(12) United States Patent
Fujimori

(10) Patent No.: US 9,879,182 B2
(45) Date of Patent: Jan. 30, 2018

(54) LIQUID CRYSTAL COMPOUND HAVING XANTHENE SKELETON AND EXHIBITING NEGATIVE DIELECTRIC ANISOTROPY, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventor: Sayaka Fujimori, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/784,958

(22) PCT Filed: Mar. 25, 2014

(86) PCT No.: PCT/JP2014/058240
§ 371 (c)(1),
(2) Date: Oct. 16, 2015

(87) PCT Pub. No.: WO2014/171272
PCT Pub. Date: Oct. 23, 2014

(65) Prior Publication Data
US 2016/0068754 A1    Mar. 10, 2016

(30) Foreign Application Priority Data
Apr. 19, 2013    (JP) .................... 2013-088664

(51) Int. Cl.
| G02F 1/1333 | (2006.01) |
| C09K 19/34 | (2006.01) |
| C07D 311/82 | (2006.01) |
| C07D 407/04 | (2006.01) |
| C07D 407/06 | (2006.01) |
| C07D 407/12 | (2006.01) |
| C09K 19/32 | (2006.01) |
| C07D 407/02 | (2006.01) |

(52) U.S. Cl.
CPC ........ *C09K 19/3402* (2013.01); *C07D 311/82* (2013.01); *C07D 407/02* (2013.01); *C07D 407/04* (2013.01); *C07D 407/06* (2013.01); *C07D 407/12* (2013.01); *C09K 19/32* (2013.01); *C09K 2019/3425* (2013.01)

(58) Field of Classification Search
CPC ... G02F 1/1333; C09K 19/3402; C09K 19/32; C09K 2019/3425; C07D 407/02; C07D 407/12; C07D 407/06; C07D 407/04; C07D 311/82
USPC .......... 252/299.01, 299.61; 428/1.1
See application file for complete search history.

(56) References Cited

U.S. PATENT DOCUMENTS 7,282,246 B2 * 10/2007 Schmidt ............... C07D 311/82
                                                      252/299.61
2005/0274929 A1  12/2005 Schmidt et al.
2012/0261614 A1  10/2012 Goto et al.

FOREIGN PATENT DOCUMENTS

| JP | 2005-314417 | 11/2005 |
| WO | 2012/086437 | 6/2012 |
| WO | 2012/132796 | 10/2012 |
| WO | 2012/144321 | 10/2012 |

OTHER PUBLICATIONS

"International Search Report (Form PCT/ISA/210)", dated Apr. 22, 2014, with English translation thereof, pp. 1-5.
"Office Action of China Counterpart Application", dated Aug. 19, 2016, p. 1-p. 20, with English translation thereof.
"Second Office Action of China Counterpart Application" with English translation thereof, dated Apr. 5, 2017, p. 1-p. 22.
"Manufacturing technology of liquid crystal display devices", Electronic industry professional skills identification guidance center, Jul. 31, 2009, pp. 45-53, with partial English translation thereof(lines 1-4 of p. 47, "Raw materials of liquid crystal display devices").
"Office Action of Taiwan Counterpart Application," with English translation thereof, dated Aug. 11, 2017, p. 1-p. 14.

(Continued)

Primary Examiner — Geraldina Visconti
(74) Attorney, Agent, or Firm — JCIPRNet

(57) ABSTRACT

A liquid crystal compound satisfies at least one of physical properties such as a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds.
The compound is represented by formula (1).

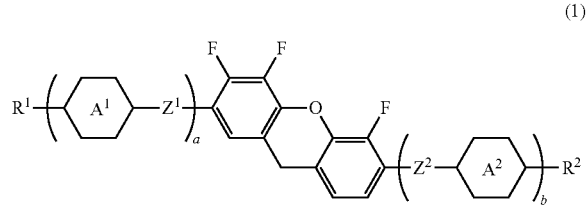

In the formula, for example, $R^1$ and $R^2$ are alkyl having 1 to 15 carbons; ring $A^1$ and ring $A^2$ are 1,4-cyclohexylene or 1,4-phenylene, $Z^1$ and $Z^2$ are a single bond, $-(CH_2)_2-$, $-CH=CH-$, $-C\equiv C-$, $-COO-$, $-OCO-$, $-CH_2O-$, $-OCH_2-$, $-CF_2O-$, $-OCF_2-$ or $-CF=CF-$, a and b are 0, 1 or 2, and a sum of a and b is 1 or 2.

12 Claims, No Drawings

(56) References Cited

OTHER PUBLICATIONS

"Office Action of China Counterpart Application," with English translation thereof, dated Sep. 19, 2017.

* cited by examiner

LIQUID CRYSTAL COMPOUND HAVING XANTHENE SKELETON AND EXHIBITING NEGATIVE DIELECTRIC ANISOTROPY, LIQUID CRYSTAL COMPOSITION AND LIQUID CRYSTAL DISPLAY DEVICE

CROSS-REFERENCE TO RELATED APPLICATION

This application is a 371 application of an international PCT application serial no. PCT/JP2014/058240, filed on Mar. 25, 2014, which claims the priority benefit of Japan application no. 2013-088664, filed on Apr. 19, 2013. The entirety of each of the abovementioned patent applications is hereby incorporated by reference herein and made a part of this specification.

TECHNICAL FIELD

The invention relates to a liquid crystal compound, a liquid crystal composition and a liquid crystal display device. More specifically, the invention relates to a compound that has a trifluoroxanthene skeleton and a ring structure bonded therewith and has a negative dielectric anisotropy, a liquid crystal composition containing the compound, and a liquid crystal display device including the composition.

BACKGROUND ART

A liquid crystal display device is widely used for a display of a personal computer, a television and so forth. The device utilizes optical anisotropy, dielectric anisotropy and so forth of a liquid crystal compound. As an operating mode of the liquid crystal display device, a variety of modes are known, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

Among the modes, the IPS mode, the FFS mode and the VA mode are known to improve narrowness of a viewing angle, being a disadvantage of operating modes such as the TN mode and the STN mode. In the liquid crystal display device having the mode of the kind, a liquid crystal composition having a negative dielectric anisotropy is mainly used. In order to further improve characteristics of the liquid crystal display device, a liquid crystal compound contained in the composition preferably has preferably physical properties described in the following (1) to (8):

(1) high stability to heat, light and so forth;
(2) a high clearing point;
(3) a low minimum temperature of a liquid crystal phase;
(4) small viscosity ($\eta$);
(5) suitable optical anisotropy ($\Delta n$);
(6) large negative dielectric anisotropy ($\Delta \in$);
(7) a suitable elastic constant ($K_{33}$: bend elastic constant); and
(8) excellent compatibility with other liquid crystal compounds.

An effect of the physical properties of the liquid crystal compound on the characteristics of the device is as described below. A compound having the high stability to heat, light and so forth as described in (1) increases a voltage holding ratio of the device. Thus, a service life of the device becomes longer. A compound having the high clearing point as described in (2) extends a temperature range in which the device can be used. A compound having the low minimum temperature of the liquid crystal phase such as a nematic phase and a smectic phase, as described in (3), in particular, a compound having the low minimum temperature of the nematic phase, also extends the temperature range in which the device can be used. A compound having the small viscosity as described in (4) decreases a response time of the device.

A compound having the suitable optical anisotropy as described in (5) improves contrast of the device. According to a design of the device, a compound having a large optical anisotropy or a small optical anisotropy, more specifically a compound having the suitable optical anisotropy is required. When decreasing the response time by decreasing a cell gap of the device, a compound having the large optical anisotropy is suitable. A compound having the large negative dielectric anisotropy as described in (6) decreases a threshold voltage of the device. Thus, an electric power consumption of the device is decreased.

With regard to (7), a compound having the large elastic constant decreases the response time of the device. A compound having the small elastic constant decreases the threshold voltage of the device. Therefore, a suitable elastic constant is required according to characteristics that are desirably improved. A compound having the excellent compatibility with other liquid crystal compound as described in (8) is preferred. The reason is that the physical properties of a composition are adjusted by mixing liquid crystal compounds that have different physical properties.

A variety of liquid crystal compounds having the large negative dielectric anisotropy have so far been prepared (for example, Patent literature No. 1). Patent literature No. 1 discloses compound (C-1). However, compound (C-1) has neither sufficiently high clearing point nor sufficiently high compatibility with other compounds.

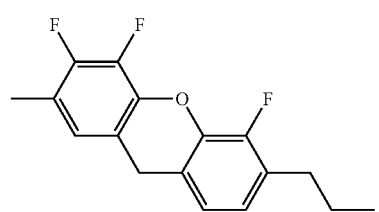

(C-1)

In view of such a situation, development has been desired for a compound having excellent physical properties and a suitable balance regarding the physical properties with regard to (1) to (8) as described above. In particular, a compound having the large negative dielectric anisotropy, the high clearing point and the high compatibility with other compounds has been required.

CITATION LIST

Patent Literature

Patent literature No. 1: JP 2005-314417 A.

SUMMARY OF INVENTION

Technical Problem

The invention provides a liquid crystal compound satisfying at least one of physical properties such as a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. In particular, the invention provides a compound having a large negative dielectric anisotropy and a high clearing point and a high compatibility with other compounds. The invention further provides a liquid crystal composition that contains the compound and satisfies at least one of physical properties such as a high maximum temperature of a nematic phase, a low minimum temperature of the nematic phase, a small viscosity, a suitable optical anisotropy, a large negative dielectric anisotropy and a suitable elastic constant. The invention provides a liquid crystal composition having a suitable balance regarding at least two of the physical properties. The invention also provides a liquid crystal display device that includes the composition, and has a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound, and a liquid crystal display device including the composition.

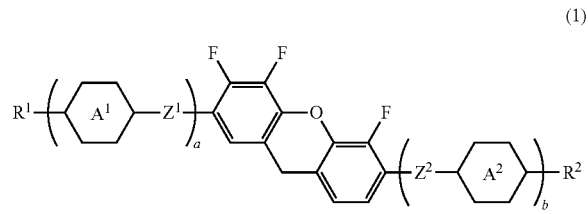

(1)

In formula (1), $R^1$ and $R^2$ are independently alkyl having 1 to 15 carbons, and in the alkyl, at least one of —$CH_2$— may be replaced by —O— or —S—, at least one of —$(CH_2)_2$— may be replaced by —CH═CH—, and in the groups, at least one of hydrogen may be replaced by halogen;

ring $A^1$ and ring $A^2$ are independently 1,4-cyclohexylene, 1,4-cyclohexenylene, 1,4-phenylene, 1,3-dioxane-2,5-diyl or tetrahydropyran-2,5-diyl, and in the rings, at least one of hydrogen may be replaced by halogen;

$Z^1$ and $Z^2$ are independently a single bond, —$(CH_2)_2$—, —CH═CH—, —C≡C—, —COO—, —OCO—, —$CH_2O$—, —$OCH_2$—, —$CF_2O$—, —$OCF_2$— or —CF═CF—; and a and b are independently 0, 1 or 2, and when a or b is 2, two of ring $A^1$, two of ring $A^2$, two of $Z^1$ and two of $Z^2$ may be identical or different, and a sum of a and b is 1 or 2.

The compound represented by formula (1) has a large negative dielectric anisotropy and a high clearing point and a high compatibility with other liquid crystal compounds by having a trifluoroxanthene skeleton and a ring structure bonded therewith.

Advantageous Effects of Invention

A first advantage of the invention is to provide a liquid crystal compound satisfying at least one of physical properties such as a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. The advantage is particularly to provide a compound having a large negative dielectric anisotropy and a high clearing point and a high compatibility with other compounds. A second advantage is to provide a liquid crystal composition that contains the compound and satisfies at least one of physical properties such as a high maximum temperature of a nematic phase, a low minimum temperature of the nematic phase, a small viscosity, a suitable optical anisotropy, a large negative dielectric anisotropy and a suitable elastic constant. A third advantage is to provide a liquid crystal display device that includes the composition and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase or a smectic phase, and also a compound having no liquid crystal phase but being useful as a component of the liquid crystal composition. The liquid crystal compound, the liquid crystal composition and a liquid crystal display device may be occasionally abbreviated as "compound," "composition" and "device," respectively. The liquid crystal display device is a generic term for a liquid crystal display panel and a liquid crystal display module. A clearing point is a transition temperature between the liquid crystal phase and an isotropic phase in the liquid crystal compound. A minimum temperature of the liquid crystal phase is a transition temperature between a solid and the liquid crystal phase (a smectic phase, a nematic phase or the like) in the liquid crystal compound. A maximum temperature of the nematic phase is a transition temperature between the nematic phase and the isotropic phase in the liquid crystal composition, and may be occasionally abbreviated as the maximum temperature. A minimum temperature of the nematic phase may be occasionally abbreviated as the minimum temperature. The compound represented by formula (1) may be abbreviated as "compound (1)." A same abbreviation may apply occasionally also to a compound represented by formula (2) or the like. In formula (1), formula (2) or the like, a symbol $A^1$, $D^1$ or the like surrounded by a hexagonal shape corresponds to ring $A^1$, ring $D^1$ or the like, respectively. A plurality of ring $A^1$ are described in one formula or in different formulas. In the compounds, two groups represented by two of arbitrary ring $A^1$ may be identical or different. A same rule also applies to a symbol ring $A^2$, $Z^2$ or the like. Moreover, the same rule also applies to two of ring $A^1$ when 1 is 2. An amount of a compound expressed in terms of "percent" is expressed in terms of "weight percent (% by weight)" based on the total amount of the composition.

An expression "at least one of "A" may be replaced by "B"" means that a position of "A" is arbitrary when the number of "A" is 1, and the positions can be selected without limitation also when the number of "A" is 2 or more. An expression "at least one of A may be replaced by B, C or D" means a case where arbitrary A is replaced by B, a case where arbitrary A is replaced by C, a case where arbitrary A is replaced by D, and further a case where a plurality of A are replaced by at least two of B, C and D. For example, alkyl in which at least one of —CH$_2$— may be replaced by —O— or —CH=CH— includes alkyl, alkenyl, alkoxy, alkoxyalkyl, alkoxyalkenyl and alkenyloxyalkyl. In addition, such a case where replacement of two successive —CH$_2$— by —O— results in forming —O—O— is not preferred. In alkyl or the like, a case where replacement of —CH$_2$— of a methyl part (—CH$_2$—H) by —O— results in forming —O—H is not preferred, either.

Then, 2-fluoro-1,4-phenylene means two divalent groups described below. Fluorine may be leftward or rightward. A same rule also applies to a divalent group in an asymmetrical ring such as tetrahydropyran-2,5-diyl.

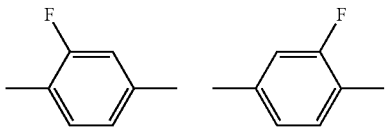

The invention includes a content described in items 1 to 13 as described below.

Item 1. A compound represented by formula (1):

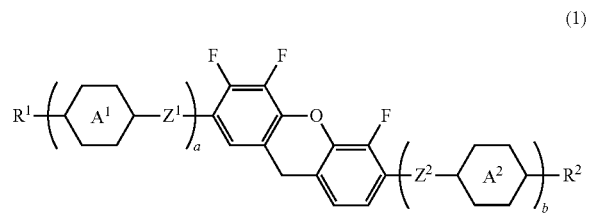

(1)

wherein, in formula (1), $R^1$ and $R^2$ are independently alkyl having 1 to 15 carbons, and in the alkyl, at least one of —CH$_2$— may be replaced by —O— or —S—, at least one of —(CH$_2$)$_2$— may be replaced by —CH=CH—, and in the groups, at least one of hydrogen may be replaced by halogen;

ring $A^1$ and ring $A^2$ are independently 1,4-cyclohexylene, 1,4-cyclohexenylene, 1,4-phenylene, 1,3-dioxane-2,5-diyl or tetrahydropyran-2,5-diyl, and in the rings, arbitrary hydrogen may be replaced by halogen;

$Z^1$ and $Z^2$ are independently a single bond, —(CH$_2$)$_2$—, —CH=CH—, —C≡C—, —COO—, —OCO—, —CH$_2$O—, —OCH$_2$—, —CF$_2$O—, —OCF$_2$— or —CF=CF—; and a and b are independently 0, 1 or 2, and when a or b is 2, two of ring $A^1$, two of ring $A^2$, two of $Z^1$ and two of $Z^2$ may be identical or different, and a sum of a and b is 1 or 2.

Item 2. The compound according to item 1, represented by any one of formulas (1-A) to (1-C):

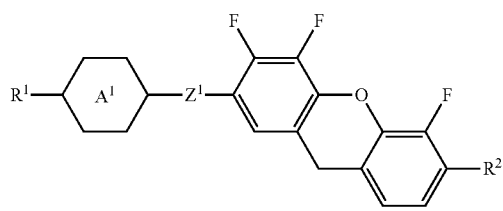

(1-A)

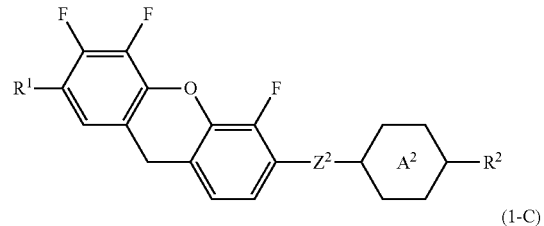

(1-B)

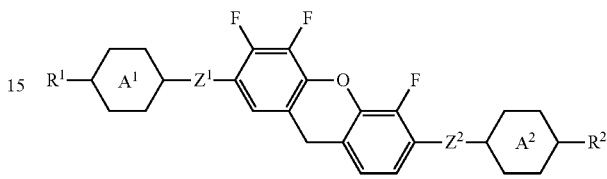

(1-C)

wherein, in formulas (1-A) to (1-C), $R^1$ and $R^2$ are independently alkyl having 1 to 15 carbons, and in the alkyl, at least one of —CH$_2$— may be replaced by —O—, at least one of —(CH$_2$)$_2$— may be replaced by —CH=CH—, and in the groups, at least one of hydrogen may be replaced by halogen;

ring $A^1$ and ring $A^2$ are independently 1,4-cyclohexylene, 1,4-cyclohexenylene, 1,4-phenylene, 1,4-phenylene in which at least one of hydrogen is replaced by fluorine, 1,3-dioxane-2,5-diyl or tetrahydropyran-2,5-diyl; and $Z^1$ and $Z^2$ are independently a single bond, —(CH$_2$)$_2$—, —CH=CH—, —COO—, —OCO—, —CH$_2$O—, —OCH$_2$—, —CF$_2$O— or —OCF$_2$—.

Item 3. The compound according to item 1, represented by formula (1-D) or (1-E):

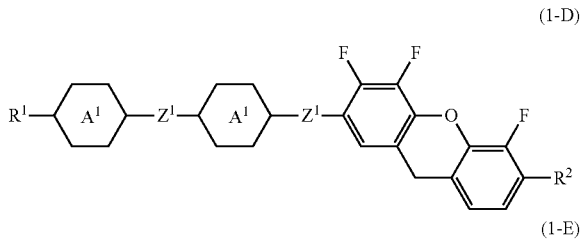

(1-D)

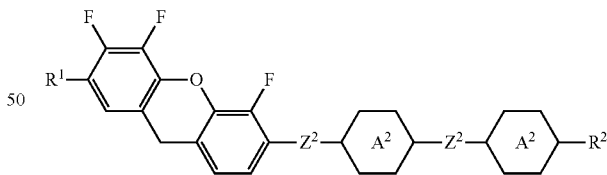

(1-E)

wherein, in formulas (1-D) and (1-E), $R^1$ and $R^2$ are independently alkyl having 1 to 15 carbons, and in the alkyl, at least one of —CH$_2$— may be replaced by —O—, at least one of —(CH$_2$)$_2$— may be replaced by —CH=CH—, and in the groups, at least one of hydrogen may be replaced by halogen;

ring $A^1$ and ring $A^2$ are independently 1,4-cyclohexylene, 1,4-cyclohexenylene, 1,4-phenylene, 1,4-phenylene in which at least one of hydrogen is replaced by fluorine, 1,3-dioxane-2,5-diyl or tetrahydropyran-2,5-diyl; and $Z^1$ and $Z^2$ are independently a single bond, —(CH$_2$)$_2$—, —CH=CH—, —COO—, —OCO—, —CH$_2$O—, —OCH$_2$—, —CF$_2$O— or —OCF$_2$—.

Item 4. The compound according to any one of items 1 to 3, wherein at least one of ring $A^1$ and ring $A^2$ is tetrahydropyran-2,5-diyl.
Item 5. The compound according to item 2, represented by any one of formulas (1-A-1) to (1-A-6), formulas (1-B-1) to (1-B-6) and formulas (1-C-1) to (1-C-4):
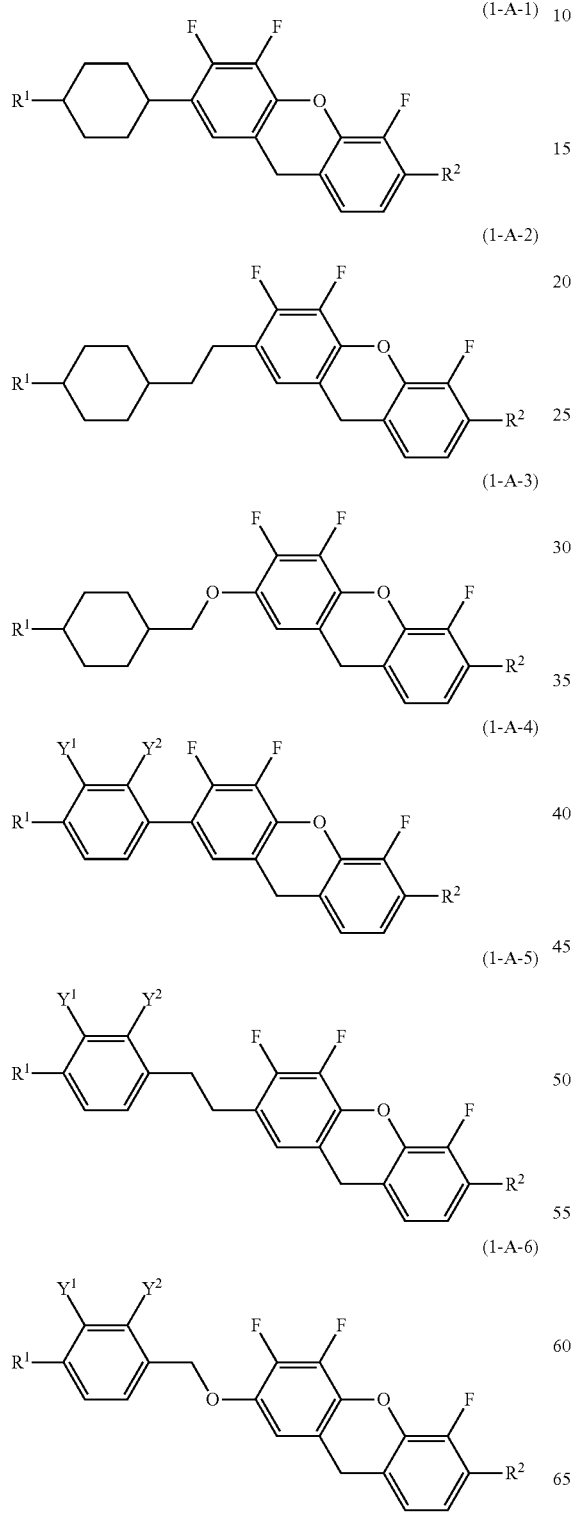
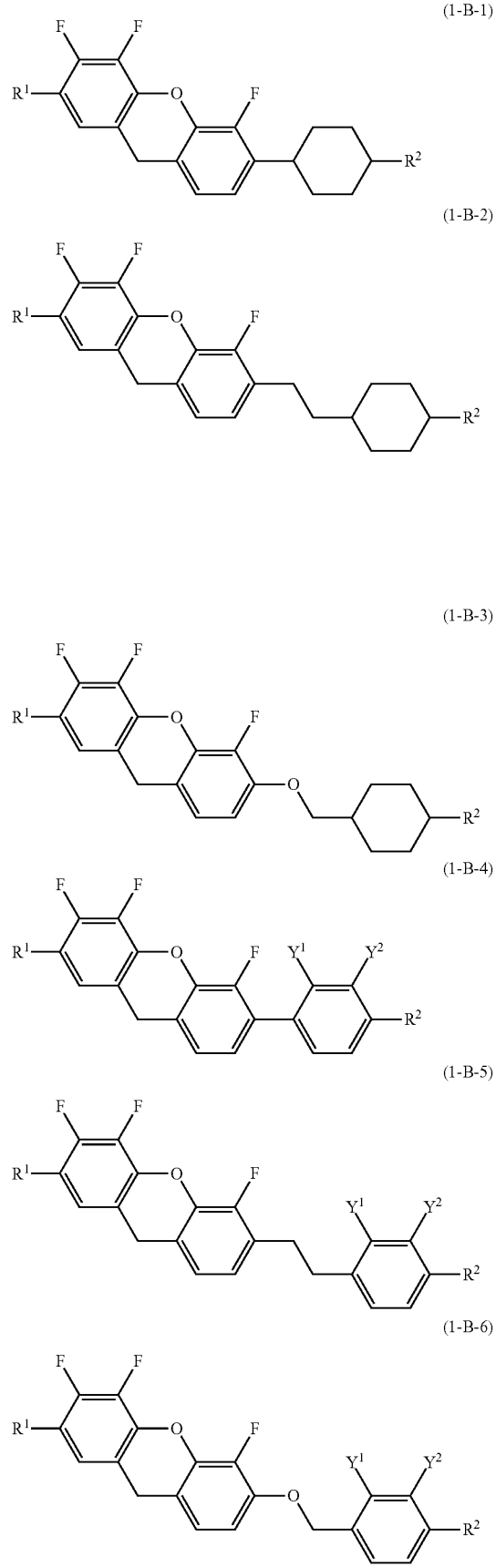

(1-C-1)
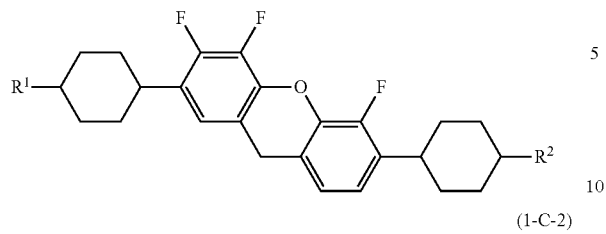
(1-C-2)
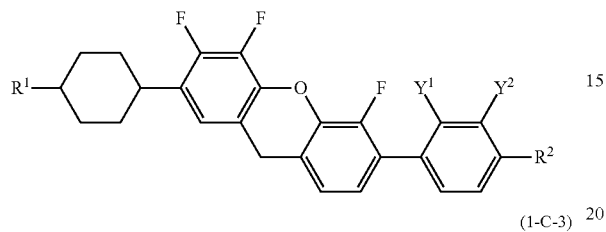
(1-C-3)
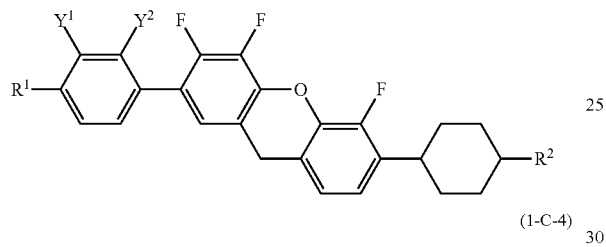
(1-C-4)
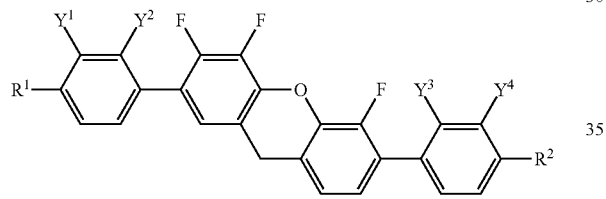
wherein, in formulas (1-A-1) to (1-A-6), formulas (1-B-1) to (1-B-6) and formulas (1-C-1) to (1-C-4), $R^1$ and $R^2$ are independently alkyl having 1 to 10 carbons, alkenyl having 2 to 10 carbons or alkoxy having 1 to 9 carbons, and $Y^1$, $Y^2$, $Y^3$ and $Y^4$ are independently hydrogen or fluorine.
Item 6. The compound according to item 2, represented by any one of formulas (1-A-7) to (1-A-12) and formulas (1-B-7) to (1-B-12):
(1-A-7)
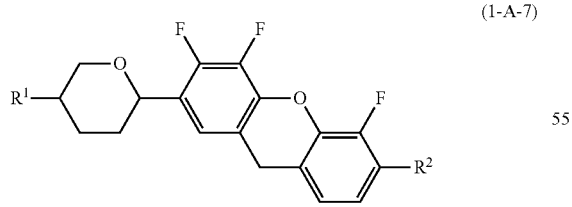
(1-A-8)
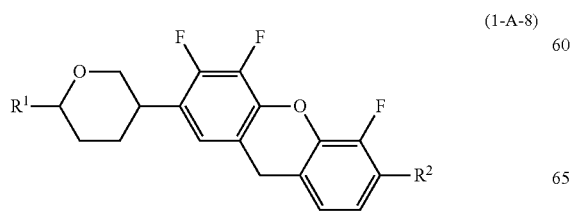
(1-A-9)
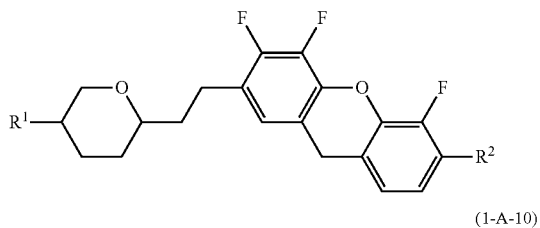
(1-A-10)
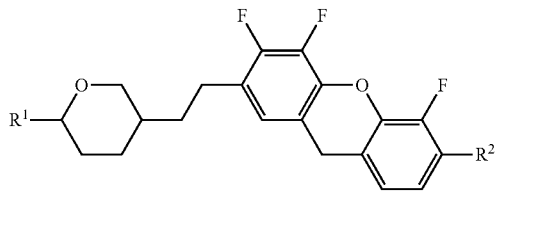
(1-A-11)
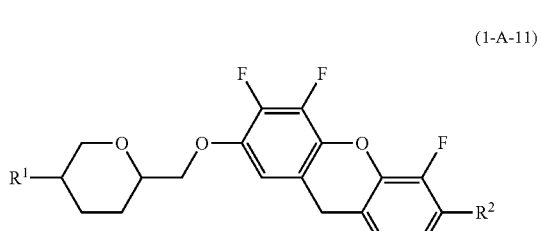
(1-A-12)
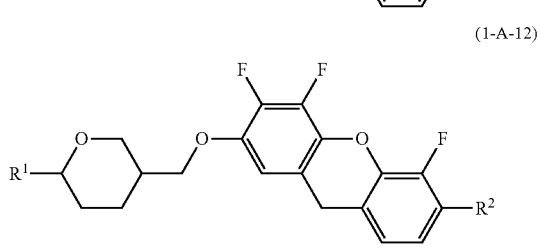
(1-B-7)
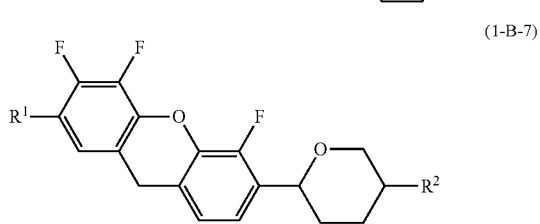
(1-B-8)
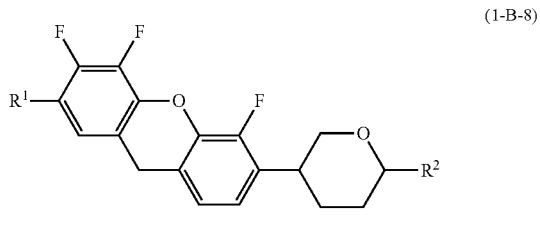
(1-B-9)
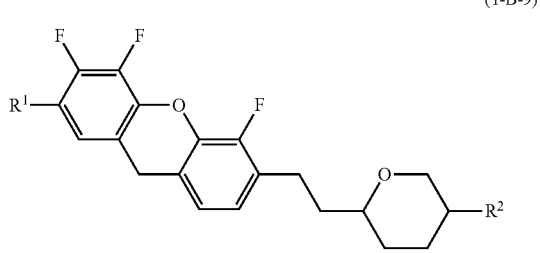

(1-B-10)

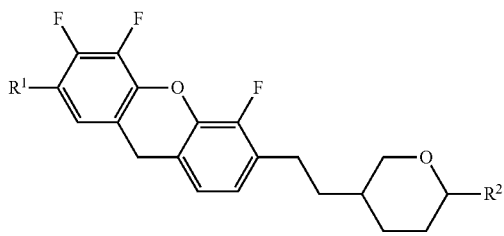

(1-B-11)

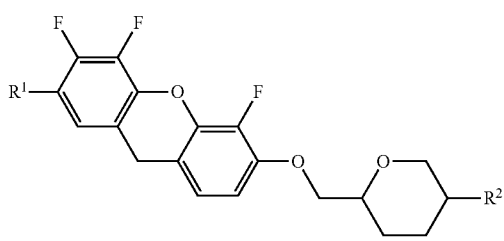

(1-B-12)

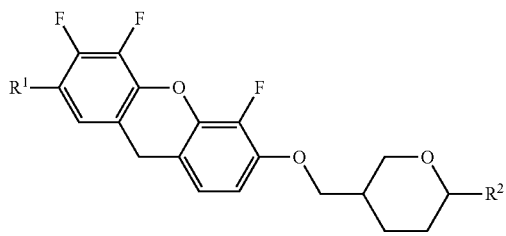

wherein, in formulas (1-A-7) to (1-A-12) and formulas (1-B-7) to (1-B-12), $R^1$ and $R^2$ are independently alkyl having 1 to 10 carbons, alkenyl having 2 to 10 carbons or alkoxy having 1 to 9 carbons.

Item 7. Use of at least one of the compounds according to any one of items 1 to 6 as a component of a liquid crystal composition.

Item 8. A liquid crystal composition, containing at least one of the compounds according to any one of items 1 to 6.

Item 9. The liquid crystal composition according to item 8, further containing at least one compound selected from the group of compounds represented by formulas (6) to (12):

(6)

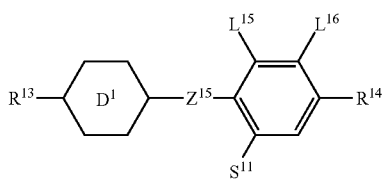

(7)

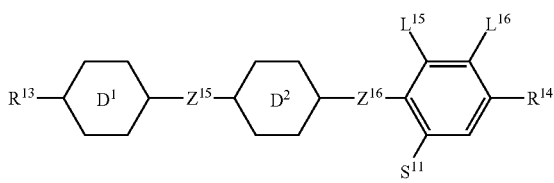

(8)

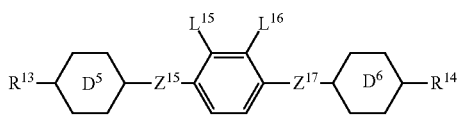

(9)

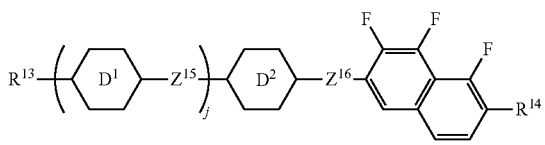

(10)

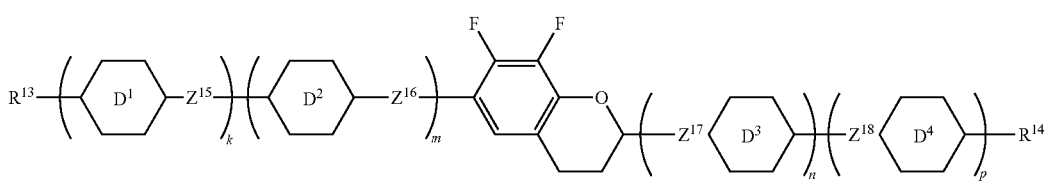

(11)

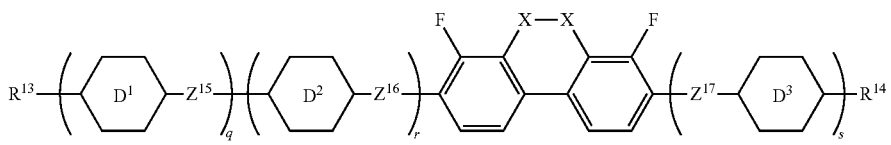

(12)

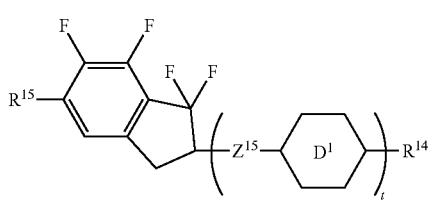

wherein, in formulas (6) to (12), $R^{13}$ is alkyl having 1 to 10 carbons or alkenyl having 2 to 10 carbons, and in the alkyl and the alkenyl, at least one of —$CH_2$— may be replaced by —O— and at least one of hydrogen may be replaced by fluorine;

$R^{14}$ is alkyl having 1 to 10 carbons, and in the alkyl, at least one of —$CH_2$— may be replaced by —O— and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of —$CH_2$— may be replaced by —O— and at least one of hydrogen may be replaced by fluorine;

$S^{11}$ is hydrogen or methyl;

X is —$CF_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 10. The liquid crystal composition according to item 8 or 9, further containing at least one compound selected from the group of compounds represented by formulas (13) to (15):

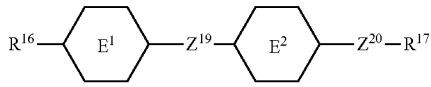

(13)

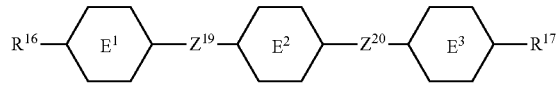

(14)

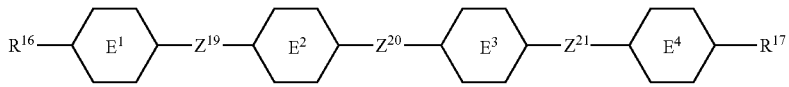

(15)

wherein, in formulas (13) to (15), $R^{16}$ and $R^{17}$ are independently alkyl having 1 to 10 carbons or alkenyl having 2 to 10 carbons, and in the alkyl or the alkenyl, at least one of —$CH_2$— may be replaced by —O— and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —$CH_2CH_2$—, —CH=CH—, —C≡C— or —COO—.

Item 11. The liquid crystal composition according to any one of items 8 to 10, further containing at least one compound selected from the group of compounds represented by formulas (2) to (4):

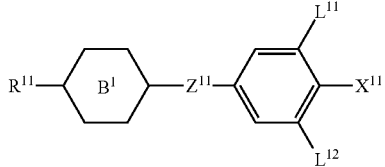

(2)

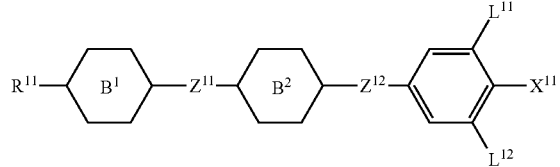

(3)

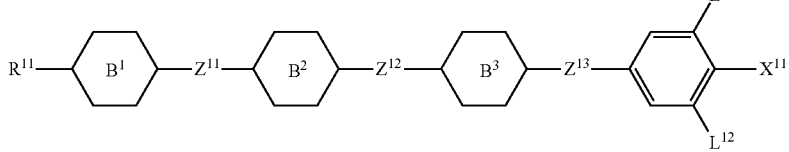

(4)

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine and at least one of —CH$_2$— may be replaced by —O—;

$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring B$^1$, ring B$^2$ and ring B$^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and $L^{11}$ and $L^{12}$ are independently hydrogen or fluorine.

Item 12. The liquid crystal composition according to any one of items 8 to 11, further containing at least one compound selected from the group of compounds represented by formula (5):

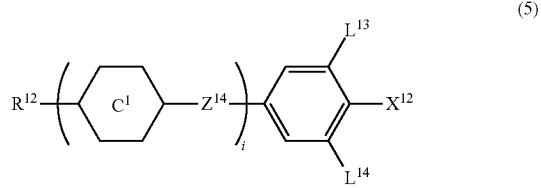

(5)

wherein, in formula (5), $R^{12}$ is alkyl having 1 to 10 carbons or alkenyl having 2 to 10 carbons, and in the alkyl and alkenyl, at least one of hydrogen may be replaced by fluorine and at least one of —CH$_2$— may be replaced by —O—;

$X^{12}$ is —C≡N or —C≡C—C≡N;

ring C$^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, —CH$_2$CH$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

Item 13. The liquid crystal composition according to any one of items 8 to 12, further containing at least one optically active compound and/or at least one polymerizable compound.

Item 14. The liquid crystal composition according to any one of items 8 to 13, further containing at least one antioxidant and/or at least one ultraviolet light absorber.

Item 15. A liquid crystal display device, including the liquid crystal composition according to any one of items 8 to 14.

The compound, the liquid crystal composition and the liquid crystal display device of the invention are described in the order.

1-1. Compound (1)

Compound (1) of the invention will be described. Preferred examples of a terminal group, a ring structure and a bonding group in compound (1), and an effect of the groups on physical properties are also applied to a compound represented by a subordinate formula of compound (1).

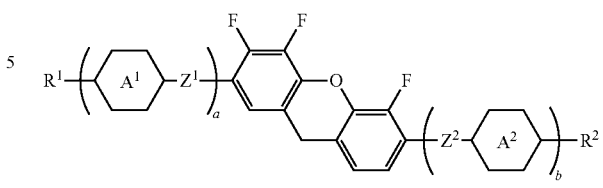

(1)

In formula (1), $R^1$ and $R^2$ are independently alkyl having 1 to 15 carbons, and in the alkyl, at least one of —CH$_2$— may be replaced by —O— or —S—, at least one of —(CH$_2$)$_2$— may be replaced by —CH=CH—, and in the groups, at least one of hydrogen may be replaced by halogen. The groups have a straight chain or a branched chain, and do not include a cyclic group such as cyclohexyl. In the groups, the straight chain is preferred to the branched chain.

A preferred configuration of —CH=CH— in alkenyl depends on a position of a double bond. A trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in alkenyl having the double bond at an even-numbered position, such as —CH$_2$CH=CHCH$_3$, —CH$_2$CH=CHC$_2$H$_5$ and —CH$_2$CH=CHC$_3$H$_7$. An alkenyl compound having the preferred configuration has a high clearing point or a wide temperature range of a liquid crystal phase. A detailed description is found in Mol. Cryst. Liq. Cryst., 1985, 131, 109 and Mol. Cryst. Liq. Cryst., 1985, 131, 327.

Preferred examples of $R^1$ or $R^2$ include alkyl, alkoxy, alkenyl and alkenyloxy. Further preferred examples of $R^1$ and $R^2$ include alkyl, alkoxy and alkenyl.

Specific examples of alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Specific examples of alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Specific examples of alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

Specific examples of alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

Specific examples of alkenyloxy include —OCH$_2$CH=CH$_2$, —OCH$_2$CH=CHCH$_3$ and —OCH$_2$CH=CHC$_2$H$_5$.

Specific examples of alkyl in which at least one of hydrogen is replaced by halogen include —CH$_2$F, —CHF$_2$, —CF$_3$, —(CH$_2$)$_2$—F, —CF$_2$CH$_3$, —CF$_2$CH$_2$F, —CF$_2$CHF$_2$, —CH$_2$CF$_3$, —CF$_2$CF$_3$, —(CH$_2$)$_3$—F, —CF$_2$CH$_2$CH$_3$, —CH$_2$CHFCH$_3$, —CH$_2$CF$_2$CH$_3$, —(CF$_2$)$_3$—F, —CF$_2$CHFCF$_3$, —CHFCF$_2$CF$_3$, —(CH$_2$)$_4$—F, —CF$_2$(CH$_2$)$_2$CH$_3$, —(CF$_2$)$_4$—F, —(CH$_2$)$_5$—F, —(CF$_2$)$_5$—F, —CH$_2$Cl, —CHCl$_2$, —CCl$_3$, —(CH$_2$)$_2$—Cl, —CCl$_2$CH$_3$, —CCl$_2$CH$_2$Cl, —CCl$_2$CHCl$_2$, —CH$_2$CCl$_3$, —CCl$_2$CCl$_3$, —(CH$_2$)$_3$—Cl, —CCl$_2$CH$_2$CH$_3$, —(CCl$_2$)$_3$—Cl, —CCl₂CHClCCl₃, —CHClCCl₂CCl₃, —(CH₂)₄—Cl, —(CCl₂)₄—Cl, —CCl₂(CH₂)₂CH₃, —(CH₂)₅—Cl and —(CCl₂)₅—Cl.

Specific examples of alkoxy in which at least one of hydrogen is replaced by halogen include —OCH₂F, —OCHF₂, —OCF₃, —O—(CH₂)₂—F, —OCF₂CH₂F, —OCF₂CHF₂, —OCH₂CF₃, —O—(CH₂)₃—F, —O—(CF₂)₃—F, —OCF₂CHFCF₃, —OCHFCF₂CF₃, —O(CH₂)₄—F, —O—(CF₂)₄—F, —O—(CH₂)₅—F, —O—(CF₂)₅—F, —OCH₂CHFCH₂CH₃, —OCH₂Cl, —OCHCl₂, —OCCl₃, —O—(CH₂)₂—Cl, —OCCl₂CH₂Cl, —OCCl₂CHCl₂, —OCH₂CCl₃, —O—(CH₂)₃—Cl, —O—(CCl₂)₃—Cl, —OCCl₂CHClCCl₃, —OCHClCCl₂CCl₃, —O(CH₂)₄—Cl, —O—(CCl₂)₄—Cl, —O—(CH₂)₅—Cl and —O—(CCl₂)₅—Cl.

Specific examples of alkenyl in which at least one of hydrogen is replaced by halogen include —CH═CHF, —CH═CF₂, —CF═CHF, —CH═CHCH₂F, —CH═CHCF₃, —(CH₂)₂—CH═CF₂, —CH₂CH═CHCF₃, —CH═CHCF₂CF₃, —CH═CHCl, —CH═CCl₂, —CCl═CHCl, —CH═CHCH₂C₁, —CH═CHCCl₃, —(CH₂)₂—CH═CCl₂, —CH₂CH═CHCCl₃ and —CH═CHCCl₂CCl₃.

In formula (1), ring $A^1$ and ring $A^2$ are independently 1,4-cyclohexylene, 1,4-cyclohexenylene, 1,4-phenylene, 1,3-dioxane-2,5-diyl or tetrahydropyran-2,5-diyl, and in the rings, arbitrary hydrogen may be replaced by halogen.

Preferred examples of ring $A^1$ or ring $A^2$ include 1,4-cyclohexylene, 1,4-cyclohexenylene, 1,4-phenylene, 1,4-phenylene in which at least one of hydrogen is replaced by fluorine, and tetrahydropyran-2,5-diyl. Further preferred examples include 1,4-cyclohexylene, 1,4-phenylene and tetrahydropyran-2,5-diyl. Then, 1,4-cyclohexylene has cis and trans configurations. From a viewpoint of a high maximum temperature, the trans configuration is preferred.

Preferred examples of 1,4-phenylene in which at least one of hydrogen is replaced by halogen include rings (A-1) to (A-17). In order to have a large negative dielectric anisotropy, groups (A-1), (A-5), (A-6), (A-7), (A-8), (A-9), (A-10) and (A-11) are further preferred.

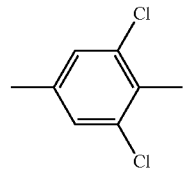

(A-1)

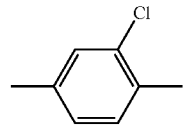

(A-2)

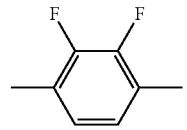

(A-3)

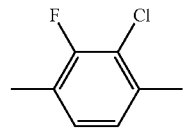

(A-4)


(A-5)


(A-6)


(A-7)

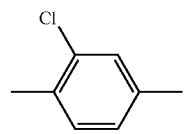

(A-8)

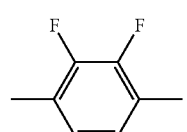

(A-9)

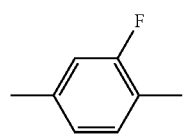

(A-10)

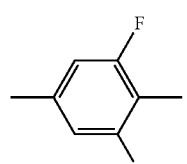

(A-11)

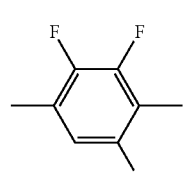

(A-12)

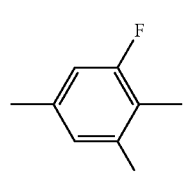

(A-13)

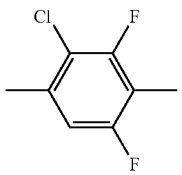

(A-14)

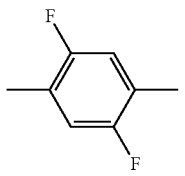

(A-15)

(A-16)

(A-17)

In formula (1), $Z^1$ and $Z^2$ are independently a single bond, —(CH$_2$)$_2$—, —CH=CH—, —COO—, —OCO—, —CH$_2$O—, —OCH$_2$—, —CF$_2$O—, —OCF$_2$— or —CF=CF—. Preferred examples of $Z^1$ and $Z^2$ include a single bond, —(CH$_2$)$_2$—, —COO—, —OCO—, —CH$_2$O—, —OCH$_2$—, —CF$_2$O— or —OCF$_2$—.

In formula (1), a and b are independently 0, 1 or 2. Two of arbitrary ring $A^1$ when a is 2 may be identical or different, and two of arbitrary ring $Z^1$ may be identical or different. Two of arbitrary ring $A^2$ when b is 2 may be identical or different, and two of arbitrary $Z^2$ may be identical or different. A sum of a and b is 1 or 2. Preferred combinations of a and b include combinations: (a=1, b=0), (a=0, b=1), (a=2, b=0) and (a=1, b=1). Further preferred combinations of a and b include combinations: (a=1, b=0) and (a=0, b=1).

1-2. Physical Properties of Compound (1)

Physical properties such as a clearing point, optical anisotropy and dielectric anisotropy can be arbitrarily adjusted by appropriately selecting a kind of $R^1$, $R^2$, ring $A^1$, ring $A^2$, $Z^1$ and $Z^2$ in compound (1). Compound (1) may contain an isotope such as 2H (deuterium) and $^{13}$C in an amount larger than an amount of natural abundance because no significant difference exists in physical properties of the compound. Main effects of kinds of $R^1$ or the like on the physical properties of compound (1) are described below.

When $R^1$ or $R^2$ has a straight chain, a temperature range of the liquid crystal phase is wide and viscosity is small. When $R^1$ or $R^2$ has a branched chain, compatibility with other liquid crystal compounds is good. A compound in which $R^1$ or $R^2$ is optically active is useful as a chiral dopant. A reverse twisted domain that is generated in the liquid crystal display device can be prevented by adding the compound to the composition. A compound in which $R^1$ or $R^2$ is not optically active is useful as a component of the composition. When $R^1$ or $R^2$ is alkenyl, the preferred configuration depends on the position of the double bond. The alkenyl compound having the preferred configuration has a small viscosity, a high maximum temperature or a wide temperature range of the liquid crystal phase. When $R^1$ or $R^2$ is alkoxy, the compound has a high maximum temperature.

When both of ring $A^1$ and ring $A^2$ are 1,4-cyclohexylene, the clearing point is high and the viscosity is small. When at least one of ring $A^1$ and ring $A^2$ is 1,4-phenylene, or 1,4-phenylene in which at least one of hydrogen is replaced by halogen, the optical anisotropy is comparatively large and an orientational order parameter is comparatively large. When both of ring $A^1$ and ring $A^2$ are 1,4-phenylene, 1,4-phenylene in which at least one of hydrogen is replaced by halogen, or a combination thereof, the optical anisotropy is particularly large. When at least one of ring $A^1$ and ring $A^2$ is 2-fluoro-1,4-phenylene, 2-chloro-1,4-phenylene, 2,3-difluoro-1,4-phenylene, 2,3-dichloro-1,4-phenylene, 2-chloro-3-fluoro-1,4-phenylene or tetrahydropyran-2,5-diyl, a negative dielectric anisotropy is particularly large.

When at least one of $Z^1$ and $Z^2$ is a single bond, —CH$_2$CH$_2$—, —CH=CH— or —CF$_2$O—, —OCF$_2$—, the viscosity is small. When at least one of $Z^1$ and $Z^2$ is —CH=CH—, —CH$_2$O— or —OCH$_2$—, the temperature range of the liquid crystal phase is wide, and an elastic constant (K) is large. When at least one of $Z^1$ and the $Z^2$ is a single bond, —CH=CH—, —C≡C—, —COO—, —OCO— or —CF=CF—, the clearing point is high. When at least one of $Z^1$ and $Z^2$ is —CH=CH—, —C≡C— or —CF=CF—, the optical anisotropy is large. When at least one of $Z^1$ and $Z^2$ is —CH$_2$O— or —OCH$_2$—, the negative dielectric anisotropy is large. When both of $Z^1$ and $Z^2$ are a single bond, —CH$_2$CH$_2$—, —CH$_2$O— or —OCH$_2$—, chemical stability is high. When a combination of a and b includes (a=1, b=0) and $Z^1$ is —CH$_2$O—, a negative dielectric anisotropy is large and compatibility with other liquid crystal compounds is excellent. When the combination of a and b includes (a=1, b=0), $Z^1$ is —CH$_2$O— and $R^2$ is alkoxy, the negative dielectric anisotropy is particularly large. When the combination of a and b includes (a=0, b=1), and $Z^2$ is —OCH$_2$—, the negative dielectric anisotropy is large. When the combination of a and b includes (a=1, b=0) or (a=0, b=1), $Z^1$ and $Z^2$ are a single bond and $R^1$ or $R^2$ is alkoxy, the compound has a large negative dielectric anisotropy. When the combination of a and b includes (a=2, b=0) or (a=1, b=1), the clearing point is high.

1-3. Preferred Compound

Preferred examples of compound (1) include compounds (1-A) to (1-E) described in items 2 and 3.

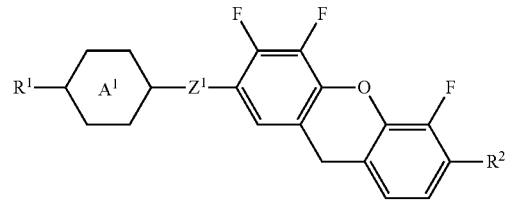

(1-A)

-continued

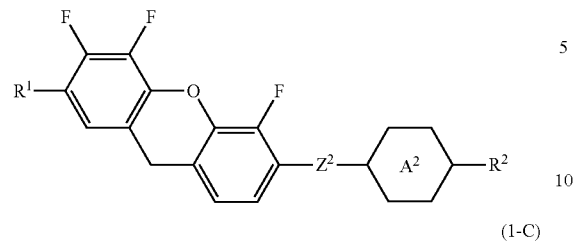
(1-B)

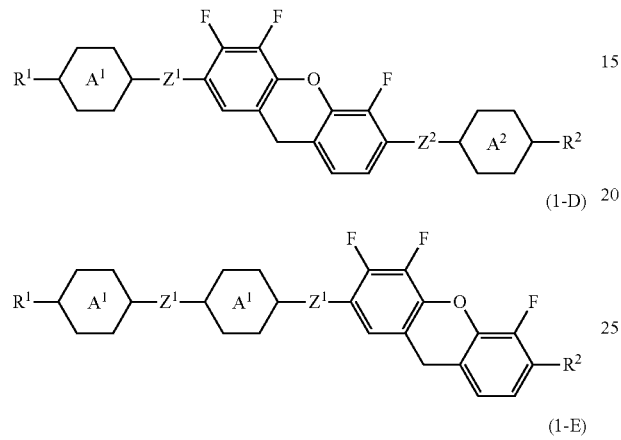
(1-C)

(1-D)

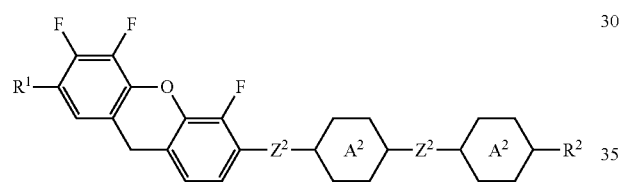
(1-E)

In formulas (1-A) to (1-E), $R^1$ and $R^2$ are independently alkyl having 1 to 10 carbons, alkenyl having 2 to 10 carbons or alkoxy having 1 to 9 carbons;

ring $A^1$ and ring $A^2$ are independently 1,4-cyclohexylene, 1,4-cyclohexenylene, 1,4-phenylene, 1,4-phenylene in which at least one of hydrogen is replaced by fluorine or tetrahydropyran-2,5-diyl; and $Z^1$ and $Z^2$ are independently a single bond, —(CH$_2$)$_2$—, —CH=CH—, —COO—, —OCO—, —CH$_2$O—, —OCH$_2$—, —CF$_2$O— or —OCF$_2$—.

Further preferred examples of compound (1) include compounds (1-A-1) to (1-A-12), compounds (1-B-1) to (1-B-12) and compound (1-C-1) to (1-C-4) described in items 5 and 6.

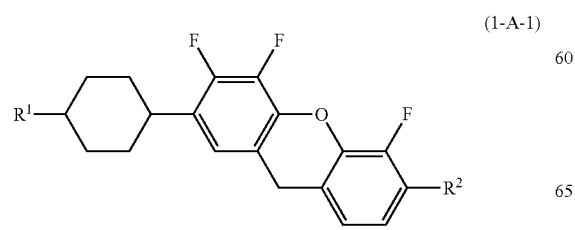
(1-A-1)

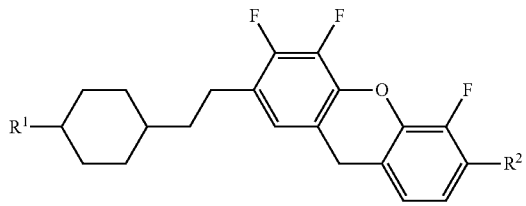
(1-A-2)

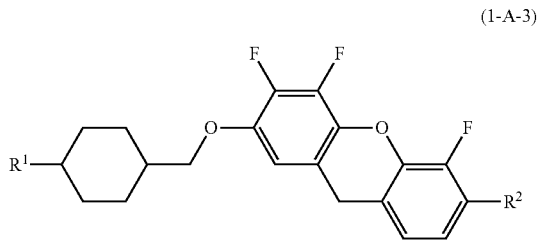
(1-A-3)

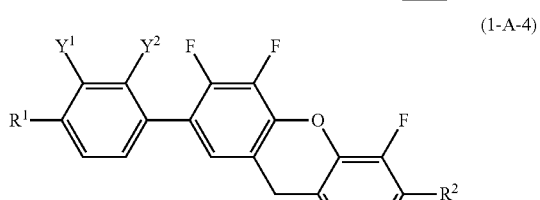
(1-A-4)

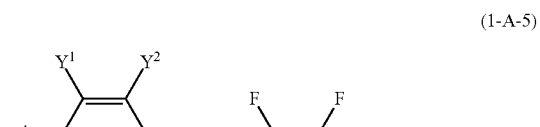
(1-A-5)

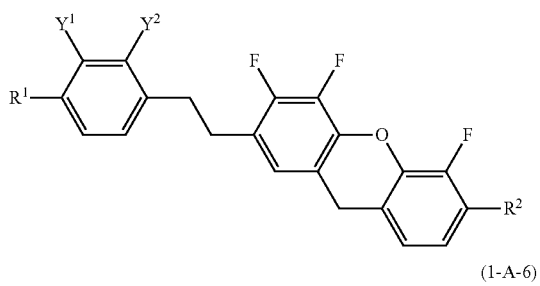
(1-A-6)

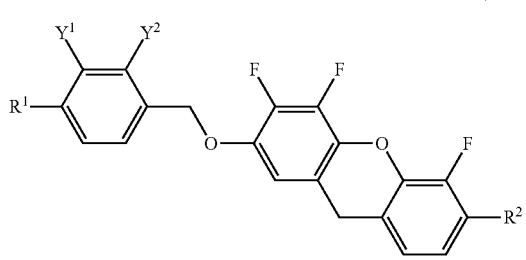

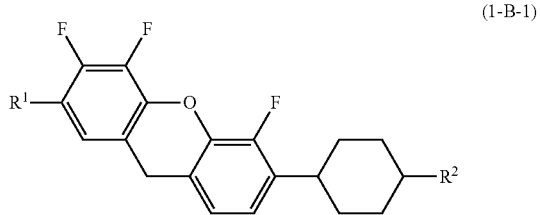
(1-B-1)

(1-B-2)
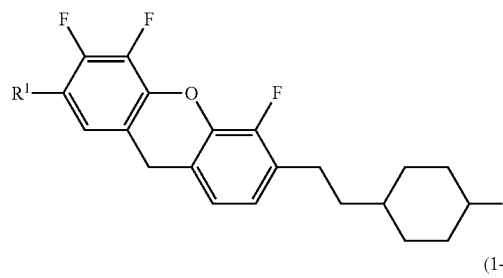
(1-B-3)
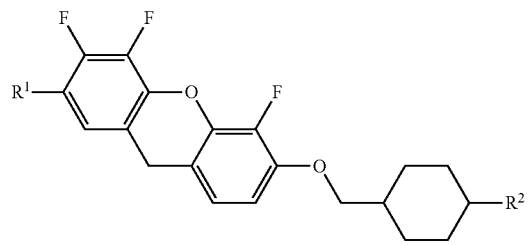
(1-B-4)
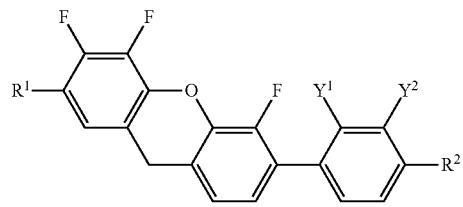
(1-B-5)
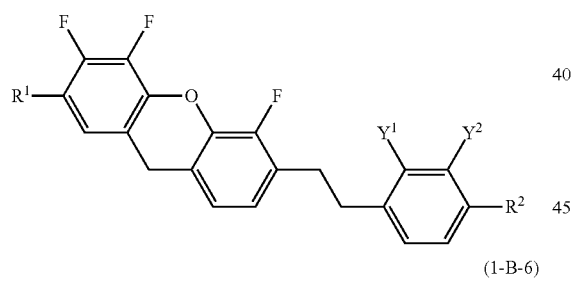
(1-B-6)
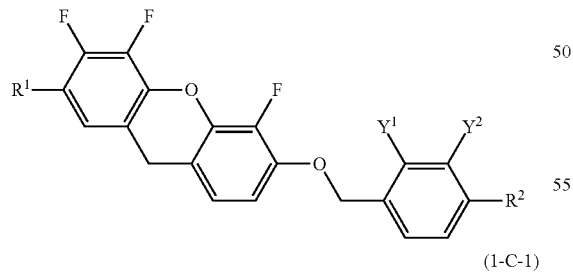
(1-C-1)
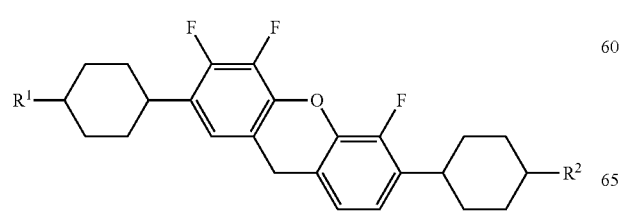
(1-C-2)
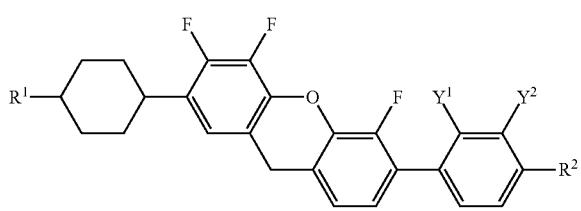
(1-C-3)
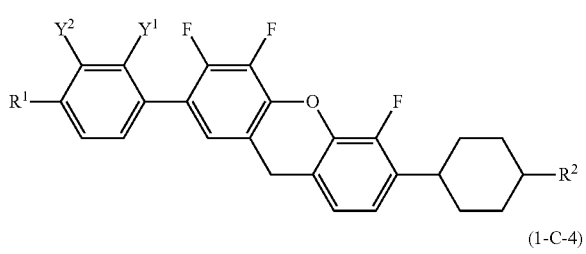
(1-C-4)
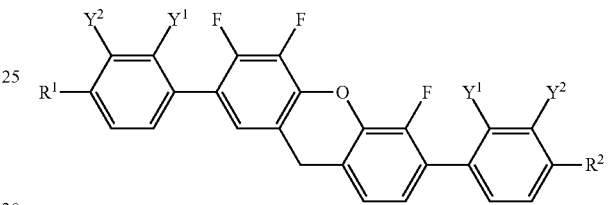
(1-A-7)
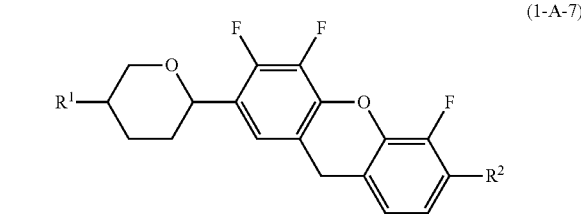
(1-A-8)
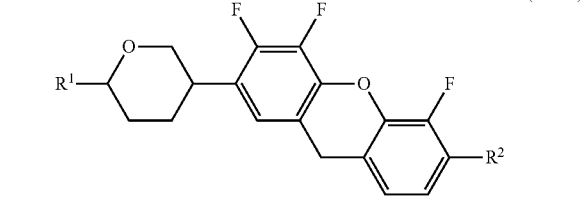
(1-A-9)
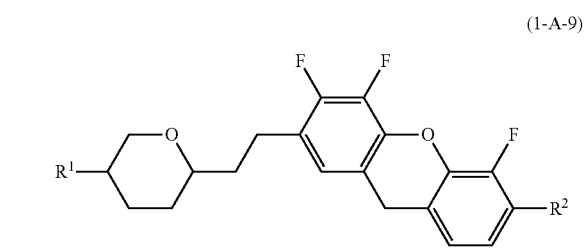
(1-A-10)

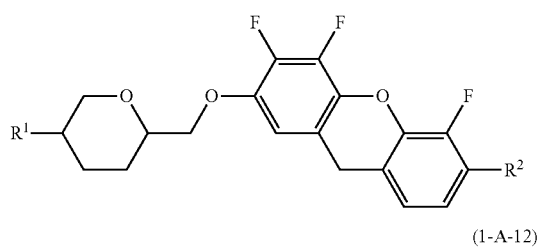

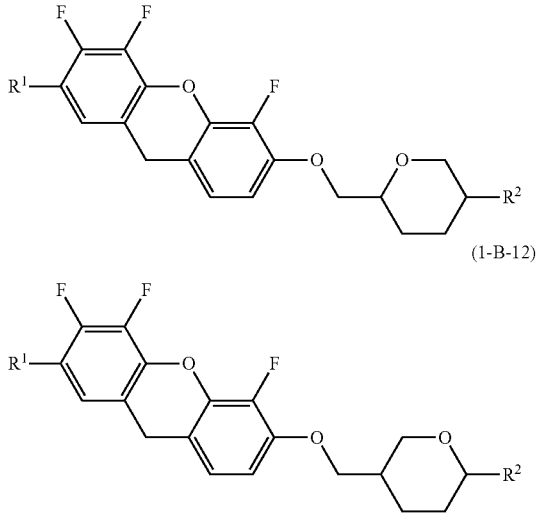

In formulas (1-A-1) to (1-A-12), formulas (1-B-1) to (1-B-12) and formulas (1-C-1) to (1-C-4), $R^1$ and $R^2$ are independently alkyl having 1 to 10 carbons, alkenyl having 2 to 10 carbons and alkoxy having 1 to 9 carbons, and $Y^1$, $Y^2$, $Y^3$ and $Y^4$ are independently hydrogen or fluorine.

1-4. Synthesis of Compound (1)

A method for preparing compound (1) will be described. Compound (1) can be prepared by suitably combining techniques of synthetic organic chemistry. A method for introducing an objective terminal group, ring and bonding group into a starting material is described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

1-4-1. Formation of a Bonding Group

An example of a method for forming a bonding group in compound (1) is as described in a scheme below. In the scheme, $MSG^1$ (or $MSG^2$) is a monovalent organic group having at least one ring. Monovalent organic groups represented by a plurality of $MSG^1$ (or $MSG^2$) may be identical or different. Compound (1A) to compound (1G) correspond to compound (1) or an intermediate of compound (1).

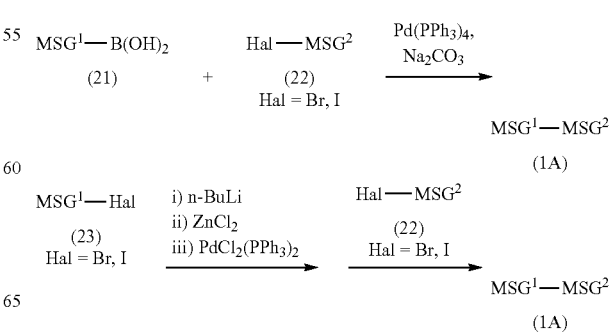

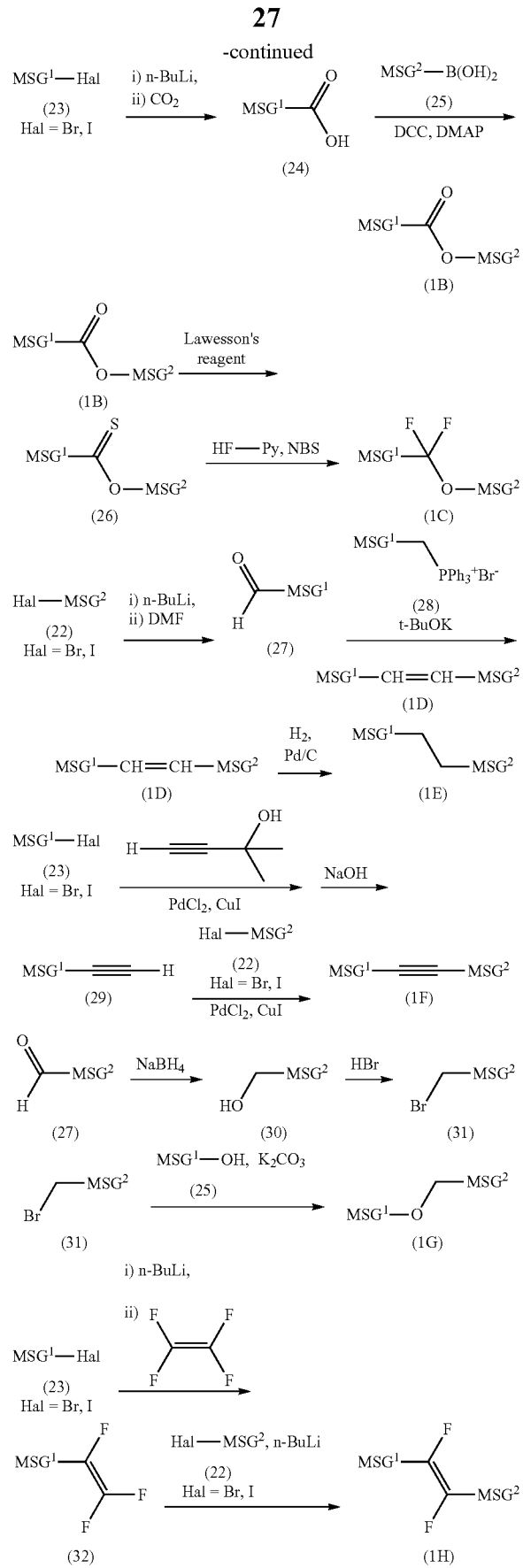

(I) Formation of a Single Bond

Compound (1A) is prepared by allowing arylboronic acid (21) to react with compound (22) in the presence of carbonate and a tetrakis(triphenylphosphine)palladium catalyst. The compound (1A) is also prepared by allowing compound (23) to react with n-butyllithium and subsequently with zinc chloride, and further with compound (22) in the presence of a dichlorobis(triphenylphosphine)palladium catalyst.

(II) Formation of —COO— and —OCO—

Carboxylic acid (24) is obtained by allowing compound (23) to react with n-butyllithium and then with carbon dioxide. Compound (1B) having —COO— is prepared by dehydrating the carboxylic acid (24) and phenol (25) derived from compound (21) in the presence of 1,3-dicyclohexylcarbodiimide (DCC) and 4-dimethylaminopyridine (DMAP). A compound having —OCO— is also prepared according to the method.

(III) Formation of —CF$_2$O— and —OCF$_2$—

Compound (26) is obtained by sulfurizing compound (1B) with Lawesson's reagent. Compound (1C) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino)sulfur trifluoride (DAST). Refer to W. H. Bunnelle et al., J. Org. Chem. 1990, 55, 768. A compound having —OCF$_2$— is also prepared according to the method.

(IV) Formation of —CH═CH—

Aldehyde (27) is obtained by allowing compound (22) to react with n-butyllithium and then with N,N-dimethylformamide (DMF). Compound (1D) is prepared by allowing aldehyde (27) to react with aldehyde (27) generated by allowing phosphonium salt (28) to react with potassium tert-butoxide. A cis isomer is generated depending on reaction conditions, and therefore the cis isomer is isomerized into a trans isomer according to a known method, when necessary.

(V) Formation of —CH$_2$CH$_2$—

Compound (1E) is prepared by hydrogenating compound (1D) in the presence of a palladium-on-carbon catalyst.

(VI) Formation of —C≡C—

Compound (29) is obtained by allowing compound (23) to react with 2-methyl-3-butyn-2-ol in the presence of a catalyst including dichloropalladium and copper iodide, and then performing deprotection under basic conditions. Compound (1F) is prepared by allowing compound (29) to react with compound (22) in the presence of a catalyst including dichlorobis(triphenylphosphine)palladium and copper halide.

(VII) Formation of —Cl$_2$O— and —OCH$_2$—

Compound (30) is obtained by reducing compound (27) with sodium borohydride. Compound (31) is obtained by brominating compound (30) with hydrobromic acid. Compound (1G) is prepared by allowing compound (25) to react with compound (31) in the presence of potassium carbonate. A compound having —OCH$_2$— is also prepared according to the method.

(VIII) Formation of —CF═CF—

Compound (32) is obtained by treating compound (23) with n-butyllithium and then allowing the treated compound to react with tetrafluoroethylene. Compound (1H) is prepared by treating compound (22) with n-butyllithium and then allowing the treated compound to react with compound (32).

1-4-2. Formation of Ring A$^1$ and Ring A$^2$

With regard to a ring such as 1,4-cyclohexylene, 1,4-cyclohexenylene, 1,4-phenylene, 2-fluoro-1,4-phenylene, 2,3-difluoro-1,4-phenylene, tetrahydropyran-2,5-diyl and 1,3-dioxane-2,5-diyl, a starting material is commercially available or a synthetic process is well known.

1-4-3. Synthesis Example

An example of a method for preparing compound (1) is as described below. In the compounds, $R^1$, $R^2$, ring $A^1$, ring $A^2$, $Z^1$, $Z^2$, a and b are defined in a manner identical with definitions as in item 1 described above.

An example of a method for preparing compound (1) is as described below. Compound (52) is obtained by allowing s-butyllithium, triisopropyl borate, acetic acid and hydrogen peroxide to act on compound (51) prepared by a publicly known method. Compound (53) is obtained by allowing sodium hydride and chloromethyl methyl ether to act on compound (52). Compound (55) is obtained by allowing s-butyllithium and N,N'-dimethylformamide to act on compound (54) prepared by a publicly known method. Compound (56) is obtained by allowing s-butyllithium and compound (55) to act on compound (53). Compound (57) is obtained by allowing triethylsilane and a boron trifluoride-diethyl ether complex to act on compound (56). Compound (1) is obtained by allowing sodium hydride to act on compound (57).

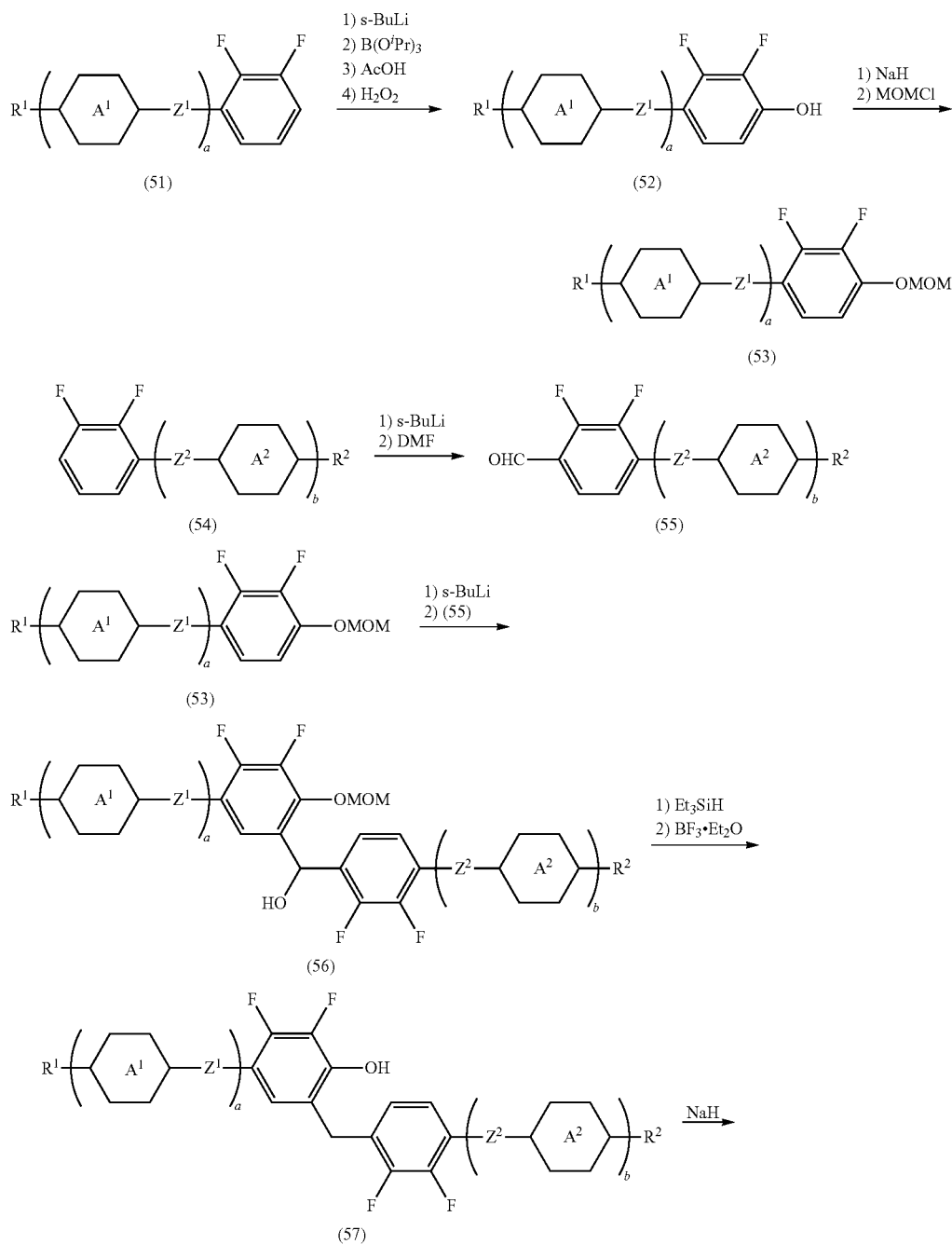

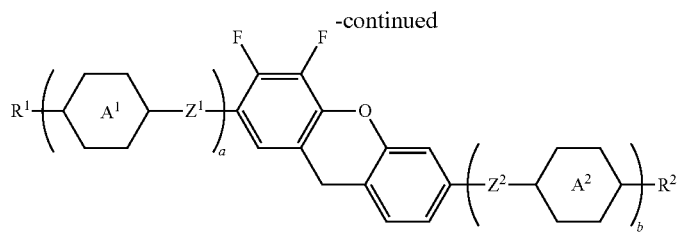

(1)

2. Composition (1)

Liquid crystal composition (1) of the invention will be described below. Composition (1) contains at least one compound (1) as component A. Composition (1) may contain two or more kinds of compound (1). Composition (1) may contain only compound (1) as a component of the liquid crystal composition. Composition (1) preferably contains at least one of compound (1) in the range of 1 to 99% by weight in order to develop excellent physical properties. In a composition having a positive dielectric anisotropy, a preferred content of compound (1) is in the range of 5 to 60% by weight. In a composition having a negative dielectric anisotropy, a preferred content of compound (1) is 30% or less by weight. Composition (1) may also contain compound (1) and various kinds of liquid crystal compounds that are not described herein.

A preferred composition contains a compound selected from components B, C, D and E shown below. When composition (1) is prepared, a component thereof can be selected, for example, by taking dielectric anisotropy of liquid crystal compound (1) into consideration. A composition prepared by suitably selecting a component has a high maximum temperature of the nematic phase, a low minimum temperature of the nematic phase, a small viscosity, a suitable optical anisotropy, a large dielectric anisotropy and a suitable elastic constant.

Component B includes compounds (2) to (4). Component C includes compound (5). Component D includes compounds (6) to (12). Component E includes compounds (13) to (15). The components will be described in the order.

Component B includes a compound having a halogen-containing group or a fluorine-containing group at a right terminal. Preferred examples of component B include compounds (2-1) to (2-16), compounds (3-1) to (3-113) and compounds (4-1) to (4-57).

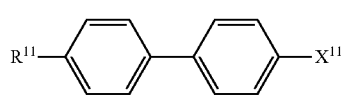
(2-1)

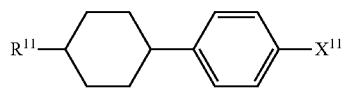
(2-2)

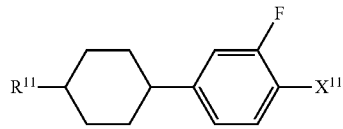
(2-3)

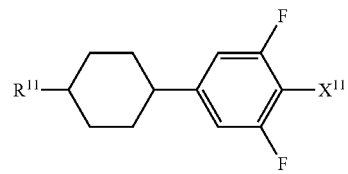
(2-4)

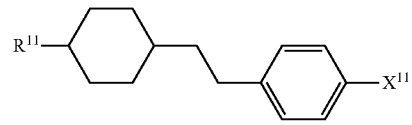
(2-5)

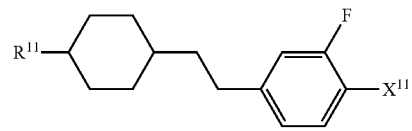
(2-6)

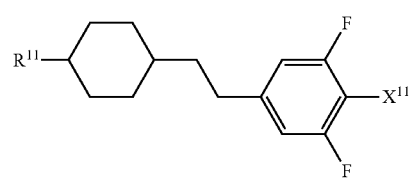
(2-7)

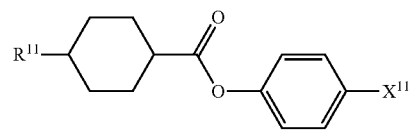
(2-8)

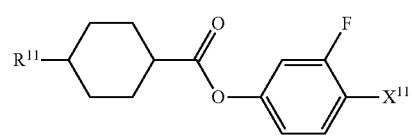
(2-9)

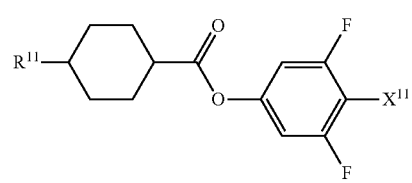
(2-10)

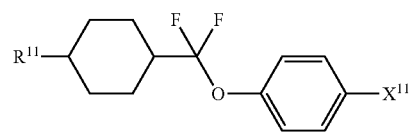
(2-11)

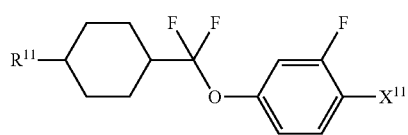
(2-12)
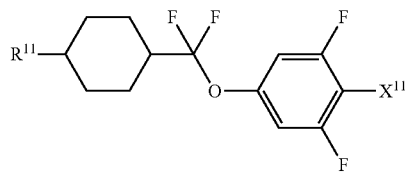
(2-13)
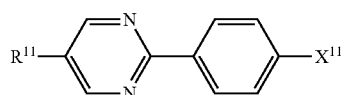
(2-14)
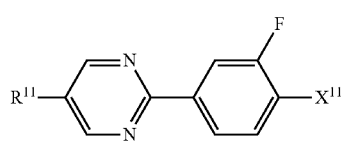
(2-15)
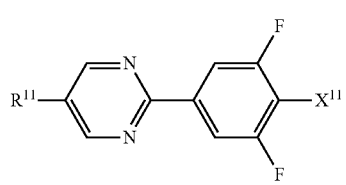
(2-16)
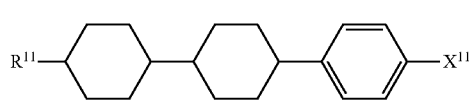
(3-1)
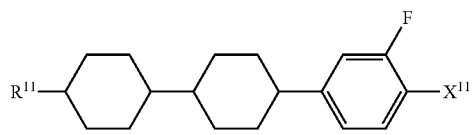
(3-2)
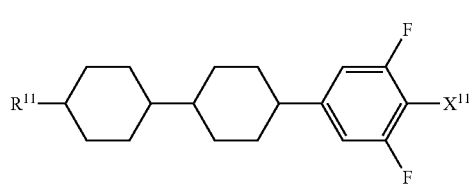
(3-3)
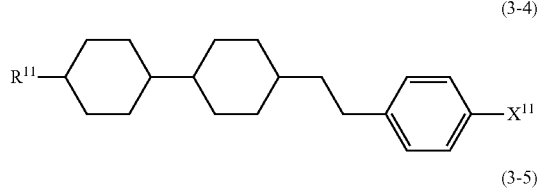
(3-4)
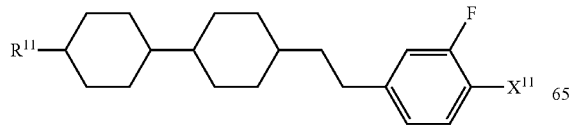
(3-5)
(3-6)
(3-7)
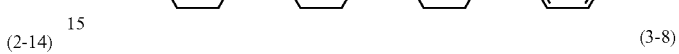
(3-8)
(3-9)
(3-10)
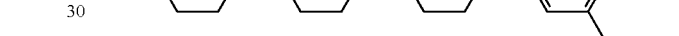
(3-11)
(3-12)
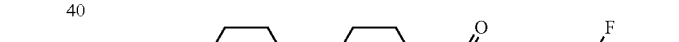
(3-13)
(3-14)

(3-15)
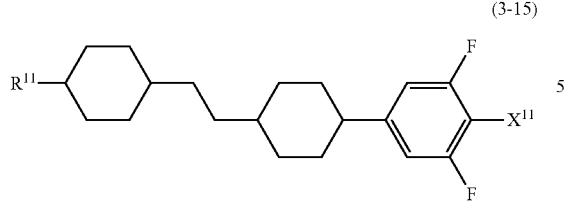
(3-16)
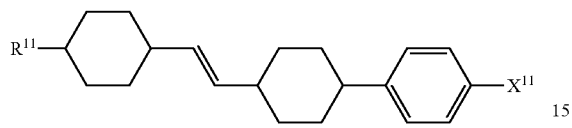
(3-17)
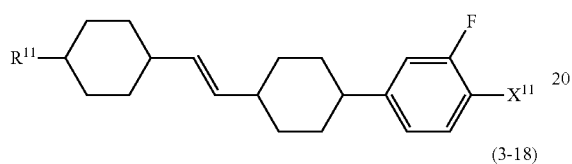
(3-18)
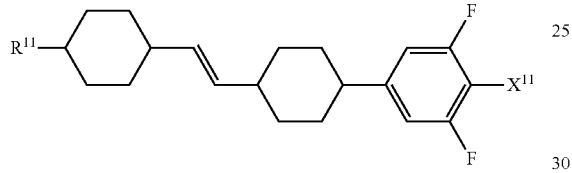
(3-19)
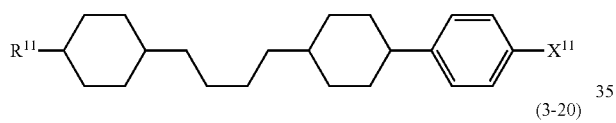
(3-20)
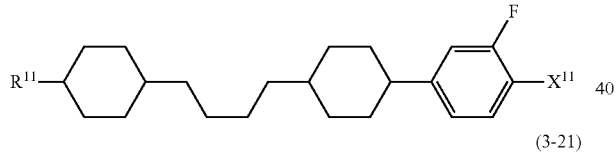
(3-21)
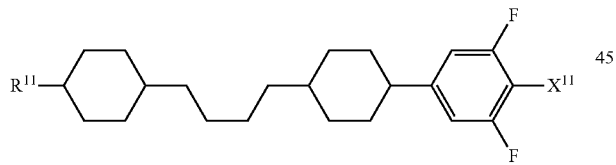
(3-22)
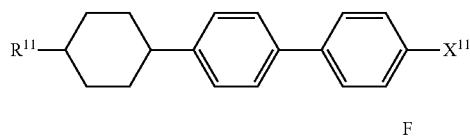
(3-23)
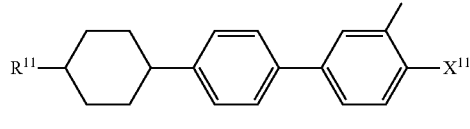
(3-24)
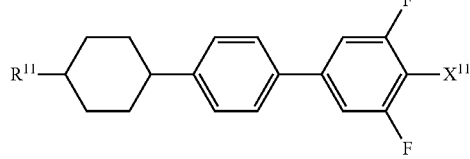
(3-25)
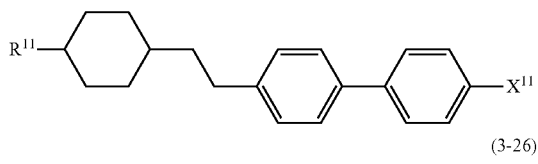
(3-26)
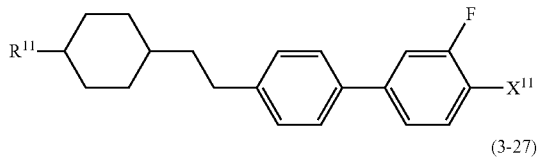
(3-27)
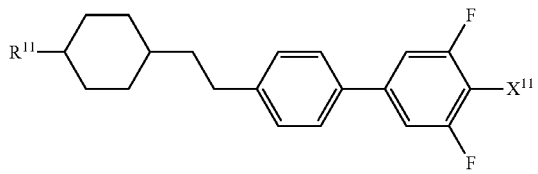
(3-28)
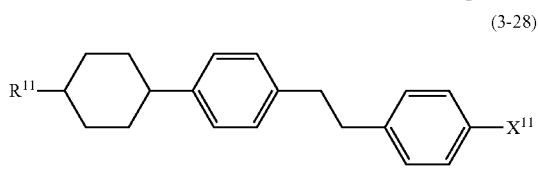
(3-29)
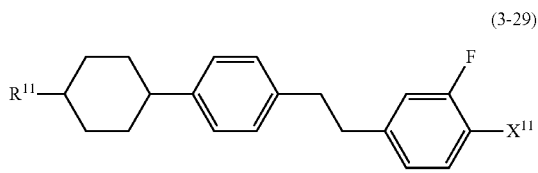
(3-30)
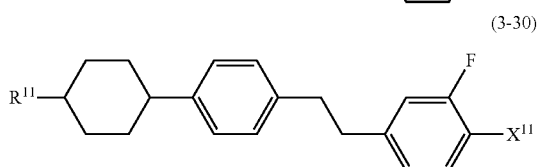
(3-31)
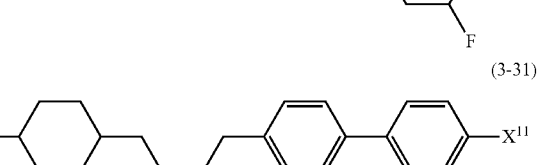
(3-32)
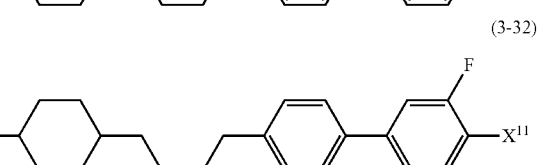
(3-33)
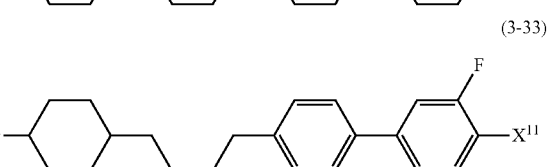
(3-34)

(3-35) 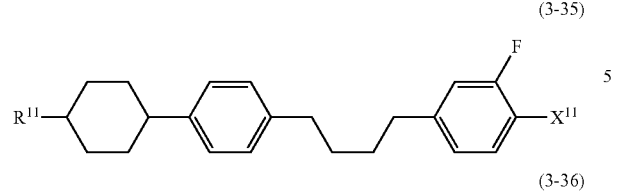
(3-36) 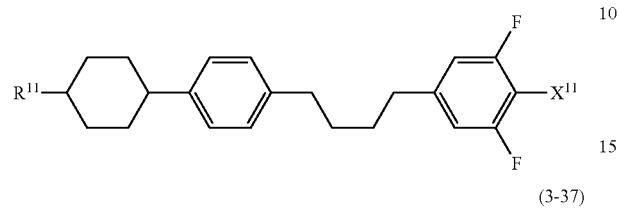
(3-37) 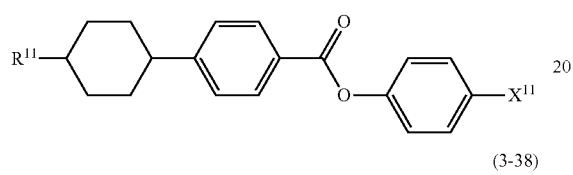
(3-38) 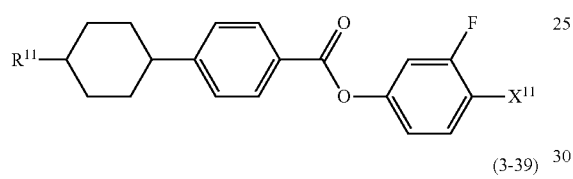
(3-39) 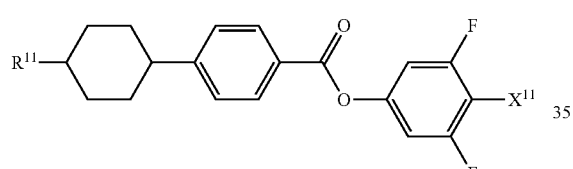
(3-40) 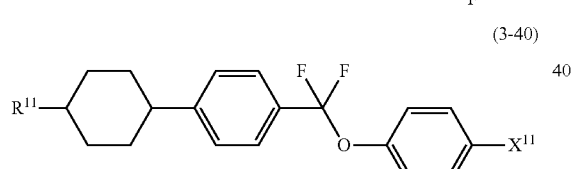
(3-41) 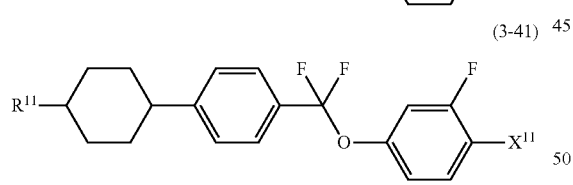
(3-42) 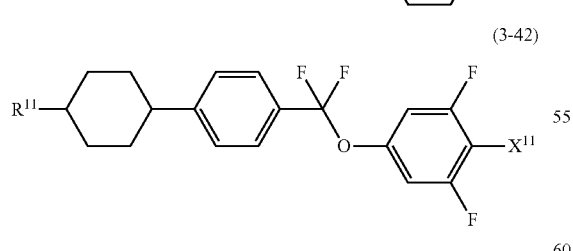
(3-43) 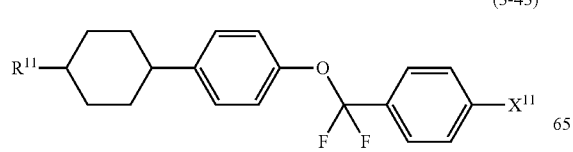
(3-44) 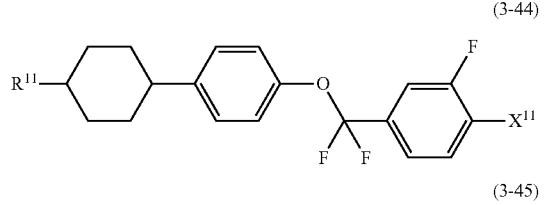
(3-45) 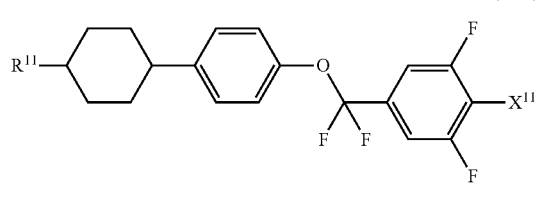
(3-46) 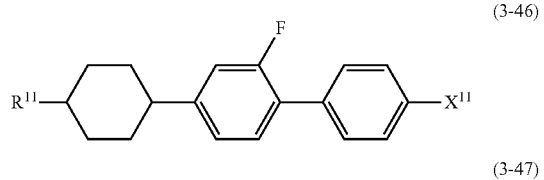
(3-47) 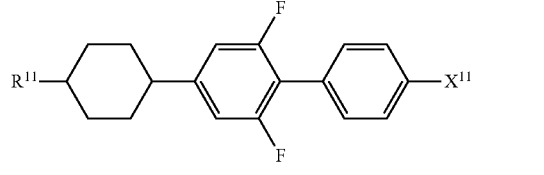
(3-48) 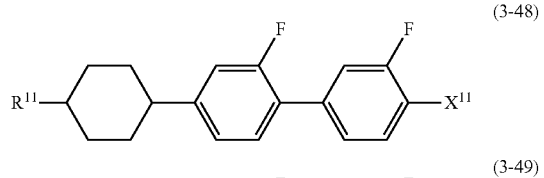
(3-49) 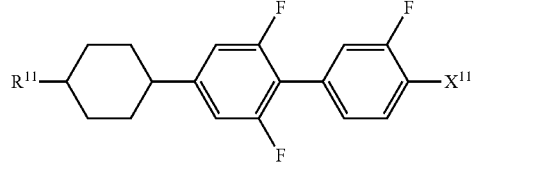
(3-50) 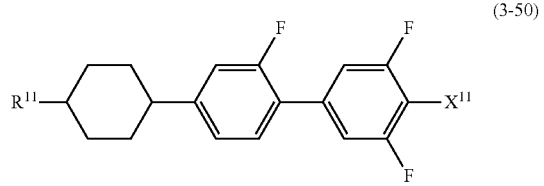
(3-51) 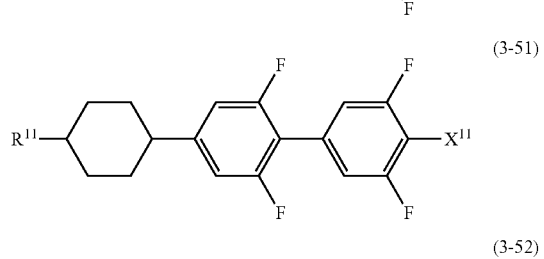
(3-52) 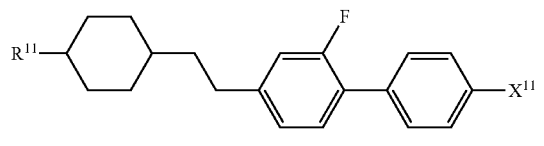

(3-53) 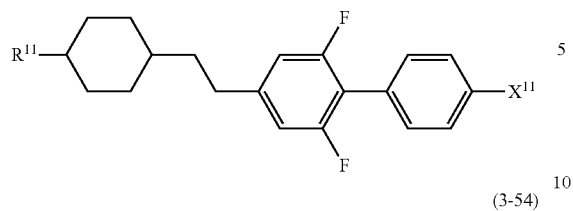
(3-54) 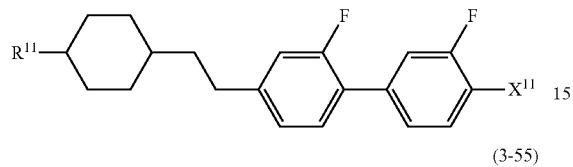
(3-55) 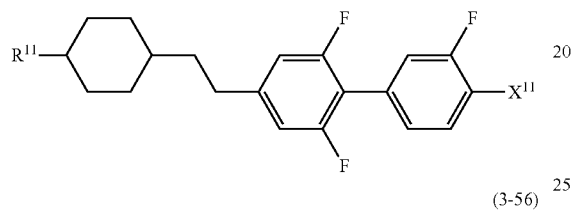
(3-56) 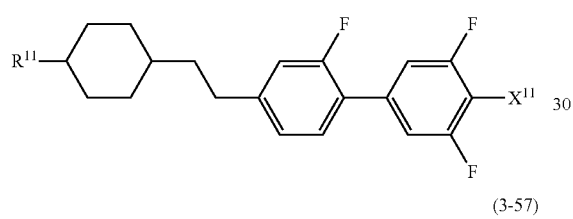
(3-57) 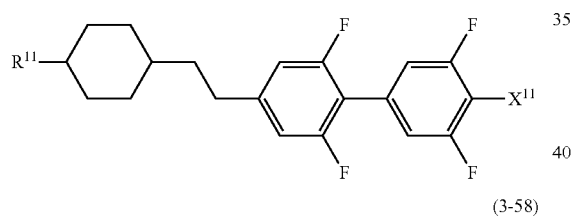
(3-58) 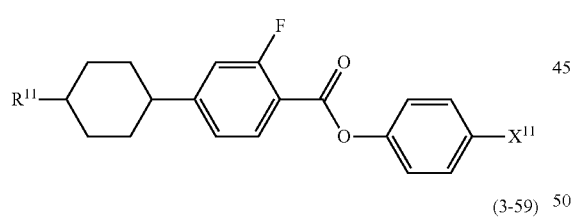
(3-59) 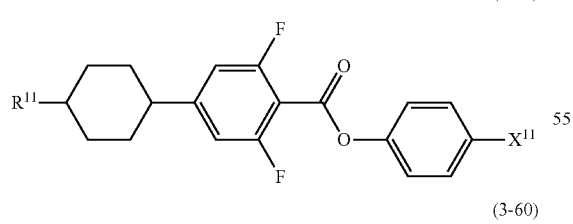
(3-60) 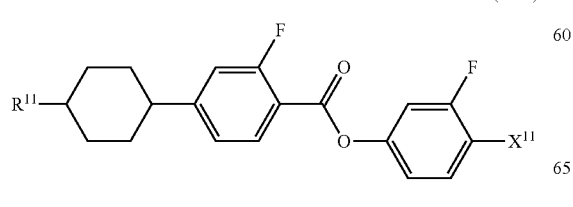
(3-61) 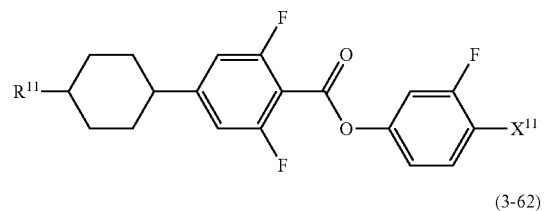
(3-62) 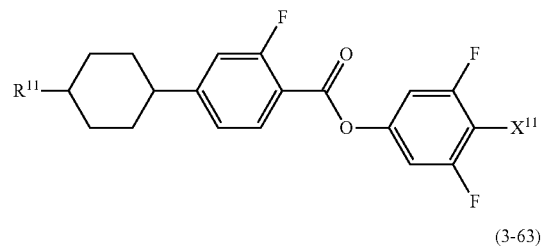
(3-63) 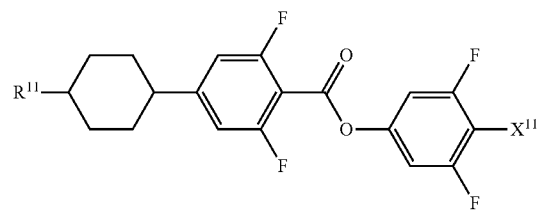
(3-64) 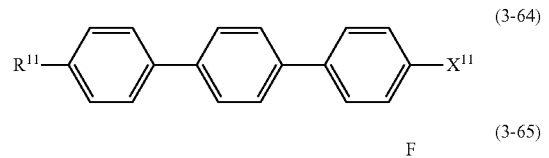
(3-65) 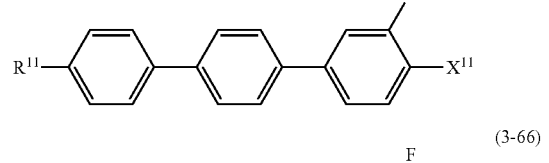
(3-66) 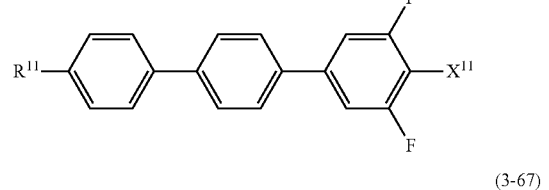
(3-67) 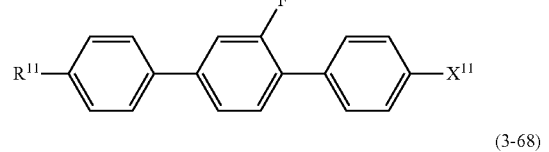
(3-68), (3-69) 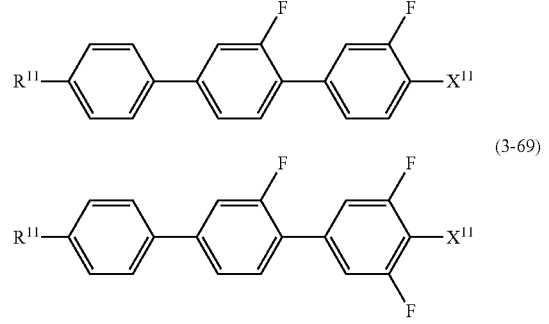

(3-70) 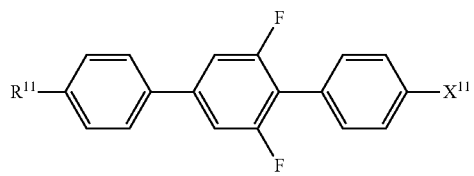
(3-71) 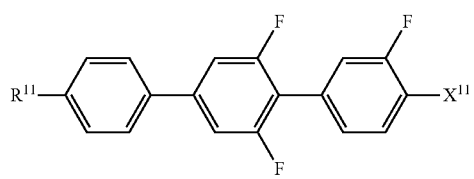
(3-72) 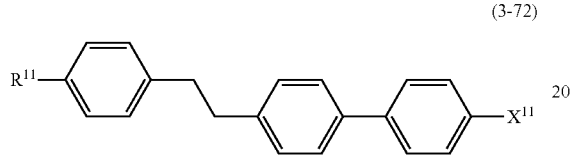
(3-73) 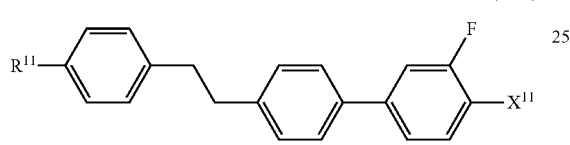
(3-74) 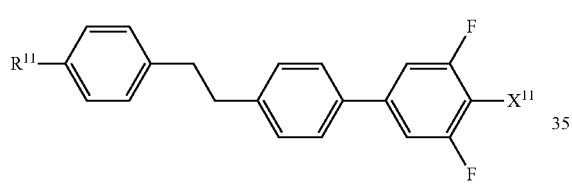
(3-75) 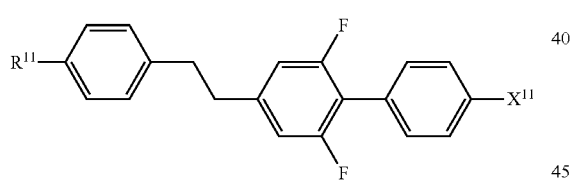
(3-76) 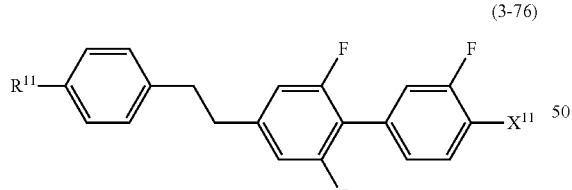
(3-77) 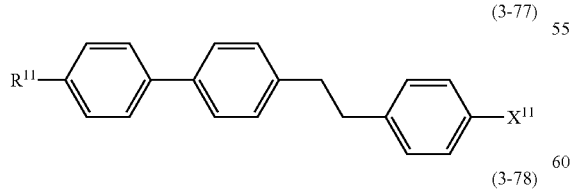
(3-78) 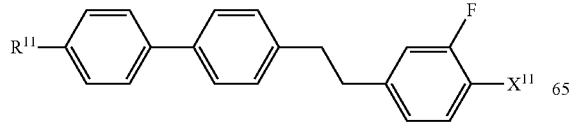
(3-79) 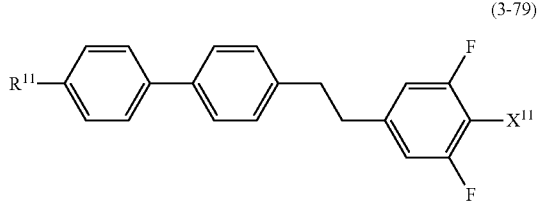
(3-80) 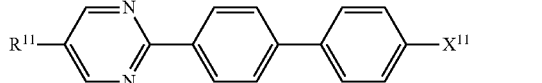
(3-81) 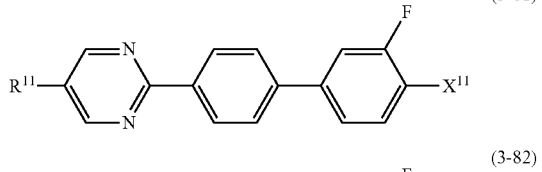
(3-82) 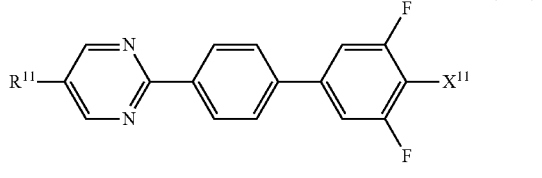
(3-83) 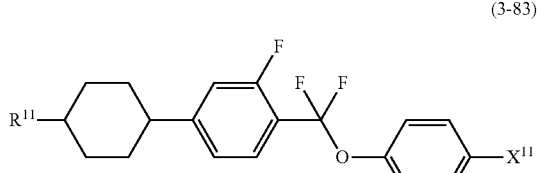
(3-84) 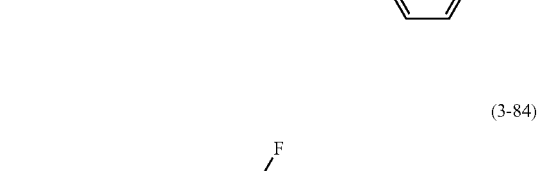
(3-85) 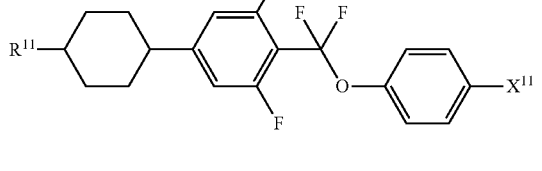
(3-86) 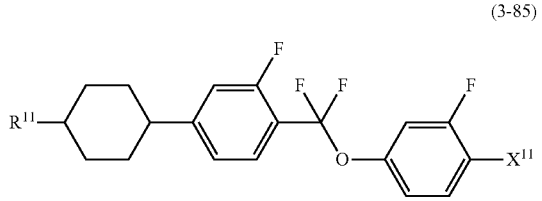
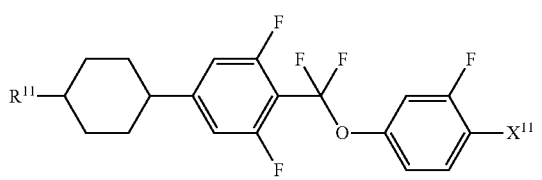

(3-87)
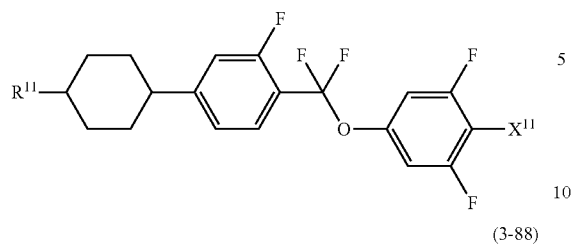
(3-88)
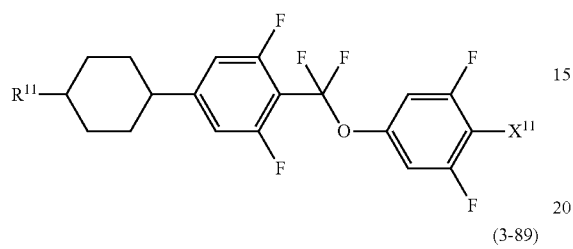
(3-89)
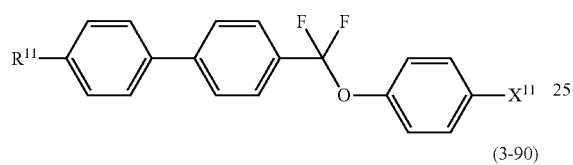
(3-90)
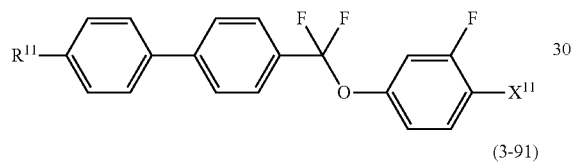
(3-91)
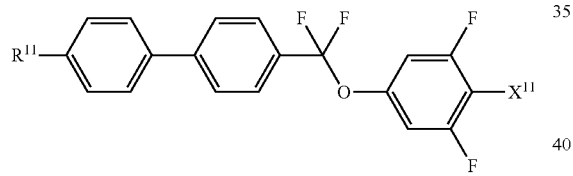
(3-92)
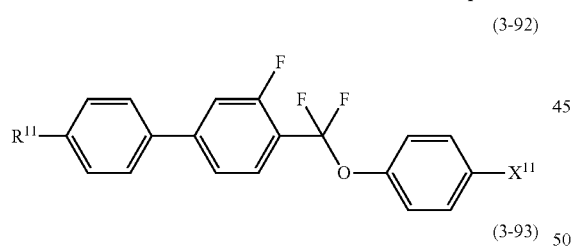
(3-93)
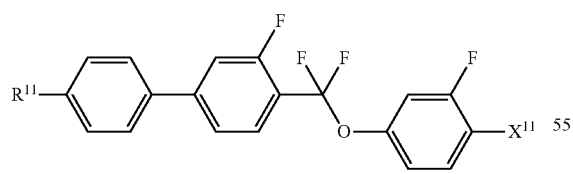
(3-94)
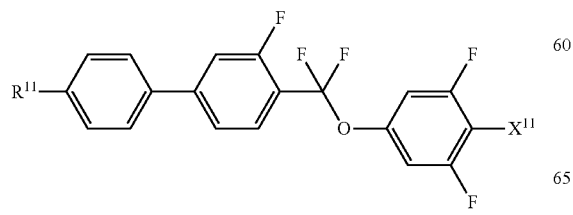
(3-95)
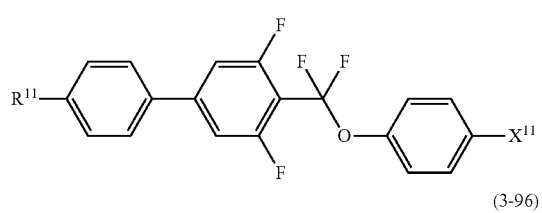
(3-96)
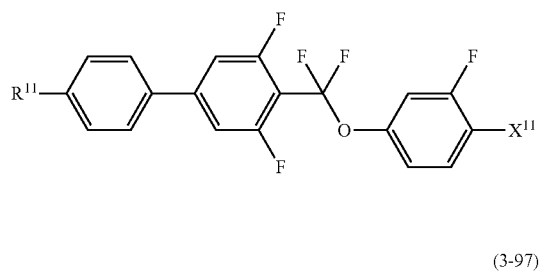
(3-97)
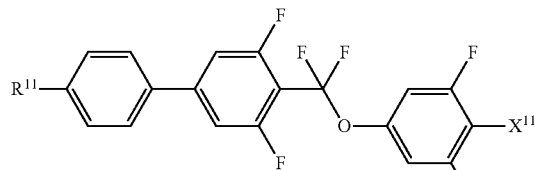
(3-98)
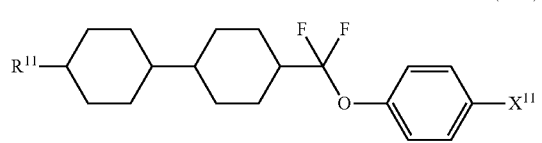
(3-99)
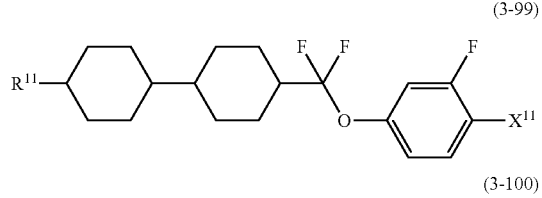
(3-100)
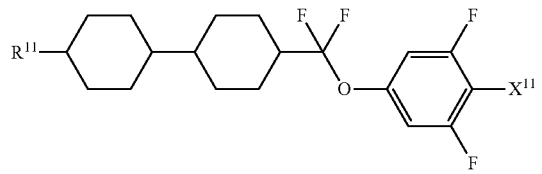
(3-101)
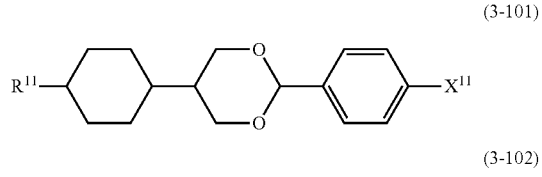
(3-102)
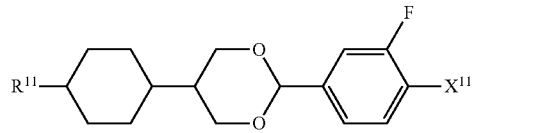

(3-103)
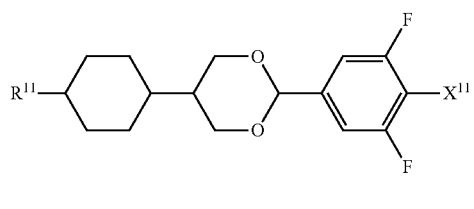
(3-104)
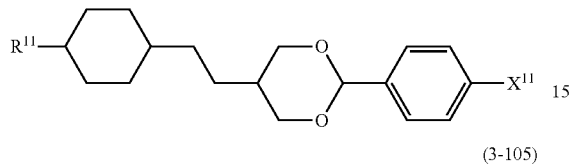
(3-105)
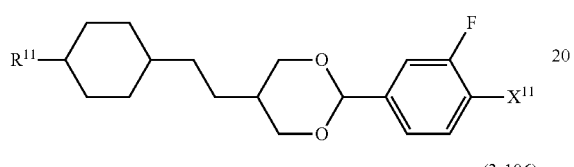
(3-106)
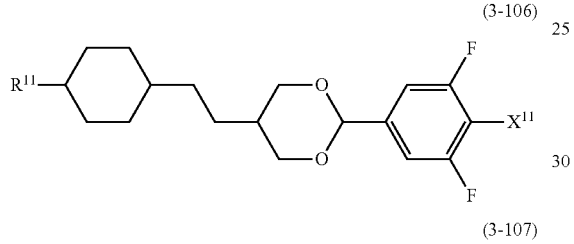
(3-107)
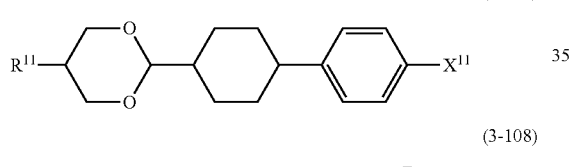
(3-108)
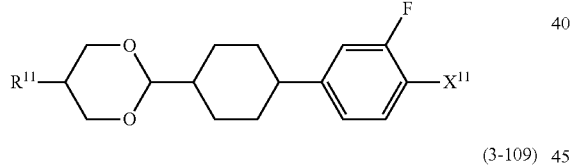
(3-109)
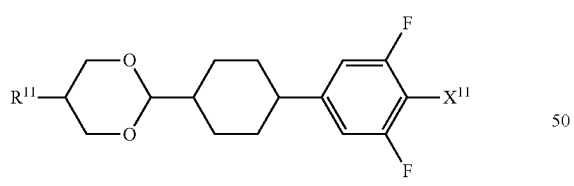
(3-110)
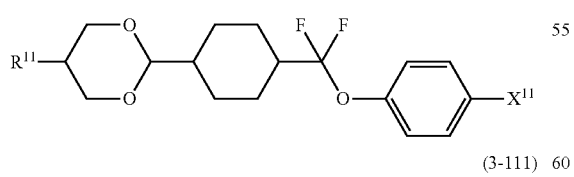
(3-111)
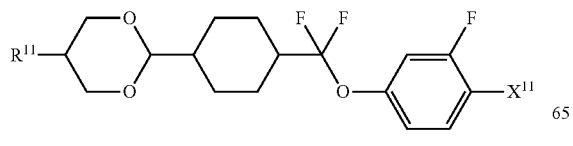
(3-112)
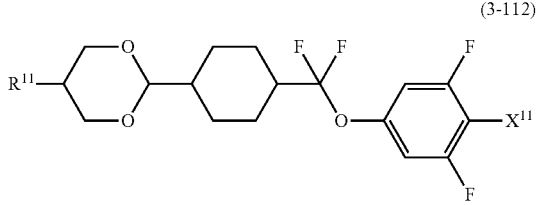
(3-113)
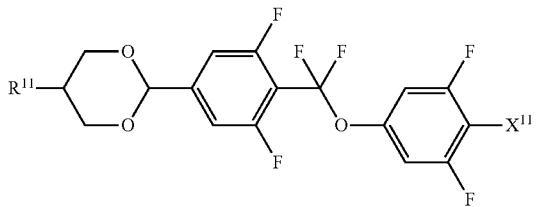
(4-1)
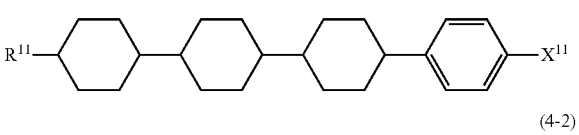
(4-2)
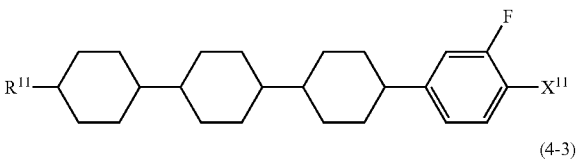
(4-3)
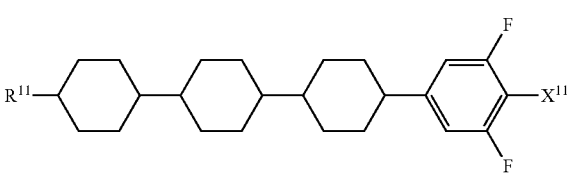
(4-4)
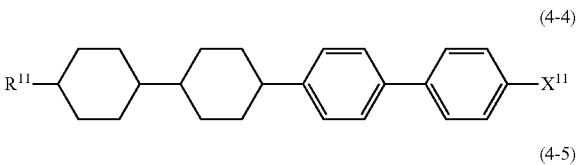
(4-5)
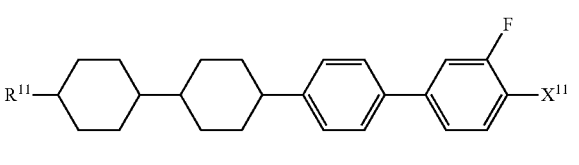
(4-6)
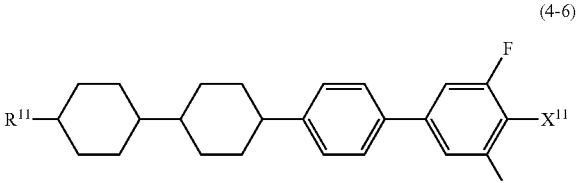
(4-7)
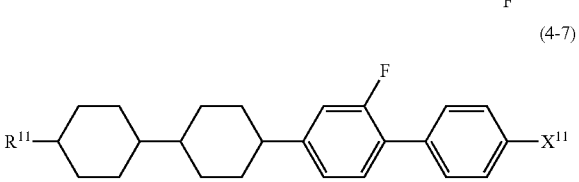

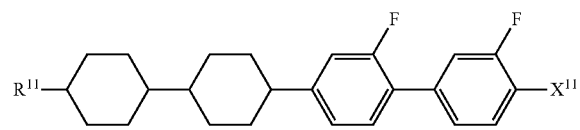
(4-8)
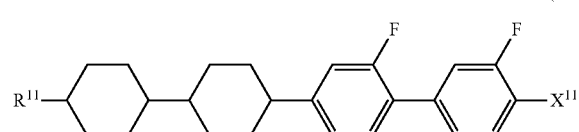
(4-9)
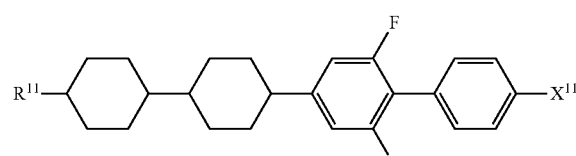
(4-10)
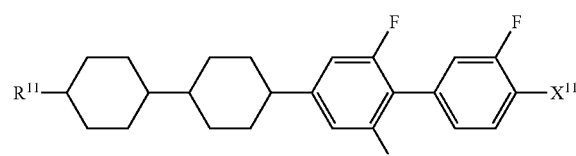
(4-11)
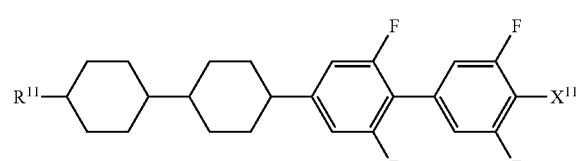
(4-12)
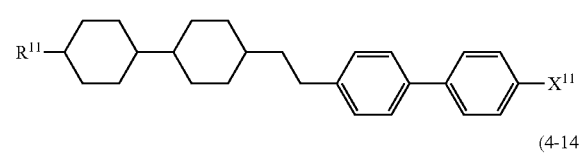
(4-13)
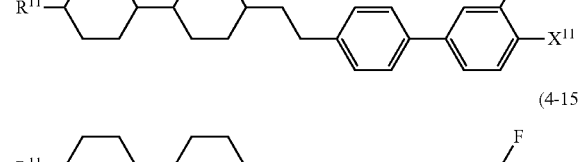
(4-14)
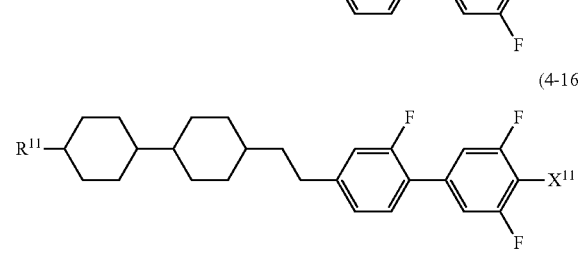
(4-15)
(4-16)
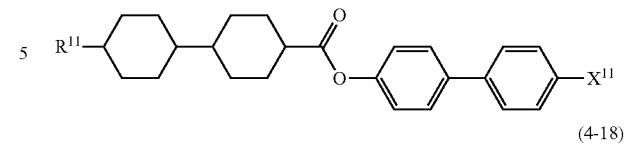
(4-17)
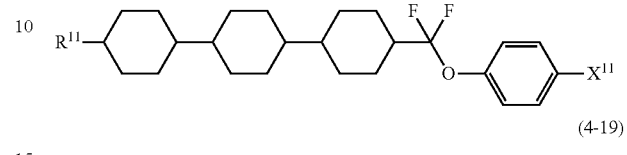
(4-18)
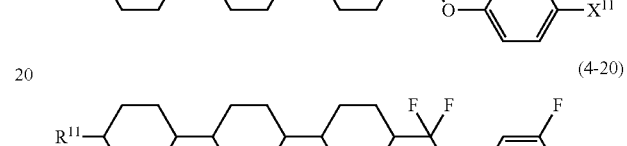
(4-19)
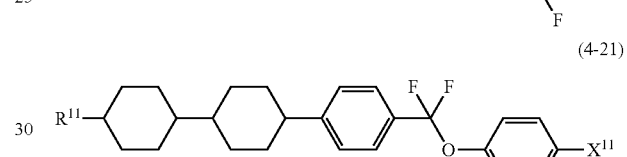
(4-20)
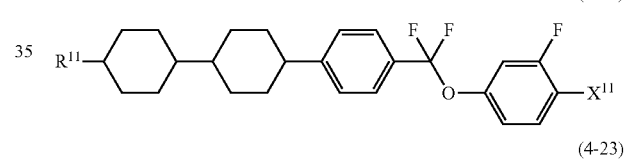
(4-21)
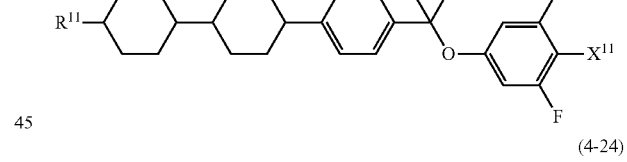
(4-22)
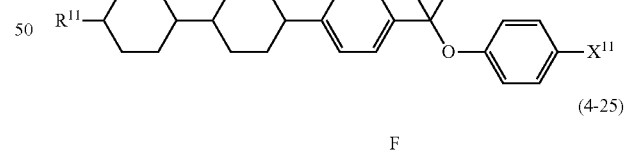
(4-23)
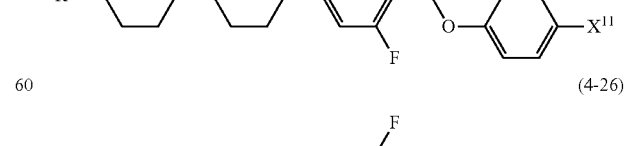
(4-24)
(4-25)
(4-26)

(4-27)
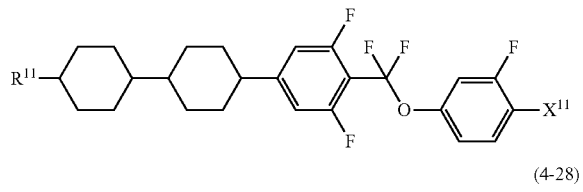
(4-28)
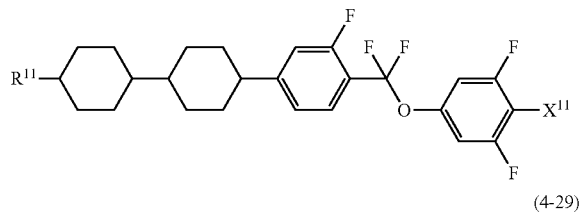
(4-29)
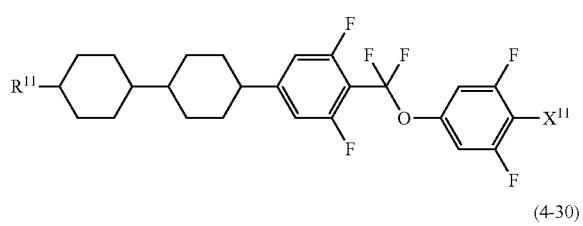
(4-30)
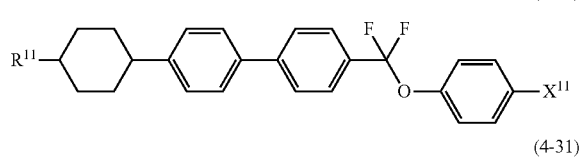
(4-31)
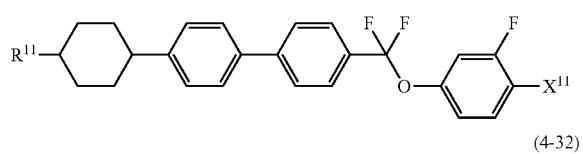
(4-32)
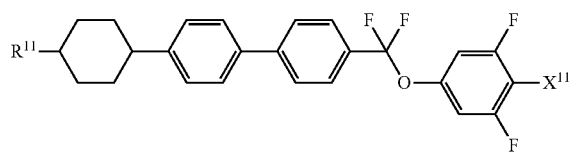
(4-33)
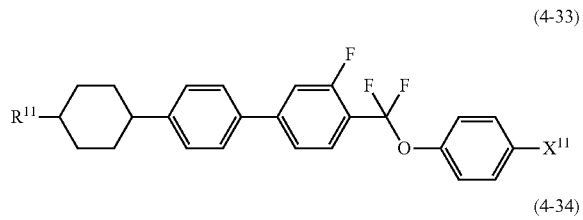
(4-34)
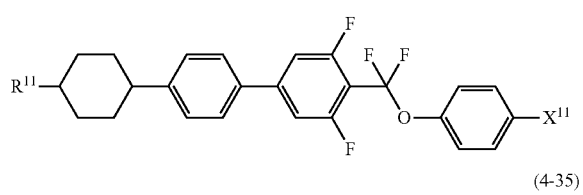
(4-35)
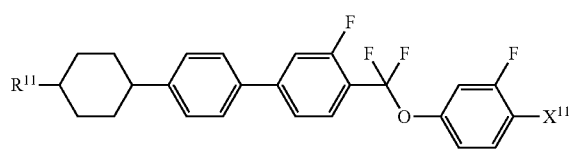
(4-36)
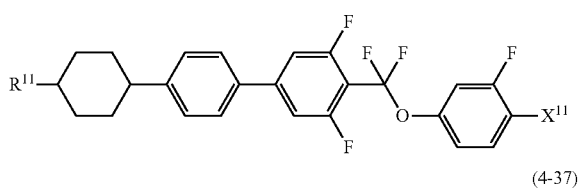
(4-37)
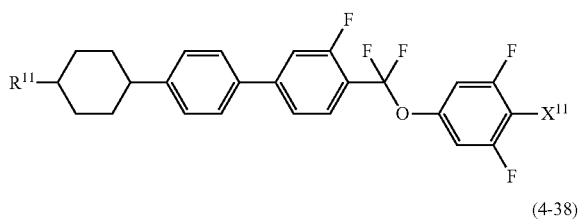
(4-38)
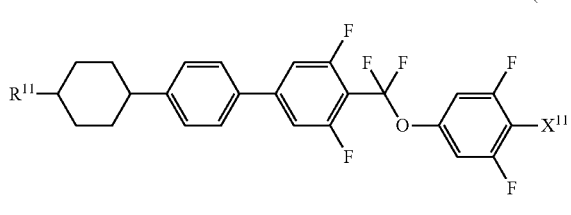
(4-39)
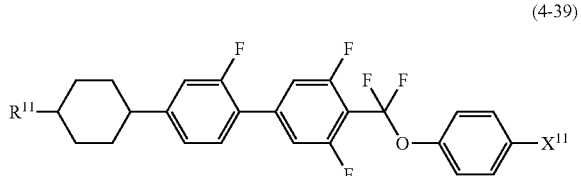
(4-40)
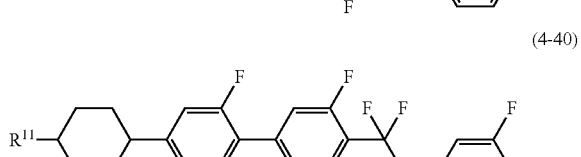
(4-41)
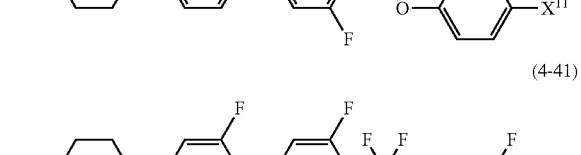
(4-42)
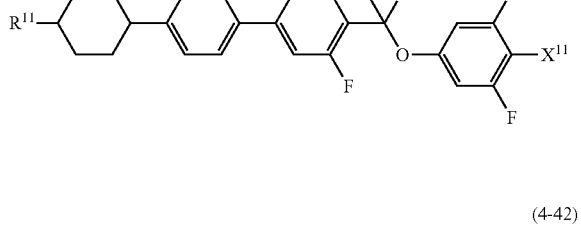
(4-43)
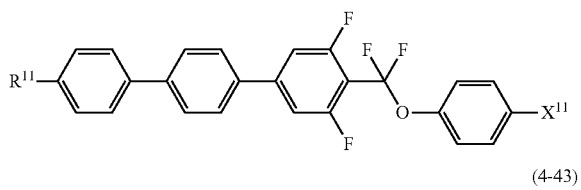
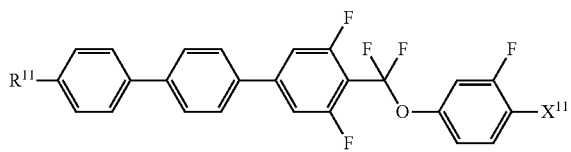

(4-44)
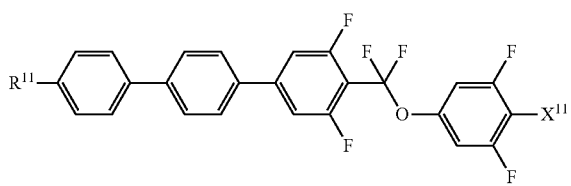

(4-45)
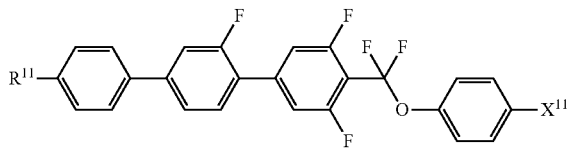

(4-46)
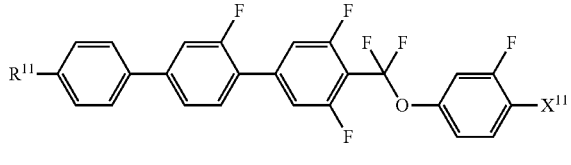

(4-47)
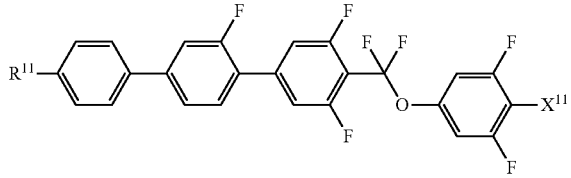

(4-48)
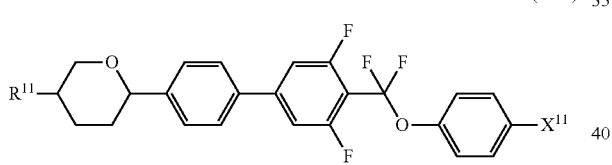

(4-49)
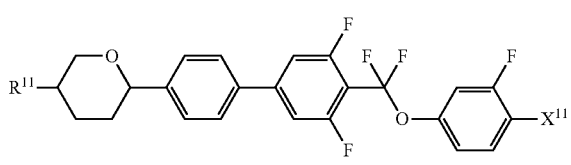

(4-50)
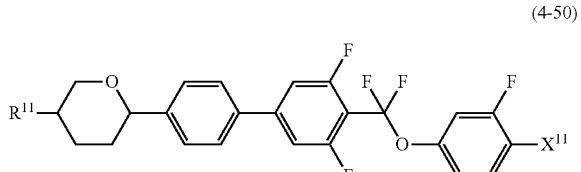

(4-51)
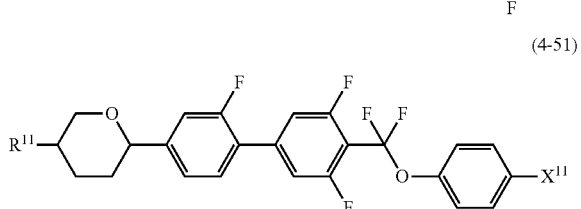

(4-52)
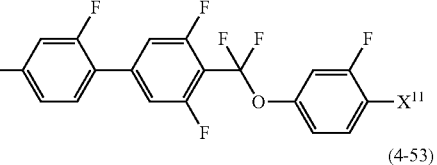

(4-53)
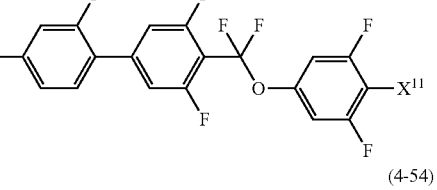

(4-54)
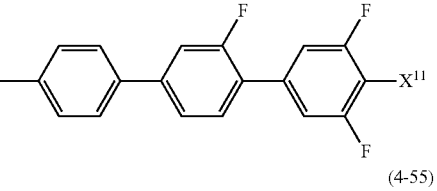

(4-55)
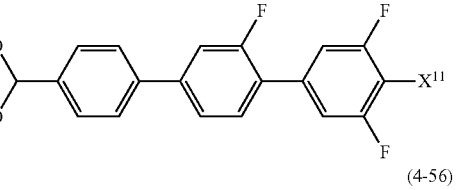

(4-56)
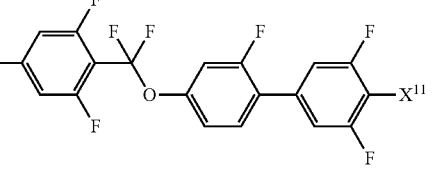

(4-57)
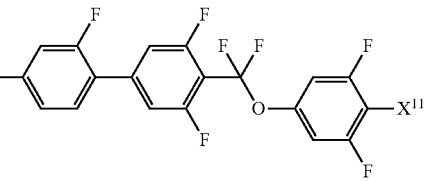

In the compounds (component B), $R^{11}$ and $X^{11}$ are defined in a manner identical with the definitions in formulas (2) to (4) described in item 11.

Component B has a positive dielectric anisotropy and a superb stability to heat, light and so forth, and therefore is used for preparing a composition for the TFT mode or the PSA mode. A content of component B is suitably in the range of 1 to 99% by weight, preferably in the range of 10 to 97% by weight, and further preferably in the range of 40 to 95% by weight, based on the total weight of the composition. The viscosity of the composition can be adjusted by further adding compounds (12) to (14) (component E) thereto.

Component C includes compound (5) having —C≡N or —C≡C—C≡N as a right terminal group. Preferred examples of component C include compounds (5-1) to (5-64).

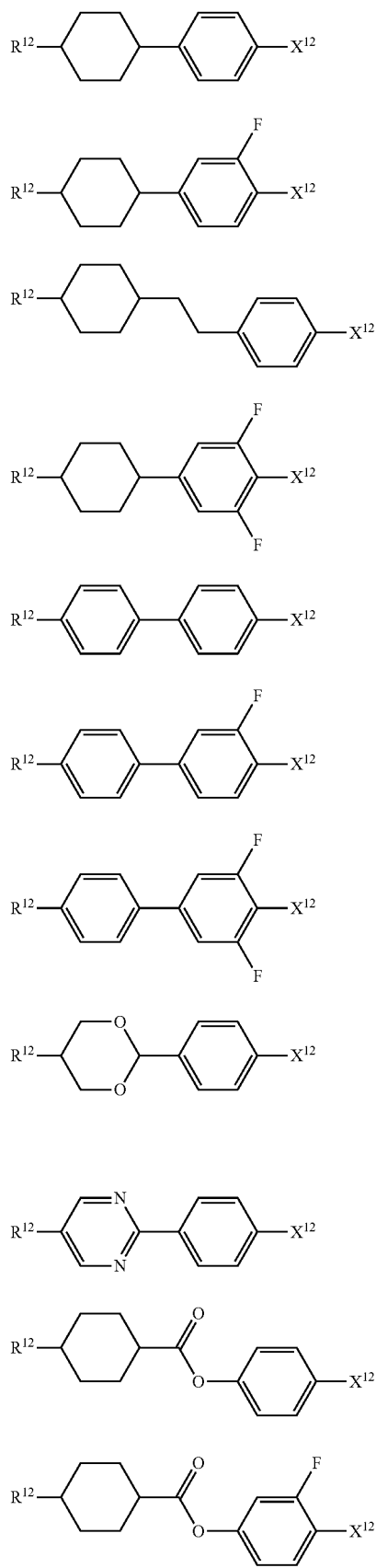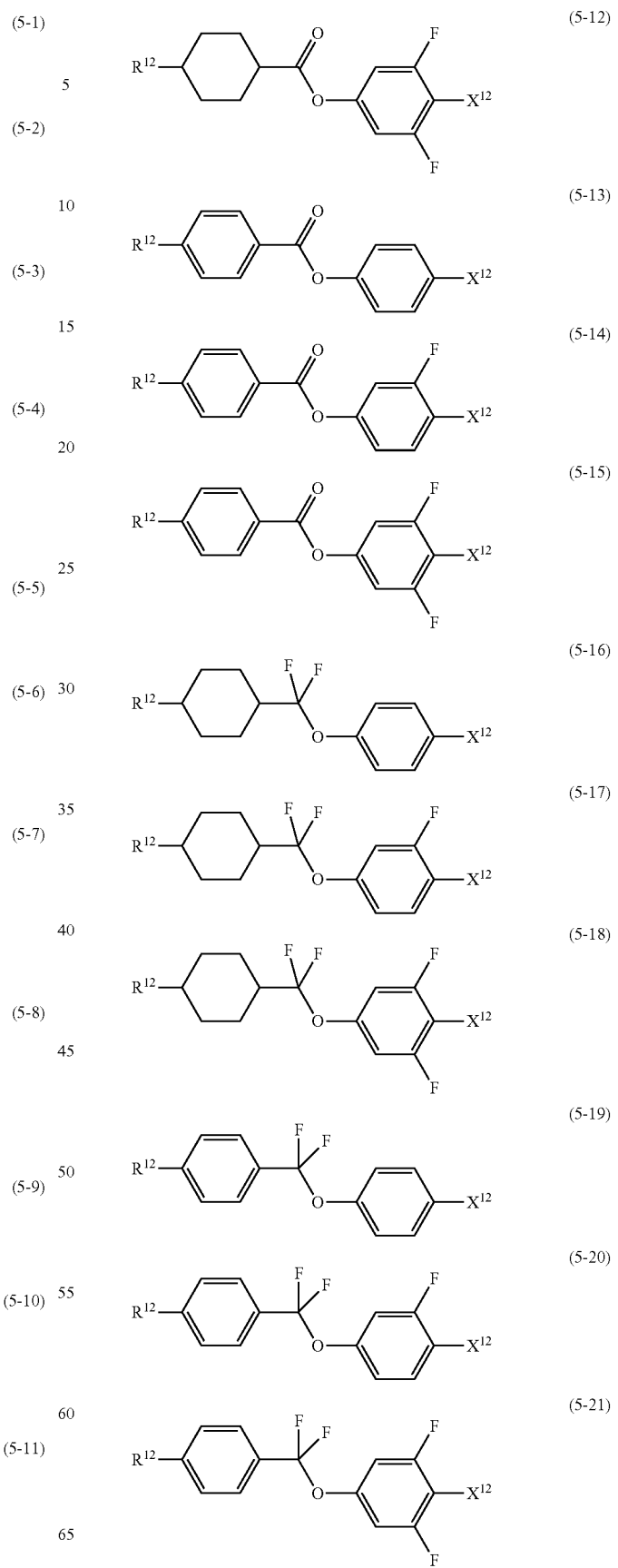

(5-22) 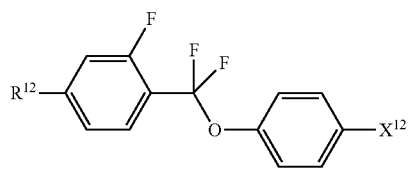
(5-23) 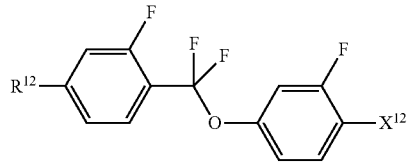
(5-24) 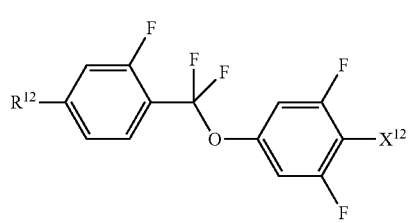
(5-25) 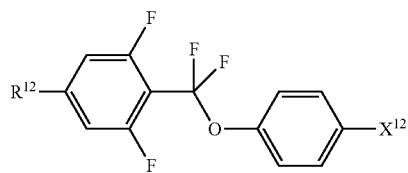
(5-26) 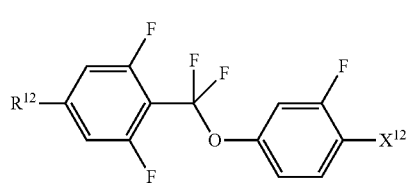
(5-27) 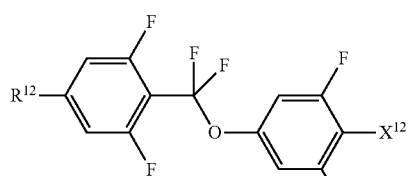
(5-28) 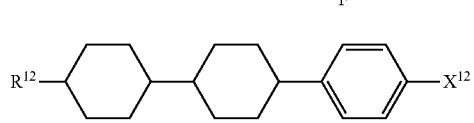
(5-29) 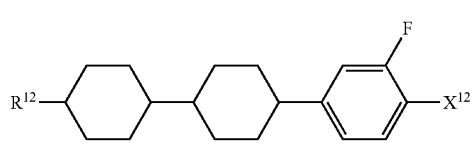
(5-30) 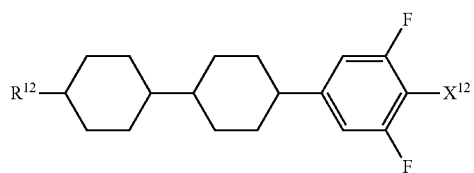
(5-31) 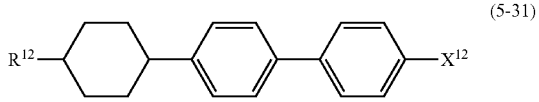
(5-32) 
(5-33) 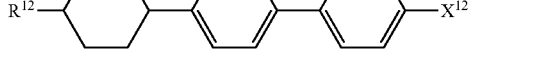
(5-34) 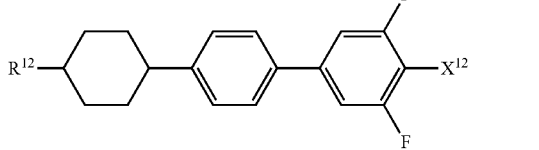
(5-35) 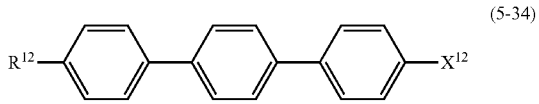
(5-36) 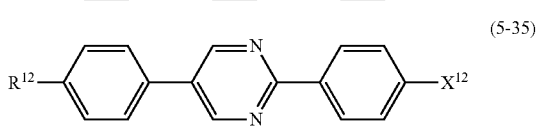
(5-37) 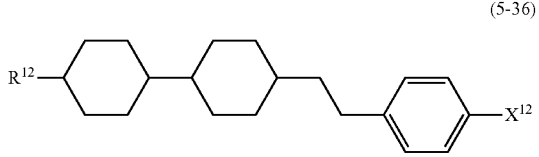
(5-38) 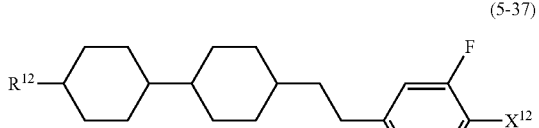
(5-39) 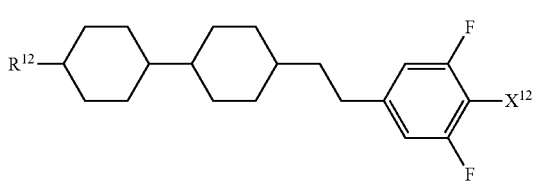
(5-40) 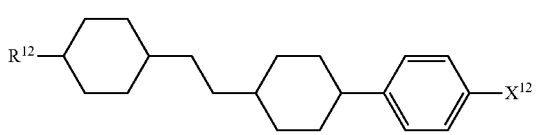
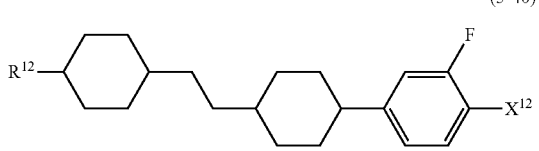

(5-41) 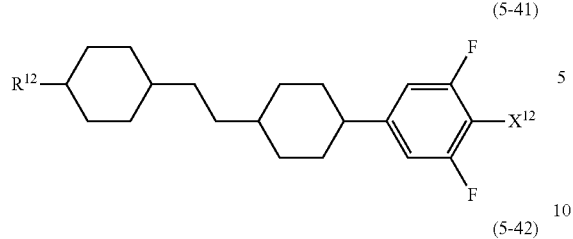
(5-42) 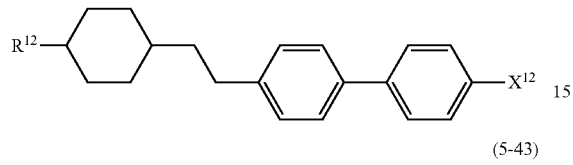
(5-43) 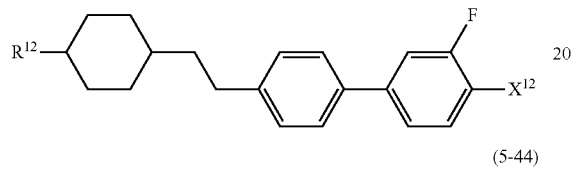
(5-44) 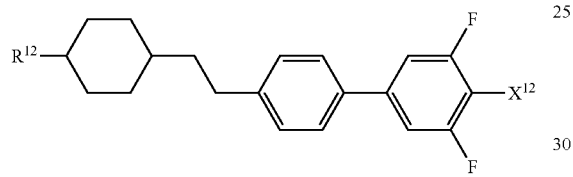
(5-45) 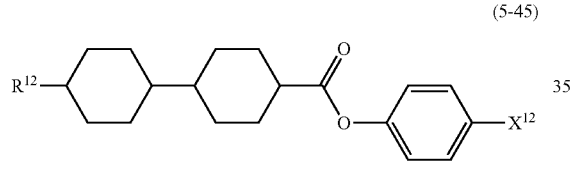
(5-46) 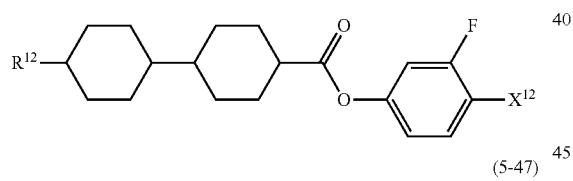
(5-47) 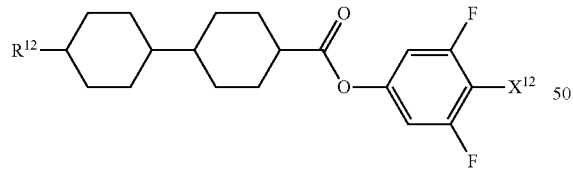
(5-48) 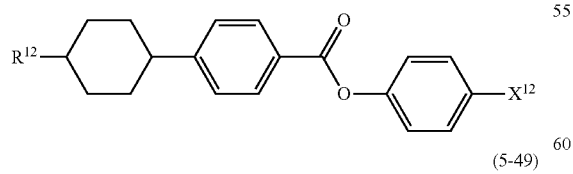
(5-49) 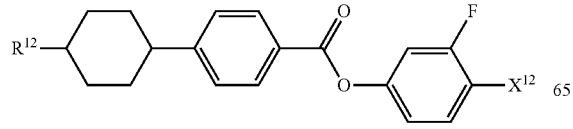
(5-50) 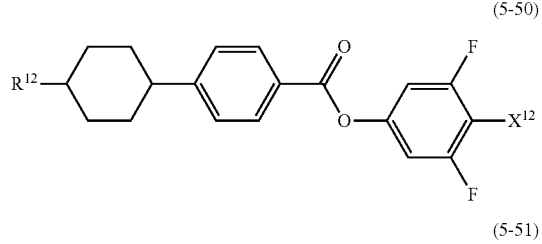
(5-51) 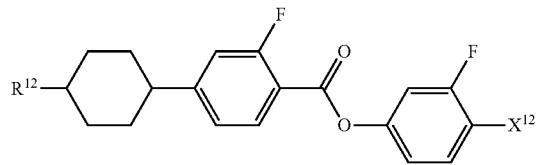
(5-52) 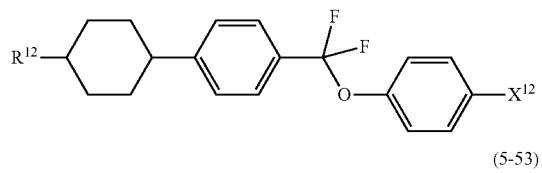
(5-53) 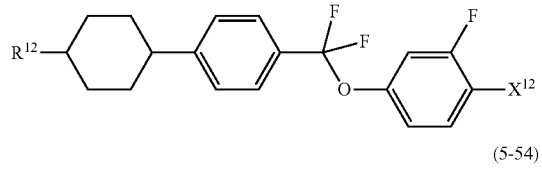
(5-54) 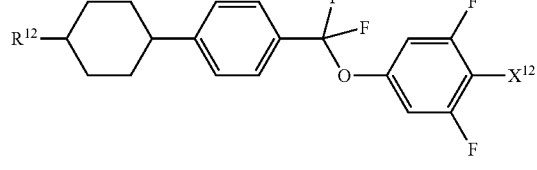
(5-55) 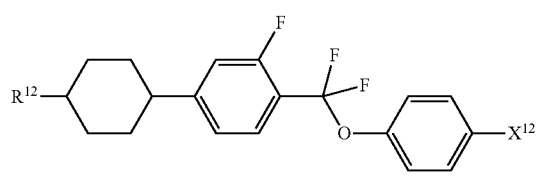
(5-56) 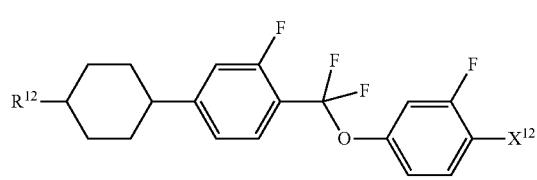
(5-57) 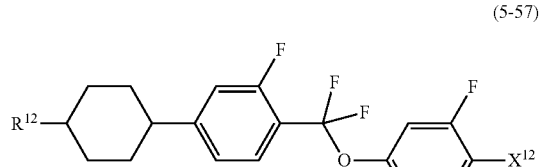

-continued

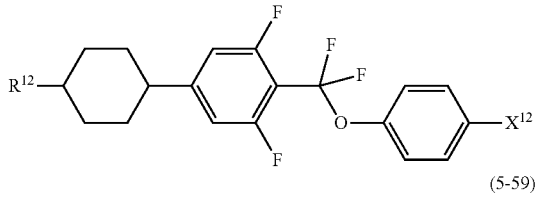
(5-58)

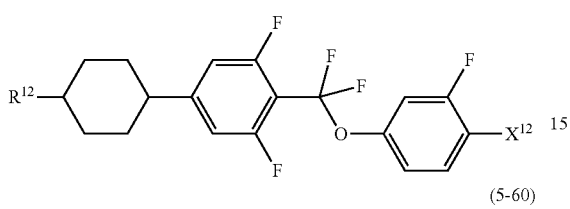
(5-59)

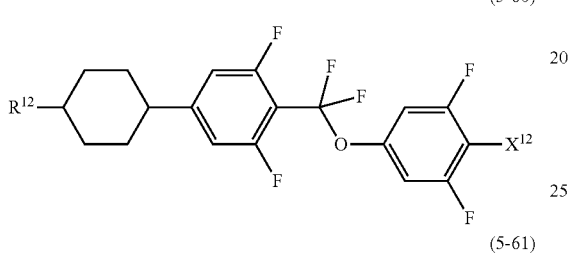
(5-60)

(5-61)

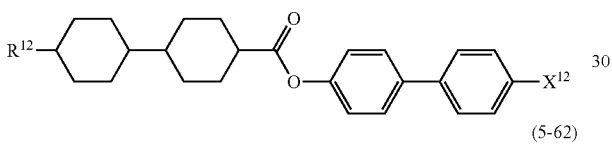
(5-62)

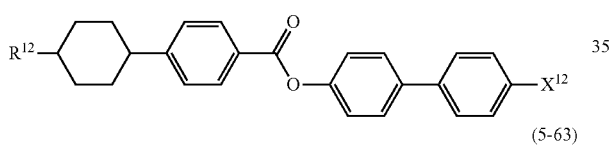
(5-63)

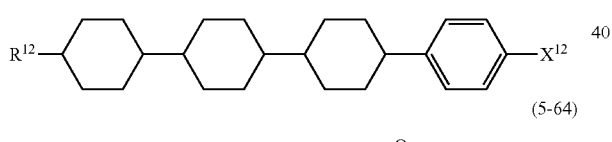
(5-64)

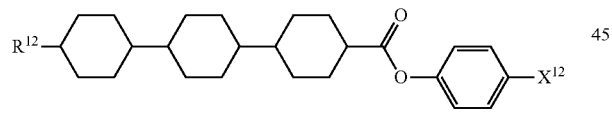

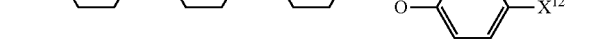

In the compounds (component C), $R^{12}$ and $X^{12}$ are defined in a manner identical with the definitions in formula (5) described in item 12.

Component C has a large value of positive dielectric anisotropy, and therefore is mainly used for preparing a composition for the STN mode, the TN mode or the PSA mode. Dielectric anisotropy of the composition can be increased by adding component C thereto. Component C is effective in extending the temperature range of the liquid crystal phase, adjusting the viscosity or adjusting the optical anisotropy. Component C is useful also for adjustment of a voltage-transmittance curve of the device.

When a composition for the STN mode or the TN mode is prepared, a content of component C is preferably in the range of 1 to 99% by weight, preferably in the range of 10 to 97% by weight, and further preferably in the range of 40 to 95% by weight, based on the total weight of the composition. The temperature range of the liquid crystal phase, the viscosity, the optical anisotropy, the dielectric anisotropy or the like of the composition can be adjusted by adding component E thereto.

Component D includes compounds (6) to (12). The compounds have a benzene ring in which atoms in lateral positions are replaced by two halogen atoms, such as 2,3-difluoro-1,4-phenylene. Preferred examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3).

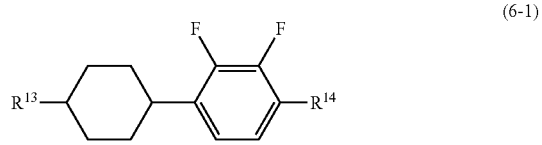
(6-1)

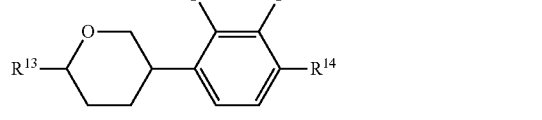
(6-2)

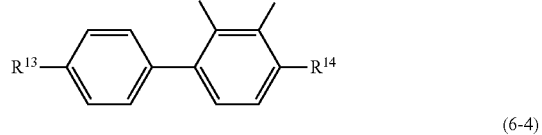
(6-3)

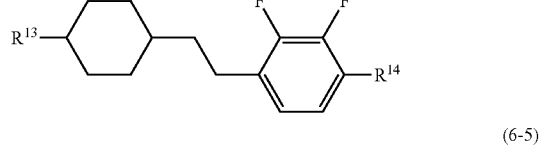
(6-4)

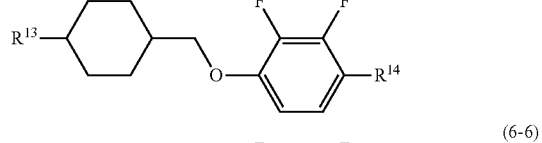
(6-5)

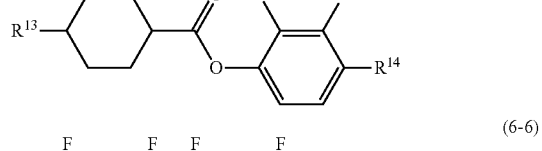
(6-6)

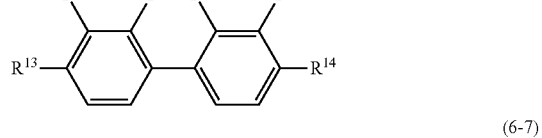
(6-6)

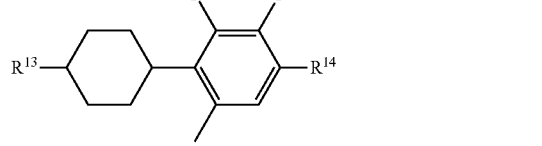
(7-1)

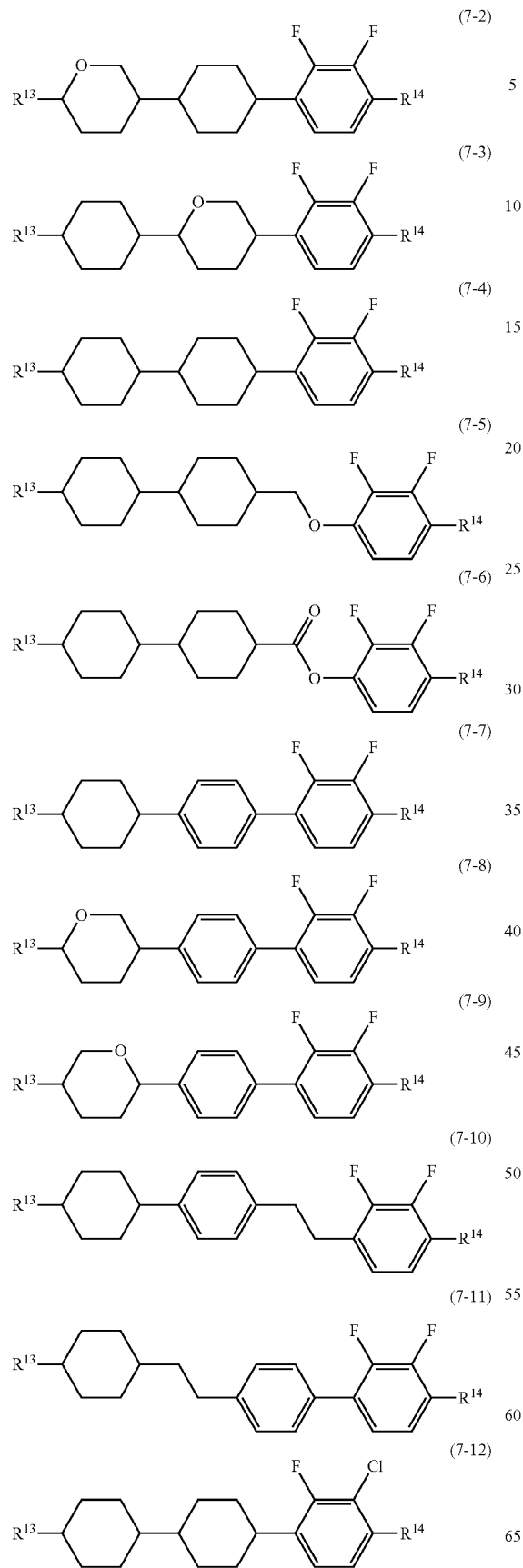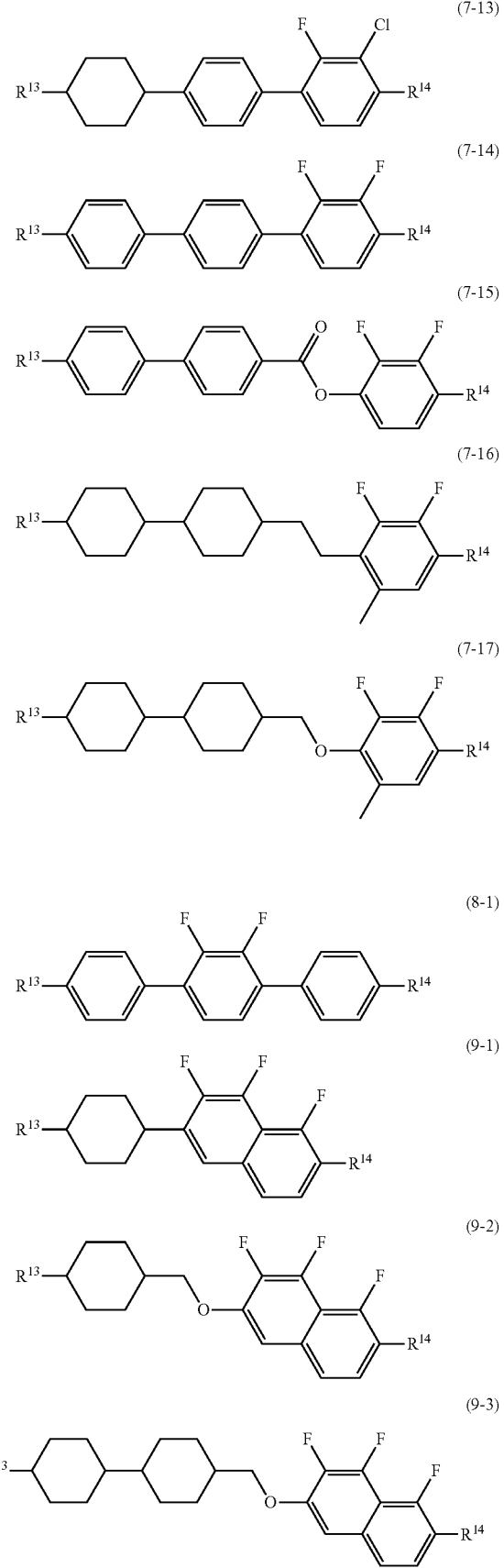

-continued
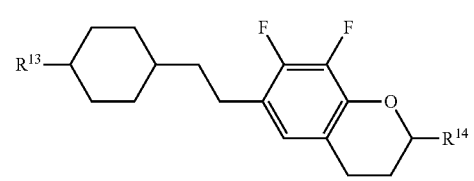 (10-1)
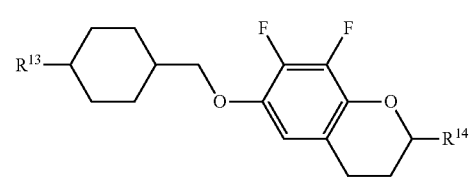 (10-2)
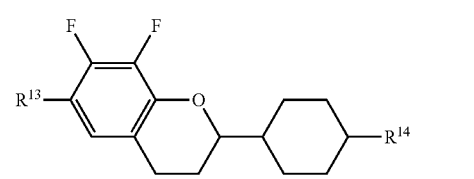 (10-3)
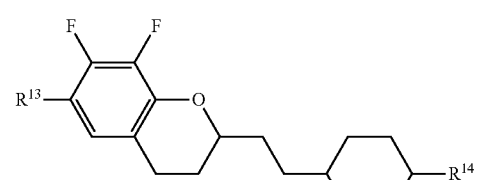 (10-4)
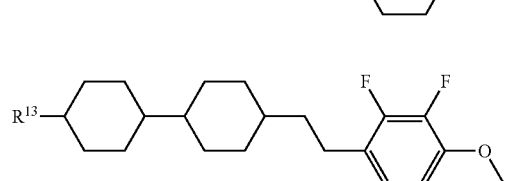 (10-5)
 (10-6)
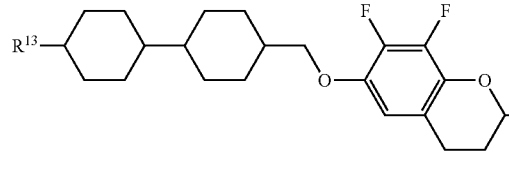 (10-7)
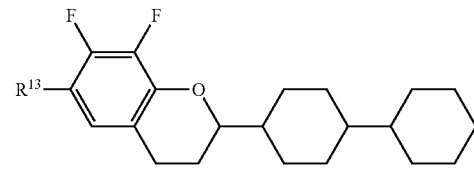 (10-8)
-continued
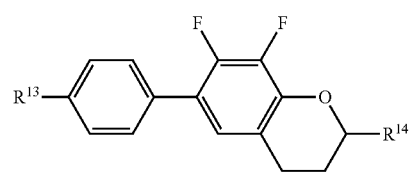 (10-9)
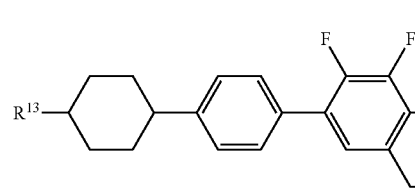 (10-10)
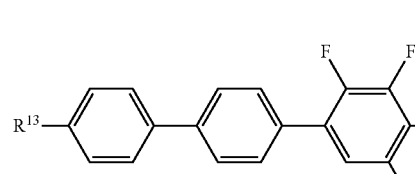 (10-11)
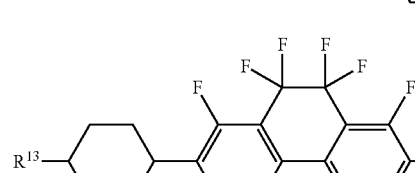 (11-1)
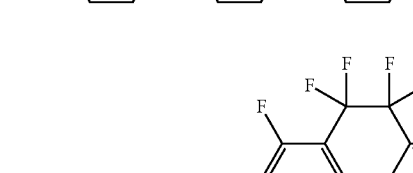 (11-2)
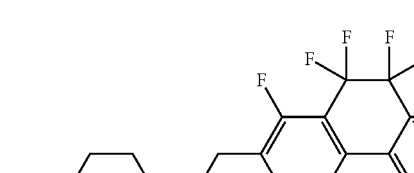 (11-3)
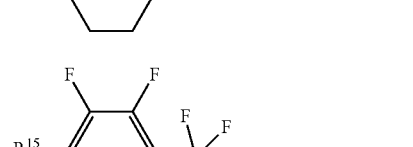 (12-1)
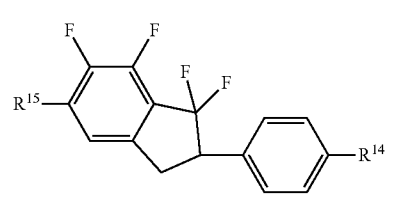 (12-2)

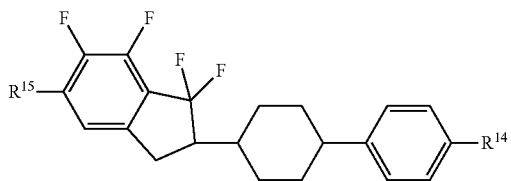
(12-3)

In the compounds (component D), $R^{13}$, $R^{14}$ and $R^{15}$ are defined in a manner identical with the definitions in formula (6) to (12) according to item 9.

Component D includes a compound having a negative dielectric anisotropy. Component D is mainly used for preparing a composition for the VA mode or the PSA mode. Among types of component D, compound (6) is a bicyclic compound, and therefore is effective mainly in adjusting the viscosity, adjusting the optical anisotropy or adjusting the dielectric anisotropy. Compounds (7) and (8) are a tricyclic compound, and therefore effective in increasing the maximum temperature, the optical anisotropy or the dielectric anisotropy. Compounds (9) to (12) are effective in increasing the dielectric anisotropy.

When a composition for the VA mode or the PSA mode is prepared, a content of component D is preferably 40% by weight or more, and further preferably in the range of 50 to 95% by weight, based on the total weight of the composition. When component D is added to a composition having a positive dielectric anisotropy, a content of component D is preferably 30% or less based on the total weight of the composition. When component D is added, the elastic constant of the composition and the voltage-transmittance curve of the device can be adjusted.

Component E includes a compound in which two terminal groups are alkyl or the like. Preferred examples of component E include compounds (13-1) to (13-11), compounds (14-1) to (14-19) and compounds (15-1) to (15-7).

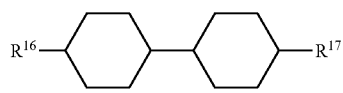
(13-1)

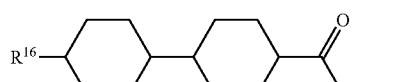
(13-2)

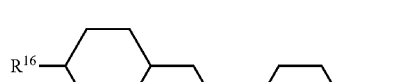
(13-3)

(13-4)

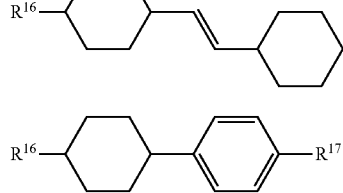
(13-5)

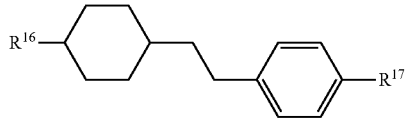
(13-6)

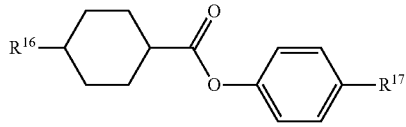
(13-7)

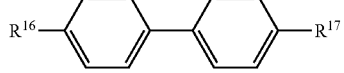
(13-8)

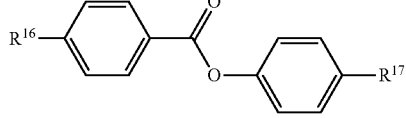
(13-9)

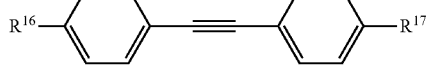
(13-10)

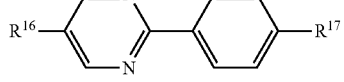
(13-11)

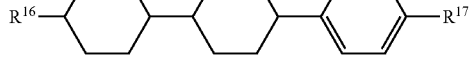
(14-1)

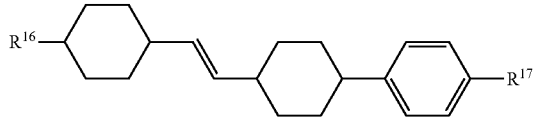
(14-2)

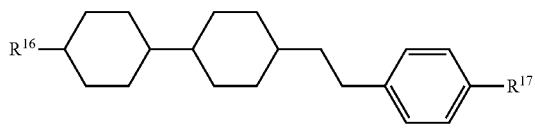
(14-3)

(14-4)

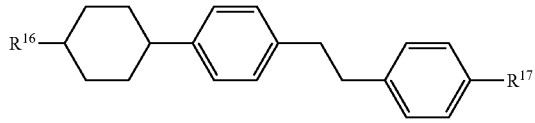
(14-5)

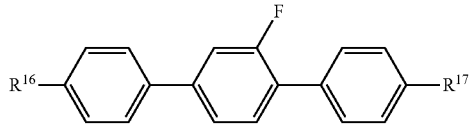
(14-6)

(14-7) 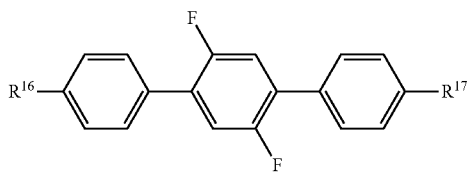

(14-8) 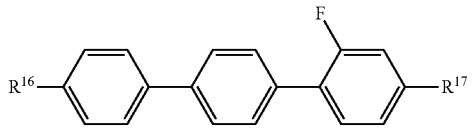

(14-9) 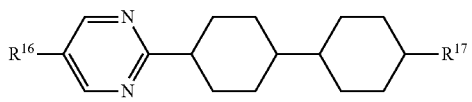

(14-10) 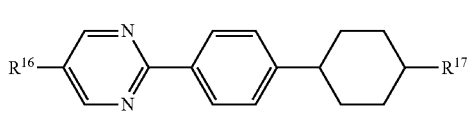

(14-11) 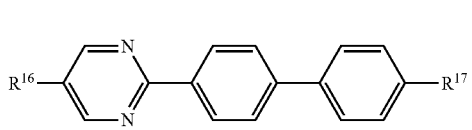

(14-12) 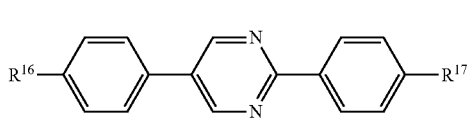

(14-13) 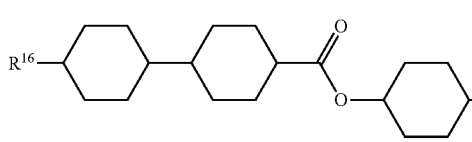

(14-14) 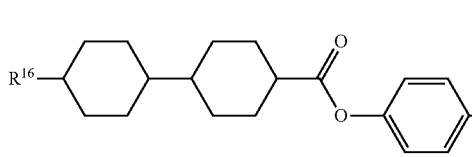

(14-15) 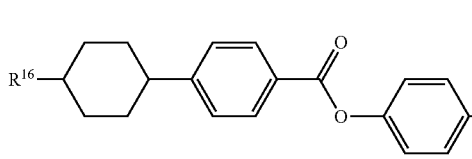

(14-16) 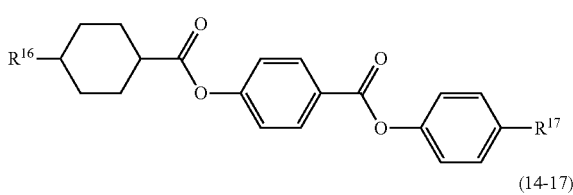

(14-17)

(14-18) 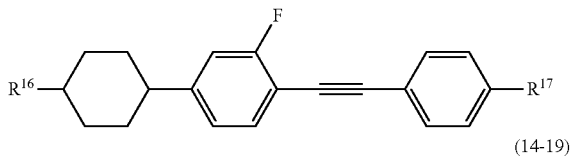

(14-19) 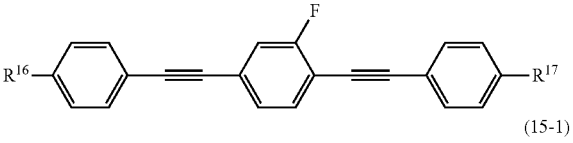

(15-1) 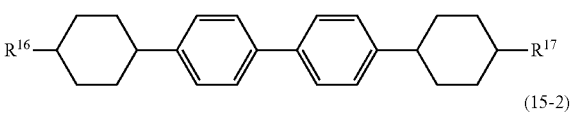

(15-2) 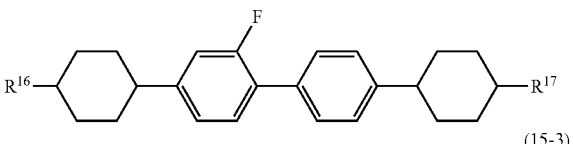

(15-3) 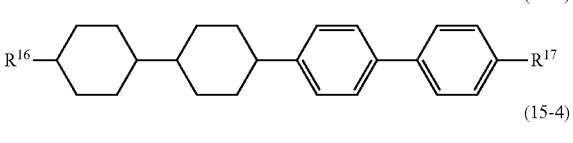

(15-4) 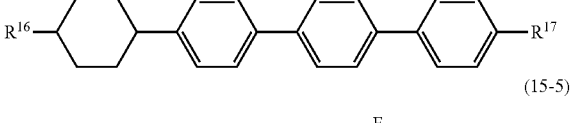

(15-5) 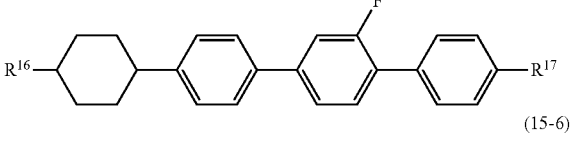

(15-6) 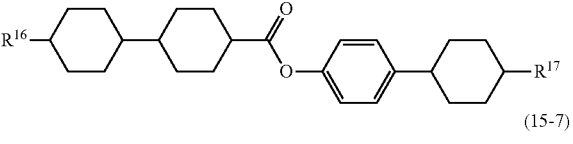

(15-7) 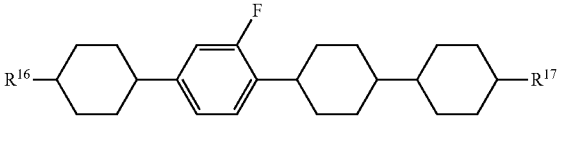

In the compounds (component E), $R^{16}$ and $R^{17}$ are defined in a manner identical with the definitions in formula (13) to (15) described in item 10.

Component E has a small absolute value of dielectric anisotropy, and therefore is a compound close to neutrality. Compound (13) is effective mainly in adjusting the viscosity or the optical anisotropy. Compounds (14) and (15) are effective in extending the temperature range of the nematic phase by increasing the maximum temperature, or in adjusting the optical anisotropy.

When a content of component E is increased, the viscosity of the composition decreases, but the dielectric anisotropy also decreases. Thus, as long as a desired value of threshold voltage of the device is met, the content is preferably as large as possible. Therefore, when a composition for the VA mode or the PSA mode is prepared, the content of component E is preferably 30% by weight or more, and further preferably 40% by weight or more, based on the total weight of the composition.

Composition (1) is prepared by a method for dissolving necessary components at a high temperature, or the like. According to an application, an additive may be added to the composition. Examples of the additive include an optically active compound, a polymerizable compound, a polymerization initiator, an antioxidant, an ultraviolet light absorber, a light stabilizer, a heat stabilizer and a defoaming agent. Such additives are well known to those skilled in the art, and are described in literature.

Composition (1) may further contain at least one optically active compound. A publicly known chiral dopant can be added as the optically active compound. The chiral dopant is effective in inducing a helical structure in liquid crystal molecules to give a necessary twist angle, thereby preventing a reverse twist. Preferred examples of the chiral dopant include compounds (Op-1) to (Op-18) below. In compound (Op-18), ring J is 1,4-cyclohexylene or 1,4-phenylene, and $R^{24}$ is alkyl having 1 to 10 carbons.

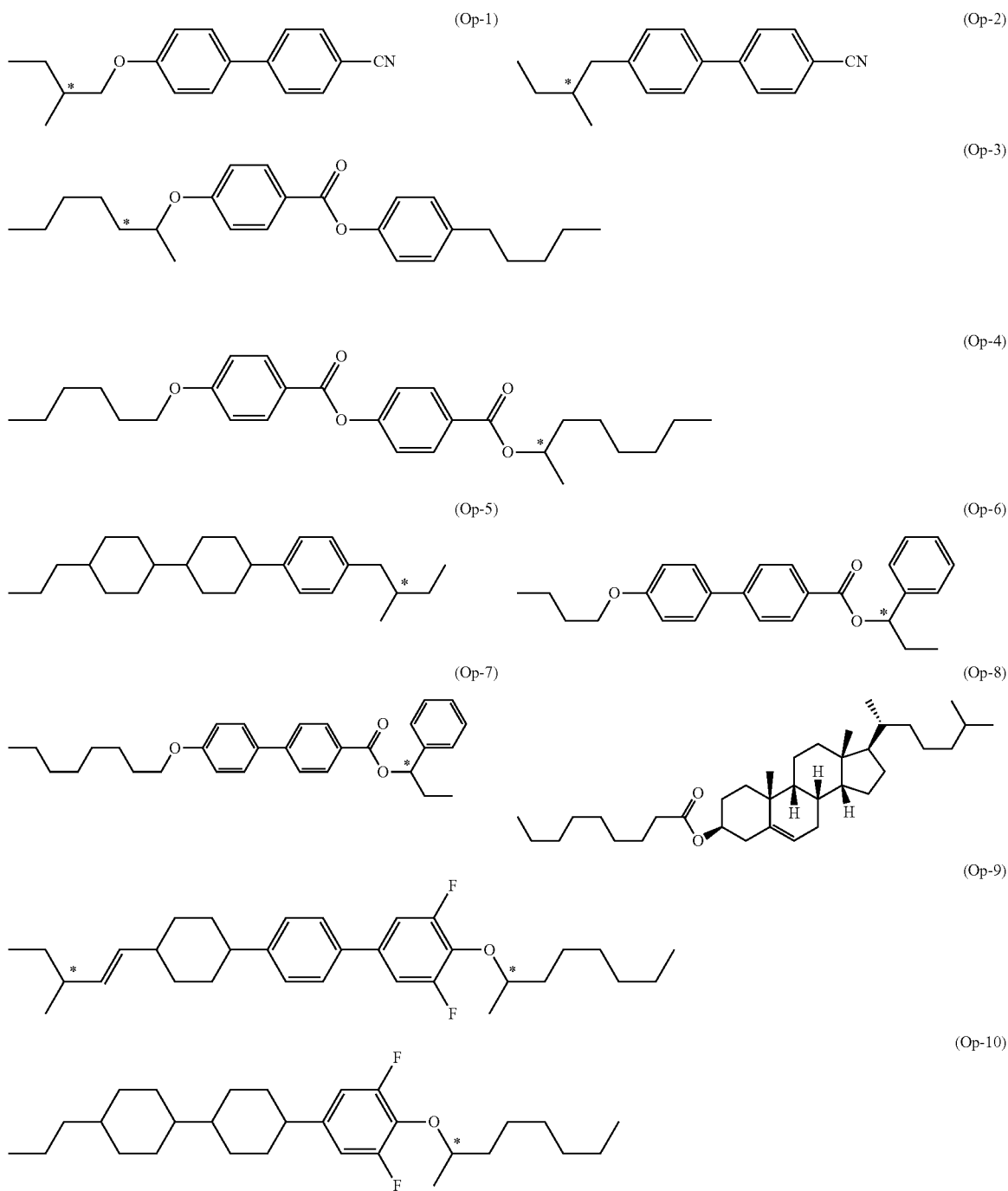

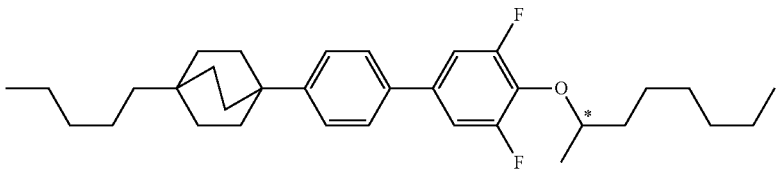

(Op-11)

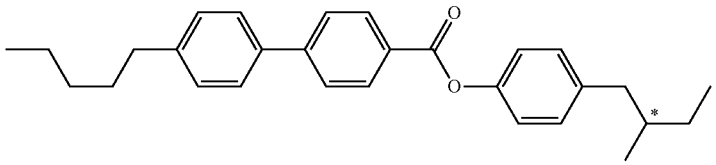

(Op-12)

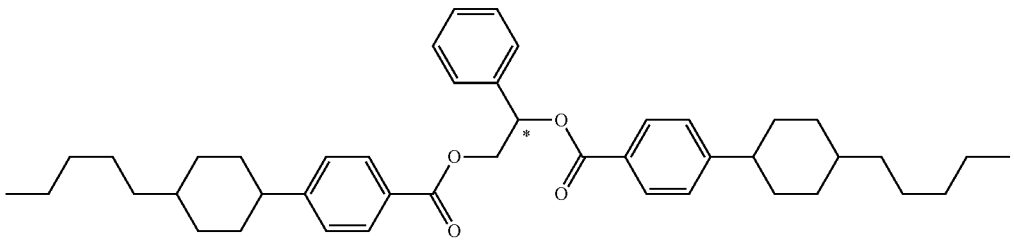

(Op-13)

(Op-14)

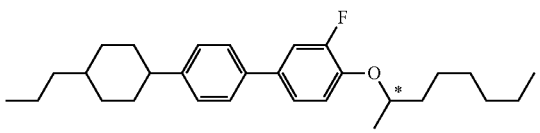

(Op-15)

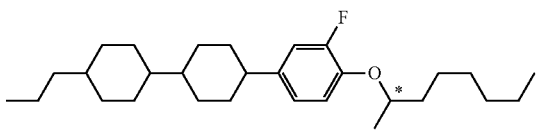

(Op-16)

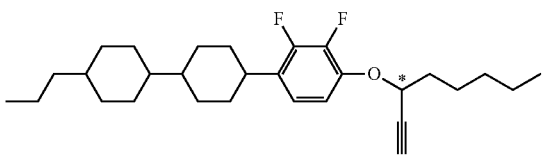

(Op-17)

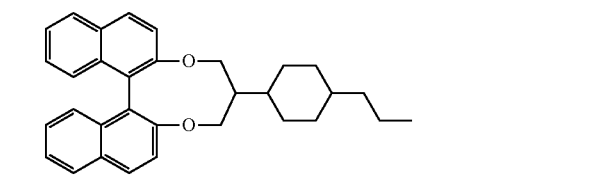

(Op-18)

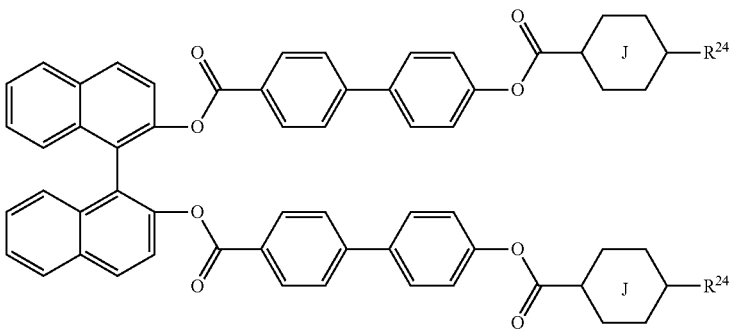

In composition (1), a helical pitch is adjusted by addition of such an optically active compound. The helical pitch is preferably adjusted to the range of 40 to 200 micrometers in a composition for the TFT mode and the TN mode. The helical pitch is preferably adjusted to the range of 6 to 20 micrometers in a composition for the STN mode. In the case of a composition for the BTN mode, the helical pitch is preferably adjusted to the range of 1.5 to 4 micrometers. Two or more optically active compounds may be added for the purpose of adjusting temperature dependence of the helical pitch.

Composition (1) can also be used in the PSA mode by adding a polymerizable compound. Examples of the polymerizable compound include acrylate, methacrylate, a vinyl compound, a vinyloxy compound, propenyl ether, an epoxy compound (oxirane, oxetane) and vinyl ketone. Preferred examples include compounds (M-1) to (M-12) below. The polymerizable compound polymerizes by irradiation with ultraviolet light or the like. The compound may be polymerized in the presence of a suitable initiator such as a photopolymerization initiator. Suitable conditions for polymerization, suitable types of the initiator and suitable amounts thereof are known to a person skilled in the art and are described in literature.

In compounds (M-1) to (M-12), $R^{20}$ is hydrogen or methyl; s is 0 or 1; and t and u are independently an integer from 1 to 10. A parenthesized symbol F stands for hydrogen or fluorine.
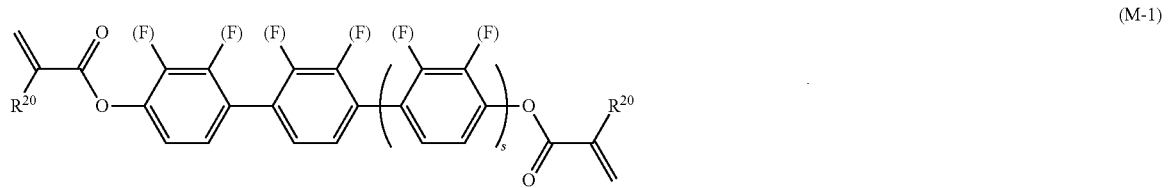
(M-1)
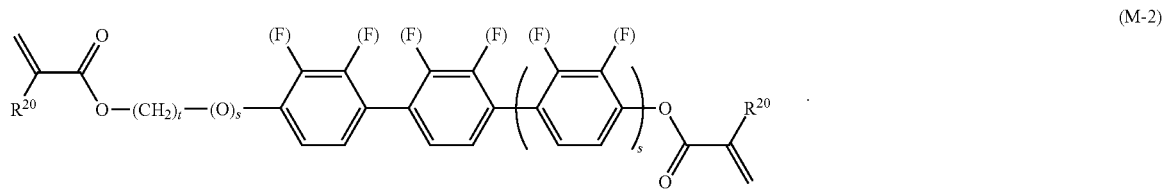
(M-2)
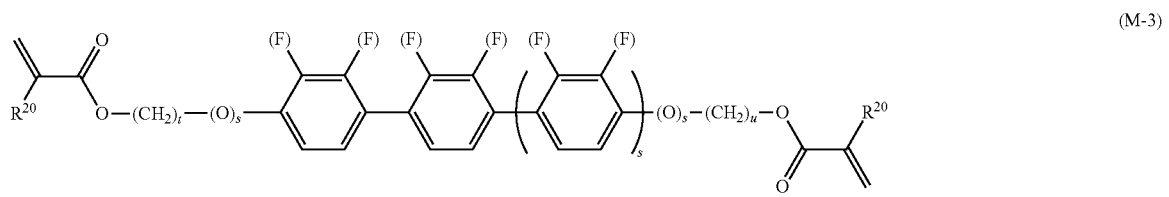
(M-3)
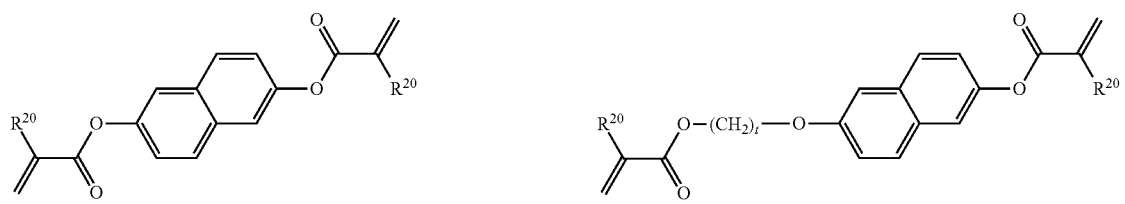
(M-4) (M-5)
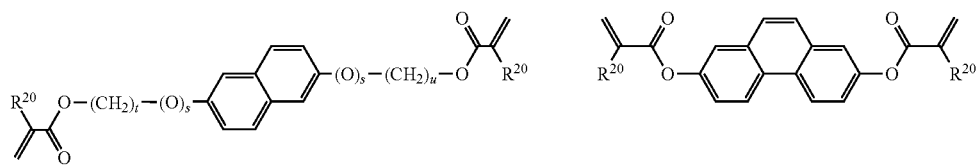
(M-6) (M-7)
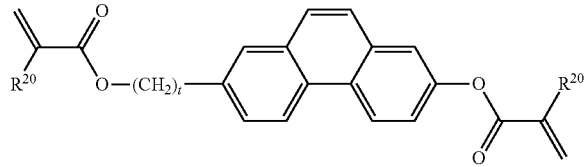
(M-8)
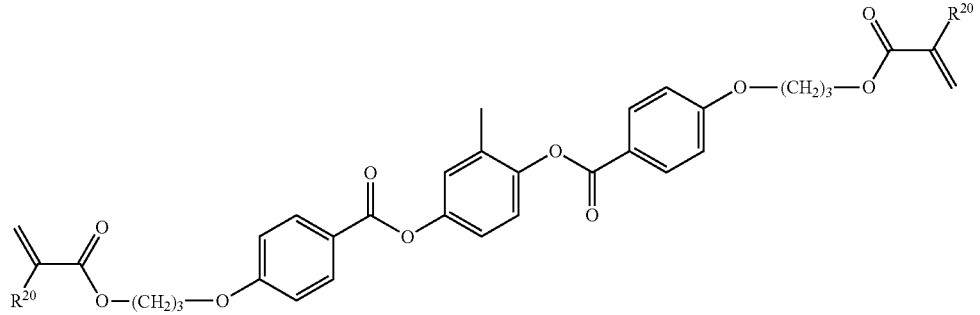
(M-9)

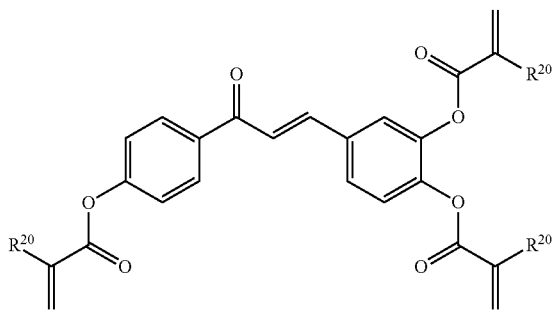
(M-10)

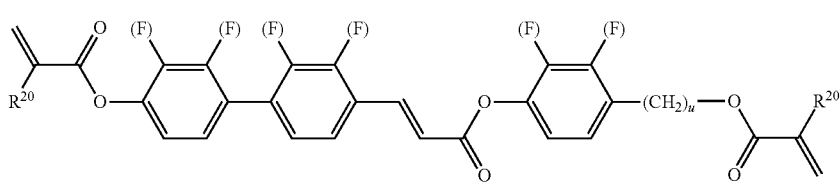
(M-11)

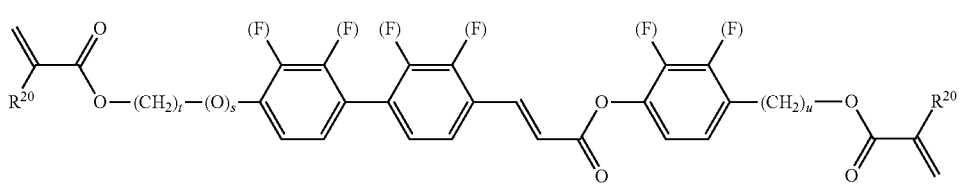
(M-12)

The antioxidant is effective for maintaining a large voltage holding ratio. Preferred examples of the antioxidant include compounds (AO-1) and (AO-2) below; IRGANOX 415, IRGANOX 565, IRGANOX 1010, IRGANOX 1035, IRGANOX 3114 and IRGANOX 1098 (trade names: BASF). The ultraviolet light absorber is effective for preventing a decrease of the maximum temperature. Preferred examples of the ultraviolet light absorber include a benzophenone derivative, a benzoate derivative and a triazole derivative. Specific examples include compounds (AO-3) and (AO-4) below; TINUVIN329, TINUVIN P, TINUVIN 326, TINUVIN 234, TINUVIN 213, TINUVIN 400, TINUVIN 328 and TINUVIN 99-2 (trade names: BASF); and 1,4-diazabicyclo[2.2.2]octane (DABCO).

A light stabilizer such as amine having steric hindrance is preferred for maintaining a large voltage holding ratio. Preferred examples of the light stabilizer include compounds (AO-5) and (AO-6) below; TINUVIN 144, TINUVIN 765 and TINUVIN 770DF (trade names: BASF). The heat stabilizer is also effective for maintaining a large voltage holding ratio, and preferred examples include IRGAFOS 168 (trade name: BASF). The defoaming agent is effective for preventing foam formation. Preferred examples of the defoaming agent include dimethyl silicone oil and methylphenyl silicone oil.

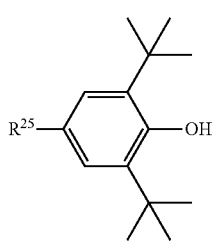
(AO-1)

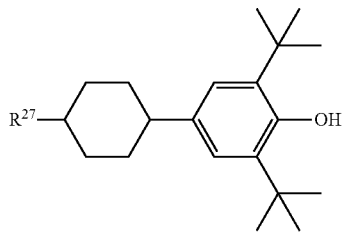
(AO-2)

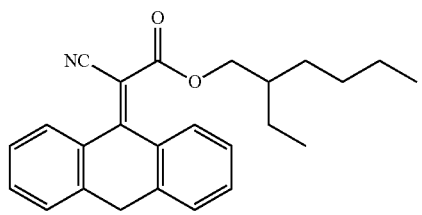
(AO-3)

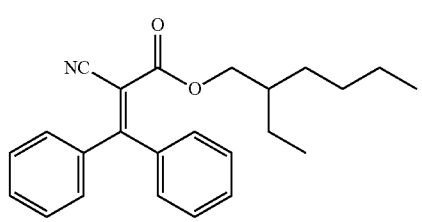
(AO-4)

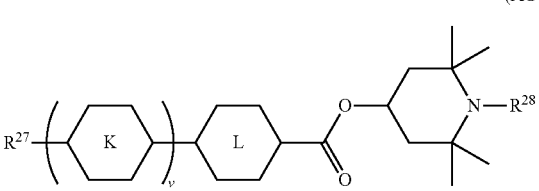
(AO-5)

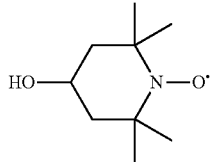
(AO-6)

In compound (AO-1), $R^{25}$ is alkyl having 1 to 20 carbons, alkoxy having 1 to 20 carbons, —COOR$^{26}$ or —CH$_2$CH$_2$COOR$^{26}$; and $R^{26}$ is alkyl having 1 to 20 carbons. In compounds (AO-2) and (AO-5), $R^{27}$ is alkyl having 1 to 20 carbons. In compound (AO-5), ring K and ring L are 1,4-cyclohexylene or 1,4-phenylene, v is 0, 1 or 2, and $R^{28}$ is hydrogen, methyl or O'.

Composition (1) can be used in a guest host (GH) mode by addition of a dichroic dye of a merocyanine type, a styryl type, an azo type, an azomethine type, an azoxy type, a quinophthalone type, an anthraquinone type, a tetrazine type or the like.

In composition (1), the maximum temperature can be adjusted to be 70° C. or higher and the minimum temperature can be adjusted to be −10° C. or lower by appropriately adjusting a kind and a ratio of component compounds, and thus the temperature range of the nematic phase is wide. Accordingly, a liquid crystal display device including the composition can be used in a wide temperature range.

In composition (1), the optical anisotropy can be adjusted to the range of 0.10 to 0.13 or 0.05 to 0.18 by appropriately adjusting a kind and a ratio of component compounds. In a similar manner, the dielectric anisotropy can be adjusted to the range of −5.0 to −2.0. Preferred dielectric anisotropy is in the range of −4.5 to −2.5. Composition (1) having the dielectric anisotropy in the range can be suitably used in a liquid crystal display device that operates in the IPS mode, VA mode or PSA mode.

3. Liquid Crystal Display Device

Composition (1) can be used in the AM device. The composition can also be used in a PM device. The composition can be used in an AM device and a PM device having a mode such as PC, TN, STN, ECB, OCB, IPS, FFS, VA, PSA or FPA. Use in an AM device having the TN, OCB, IPS or FFS mode is particularly preferred. In an AM device having the IPS mode or FFS mode, alignment of liquid crystal molecules in a state in which no voltage is applied may be parallel or perpendicular to a panel substrate. The devices may be of a reflective type, a transmissive type or a transflective type. Use in the transmissive device is preferred. The composition can also be used in an amorphous silicon-TFT device or a polycrystal silicon-TFT device. The composition can also be used in a nematic curvilinear aligned phase (NCAP) device prepared by microencapsulating the composition, and in a polymer dispersed (PD) device in which a three-dimensional network-polymer is formed in the composition.

Composition (1) has a negative dielectric anisotropy, and therefore can be preferably used in a liquid crystal display device that has an operating mode such as the VA mode, the IPS mode or the PSA mode, and is driven by an AM mode. The composition can be particularly preferably used in a liquid crystal display device that has the VA mode and driven by the AM mode.

In the liquid crystal display device that operates in the TN mode, VA mode or the like, a direction of an electric field is perpendicular to a direction of a liquid crystal layer. On the other hand, in the liquid crystal display device that operates in the IPS mode or the like, the direction of the electric field is parallel to the direction of the liquid crystal layer. A structure of the liquid crystal display device that operates in the VA mode is reported by K. Ohmura, S. Kataoka, T. Sasaki and Y. Koike, SID '97 Digest of Technical Papers, 28, 845 (1997). A structure of the liquid crystal display device that operates in the IPS mode is reported in WO 91/10936 A (family: U.S. Pat. No. 5,576,867 B).

EXAMPLES

The invention will be described in greater detail by way of Examples. The invention is not restricted by the Examples.

1-1. Example of Compound (1-1)

Compound (1-1) was prepared by procedures as described below. A prepared compound was identified by a method such as NMR analysis. Physical properties of the compound were measured by methods as described below.
NMR Analysis As a measuring apparatus, DRX-500 (made by Bruker BioSpin Corporation) was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using CFCl$_3$ as an internal standard. In the explanation of nuclear magnetic resonance spectra, s, d, t, q, quin, sex, m and br stand for a singlet, a doublet, a triplet, a quartet, a quintet, a sextet, a multiplet and being broad, respectively.
Sample for Measurement In measuring a phase structure and a transition temperature, a liquid crystal compound itself was used as a sample. In measuring physical properties such as a maximum temperature of a nematic phase, viscosity, optical anisotropy and dielectric anisotropy, a composition prepared by mixing the compound with a base liquid crystal was used as the sample.

In the case where the sample prepared by mixing the compound with the base liquid crystal was used, measurement was carried out according to the method described below. The sample was prepared by mixing 15% by weight of the compound and 85% of the base liquid crystal. An extrapolated value was calculated from a measured value of the sample according to an extrapolation method based on an equation below, and the extrapolated value was described. (Extrapolated value)=(100×(measured value of a sample)−(% of a base liquid crystal)×(measured value of a base liquid crystal))/(% of a compound).

When crystals (or a smectic phase) precipitated at 25° C. even at the above ratio of the compound to the base liquid crystal, a ratio of the compound to the base liquid crystal was changed in the order of (10% by weight: 90% by weight), (5% by weight: 95% by weight) and (1% by weight: 99% by weight). Physical properties of the sample were measured at a ratio at which no crystals (or no smectic phase) precipitated at 25° C. In addition, unless otherwise noted, the ratio of the compound to the base liquid crystal is 15% by weight: 85% by weight.

As the base liquid crystal, base liquid crystal (i) below was used. Ratios of components of base liquid crystal (i) are expressed in terms of % by weight.

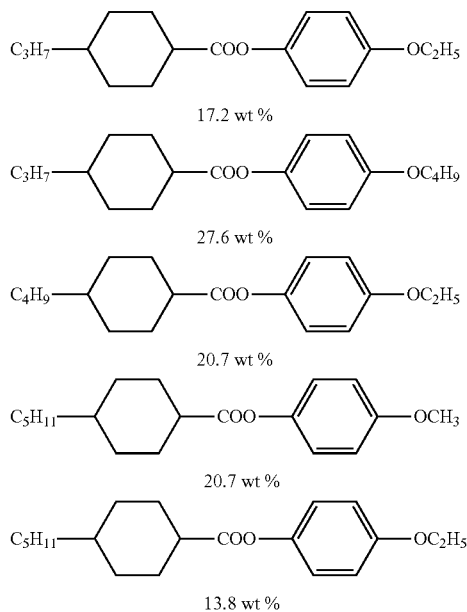

Measurement Method

Physical properties of a compound were measured according to the methods described below. Most of the measurement methods are applied as described in the Standard of the Japan Electronics and Information Technology Industries Association (hereinafter, abbreviated as JEITA) (JEITA EIAJ ED-2521A) discussed and established by JEITA, or modified thereon. No TFT was attached to a TN device used for measurement.

(1) Phase Structure

A sample was placed on a hot plate of a melting point apparatus (FP52 Hot Stage made by Mettler-Toledo International Inc.) equipped with a polarizing microscope, and a state of a phase and a change thereof were observed while the polarizing microscope while the sample was heated at a rate of 3° C. per minute, and a kind of the phase was specified.

(2) Transition Temperature (° C.)

A sample was heated and then cooled at a rate of 3° C. per minute using a differential scanning calorimeter, DSC-7 System or Diamond DSC System, made by PerkinElmer, Inc. A starting point of an endothermic peak or an exothermic peak caused by a phase change of the sample was determined by extrapolation, and thus a transition temperature was determined. Temperature at which a compound undergoes transition from a solid to a liquid crystal phase such as a smectic phase and a nematic phase may be occasionally abbreviated as "minimum temperature of the liquid crystal phase." Temperature at which a compound undergoes transition from the liquid crystal phase to a liquid may be occasionally abbreviated as "clearing point."

The crystals were expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. The liquid (isotropic) was expressed as I. The transition temperature was expressed as "C 50.0 N 100.0 I," for example. The expression indicates that a transition temperature from the crystal to the nematic phase is 50.0° C., and a transition temperature from the nematic phase to the liquid is 100.0° C.

(3) Compatibility at Low Temperature

Samples in which a base liquid crystal and a compound were mixed for the compound to be 20% by weight, 15% by weight, 10% by weight, 5% by weight, 3% by weight and 1% by weight were prepared, and put in glass vials. After the glass vials were kept in freezers at –10° C. or –20° C. for a predetermined period of time, whether or not crystals (or a smectic phase) precipitated was observed.

(4) Maximum Temperature of Nematic Phase ($T_{NI}$ or NI; ° C.)

A sample was placed on a hot plate in a melting point apparatus equipped with a polarizing microscope and was heated at a rate of 1° C. per minute. Temperature when part of the sample began to change from a nematic phase to an isotropic liquid was measured. A maximum temperature of the nematic phase may be occasionally abbreviated as "maximum temperature." When the sample was a mixture of a compound and a base liquid crystal, the maximum temperature was expressed in terms of a symbol $T_{NI}$. When the sample was the mixture of the compound and component B or the like, the maximum temperature was expressed in terms of a symbol NI.

(5) Minimum Temperature of Nematic Phase ($T_C$; ° C.)

Samples each having a nematic phase were kept in freezers at temperatures of 0° C., –10° C., –20° C., –30° C. and –40° C. for 10 days, and then liquid crystal phases were observed. For example, when the sample maintained the nematic phase at –20° C. and changed to crystals or a smectic phase at –30° C., $T_c$ was expressed as $T_c \le -20°$ C. A minimum temperature of the nematic phase may be occasionally abbreviated as "minimum temperature."

(6) Viscosity (Bulk Viscosity; η; Measured at 20° C.; mPa·s)

A cone-plate (E-type) rotational viscometer was used for measurement.

(7) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. A voltage was applied stepwise to the device in the range of 30 V to 50 V at an increment of 1 V. After a period of 0.2 second with no voltage, a voltage was applied repeatedly under the conditions of only one rectangular wave (rectangular pulse; 0.2 second) and no voltage (2 seconds). A peak current and a peak time of a transient current generated by the applied voltage were measured. A value of rotational viscosity was obtained from the measured values and calculation equation (8) on page 40 of the paper presented by M. Imai et al. As dielectric anisotropy required for the calculation, a value measured in a section of dielectric anisotropy described below was used.

(8) Optical Anisotropy (Refractive Index Anisotropy; Δn; Measured at 25° C.)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (nil) was measured when the direction of polarized light was parallel to the direction of rubbing. A refractive index (n1) was measured when the direction of polarized light was perpendicular to the direction of rubbing. A value of refractive index anisotropy was calculated from an equation: $\Delta n = n\| - n\perp$.

(9) Dielectric Anisotropy ($\Delta\epsilon$; Measured at 25° C.)

A value of dielectric anisotropy was calculated from an equation: $\Delta\epsilon = \epsilon\| - \epsilon\perp$. A dielectric constant ($\epsilon\|$ and $\epsilon\perp$) was measured as described below.

1) Measurement of dielectric constant ($\epsilon\|$): An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (Ell) in the major axis direction of liquid crystal molecules was measured.

2) Measurement of dielectric constant ($\epsilon\perp$): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant ($\epsilon\perp$) in the minor axis direction of the liquid crystal molecules was measured.

(10) Elastic constant ($K_{11}$ and $K_{33}$; measured at 25° C.; pN)

Elastic Constant Measurement System Model EC-1 made by TOYO Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(11) Threshold voltage (Vth; measured at 25° C.; V)

An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the above occasion, the device was irradiated with light from a direction perpendicular to the device, and the amount of light transmitted through the device was measured. A voltage-transmittance curve was prepared, in which the maximum amount of light corresponds to 100% transmittance and the minimum amount of light corresponds to 0% transmittance. A threshold voltage is a voltage at 10% transmittance.

(12) Voltage Holding Ratio (VHR-1; Measured at 25° C.; %)

A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was obtained. Area B is an area without decay. A voltage holding ratio is a percentage of area A to area B.

(13) Voltage Holding Ratio (VHR-2; Measured at 80° C.; %)

A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was obtained. Area B is an area without decay. A voltage holding ratio is a percentage of area A to area B.

Example 1

Synthesis of Compound (1-1-1)

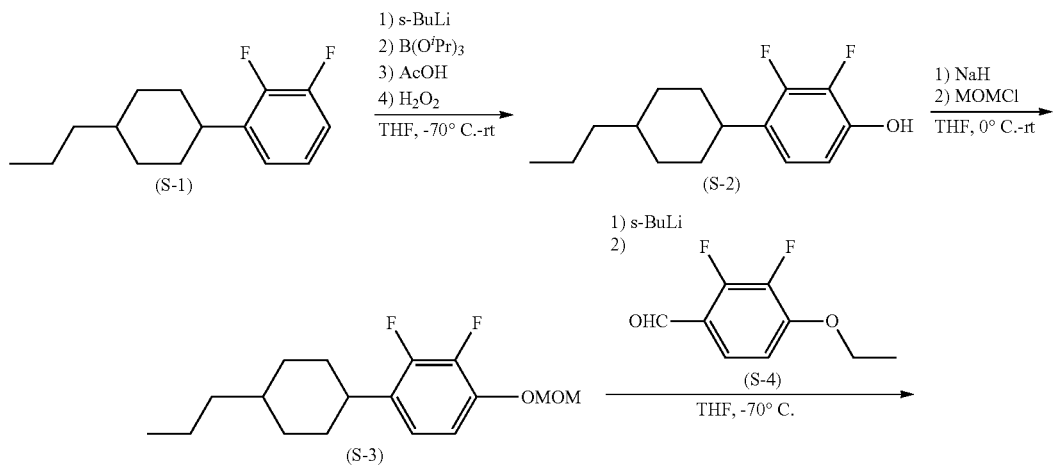

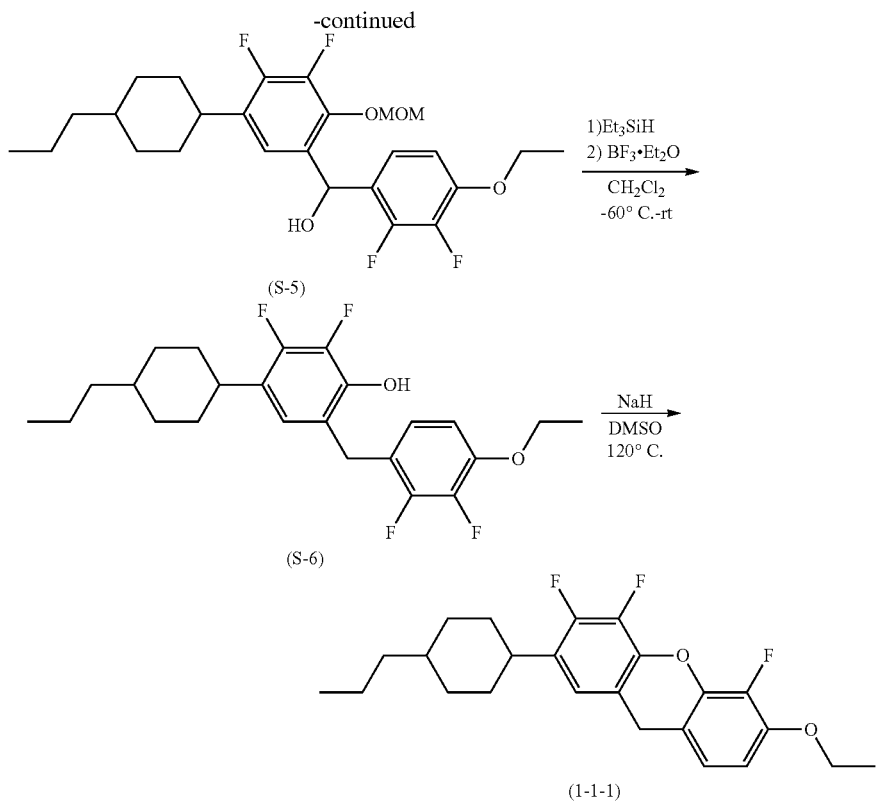

First Step

Under a nitrogen atmosphere, compound (S-1) (10.0 g) and THF (140 mL) were put in a reaction vessel and the resulting mixture was cooled to −70° C. Then, s-butyl-lithium (1.07 M cyclohexane solution, 49.0 mL) was slowly added thereto and the resulting mixture was stirred for 2 hours, and then a THF (10 mL) solution of triisopropyl borate (12.0 mL) was slowly added thereto, and the resulting mixture was stirred for 2 hours. The reaction mixture was heated to room temperature, acetic acid (3.60 mL) was added thereto, the resulting mixture was stirred for 30 minutes, and then a 30% hydrogen peroxide solution (9.52 g) was added thereto. The reaction mixture was poured into water, and a water layer was subjected to extraction with ethyl acetate. A combined organic layer was washed with water, an aqueous solution of sodium sulfite and saturated brine, and dried over anhydrous magnesium sulfate. The resulting solution was concentrated under reduced pressure, and the resulting residue was purified by silica gel chromatography (heptane:ethyl acetate=2:1 in a volume ratio) to obtain compound (S-2) (10.7 g; 100%).

Second Step

Under a nitrogen atmosphere, sodium hydride (2.20 g) and THF (80 mL) were put in a reaction vessel and the resulting mixture was cooled to 0° C. A THF solution (20 mL) of compound (S-2) (10.7 g) was added thereto and the resulting mixture was stirred for 1 hour, and then chloromethyl methyl ether (3.82 mL) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=9:1 in a volume ratio) to obtain compound (S-3) (9.69 g; 77%).

Third Step

Under a nitrogen atmosphere, compound (S-3) (9.69 g) and THF (80 mL) were put in a reaction vessel and the resulting mixture was cooled to −70° C. Then, s-butyl-lithium (1.07 M cyclohexane solution, 36.4 mL) was slowly added thereto and the resulting mixture was stirred for 1 hour, and then a THF solution (40 mL) of compound (S-4) (6.65 g) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-5) (15.7 g; 100%).

Fourth Step

Under a nitrogen atmosphere, compound (S-5) (15.7 g) and dichloromethane (140 mL) were put in a reaction vessel, and the resulting mixture was cooled to −60° C. A dichloromethane solution (10 mL) of triethylsilane (10.4 mL) was added thereto and the resulting mixture was stirred for 30 minutes, and then a boron trifluoride-diethyl ether complex (24.6 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-6) (11.9 g; 86%).

Fifth Step

Under a nitrogen atmosphere, sodium hydride (1.34 g) and dimethylsulfoxide (180 mL) were put in a reaction vessel, a dimethyl sulfoxide solution (50 mL) of compound (S-6) (11.9 g) was slowly added thereto, and the resulting mixture was heated to 120° C. and stirred for 3 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane: toluene=2:1 in a volume ratio). Further, the resulting material was purified by recrystallization from a mixed solvent of 2-propanol and ethyl acetate (1:1 in a volume ratio) to obtain compound (1-1-1) (5.11 g; 45%).

Chemical shift δ (ppm; CDCl$_3$): 6.82 (dd, J=8.2 Hz, J=1.6 Hz, 1H), 6.73 (dd, J=6.7 Hz, J=1.2 Hz, 1H) 6.70-6.65 (m, 1H), 4.12 (q, J=7.0 Hz, 2H), 3.94 (s, 2H), 2.77 (tt, J=12.4, J=3.1, 1H), 1.90-1.82 (m, 4H), 1.50-1.18 (m, 10H), 1.13-1.03 (m, 2H), 0.90 (t, J=7.4 Hz, 3H).

Physical properties of compound (1-1-1) were as described below. For measurement of maximum temperature, optical anisotropy, dielectric anisotropy and viscosity, the sample in which the ratio of the compound to the base liquid crystal was 5% by weight: 95% by weight was used.

Transition temperature: C 125.2 (N 99.9) I.

Maximum temperature (T$_{NI}$)=98.6° C.; optical anisotropy (Δn)=0.143; dielectric anisotropy (As)=−12.0; viscosity (ƒ)=88.7 mPa·s.

Example 2

Synthesis of Compound (1-2-1)

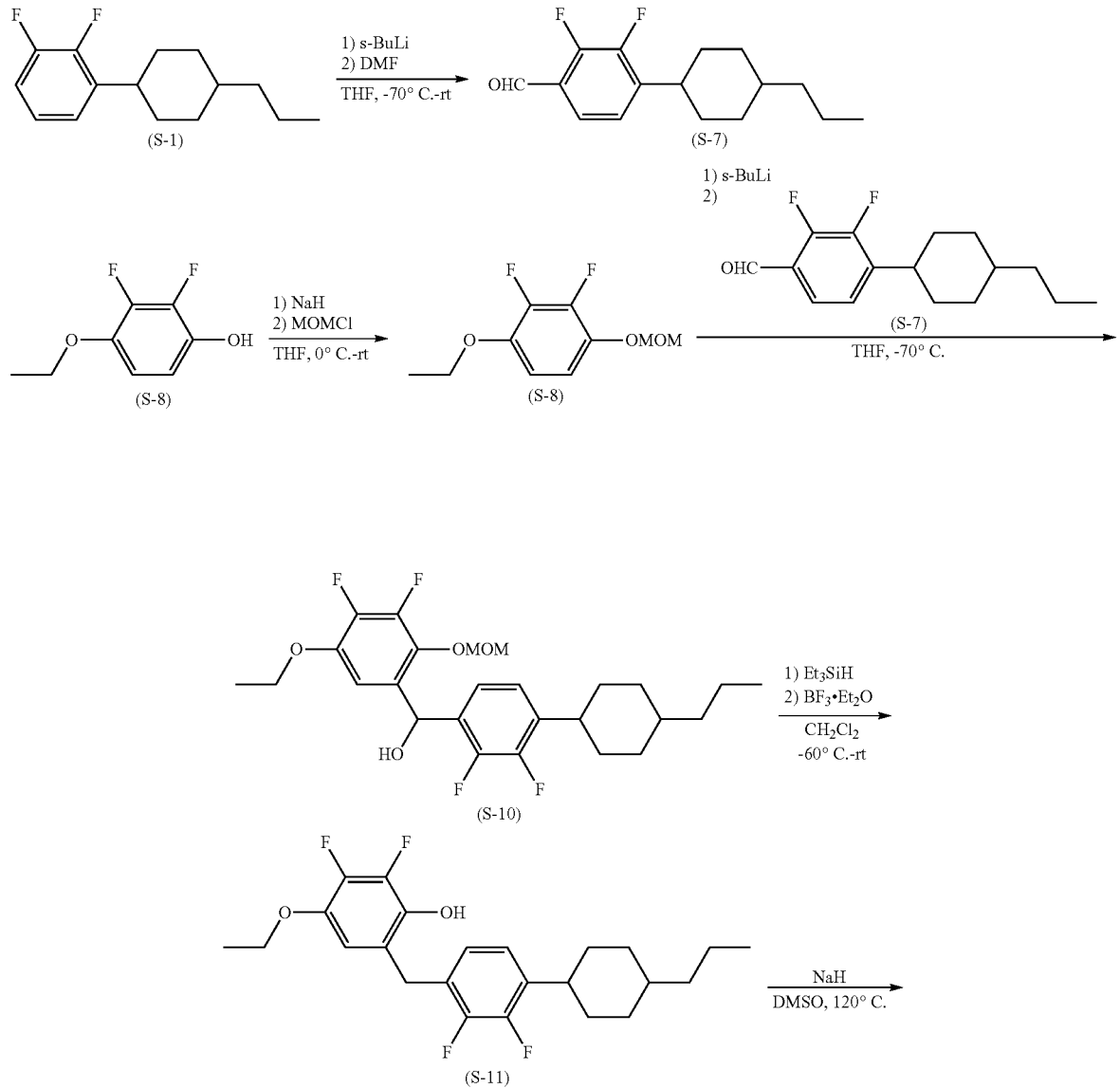

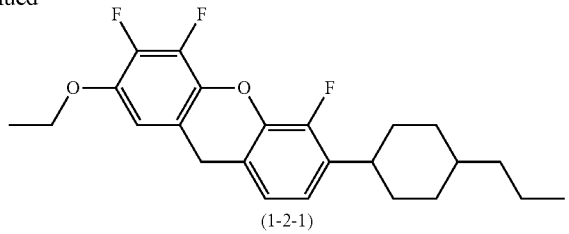

(1-2-1)

First Step

Under a nitrogen atmosphere, compound (S-1) (10.0 g) and THF (160 mL) were put in a reaction vessel and the resulting mixture was cooled to −70° C. Then, s-butyllithium (1.07 M cyclohexane solution, 47.1 ml) was slowly added thereto and the resulting mixture was stirred for 2.5 hours, and then a THF solution (40 ml) of N,N'-dimethylformamide (6.50 mL) was slowly added thereto, and temperature was increased to room temperature. The reaction mixture was poured into an ice-cooled saturated aqueous solution of ammonium chloride, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane:ethyl acetate=2:1 in a volume ratio) to obtain compound (S-7) (11.2 g; 100%).

Second Step

Under a nitrogen atmosphere, sodium hydride (6.01 g) and THF (150 mL) were put in a reaction vessel and the resulting mixture was cooled to 0° C. A THF solution (100 mL) of compound (S-8) (20.0 g) was slowly added thereto and the resulting mixture was stirred for 1 hour, and then chloromethyl methyl ether (10.5 mL) was slowly added thereto, and temperature was increased to room temperature. The reaction mixture was poured into water, and a water layer was subjected to extraction with diethyl ether. A combined organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-9) (22.5 g; 90%).

Third Step

Under a nitrogen atmosphere, compound (S-9) (4.0 g) and THF (40 mL) were put in a reaction vessel and the resulting mixture was cooled to −70° C. Then, s-butyllithium (1.07 M cyclohexane solution, 20.6 mL) was slowly added thereto and the resulting mixture was stirred for 1 hour, and then a THF solution (20 mL) of compound (S-7) (5.37 g) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-10) (8.68 g; 98%).

Fourth Step

Under a nitrogen atmosphere, compound (S-10) (8.68 g) and dichloromethane (75 mL) were put in a reaction vessel, and the resulting mixture was cooled to −60° C. A dichloromethane solution (5 mL) of triethylsilane (5.71 mL) was slowly added thereto and the resulting mixture was stirred for 45 minutes, and then a boron trifluoride-diethyl ether complex (13.6 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=2:1 in a volume ratio) to obtain compound (S-11) (6.66 g; 86%).

Fifth Step

Under a nitrogen atmosphere, sodium hydride (0.75 g) and dimethylsulfoxide (80 mL) were put in a reaction vessel, a dimethyl sulfoxide solution (50 mL) of compound (S-11) (6.66 g) was slowly added thereto, and the resulting mixture was heated to 120° C. and stirred for 5 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (eluent:heptane:toluene=1:1). Further, the resulting material was purified by recrystallization from a mixed solvent of 2-propanol and toluene (1:1 in a volume ratio) to obtain compound (1-2-1) (2.56 g; 40%).

Chemical shift δ (ppm; CDCl$_3$): 6.92-6.83 (m, 2H), 6.50 (d, J=7.9 Hz, 1H), 4.08 (q, J=7.0 Hz, 2H), 3.96 (s, 2H), 2.88-2.81 (m, 1H), 1.90-1.82 (m, 4H), 1.53-1.18 (m, 10H), 1.14-1.03 (m, 2H), 0.90 (t, J=7.2 Hz, 3H).

Physical properties of compound (1-2-1) were as described below. For measurement of maximum temperature, optical anisotropy, dielectric anisotropy and viscosity, the sample in which the ratio of the compound to the base liquid crystal was 3% by weight: 97% by weight was used.

Transition temperature: C 165.1 I.

Maximum temperature (T$_{NI}$)=104.6° C.; optical anisotropy (an)=0.147; dielectric anisotropy (Δ∈)=−11.7; viscosity (Λ)=99.9 mPa·s.

Example 3

Synthesis of Compound (1-5-1)

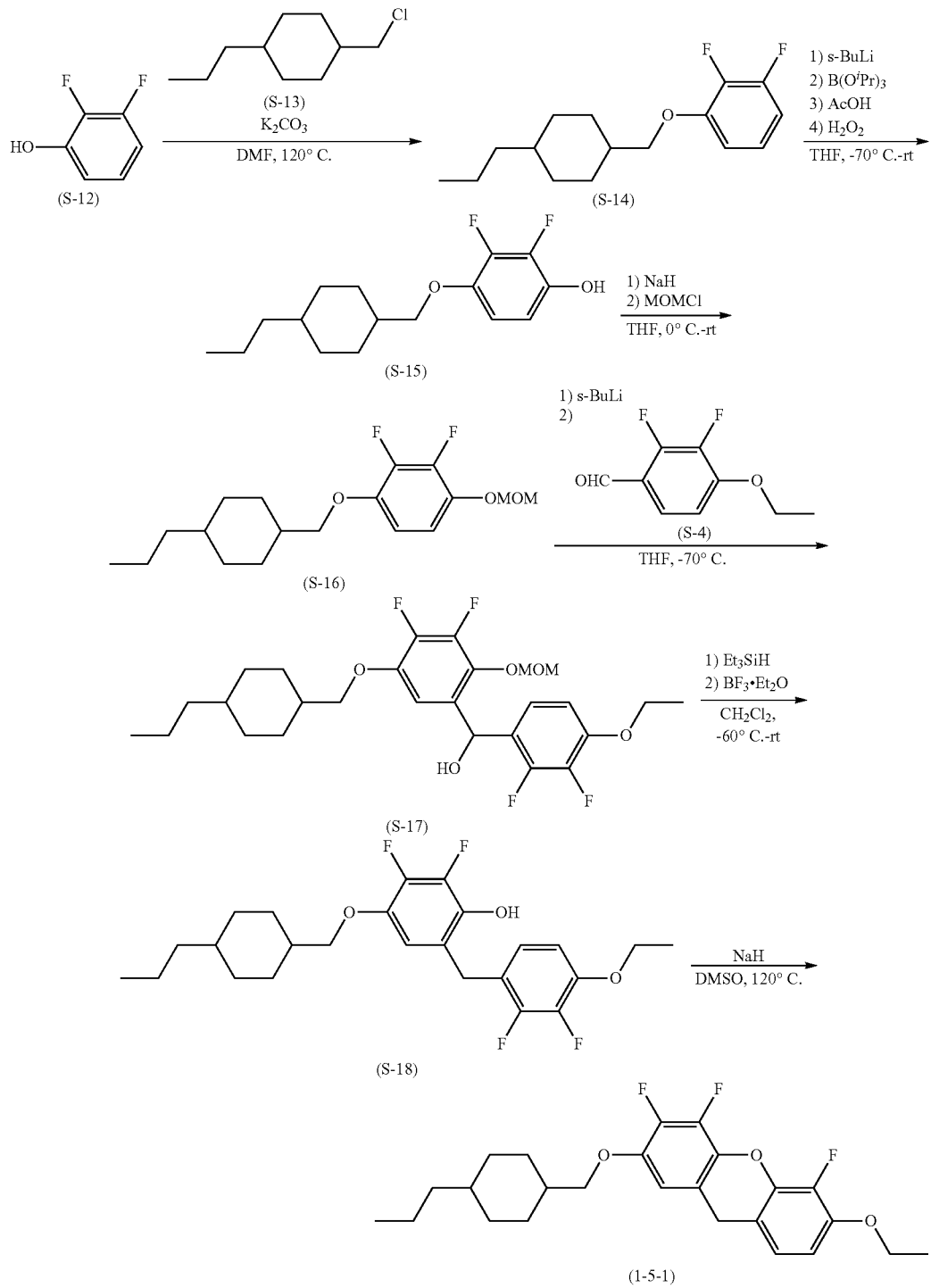

First Step

Under a nitrogen atmosphere, compound (S-12) (10.0 g), potassium carbonate (21.3 g) and N,N'-dimethylformamide (130 mL) were put in a reaction vessel, and the resulting mixture was heated to 80° C. and stirred for 30 minutes. An N,N'-dimethylformamide solution (20 mL) of compound (S-13) (13.4 g) was added thereto, and then the resulting mixture was heated to 130° C. and stirred for 5 hours. The reaction mixture was poured into water, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane) to obtain compound (S-14) (17.4 g; 85%).
Second Step Under a nitrogen atmosphere, compound (S-14) (17.4 g) and THF (230 mL) were put in a reaction vessel and the resulting mixture was cooled to −70° C. Then, s-butyllithium (1.04 M cyclohexane solution, 78.1 mL) was slowly added thereto and the resulting mixture was stirred for 2 hours, and then a THF solution (20 mL) of triisoproyl borate (18.6 mL) was slowly added thereto, and the resulting mixture was stirred for 2 hours. The reaction mixture was heated to room temperature, acetic acid (5.85 mL) was added thereto, and the resulting mixture was stirred for 30 minutes, and then a 30% hydrogen peroxide solution (14.7 g) was added thereto. The reaction mixture was poured into water, and a water layer was subjected to extraction with ethyl acetate. A combined organic layer was washed with water, an aqueous solution of sodium sulfite and saturated brine, and dried over anhydrous magnesium sulfate. The resulting solution was concentrated under reduced pressure, and the resulting residue was purified by silica gel chromatography (toluene). Further, the resulting material was purified by recrystallization from a mixed solvent of heptane and toluene (volume ratio, 1:1) to obtain compound (S-15) (18.2 g; 98%).
Third Step Under a nitrogen atmosphere, sodium hydride (3.24 g) and THF (160 mL) were put in a reaction vessel and the resulting mixture was cooled to 0° C. A THF solution (50 mL) of compound (S-15) (17.6 g) was slowly added thereto and the resulting mixture was stirred for 1 hour, and then chloromethyl methyl ether (5.65 mL) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=5:1 in a volume ratio) to obtain compound (S-16) (18.9 g; 93%).
Fourth Step Under a nitrogen atmosphere, compound (S-16) (2.0 g) and THF (20 mL) were put in a reaction vessel and the resulting mixture was cooled to −70° C. Then, s-butyllithium (1.07 M cyclohexane solution, 6.83 mL) was slowly added thereto and the resulting mixture was stirred for 1 hour, and then a THF solution (10 mL) of compound (S-4) (1.25 g) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane: ethyl acetate=4:1 in a volume ratio) to obtain compound (S-17) (2.87 g; 92%).
Fifth Step Under a nitrogen atmosphere, compound (S-17) (2.87 g) and dichloromethane (30 mL) were put in a reaction vessel, and the resulting mixture was cooled to −60° C. Triethylsilane (1.78 mL) was added thereto and the resulting mixture was stirred for 1 hour, and then a boron trifluoride-diethyl ether complex (4.22 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane: ethyl acetate=2:1 in a volume ratio) to obtain compound (S-18) (2.39 g; 94%).
Sixth Step Under a nitrogen atmosphere, sodium hydride (0.25 g) and dimethylsulfoxide (30 mL) were put in a reaction vessel, a dimethyl sulfoxide solution (20 mL) of compound (S-18) (2.39 g) was slowly added thereto, and the resulting mixture was heated to 120° C. and stirred for 3 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane:toluene=1:1 in a volume ratio). Further, the resulting material was purified by recrystallization from a mixed solvent of 2-propanol and ethyl acetate (1:1 in a volume ratio) to obtain compound (1-5-1) (1.21 g; 53%).

Chemical shift δ (ppm; $CDCl_3$): 6.81 (dd, J=9.3 Hz, J=1.6 Hz, 1H), 6.70-6.65 (m, 1H), 6.49 (dd, J=8.2 Hz, J=2.0 Hz, 1H), 4.12 (q, J=7.0 Hz, 2H), 3.93 (s, 2H), 3.78 (d, J=6.5, 2H), 1.94-1.87 (m, 2H), 1.84-1.72 (m, 3H), 1.44 (t, J=7.0 Hz, 3H), 1.37-1.28 (m, 2H), 1.27-1.15 (m, 3H), 1.05 (dq, J=13.0, J=3.2, 2H), 0.99-0.86 (m, 5H).

Physical properties of compound (1-5-1) were as described below. For measurement of maximum temperature, optical anisotropy, dielectric anisotropy and viscosity, the sample in which the ratio of the compound to the base liquid crystal was 10% by weight: 90% by weight was used.

Transition temperature: C 101.4 (N 97.6) I.

Maximum temperature ($T_{NI}$)=94.6° C.; optical anisotropy (Δn)=0.135; dielectric anisotropy (Le)=−14.3; viscosity (η)=104.0 mPa·s.

Example 4

Synthesis of Compound (1-5-2)

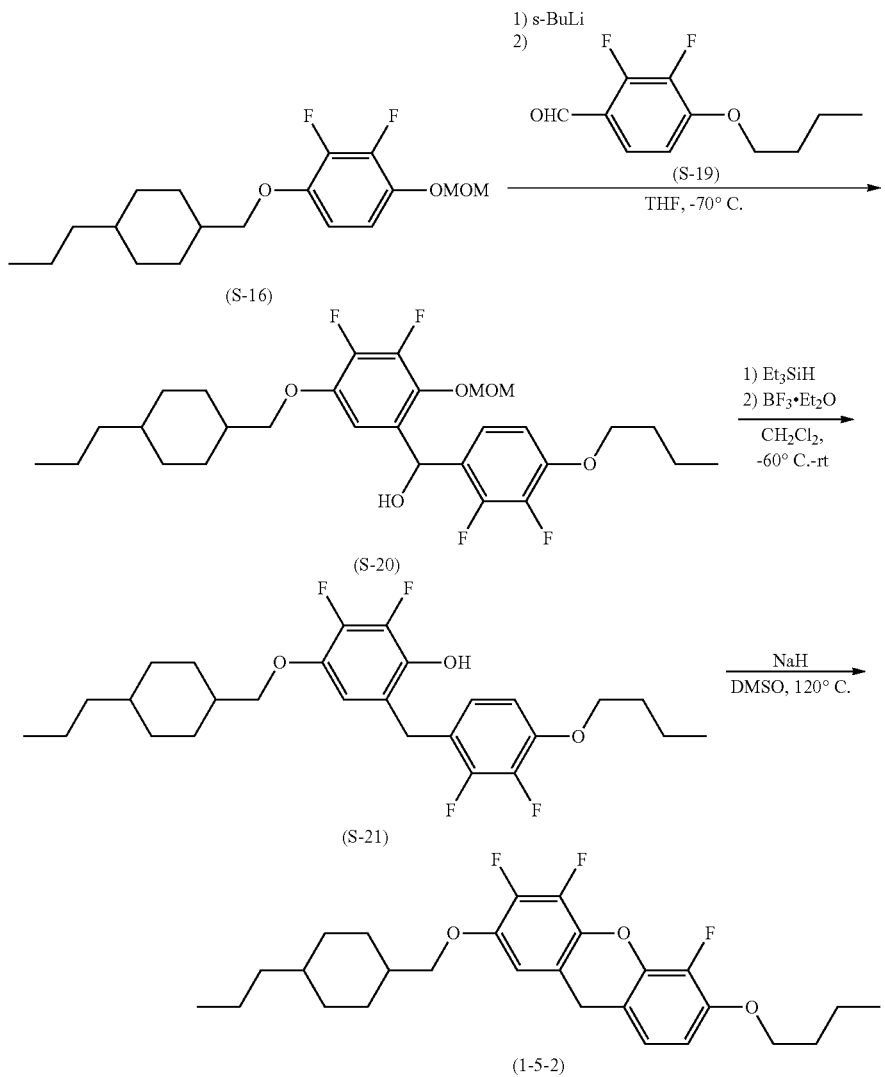

First Step

Under a nitrogen atmosphere, compound (S-16) (4.0 g) and THF (40 mL) were put in a reaction vessel and the resulting mixture was cooled to −70° C. Then, s-butyllithium (1.07 M cyclohexane solution, 13.7 mL) was slowly added thereto and the resulting mixture was stirred for 1 hour, and then a THF solution (20 mL) of compound (S-19) (2.875 g) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane: ethyl acetate=4:1 in a volume ratio) to obtain compound (S-20) (6.61 g; 100%).

Second Step

Under a nitrogen atmosphere, compound (S-20) (6.61 g) and dichloromethane (60 mL) were put in a reaction vessel, and the resulting mixture was cooled to −60° C. Triethylsilane (3.88 mL) was added thereto and the resulting mixture was stirred for 1 hour, and then a boron trifluoride-diethyl ether complex (9.22 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane: ethyl acetate=2:1 in a volume ratio) to obtain compound (S-21) (5.31 g; 90%).

Third Step

Under a nitrogen atmosphere, sodium hydride (0.53 g) and dimethylsulfoxide (60 mL) were put in a reaction vessel, a dimethyl sulfoxide solution (40 mL) of compound (S-21) (5.31 g) was slowly added thereto, and the resulting mixture was heated to 120° C. and stirred for 2 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane:toluene=1:1 in a volume ratio). Further, the resulting material was purified by recrystallization from a mixed solvent of 2-propanol and ethyl acetate (1:1 in a volume ratio) to obtain compound (1-5-2) (2.65 g; 52%).

Chemical shift δ (ppm; CDCl$_3$): 6.81 (dd, J=8.0 Hz, J=1.4 Hz, 1H), 6.71-6.65 (m, 1H), 6.49 (dd, J=8.2 Hz, J=2.1 Hz, 1H), 4.04 (t, J=6.5, 2H), 3.93 (s, 2H), 3.79 (d, J=6.5, 2H), 1.94-1.87 (m, 2H), 1.84-1.72 (m, 4H), 1.57-1.46 (m, 3H), 1.38-1.28 (m, 2H), 1.28-1.15 (m, 3H), 1.05 (dq, J=13.0, J=3.3, 2H), 1.11-0.86 (m, 8H).

Physical properties of compound (1-5-2) were as described below. For measurement of maximum temperature, optical anisotropy, dielectric anisotropy and viscosity, the sample in which the ratio of the compound to the base liquid crystal was 5% by weight: 95% by weight was used.

Transition temperature: C 124.4 (S$_A$ 66.4 N 97.5) I.

Maximum temperature (T$_{NI}$)=94.6° C.; optical anisotropy (Δn)=0.129; dielectric anisotropy (Δ∈)=−14.0; viscosity (η)=95.9 mPa·s.

Example 5

Synthesis of Compound (1-5-13)

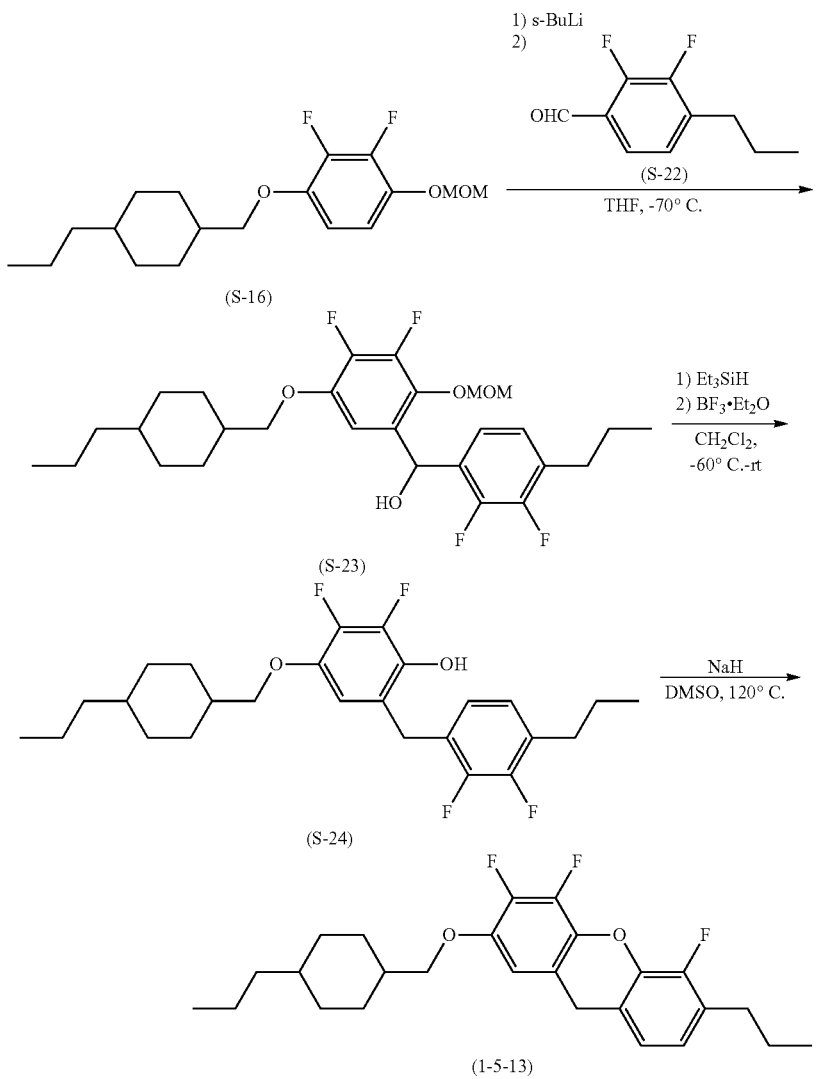

First Step

Under a nitrogen atmosphere, compound (S-16) (1.0 g) and THF (10 mL) were put in a reaction vessel and the resulting mixture was cooled to −70° C. Then, s-butyl-lithium (1.07 M cyclohexane solution, 3.42 mL) was slowly added thereto and the resulting mixture was stirred for 1 hour, and then a THF solution (6 mL) of compound (S-22) (0.59 g) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=5:1 in a volume ratio) to obtain compound (S-23) (1.29 g; 83%).

Second Step

Under a nitrogen atmosphere, compound (S-23) (1.29 g) and dichloromethane (13 mL) were put in a reaction vessel, and the resulting mixture was cooled to −60° C. Triethylsilane (0.80 mL) was added thereto and the resulting mixture was stirred for 1 hour, and then a boron trifluoride-diethyl ether complex (1.91 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=2:1 in a volume ratio) to obtain compound (S-24) (1.11 g; 97%).

Third Step

Under a nitrogen atmosphere, sodium hydride (0.12 g) and dimethylsulfoxide (12 mL) were put in a reaction vessel, a dimethyl sulfoxide solution (8 mL) of compound (S-24) (1.11 g) was slowly added thereto, and the resulting mixture was heated to 120° C. and stirred for 7 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane:toluene=4:1 in a volume ratio). Further, the resulting material was purified by recrystallization from heptane to obtain compound (1-5-13) (0.36 g; 34%).

Chemical shift δ (ppm; CDCl$_3$): 6.87-6.81 (m, 2H), 6.49 (dd, J=7.9 Hz, J=1.9 Hz, 1H), 3.96 (s, 2H), 3.79 (d, J=6.4, 2H), 2.63 (t, J=7.5 Hz, 2H), 1.94-1.87 (m, 2H), 1.84-1.72 (m, 3H), 1.64 (dt, J=14.9, J=7.6 Hz, 2H), 1.38-1.28 (m, 2H), 1.28-1.15 (m, 3H), 1.05 (dq, J=12.9, J=3.1, 2H), 1.00-0.86 (m, 8H).

Physical properties of compound (1-5-13) were as described below.

Transition temperature: C 94.6 (S$_A$ 53.4 N 66.0) I.

Maximum temperature (T$_{NI}$)=63.3° C.; optical anisotropy (Δn)=0.115; dielectric anisotropy (Δε)=−10.4; viscosity (η)=125.2 mPa·s.

Example 6

Synthesis of Compound (1-6-1)

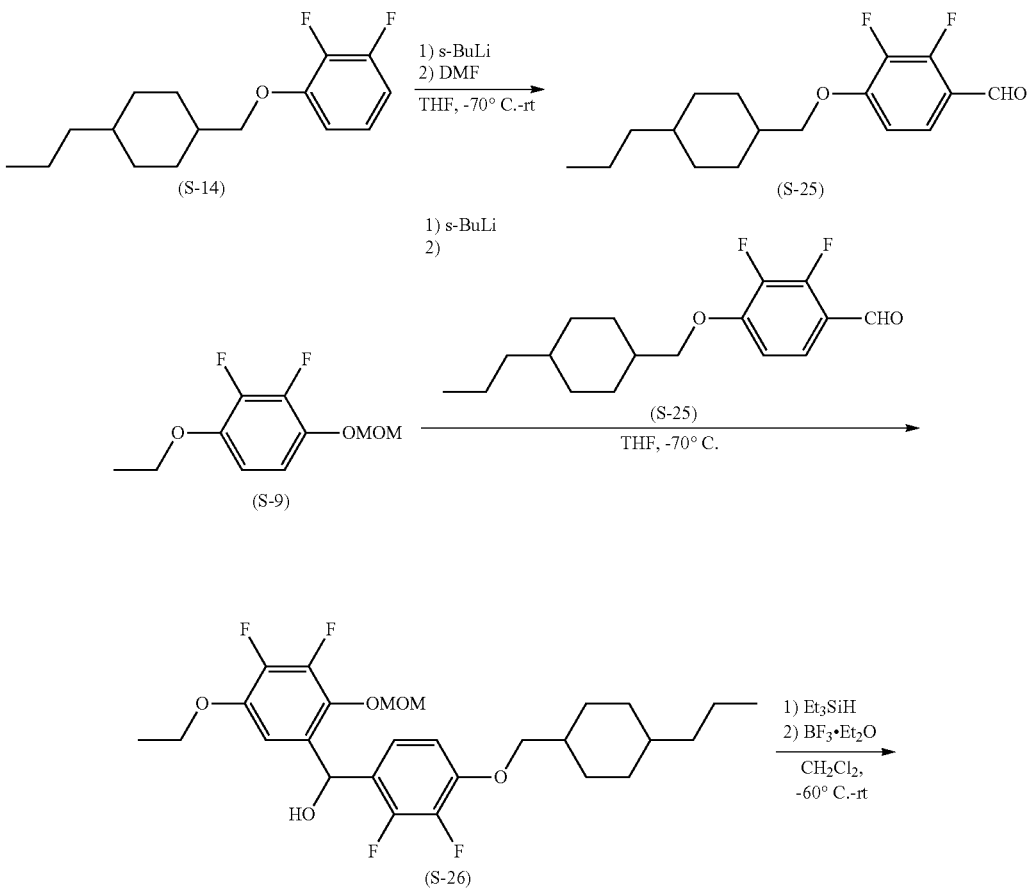

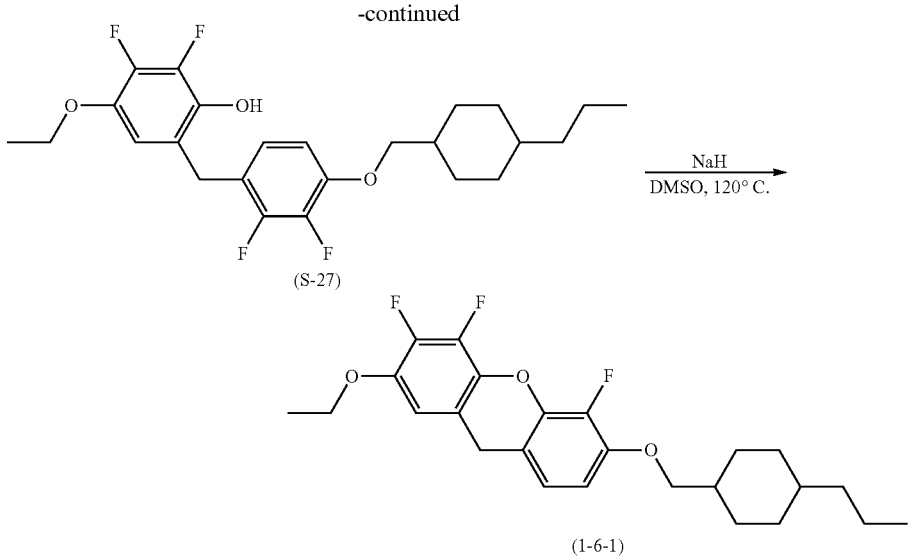

First Step

Under a nitrogen atmosphere, compound (S-14) (10.0 g) and THF (150 mL) were put in a reaction vessel and the resulting mixture was cooled to −70° C. Then, s-butyllithium (1.07 M cyclohexane solution, 41.8 mL) was slowly added thereto and the resulting mixture was stirred for 2.5 hours, and then a THF solution (50 mL) of N,N'-dimethylformamide (5.77 mL) was slowly added thereto, and temperature was increased to room temperature. The reaction mixture was poured into an ice-cooled saturated aqueous solution of ammonium chloride, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane: toluene=1:1 in a volume ratio) to obtain compound (S-25) (9.72 g; 88%).

Second Step

Under a nitrogen atmosphere, compound (S-9) (3.0 g) and THF (30 mL) were put in a reaction vessel and the resulting mixture was cooled to −70° C. Then, s-butyllithium (1.07 M cyclohexane solution, 15.4 mL) was slowly added thereto and the resulting mixture was stirred for 1 hour, and then a THF solution (15 mL) of compound (S-25) (4.48 g) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-26) (5.96 g; 84%).

Third Step

Under a nitrogen atmosphere, compound (S-26) (5.96 g) and dichloromethane (60 mL) were put in a reaction vessel, and the resulting mixture was cooled to −60° C. Triethylsilane (3.69 mL) was added thereto and the resulting mixture was stirred for 1 hour, and then a boron trifluoride-diethyl ether complex (8.77 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane: ethyl acetate=2:1 in a volume ratio) to obtain compound (S-27) (4.79 g; 91%).

Fourth Step

Under a nitrogen atmosphere, sodium hydride (0.51 g) and dimethylsulfoxide (60 mL) were put in a reaction vessel, a dimethyl sulfoxide solution (36 mL) of compound (S-27) (4.79 g) was slowly added thereto, and the resulting mixture was heated to 120° C. and stirred for 3 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (toluene, in a volume ratio). Further, the resulting material was purified by recrystallization from a mixed solvent of 2-propanol and toluene (1:1 in a volume ratio) to obtain compound (1-6-1) (2.29 g; 50%).

Chemical shift δ (ppm; CDCl$_3$): 6.81 (dd, J=8.9 Hz, J=1.3 Hz, 1H), 6.69-6.65 (m, 1H), 6.50 (dd, J=8.1 Hz, J=2.2 Hz, 1H), 4.08 (q, J=7.0, 2H), 3.93 (s, 2H), 3.83 (d, J=6.5, 2 H), 1.94-1.88 (m, 2H), 1.83-1.73 (m, 3H), 1.44 (t, J=7.0, 3H), 1.40-1.27 (m, 2H), 1.27-1.15 (m, 3H), 1.05 (dq, J=12.9, J=3.2, 2H), 0.99-0.85 (m, 5H).

Physical properties of compound (1-6-1) were as described below.

Transition temperature: C 169.3 I.

Example 7

Synthesis of Compound (1-1-11)

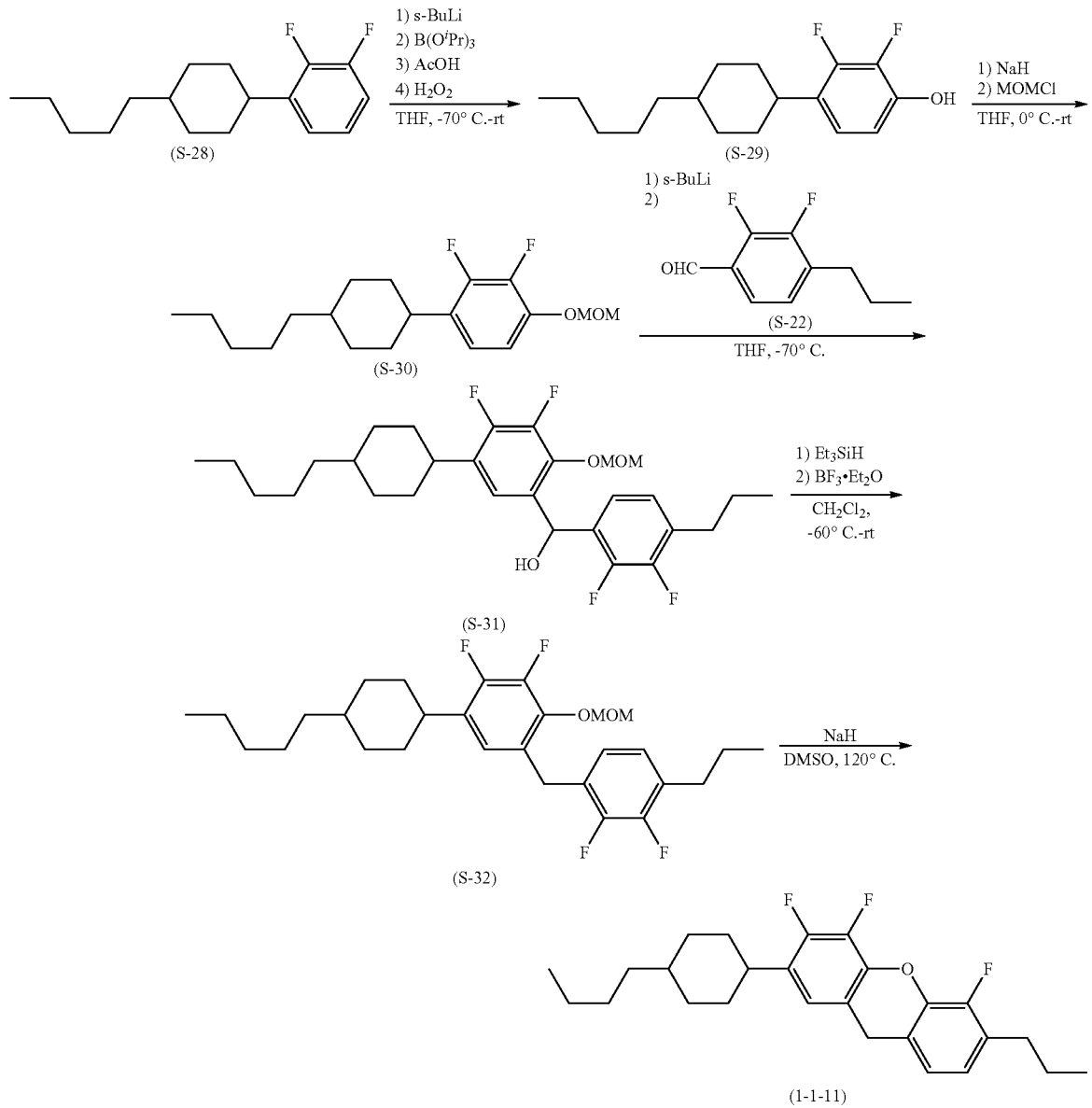

First Step

In a manner similar to the first step in Example 1, compound (S-29) (7.00 g; 98%) was obtained.

Second Step

Under a nitrogen atmosphere, sodium hydride (1.30 g) and THF (60 mL) were put in a reaction vessel and the resulting mixture was cooled to 0° C. A THE solution (10 mL) of compound (S-29) (7.00 g) was slowly added thereto and the resulting mixture was stirred for 1 hour, and then chloromethyl methyl ether (2.26 mL) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=9:1 in a volume ratio) to obtain compound (S-30) (6.86 g; 85%).

Third Step

Under a nitrogen atmosphere, compound (S-30) (4.83 g) and THF (60 mL) were put in a reaction vessel and the resulting mixture was cooled to −70° C. Then, s-butyllithium (1.07 M cyclohexane solution, 17.8 mL) was slowly added thereto and the resulting mixture was stirred for 1 hour, and then a THF solution (10 mL) of compound (S-22) (3.68 g) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=5:1 in a volume ratio) to obtain compound (S-31) (5.70 g; 75%).

Fourth Step

Under a nitrogen atmosphere, compound (S-31) (5.70 g) and dichloromethane (55 mL) were put in a reaction vessel, and the resulting mixture was cooled to −60° C. A dichloromethane solution (5 mL) of triethylsilane (2.81 mL) was added thereto and the resulting mixture was stirred for 30 minutes, and then a boron trifluoride-diethyl ether complex (6.71 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-32) (3.73 g; 94%).

Fifth Step

Under a nitrogen atmosphere, sodium hydride (0.40 g) and dimethylsulfoxide (60 mL) were put in a reaction vessel, a dimethylsulfoxide solution (20 mL) of compound (S-32) (3.73 g) was slowly added thereto, and the resulting mixture was heated to 120° C. and stirred for 6 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane). Further, the resulting material was purified by recrystallization from a mixed solvent of heptane and toluene (1:1 in a volume ratio) to obtain compound (1-1-11) (1.79 g; 50%).

Chemical shift δ (ppm; CDCl$_3$): 6.85-6.83 (m, 2H), 6.76-6.72 (m, 1H), 3.97 (s, 2H), 2.77 (tt, J=12.3, J=3.1, 1H), 2.63 (t, J=7.2, 2H), 1.90-1.82 (m, 4H), 1.64 (dt, J=14.8, J=7.5 Hz, 2H), 1.44 (dq, J=12.6, J=3.0, 2H), 1.36-1.19 (m, 9H), 1.12-1.02 (m, 2H), 0.95 (t, J=7.3, 3H), 0.90 (t, J=7.2, 3H).

Physical properties of compound (1-1-11) were as described below. For measurement of maximum temperature, optical anisotropy, dielectric anisotropy and viscosity, the sample in which the ratio of the compound to the base liquid crystal was 5% by weight: 95% by weight was used.

Transition temperature: C 119.4 I.

Maximum temperature (T$_{NI}$)=66.6° C.; optical anisotropy (Δn)=0.105; dielectric anisotropy (As)=−7.02; viscosity (η)=93.5 mPa·s.

Example 8

Synthesis of Compound (1-1-61)

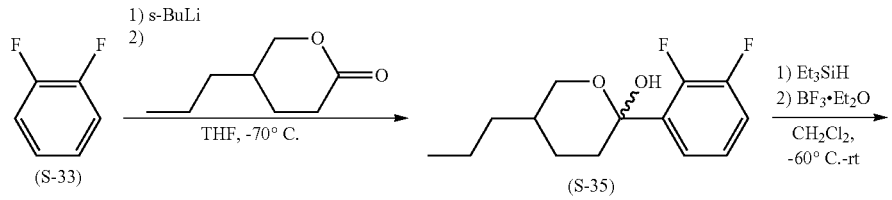

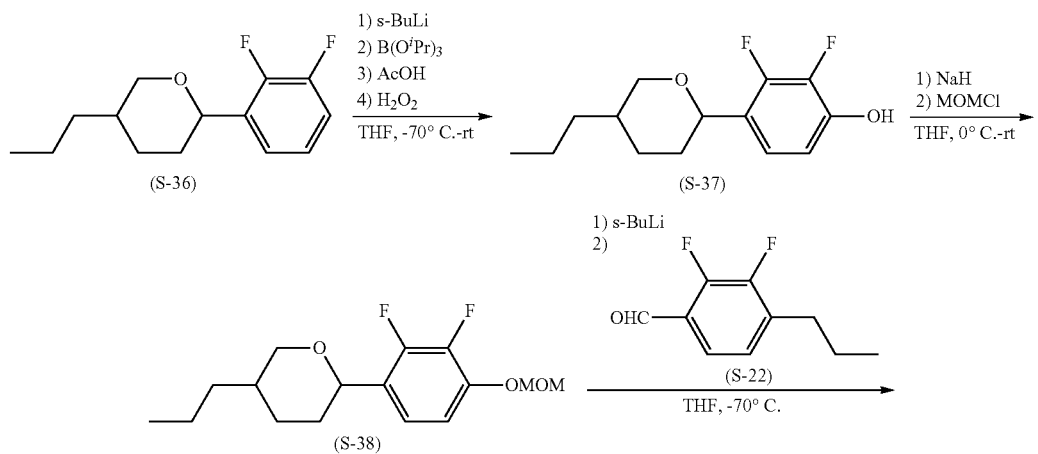

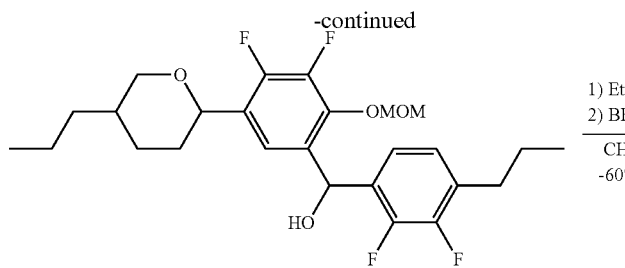
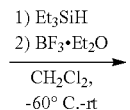
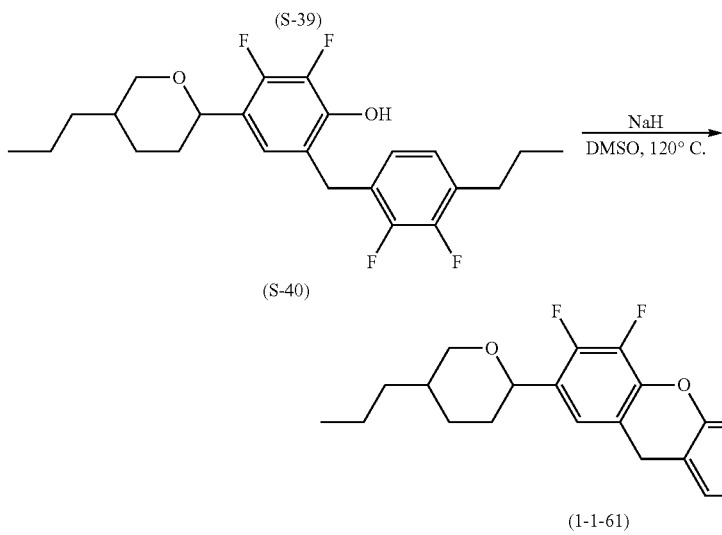

First Step

Under a nitrogen atmosphere, compound (S-33) (5.8 g) and THF (70 mL) were put in a reaction vessel and the resulting mixture was cooled to −70° C. Then, s-butyllithium (1.07 M cyclohexane solution, 49.4 mL) was slowly added thereto and the resulting mixture was stirred for 2 hours, and then a THF solution (20 mL) of compound (S-34) (6.53 g) prepared by a publicly known method was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-35) (10.55 g; 90%).

Second Step

Under a nitrogen atmosphere, compound (S-35) (10.55 g) and dichloromethane (90 mL) were put in a reaction vessel, and the resulting mixture was cooled to −60° C. A dichloromethane solution (10 mL) of triethylsilane (6.56 mL) was added thereto and the resulting mixture was stirred for 30 minutes, and then a boron trifluoride-diethyl ether complex (10.43 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=10:1 in a volume ratio) to obtain compound (S-36) (8.90 g; 90%).

Third Step

Under a nitrogen atmosphere, compound (S-36) (8.90 g) and THF (100 mL) were put in a reaction vessel and the resulting mixture was cooled to −70° C. Then, s-butyllithium (1.07 M cyclohexane solution, 43.3 mL) was slowly added thereto and the resulting mixture was stirred for 2 hours, and then a THF solution (25 mL) of triisoproyl borate (10.6 mL) was slowly added thereto, and the resulting mixture was stirred for 2 hours. The reaction mixture was heated to room temperature, acetic acid (3.18 mL) was added thereto and the resulting mixture was stirred for 30 minutes, and then a 30% hydrogen peroxide solution (8.40 g) was added thereto. The reaction mixture was poured into water, and a water layer was subjected to extraction with ethyl acetate. A combined organic layer was washed with water, an aqueous solution of sodium sulfite and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-37) (9.49 g; 100%).

Fourth Step

Under a nitrogen atmosphere, sodium hydride (1.96 g) and THF (80 mL) were put in a reaction vessel and the resulting mixture was cooled to 0° C. A THF solution (20 mL) of compound (S-37) (9.59 g) was slowly added thereto and the resulting mixture was stirred for 1 hour, and then chloromethyl methyl ether (3.41 mL) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, the resulting residue was purified by silica gel chromatography (heptane:ethyl acetate=10:1 in a volume ratio), and thus compound (S-38) (9.37 g; 83%) was obtained.

Fifth Step

Under a nitrogen atmosphere, compound (S-38) (6.24 g) and THF (90 mL) were put in a reaction vessel and the resulting mixture was cooled to −70° C. After slowly adding s-butyllithium (1.01 M cyclohexane solution, 24.7 mL) thereto and stirring the resulting mixture for 2 hours, a THF solution (10 mL) of compound (S-22) (4.45 g) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-39) (6.79 g; 67%).

Sixth Step

Under a nitrogen atmosphere, compound (S-39) (6.79 g) and dichloromethane (65 mL) were put in a reaction vessel, and the resulting mixture was cooled to −60° C. A dichloromethane solution (5 mL) of triethylsilane (4.46 mL) was added thereto and the resulting mixture was stirred for 30 minutes, and then a boron trifluoride-diethyl ether complex (10.6 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-6) (1.54 g; 26%).

Seventh Step

Under a nitrogen atmosphere, sodium hydride (0.22 g) and dimethylsulfoxide (25 mL) were put in a reaction vessel, a dimethyl sulfoxide solution (15 mL) of compound (S-6) (1.54 g) was slowly added thereto, and the resulting mixture was heated to 120° C. and stirred for 17 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane:ethyl acetate=10:1 in a volume ratio). Further, the resulting material was purified by recrystallization from a mixed solvent of heptane and ethyl acetate (1:1 in a volume ratio) to obtain compound (1-1-61) (0.26 g; 18%).

Chemical shift δ (ppm; $CDCl_3$): 7.06-7.02 (m, 1H), 6.88-6.82 (m, 2H), 4.55 (d, J=10.2 Hz, 1H), 4.11-4.06 (m, 1H), 3.99 (s, 2H), 3.24 (t, J=11.3, 1H), 2.63 (t, J=7.7 Hz, 2H), 2.01-1.94 (m, 1H), 1.93-1.87 (m, 1H), 1.74-1.48 (m, 4H), 1.44-1.07 (m, 5H), 0.98-0.88 (m, 6H).

Physical properties of compound (1-1-61) were as described below. For measurement of maximum temperature, optical anisotropy, dielectric anisotropy and viscosity, the sample in which the ratio of the compound to the base liquid crystal was 10% by weight: 90% by weight was used.

Transition temperature: C 115.9 I.

Maximum temperature ($T_{NI}$)=35.6° C.; optical anisotropy (Δn)=0.092; dielectric anisotropy (Δ∈)=−3.28; viscosity (η)=100.5 mPa·s.

Example 9

Synthesis of Compound (1-1-71)

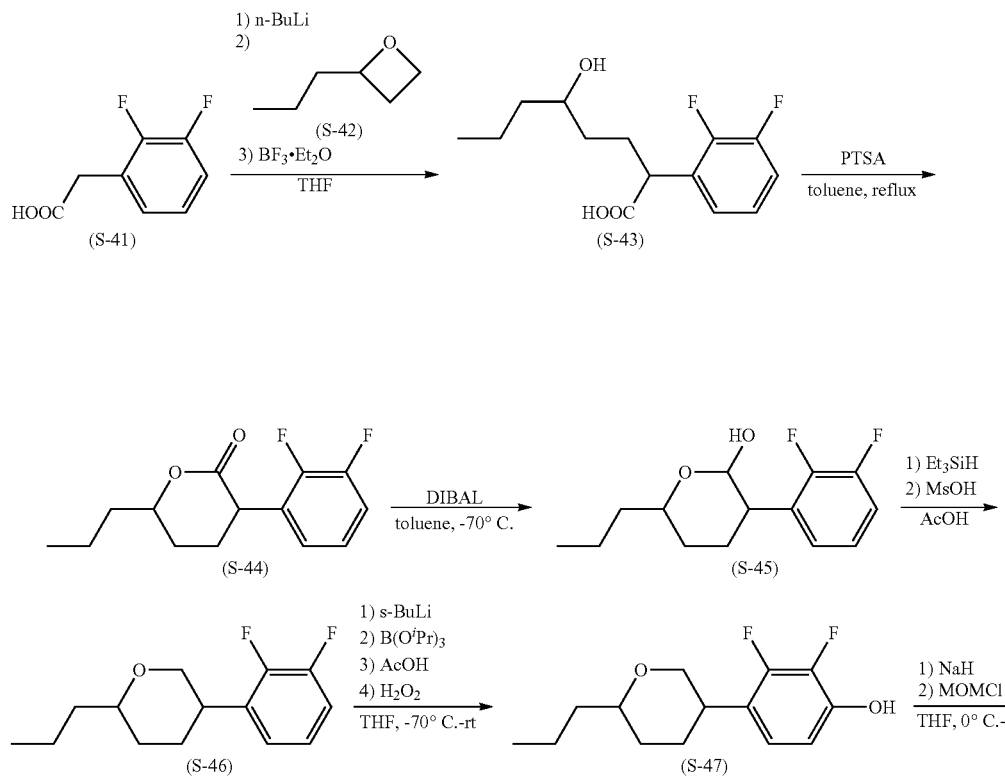

-continued

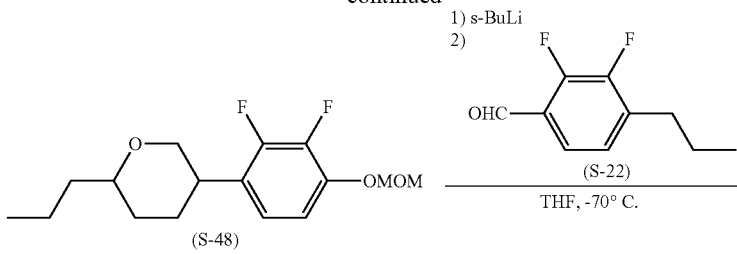

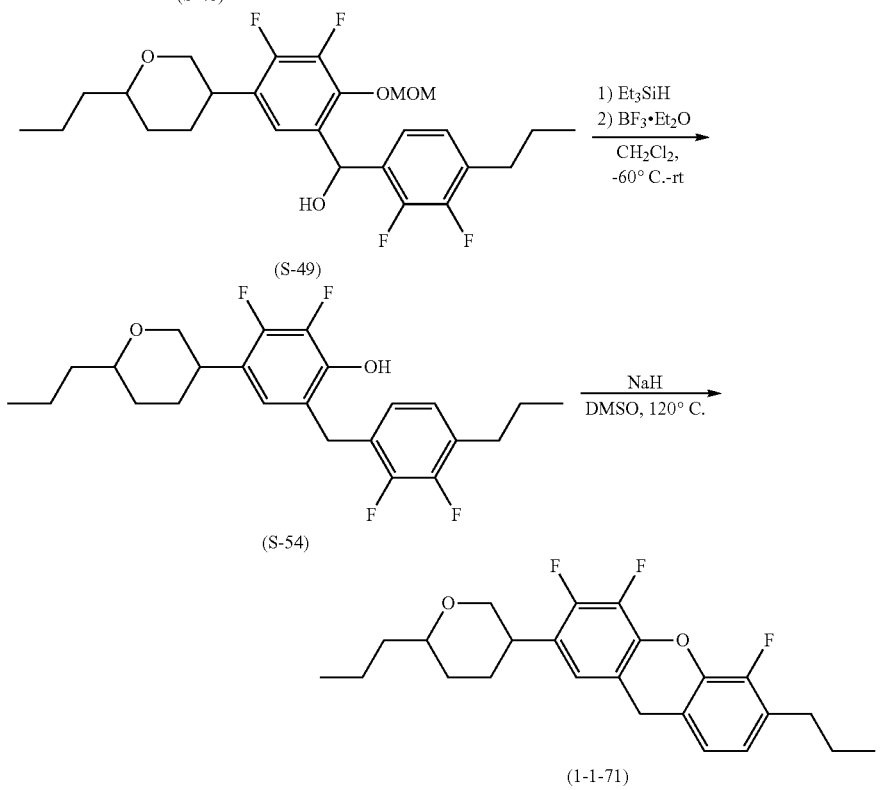

First Step

Under a nitrogen atmosphere, compound (S-41) (11.6 g) prepared by a publicly known method and THF (150 mL) were put in a reaction vessel and the resulting mixture was cooled to 0° C. Then, n-butyllithium (1.65 M cyclohexane solution, 84.0 mL) was slowly added thereto and the resulting mixture was stirred for 30 minutes, and then cooled to −70° C. A THF solution (40 mL) of compound (S-42) (6.84 g) prepared by a publicly known method was slowly added thereto. A boron trifluoride-diethyl ether complex (10.4 mL) was slowly added thereto and the resulting mixture was stirred for 40 minutes, and then temperature was increased to room temperature. The reaction mixture was poured into an 80% formic acid aqueous solution, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (ethyl acetate) to obtain compound (S-43) (18.6 g; 100%).

Second Step

Under a nitrogen atmosphere, compound (S-43) (18.6 g), p-toluenesulfonic acid monohydrate (0.56 g) and toluene (90 mL) were put in a reaction vessel, and the resulting mixture was refluxed under heating for 2 hours and 30 minutes. The reaction mixture was poured into saturated sodium bicarbonate water, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (eluent: heptane/ethyl acetate=4:1) to obtain compound (S-44) (11.9 g; 69%).

Third Step

Under a nitrogen atmosphere, compound (S-44) (11.9 g) and toluene (240 mL) were put in a reaction vessel, and the resulting mixture was cooled to −70° C. Diisobutylaluminum hydride (1.00 M toluene solution, 103.1 mL) was slowly added thereto, and the resulting mixture was stirred for 2 hours. The reaction mixture was poured into an 80% formic acid aqueous solution, and a water layer was subjected to extraction with toluene. A combined organic layer was washed with water and saturated brine, and dried over anhydrous magnesium sulfate. The resulting solution was concentrated under reduced pressure to obtain compound (S-45) (12.0 g; 100%).

Fourth Step

Under a nitrogen atmosphere, compound (S-45) (12.0 g) and dichloromethane (110 mL) were put in a reaction vessel, and the resulting mixture was stirred at room temperature. A dichloromethane solution (10 mL) of triethylsilane (11.2 mL) was added thereto and the resulting mixture was stirred for 30 minutes, and then a boron trifluoride-diethyl ether complex (4.57 mL) was slowly added thereto. The reaction mixture was poured into water, and an organic layer was washed with saturated sodium bicarbonate water, water and saturated brine, and dried over anhydrous magnesium sulfate. The resulting solution was concentrated under reduced pressure, and the resulting residue was purified by silica gel chromatography (heptane:ethyl acetate=10:1 in a volume ratio) to obtain compound (S-46) (11.3 g; 100%).

Fifth Step

Under a nitrogen atmosphere, compound (S-46) (11.3 g) and THF (200 mL) were put in a reaction vessel and the resulting mixture was cooled to −70° C. Then, s-butyl lithium (0.97 M cyclohexane solution, 60.5 mL) was slowly added thereto and the resulting mixture was stirred for 2 hours, and then a THF solution (40 mL) of triisoproyl borate (13.5 mL) was slowly added thereto, and the resulting mixture was stirred for 2 hours. The reaction mixture was heated to room temperature, acetic acid (4.03 mL) was added thereto and the resulting mixture was stirred for 30 minutes, and then a 30% hydrogen peroxide solution (10.7 g) was added thereto. The reaction mixture was poured into water, and a water layer was subjected to extraction with ethyl acetate. A combined organic layer was washed with water, a sodium sulfite aqueous solution and saturated brine, and dried over anhydrous magnesium sulfate. The resulting solution was concentrated under reduced pressure, and the resulting residue was purified by silica gel chromatography (heptane:ethyl acetate=2:1 in a volume ratio) to obtain compound (S-47) (12.0 g; 100%).

Sixth Step

Under a nitrogen atmosphere, sodium hydride (2.45 g) and THF (90 mL) were put in a reaction vessel and the resulting mixture was cooled to 0° C. A THF solution (30 mL) of compound (S-47) (12.0 g) was slowly added thereto and the resulting mixture was stirred for 1 hour, and then chloromethyl methyl ether (4.27 mL) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=5:1 in a volume ratio) to obtain compound (S-48) (11.6 g; 83%).

Seventh Step

Under a nitrogen atmosphere, compound (S-48) (6.00 g) and THF (60 mL) were put in a reaction vessel and the resulting mixture was cooled to −70° C. Then, s-butyl lithium (0.97 M cyclohexane solution, 24.7 mL) was slowly added thereto and the resulting mixture was stirred for 2 hours, and then a THF solution (30 mL) of compound (S-22) (5.47 g) was slowly added thereto, and the resulting mixture was heated to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=5:1 in a volume ratio) to obtain compound (S-49) (8.40 g; 87%).

Eighth Step

Under a nitrogen atmosphere, compound (S-49) (7.90 g) and dichloromethane (75 mL) were put in a reaction vessel, and the resulting mixture was cooled to −60° C. A dichloromethane solution (5 mL) of triethylsilane (5.19 mL) was added thereto and the resulting mixture was stirred for 30 minutes, and then a boron trifluoride-diethyl ether complex (18.5 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-54) (6.90 g; 100%).

Ninth Step

Under a nitrogen atmosphere, sodium hydride (0.72 g) and dimethylsulfoxide (80 mL) were put in a reaction vessel, a dimethyl sulfoxide solution (50 mL) of compound (S-54) (6.40 g) was slowly added thereto, and the resulting mixture was heated to 120° C. and stirred for 8 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane:ethyl acetate=5:1 in a volume ratio). Further, the resulting material was purified by recrystallization from a mixed solvent of 2-propanol and ethyl acetate (1:1 in a volume ratio) to obtain compound (1-1-71) (1.54 g; 25%).

Chemical shift δ (ppm; $CDCl_3$): 6.88-6.82 (m, 2H), 6.73-6.69 (m, 1H), 4.04-3.96 (m, 3H), 3.41 (t, J=11.0, 1H), 3.38-3.31 (m, 1H), 3.10 (tt, J=11.6, J=3.7, 1H), 2.63 (t, J=7.4, 2H), 2.02-1.95 (m, 1H), 1.83-1.72 (m, 2H), 1.69-1.34 (m, 7H), 0.98-0.92 (m, 6H).

Physical properties of compound (1-1-71) were as described below. For measurement of maximum temperature, optical anisotropy, dielectric anisotropy and viscosity, the sample in which the ratio of the compound to the base liquid crystal was 10% by weight: 90% by weight was used.

Transition temperature: C 117.7 I.

Maximum temperature ($T_{NI}$)=33.6° C.; optical anisotropy (Δn)=0.106; dielectric anisotropy (Δ∈)=−10.66; viscosity (η)=119.4 mPa·s.

Example 10

Synthesis of Compound (1-3-1)

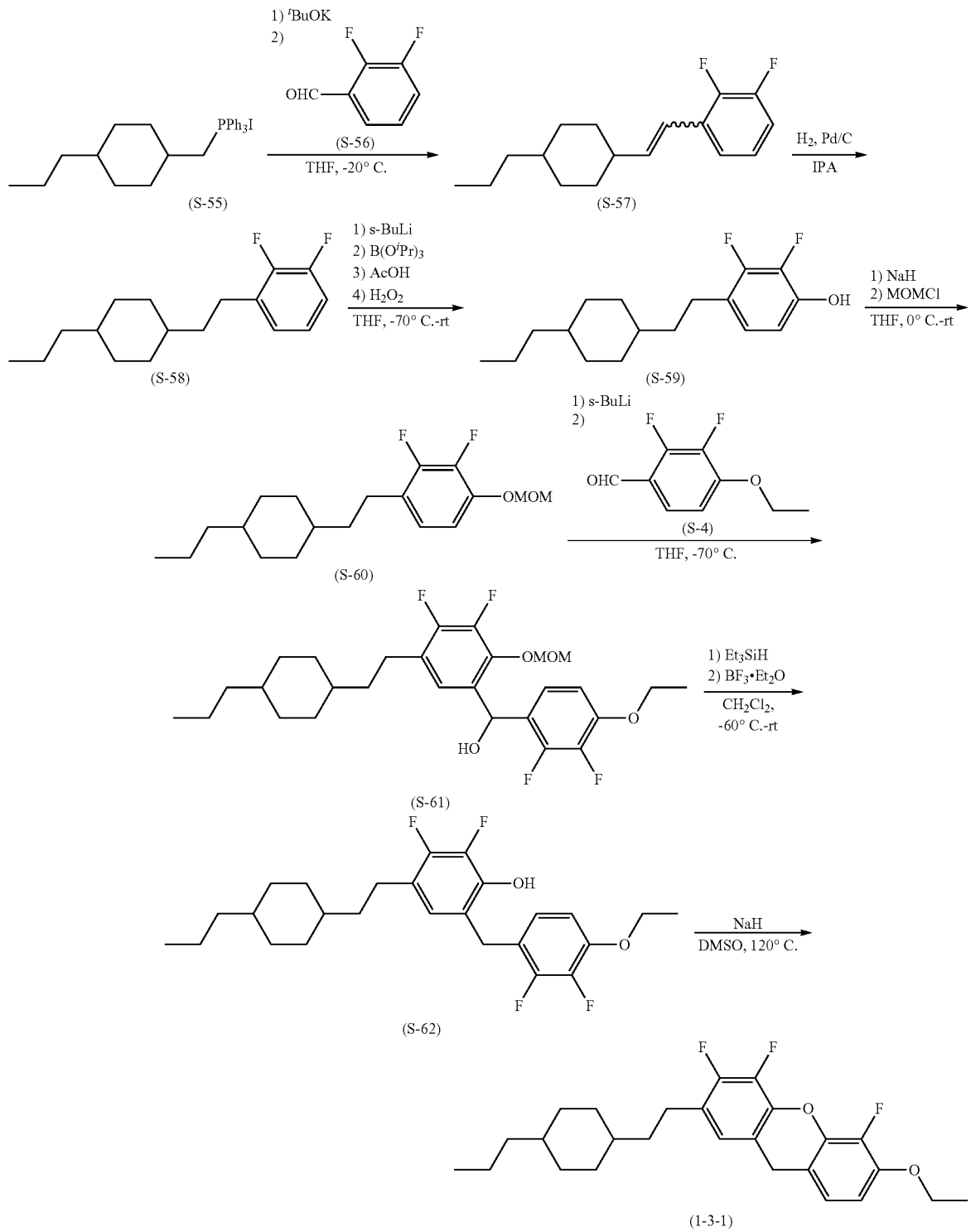

First Step

Under a nitrogen atmosphere, compound (S-55) (20.0 g) prepared by a publicly known method and THF (45 mL) were put in a reaction vessel and the resulting mixture was cooled to −20° C. Potassium t-butoxide (4.08 g) was added little by little thereto and the resulting mixture was stirred for 1 hour, and then a THF (5 mL) solution of compound (S-56) (4.30 g) prepared by a publicly known method was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (eluent: heptane) to obtain compound (S-57) (7.91 g; 99%).

Second Step

Under a hydrogen atmosphere, compound (S-57) (7.91 g), 5% palladium on carbon (0.40 g) and 2-propanol (24 mL) were put in a reaction vessel, and the resulting mixture was stirred for 12 hours. The reaction mixture was subjected filtration, and then the resulting solution was concentrated under reduced pressure, and the resulting residue was purified by silica gel chromatography (eluent: heptane) to obtain compound (S-58) (6.75 g; 85%).

Third Step

Under a nitrogen atmosphere, compound (S-58) (6.75 g) and THF (90 mL) were put in a reaction vessel and the resulting mixture was cooled to −70° C. Then, s-butyllithium (1.07 M cyclohexane solution, 29.6 mL) was slowly added thereto and the resulting mixture was stirred for 2 hours, and then a THF solution (10 mL) of triisoproyl borate (7.27 mL) was slowly added thereto, and the resulting mixture was stirred for 2 hours. The reaction mixture was heated to room temperature, acetic acid (2.18 mL) was added and the resulting mixture was stirred for 30 minutes, and then a 30% hydrogen peroxide solution (5.75 g) was added thereto. The reaction mixture was poured into water, and a water layer was subjected to extraction with ethyl acetate. A combined organic layer was washed with water, a sodium sulfite aqueous solution and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-59) (7.16 g; 100%).

Fourth Step

Under a nitrogen atmosphere, sodium hydride (1.33 g) and THF (50 mL) were put in a reaction vessel and the resulting mixture was cooled to 0° C. A THF solution (20 mL) of compound (S-59) (7.16 g) was slowly added thereto and the resulting mixture was stirred for 1 hour, and then chloromethyl methyl ether (2.31 mL) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=10:1 in a volume ratio) to obtain compound (S-60) (8.05 g; 97%).

Fifth Step

Under a nitrogen atmosphere, compound (S-60) (8.05 g) and THF (100 mL) were put in a reaction vessel and the resulting mixture was cooled to −70° C. Then, s-butyllithium (1.07 M cyclohexane solution, 29.6 mL) was slowly added thereto and the resulting mixture was stirred for 2 hours, and then a THF solution (20 mL) of compound (S-4) (4.59 g) was slowly added thereto, and the resulting mixture was heated to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane: ethyl acetate=4:1 in a volume ratio) to obtain compound (S-61) (12.6 g; 100%).

Sixth Step

Under a nitrogen atmosphere, compound (S-61) (12.6 g) and dichloromethane (110 mL) were put in a reaction vessel, and the resulting mixture was cooled to −60° C. A dichloromethane solution (10 mL) of triethylsilane (7.86 mL) was added thereto and the resulting mixture was stirred for 30 minutes, and then a boron trifluoride-diethyl ether complex (18.8 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=10:1 in a volume ratio) to obtain compound (S-62) (9.80 g; 88%).

Seventh Step

Under a nitrogen atmosphere, sodium hydride (1.04 g) and dimethylsulfoxide (160 mL) were put in a reaction vessel, a dimethyl sulfoxide solution (40 mL) of compound (S-62) (9.80 g) was slowly added thereto, and the resulting mixture was heated to 110° C. and stirred for 4 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane: toluene=2:1 in a volume ratio). Further, the resulting material was purified by recrystallization from a mixed solvent of 2-propanol and toluene (1:1 in a volume ratio) to obtain compound (1-3-1) (4.39 g; 47%).

Chemical shift δ (ppm; $CDCl_3$): 6.85-6.80 (m, 1H), 6.72-6.66 (m, 2H), 4.12 (q, J=7.0 Hz, 2H), 3.94 (s, 2H), 2.61 (t, J=7.7, 2H), 1.83-1.71 (m, 4H), 1.50-1.41 (m, 5H), 1.36-1.26 (m, 2H), 1.25-1.11 (m, 4H), 0.99-0.82 (m, 7H).

Physical properties of compound (1-3-1) were as described below. For measurement of maximum temperature, optical anisotropy, dielectric anisotropy and viscosity, the sample in which the ratio of the compound to the base liquid crystal was 1% by weight: 99% by weight was used.

Transition temperature: C 140.9 I.

Maximum temperature ($T_{NI}$)=84.6° C.; optical anisotropy (Δn)=0.147; dielectric anisotropy (ΔE)=−12.37.

Example 11

Synthesis of Compound (1-5-3)

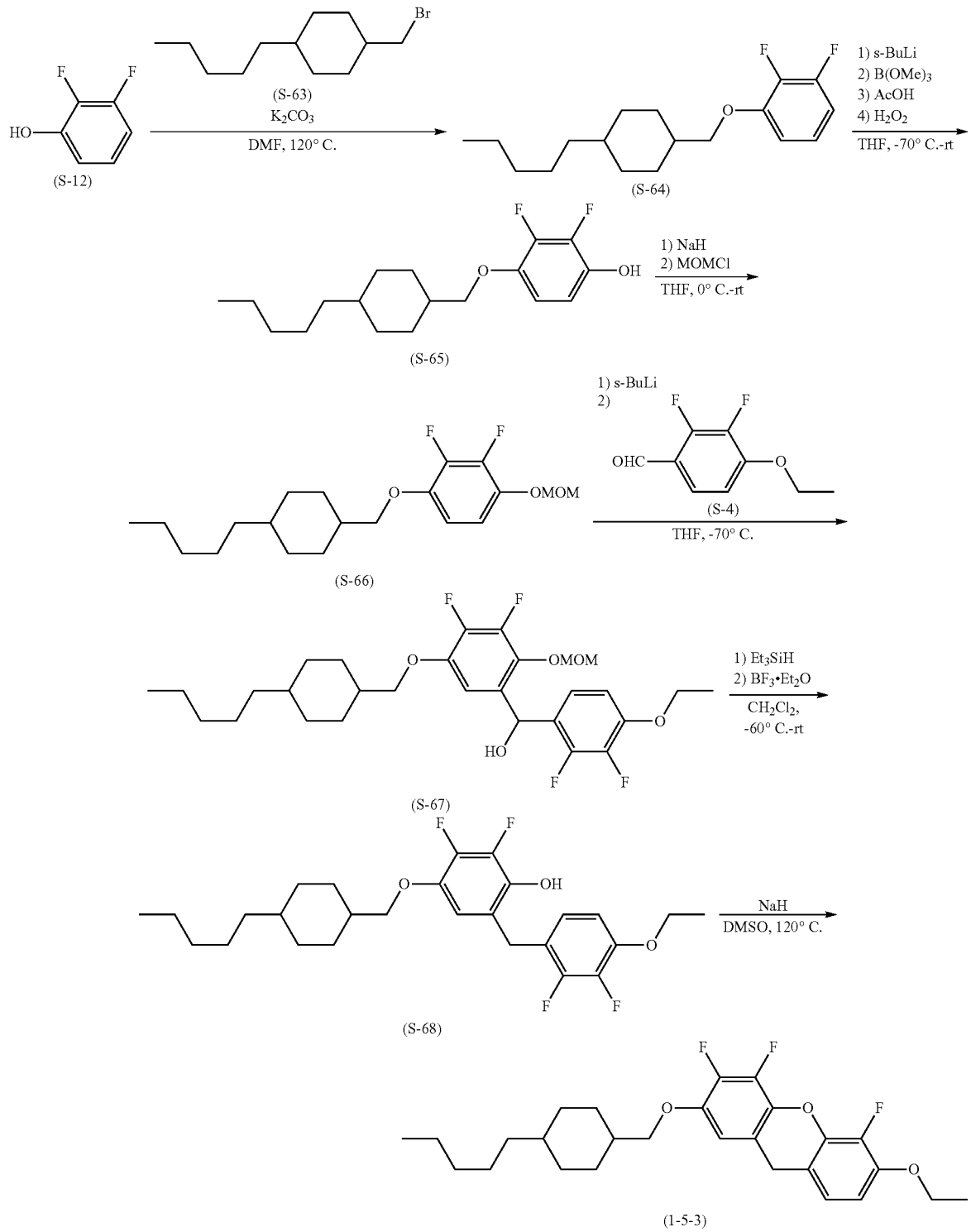

First Step

Under a nitrogen atmosphere, compound (S-12) (10.0 g), potassium carbonate (21.3 g) and N,N'-dimethylformamide (130 mL) were put in a reaction vessel, and the resulting mixture was heated to 80° C. and stirred for 30 minutes. An N,N'-dimethylformamide solution (20 mL) of compound (S-63) (13.4 g) was added thereto, and then the resulting mixture was heated to 130° C. and stirred for 4 hours. The reaction mixture was poured into water, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane). Further, the resulting material was purified by recrystallization from a mixed solvent of Solmix and heptane (volume ratio, 1:1) to obtain compound (S-64) (17.4 g; 76%).

Second Step

Under a nitrogen atmosphere, compound (S-64) (17.4 g) and THF (230 mL) were put in a reaction vessel and the resulting mixture was cooled to −70° C. Then, s-butyllithium (0.97 M cyclohexane solution, 75.5 mL) was slowly added thereto and the resulting mixture was stirred for 3 hours, and then a THF solution (20 mL) of triisoproyl borate (16.8 mL) was slowly added thereto, and the resulting mixture was stirred for 2 hours. The reaction mixture was heated to room temperature, acetic acid (5.03 mL) was added thereto and the resulting mixture was stirred for 30 minutes, and then a 30% hydrogen peroxide solution (13.3 g) was added thereto. The reaction mixture was poured into water, and a water layer was subjected to extraction with ethyl acetate. A combined organic layer was washed with water, a sodium sulfite aqueous solution and saturated brine, and dried over anhydrous magnesium sulfate. The resulting solution was concentrated under reduced pressure, and the resulting residue was purified by silica gel chromatography (heptane:ethyl acetate=5:1 in a volume ratio) to obtain compound (S-65) (17.8 g; 97%).

Third Step

Under a nitrogen atmosphere, sodium hydride (2.98 g) and THF (150 mL) were put in a reaction vessel and the resulting mixture was cooled to 0° C. A THF solution (30 mL) of compound (S-65) (17.8 g) was slowly added thereto and the resulting mixture was stirred for 1 hour, and then chloromethyl methyl ether (5.18 mL) was slowly added thereto, and temperature was increased to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=9:1 in a volume ratio) to obtain compound (S-66) (19.1 g; 94%).

Fourth Step

Under a nitrogen atmosphere, compound (S-66) (5.0 g) and THF (50 mL) were put in a reaction vessel and the resulting mixture was cooled to −70° C. Then, s-butyllithium (0.97 M cyclohexane solution, 17.4 mL) was slowly thereto and the resulting mixture was stirred for 1 hour, and then a THF solution (25 mL) of compound (S-4) (2.87 g) was slowly added thereto, and the resulting mixture was heated to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane: ethyl acetate=4:1 in a volume ratio) to obtain compound (S-67) (7.61 g; 100%).

Fifth Step

Under a nitrogen atmosphere, compound (S-67) (7.61 g) and dichloromethane (65 mL) were put in a reaction vessel, and the resulting mixture was cooled to −60° C. A dichloromethane solution (5 mL) of triethylsilane (4.47 mL) was added thereto and the resulting mixture was stirred for 20 minutes, and then a boron trifluoride-diethyl ether complex (10.6 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=2:1 in a volume ratio) to obtain compound (S-68) (6.22 g; 92%).

Sixth Step

Under a nitrogen atmosphere, sodium hydride (0.62 g) and dimethylsulfoxide (70 mL) were put in a reaction vessel, a dimethyl sulfoxide solution (55 mL) of compound (S-68) (6.22 g) was slowly added thereto, and the resulting mixture was heated to 120° C. and stirred for 3 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane:toluene=1:1 in a volume ratio). Further, the resulting material was purified by recrystallization from a mixed solvent of heptane and toluene (volume ratio, 1:1) to obtain compound (1-5-3) (2.47 g; 41%).

Chemical shift δ (ppm; $CDCl_3$): 6.82 (dd, J=9.0 Hz, J=1.5 Hz, 1H), 6.68 (t, J=8.2 Hz, 1H), 6.52-6.47 (m, 1H), 4.12 (q, J=7.0 Hz, 2H), 3.93 (s, 2H), 3.78 (d, J=6.4 Hz, 2H), 1.94-1.72 (m, 5H), 1.44 (t, J=7.0 Hz, 3H), 1.36-1.15 (m, 9H), 1.11-0.85 (m, 7H).

Physical properties of compound (1-5-3) were as described below. For measurement of maximum temperature, optical anisotropy, dielectric anisotropy and viscosity, the sample in which the ratio of the compound to the base liquid crystal was 10% by weight: 90% by weight was used.

Transition temperature: C 117.5 (N 103.8) I.

Maximum temperature ($T_{NI}$)=100.6° C.; optical anisotropy (Δn)=0.135; dielectric anisotropy (Δ∈)=−13.2; viscosity (η)=115.1 mPa·S.

Example 12

Synthesis of Compound (1-5-18)

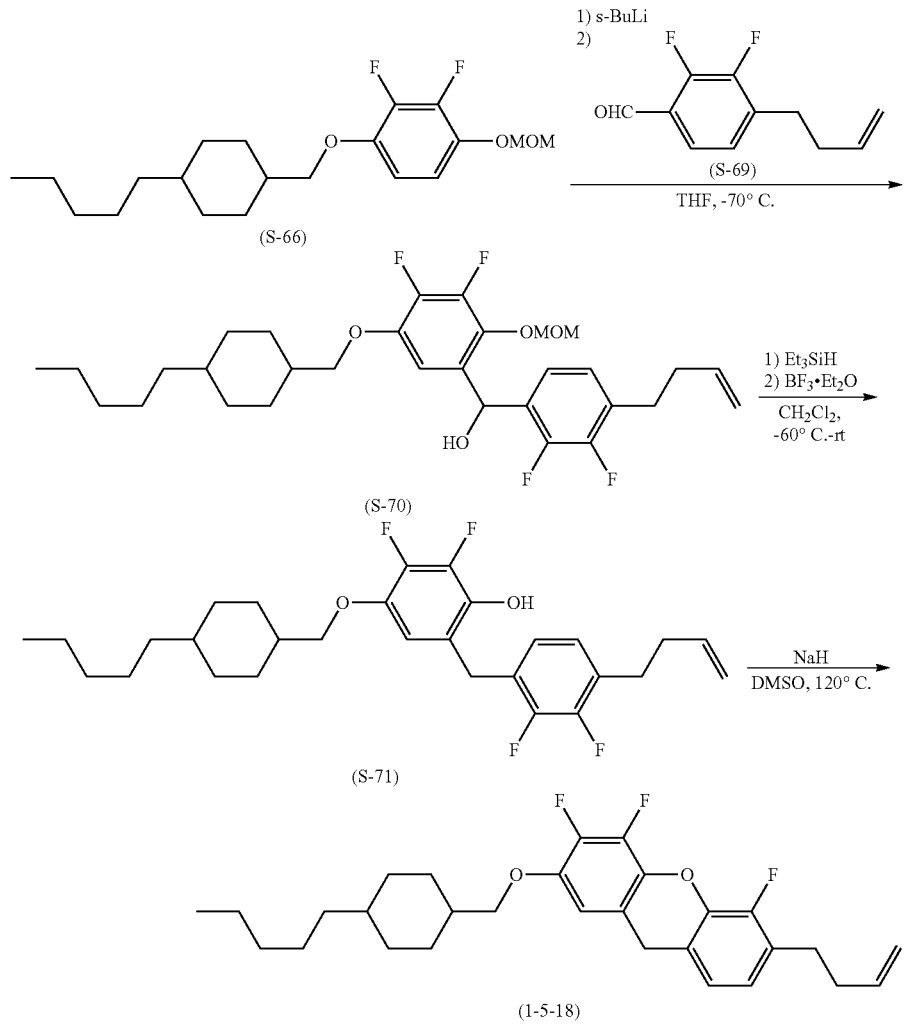

First Step

Under a nitrogen atmosphere, compound (S-66) (10.7 g) and THF (120 mL) were put in a reaction vessel and the resulting mixture was cooled to −70° C. Then, s-butyllithium (1.02 M cyclohexane solution, 35.2 mL) was slowly added thereto and the resulting mixture was stirred for 2 hours, and then a THF solution (30 mL) of compound (S-4) (6.40 g) was slowly added thereto, and the resulting mixture was heated to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-70) (15.0 g; 91%).

Second Step

Under a nitrogen atmosphere, compound (S-70) (15.0 g) and dichloromethane (110 mL) were put in a reaction vessel, and the resulting mixture was cooled to −60° C. A dichloromethane solution (10 mL) of triethylsilane (8.67 mL) was added thereto and the resulting mixture was stirred for 20 minutes, and then a boron trifluoride-diethyl ether complex (20.7 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane:ethyl acetate=8:1 in a volume ratio) to obtain compound (S-71) (9.32 g; 70%).

Third Step

Under a nitrogen atmosphere, sodium hydride (0.91 g) and dimethylsulfoxide (130 mL) were put in a reaction vessel, a dimethyl sulfoxide solution (50 mL) of compound (S-71) (9.32 g) was slowly added thereto, and the resulting mixture was heated to 120° C. and stirred for 6 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane: toluene=4:1 in a volume ratio). Further, the resulting material was purified by recrystallization from a mixed solvent of 2-propanol and ethyl acetate (1:1 in a volume ratio) to obtain compound (1-5-18) (1.42 g; 16%).

Chemical shift δ (ppm; CDCl$_3$): 6.87-6.81 (m, 2H), 6.49 (dd, J=8.1 Hz, J=2.1 Hz, 1H), 5.89-5.79 (m, 1H), 5.06-4.96 (m, 2H), 3.97 (s, 2H), 3.78 (d, J=6.4, 2H), 2.75 (t, J=7.6 Hz, 2H), 2.37 (q, J=7.5 Hz, 2H), 1.92-1.72 (m, 5H), 1.35-1.14 (m, 9H), 1.11-0.86 (m, 7H).

Physical properties of compound (1-5-18) were as described below.

Transition temperature: C 88.9 (SA 77.9 N 85.8) I.

Maximum temperature ($T_{NI}$)=75.9° C.; optical anisotropy (Δn)=0.1203; dielectric anisotropy (Δ∈)=−9.62; viscosity (η)=112.3 mPa·s.

According to the method for synthesis of compound (1) described above and synthesis procedures described in Examples 1 to 4, compounds (1-1-1) to (1-1-75), compounds (1-2-1) to (1-2-55), compounds (1-3-1) to (1-3-47), compounds (1-4-1) to (1-4-51), compounds (1-5-1) to (1-5-72), compounds (1-6-1) to (1-6-44), compounds (1-7-1) to (1-7-56), compounds (1-8-1) to (1-8-40), compounds (1-9-1) to (1-9-37), compounds (1-10-1) to (1-10-28) and compounds (1-11-1) to (1-11-27) can be prepared.

(1-1-1)

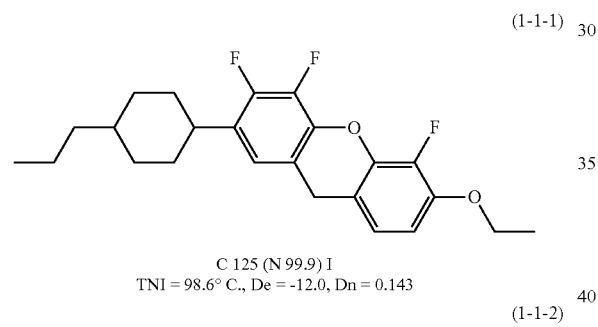

C 125 (N 99.9) I
TNI = 98.6° C., De = -12.0, Dn = 0.143

(1-1-2)

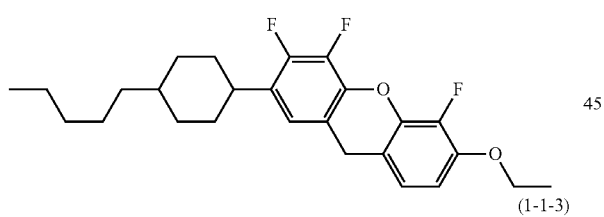

(1-1-3)

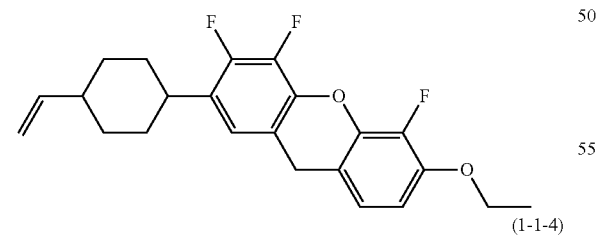

(1-1-4)

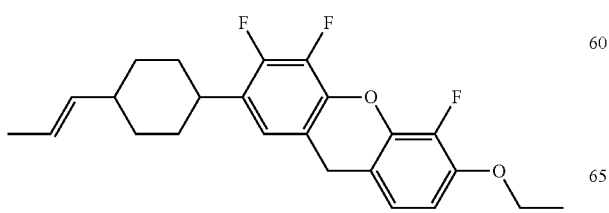

-continued (1-1-5)

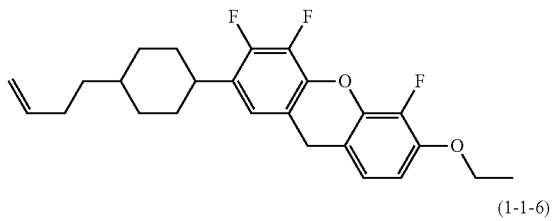

(1-1-6)

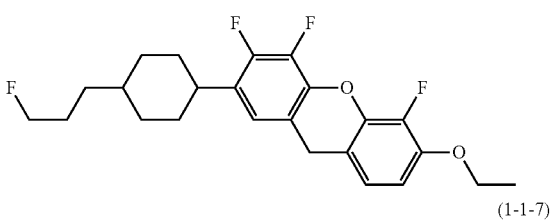

(1-1-7)

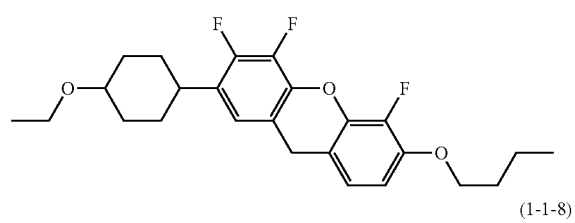

(1-1-8)

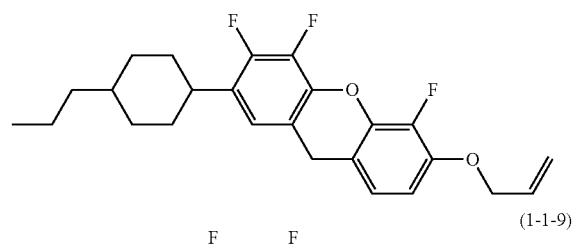

(1-1-9)

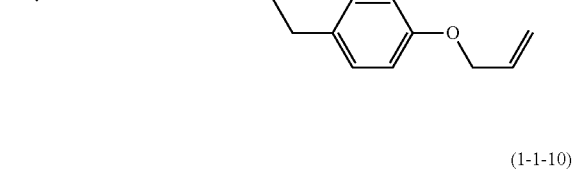

(1-1-10)

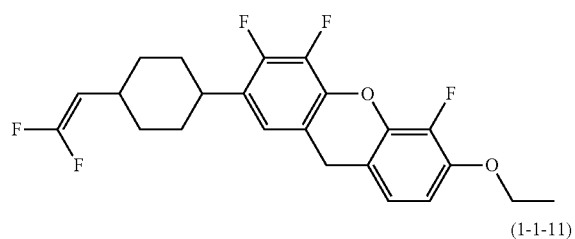

(1-1-11)

C 119 I
$T_{NI}$ = 66.6° C., Δε = -7.02, Δn = 0.105

(1-1-12)
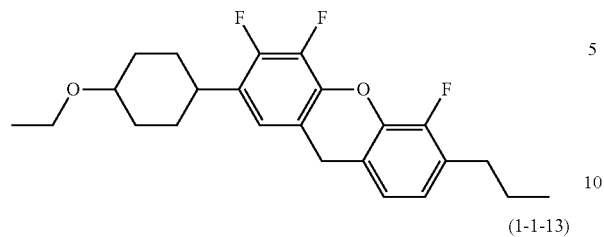
(1-1-13)
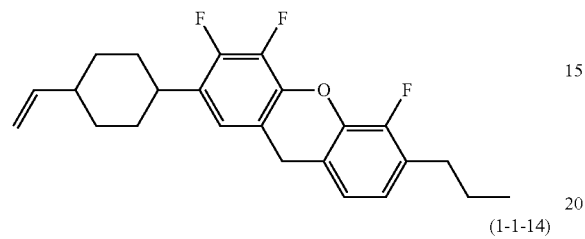
(1-1-14)
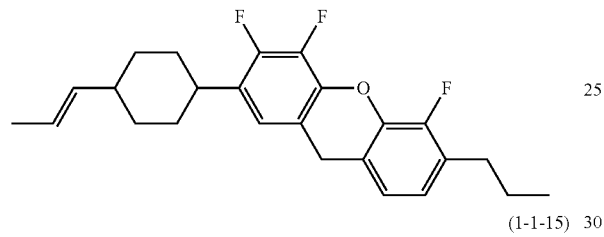
(1-1-15)
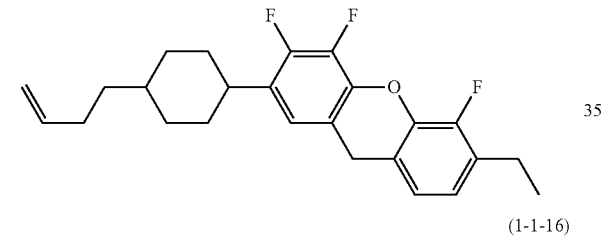
(1-1-16)
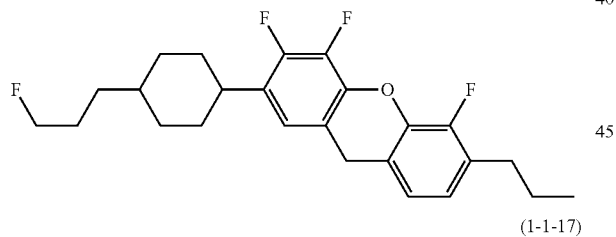
(1-1-17)
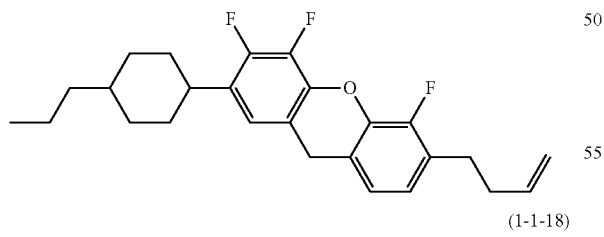
(1-1-18)
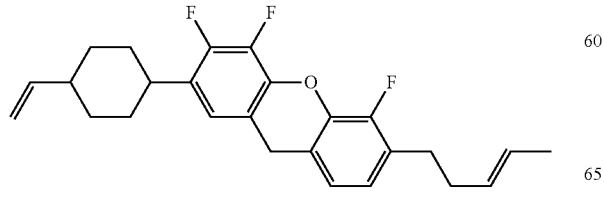
(1-1-19)
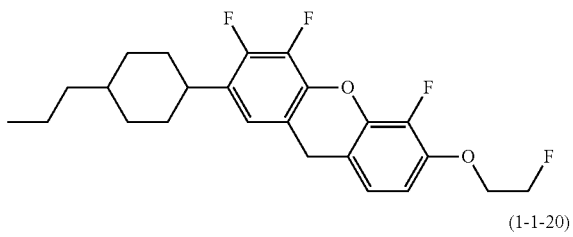
(1-1-20)
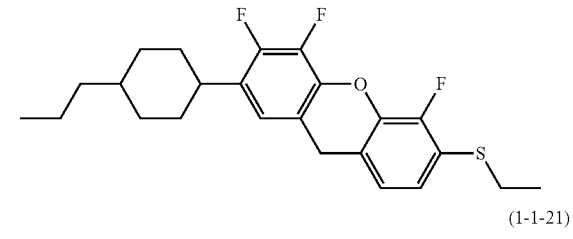
(1-1-21)
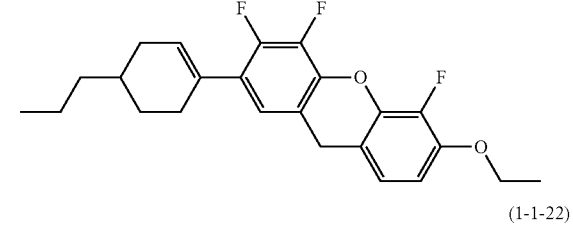
(1-1-22)
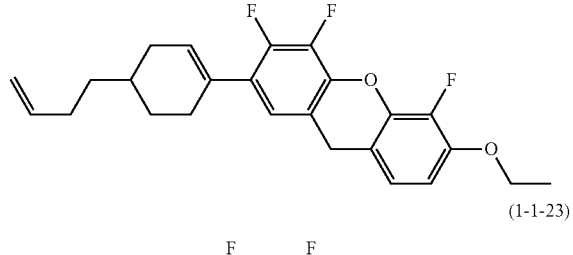
(1-1-23)
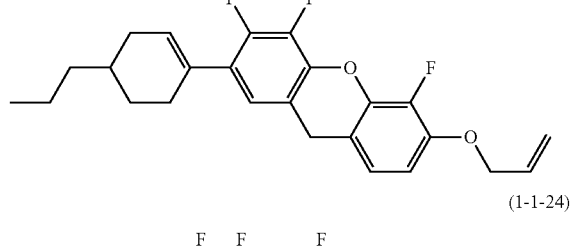
(1-1-24)
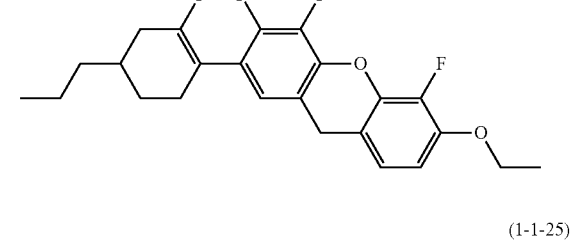
(1-1-25)
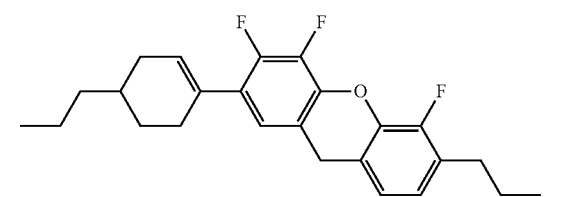

(1-1-26)
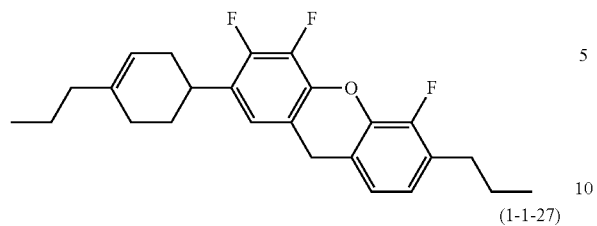
(1-1-27)
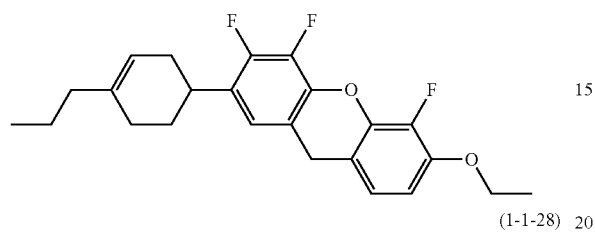
(1-1-28)
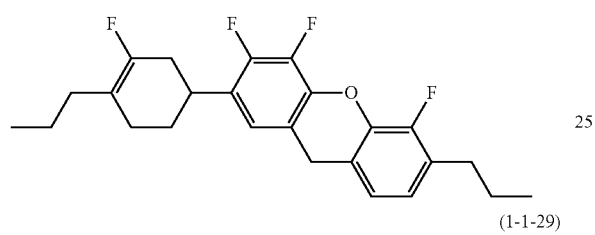
(1-1-29)
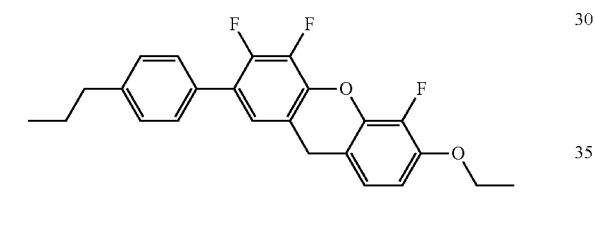
(1-1-30)
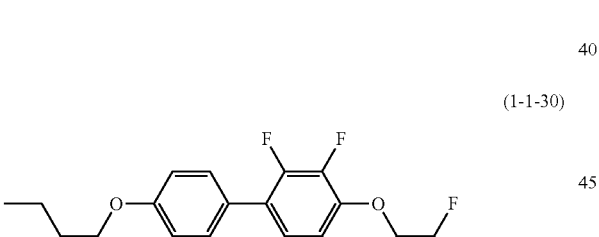
(1-1-31)
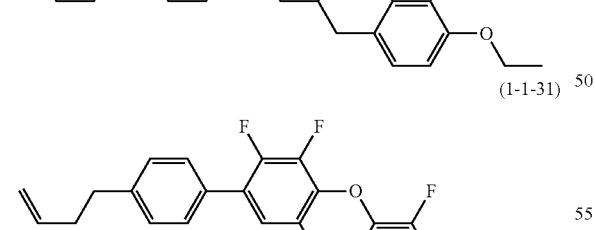
(1-1-32)
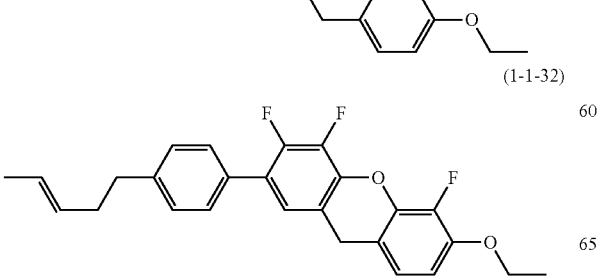
(1-1-33)
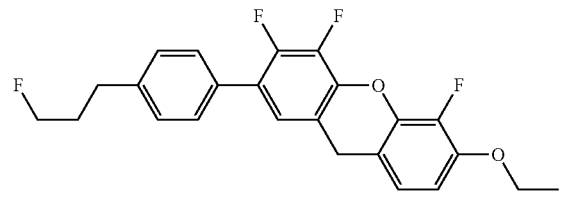
(1-1-34)
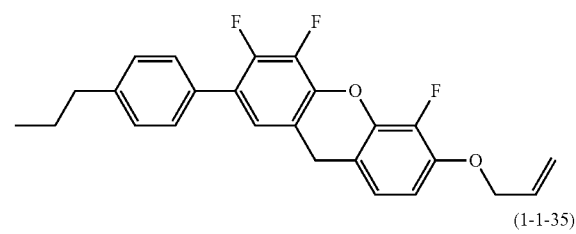
(1-1-35)
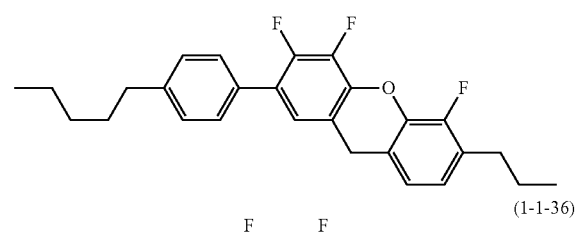
(1-1-36)
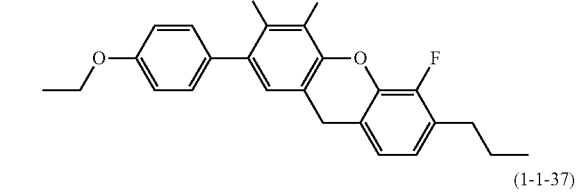
(1-1-37)
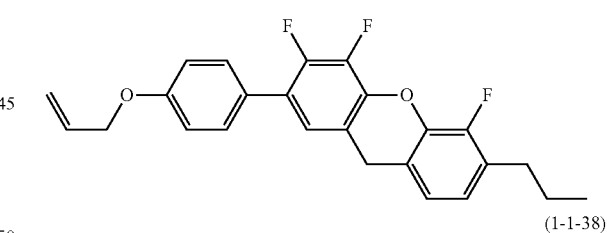
(1-1-38)
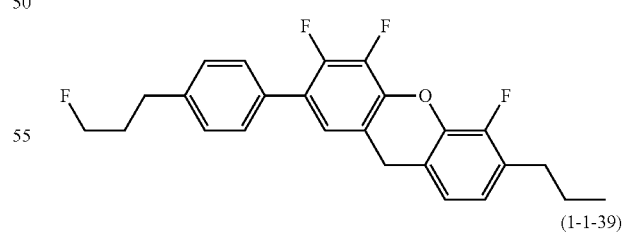
(1-1-39)
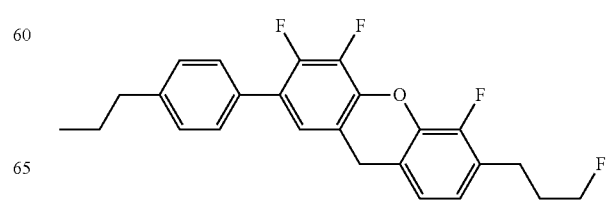

(1-1-40)
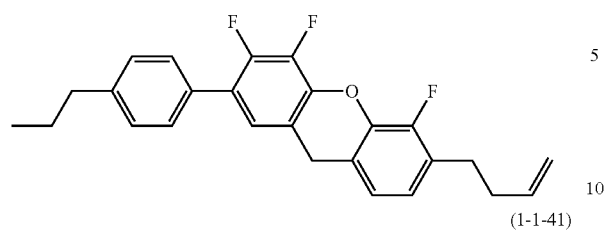
(1-1-41)
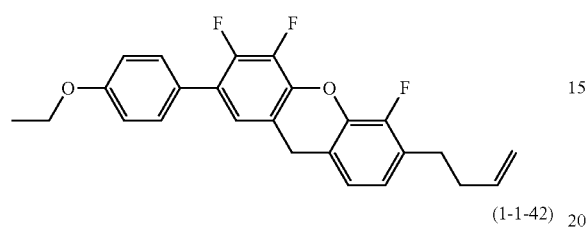
(1-1-42)
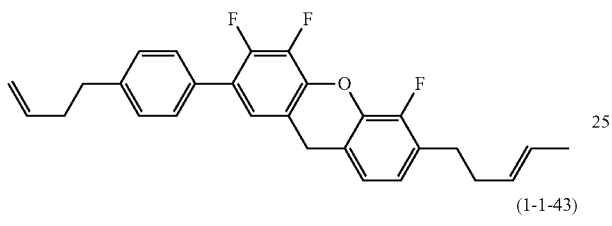
(1-1-43)
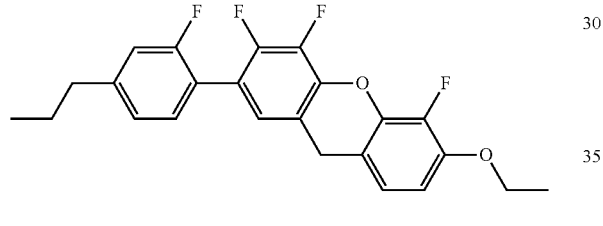
(1-1-44)
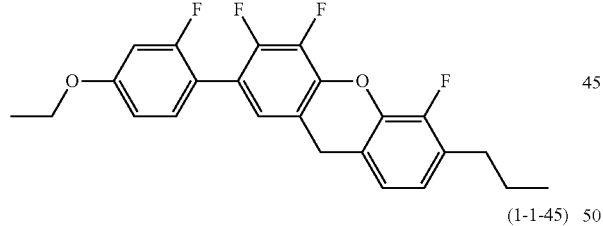
(1-1-45)
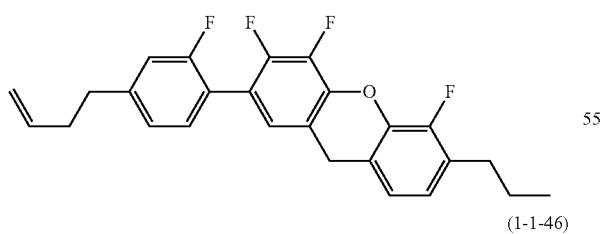
(1-1-46)
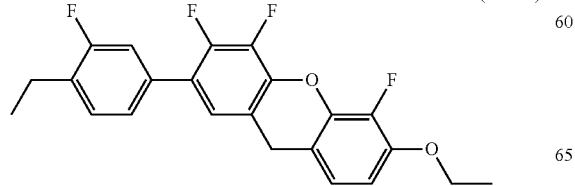
(1-1-47)
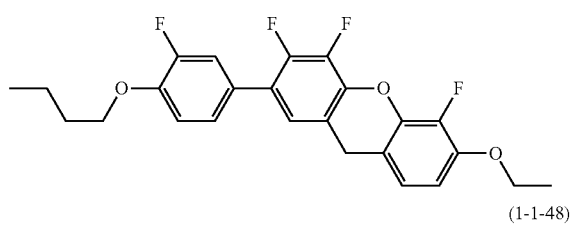
(1-1-48)
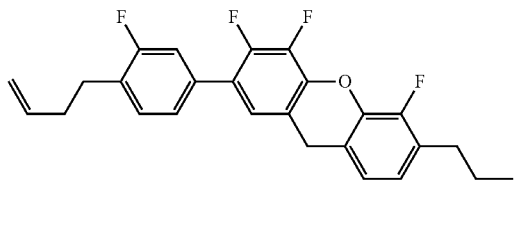
(1-1-49)
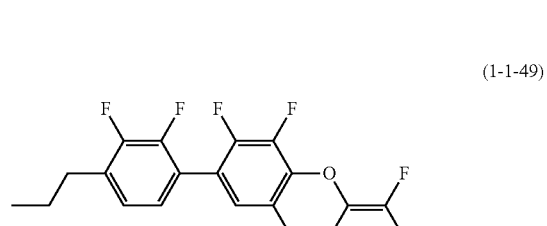
(1-1-50)
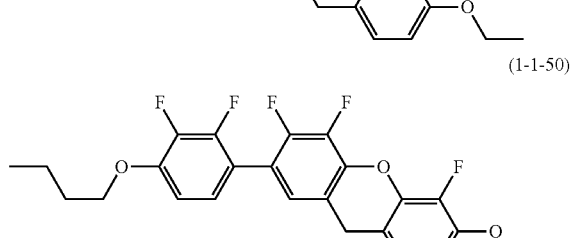
(1-1-51)
(1-1-52)
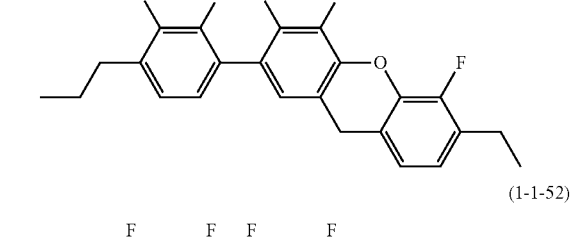
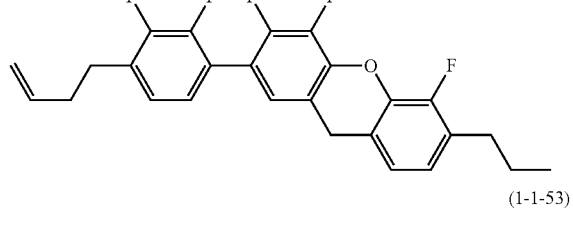
(1-1-53)
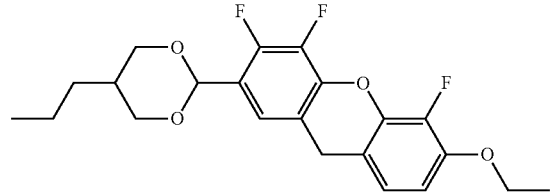

(1-1-54)
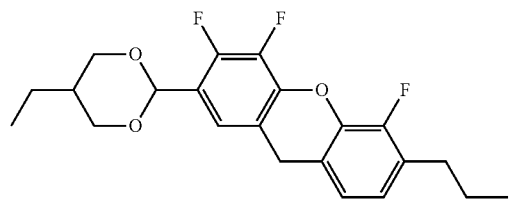
(1-1-55)
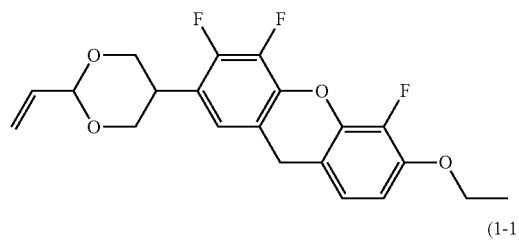
(1-1-56)
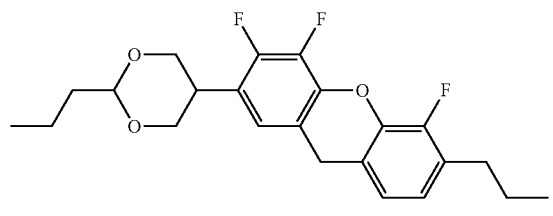
(1-1-57)
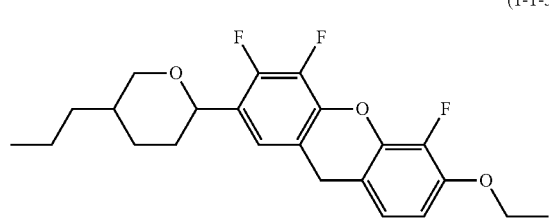
(1-1-58)
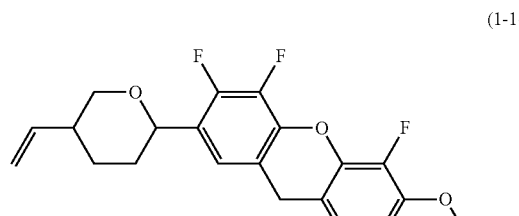
(1-1-59)
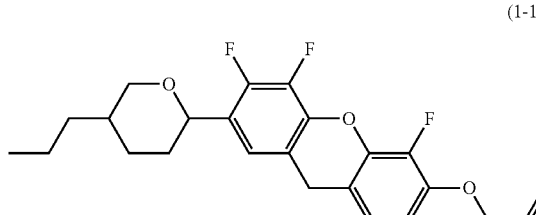
(1-1-60)
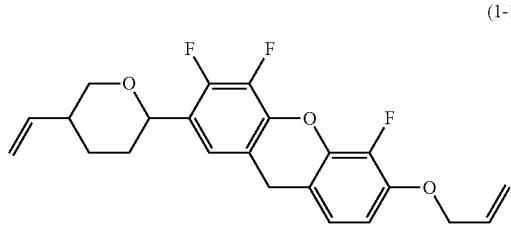
(1-1-61)
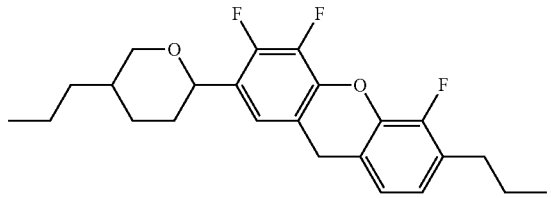
$T_{NI}$ = 35.6° C., Δε = -3.28, Δn = 0.092
(1-1-62)
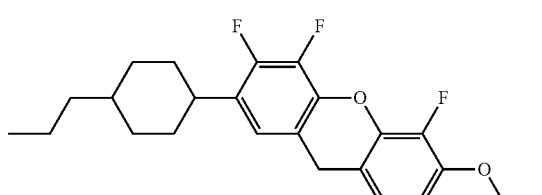
(1-1-63)
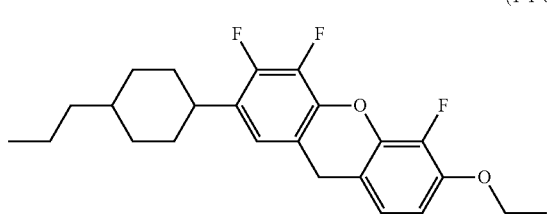
(1-1-64)
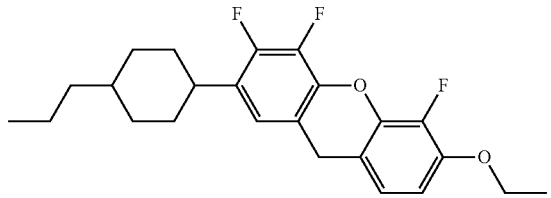
(1-1-65)
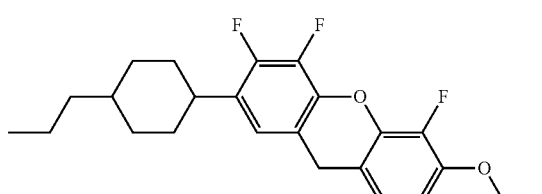
(1-1-66)
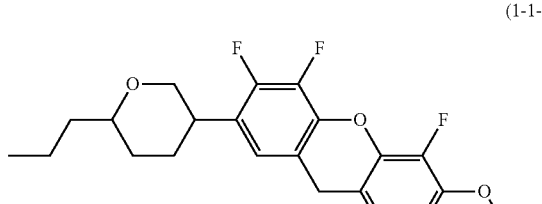
(1-1-67)
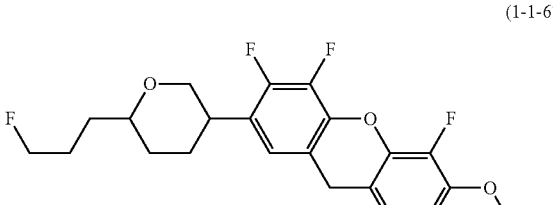

(1-1-68)
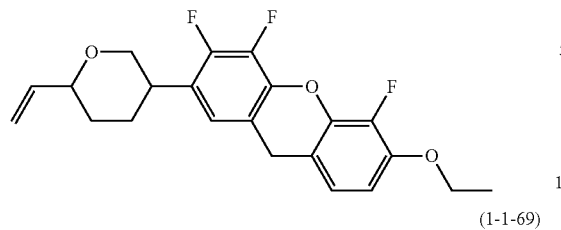
(1-1-69)
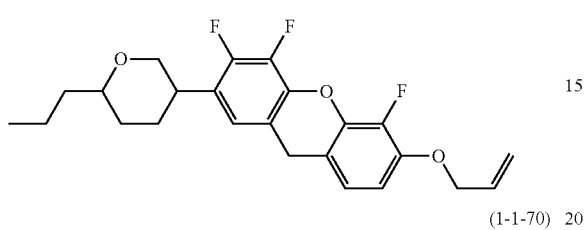
(1-1-70)
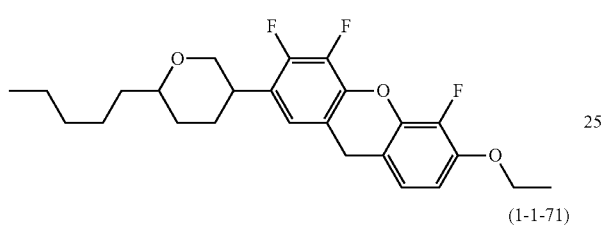
(1-1-71)
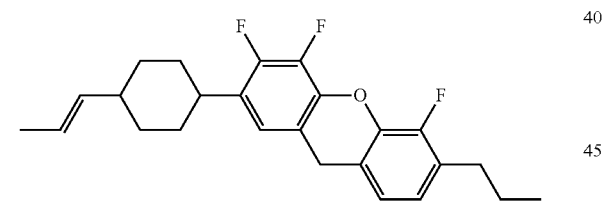
$T_{NI}$ = 33.6° C., Δε = −10.7, Δn = 0.106
(1-1-72)
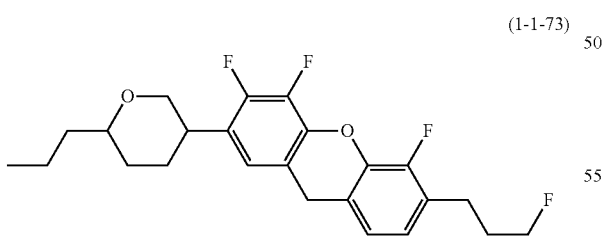
(1-1-73)
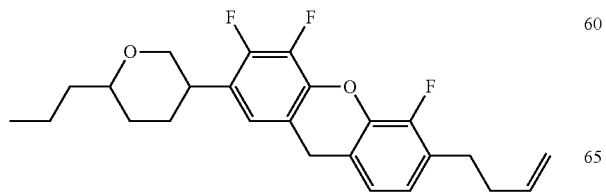
(1-1-74)
(1-1-75)
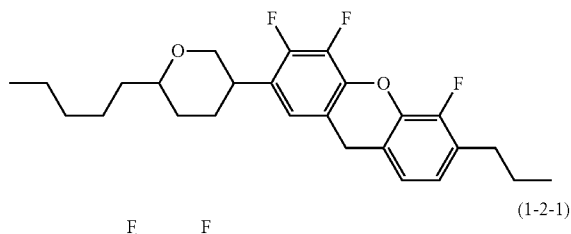
(1-2-1)
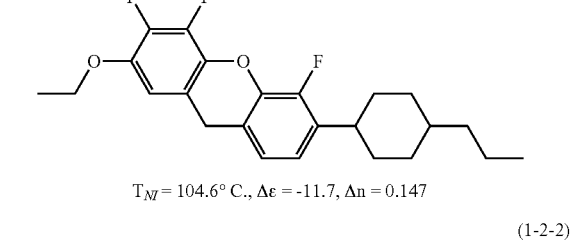
$T_{NI}$ = 104.6° C., Δε = −11.7, Δn = 0.147
(1-2-2)
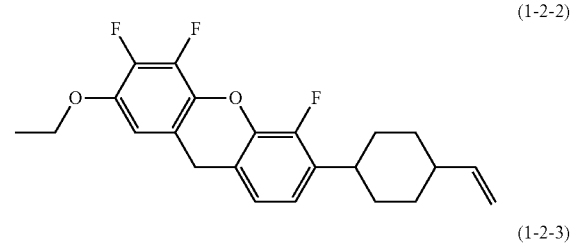
(1-2-3)
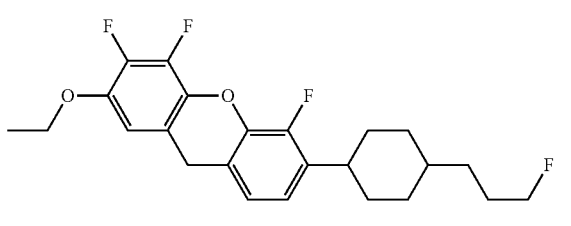
(1-2-4)
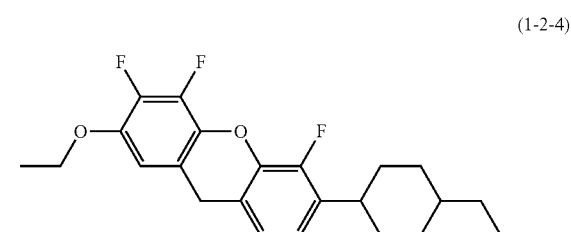
(1-2-5)
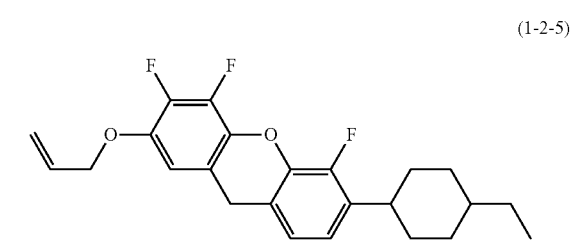
(1-2-6)
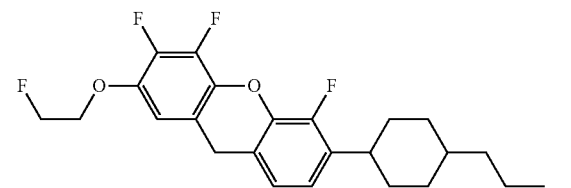

-continued
(1-2-7)
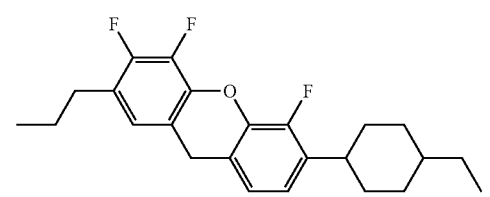
(1-2-8)
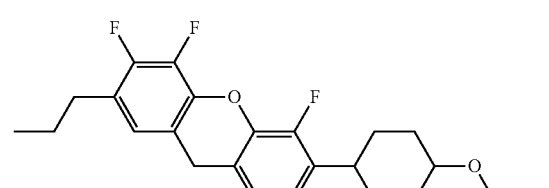
(1-2-9)
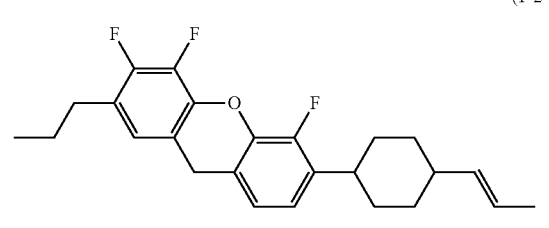
(1-2-10)
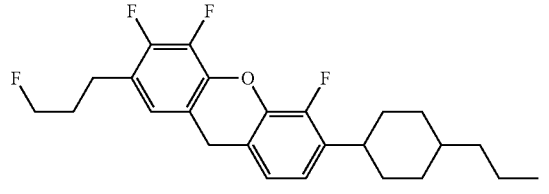
(1-2-11)
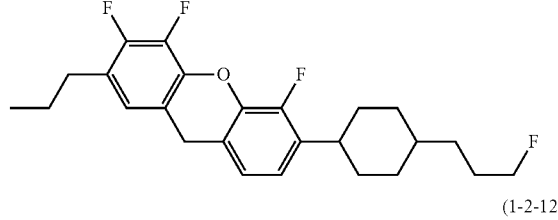
(1-2-12)
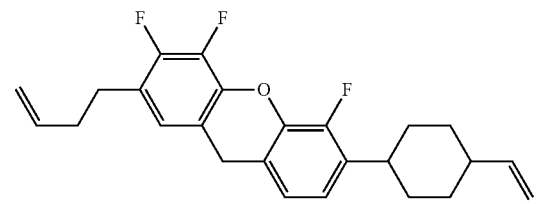
(1-2-13)
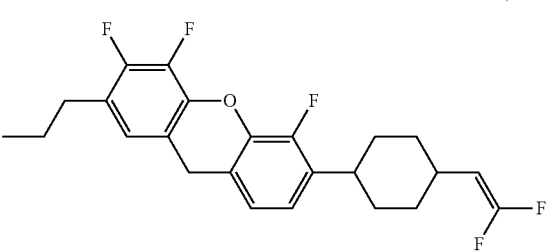
(1-2-14)
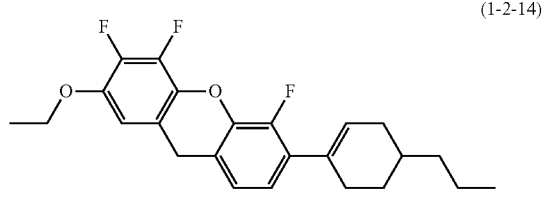
(1-2-15)
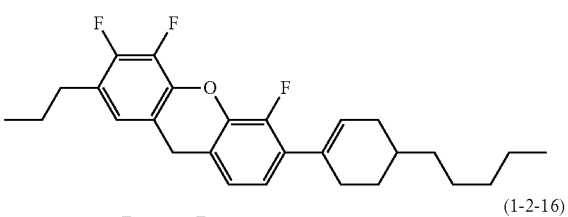
(1-2-16)
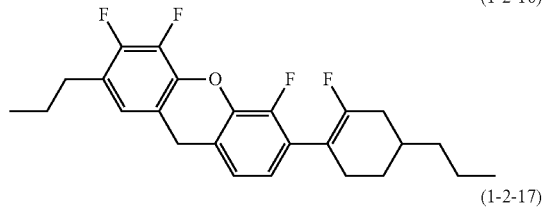
(1-2-17)
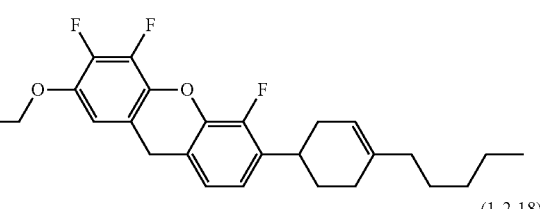
(1-2-18)
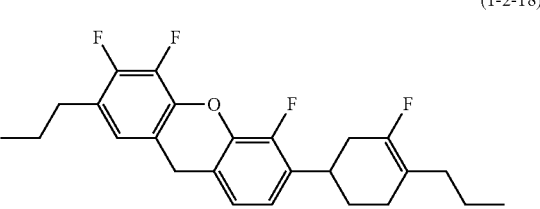
(1-2-19)
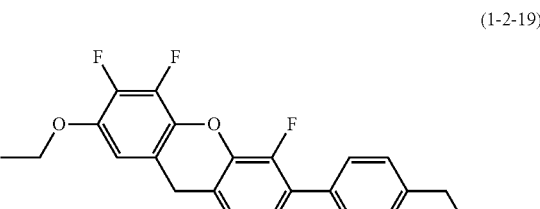
(1-2-20)
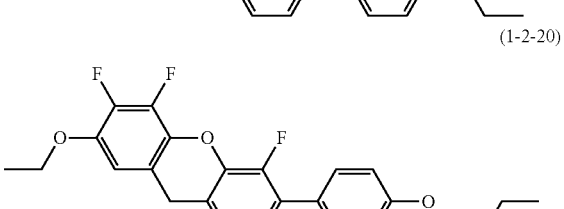
(1-2-21)
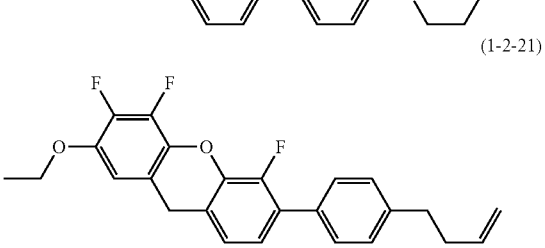

(1-2-22)
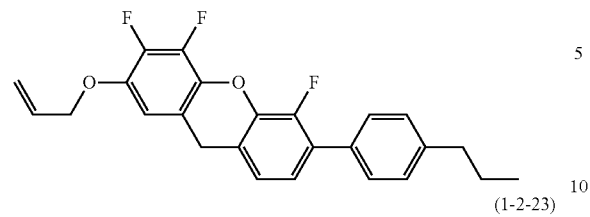
(1-2-23)
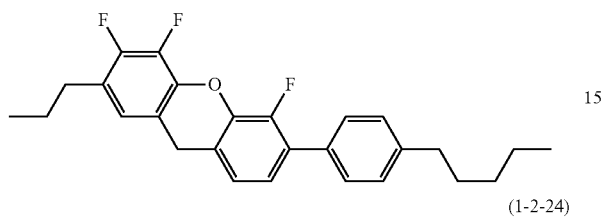
(1-2-24)
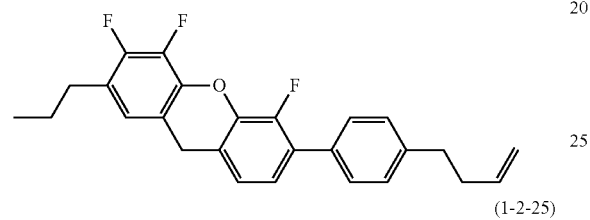
(1-2-25)
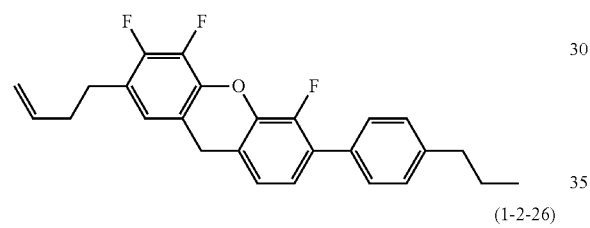
(1-2-26)
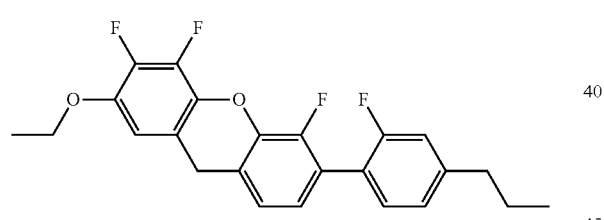
(1-2-27)
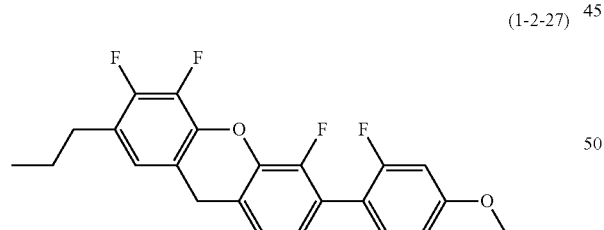
(1-2-28)
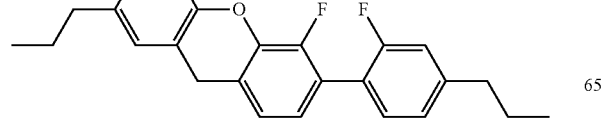
(1-2-29)
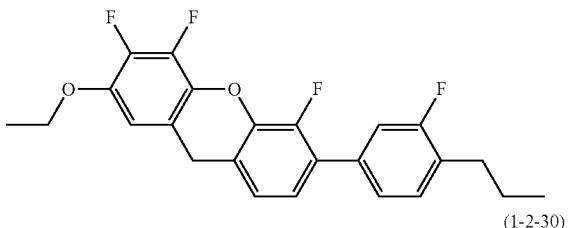
(1-2-30)
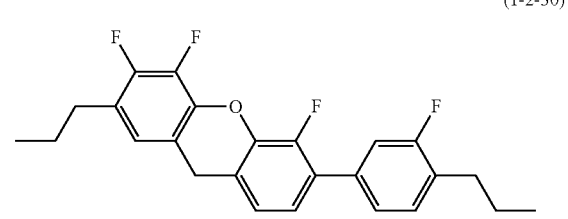
(1-2-31)
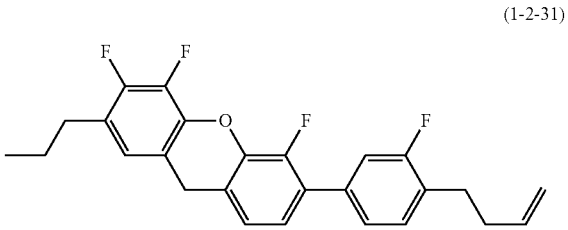
(1-2-32)
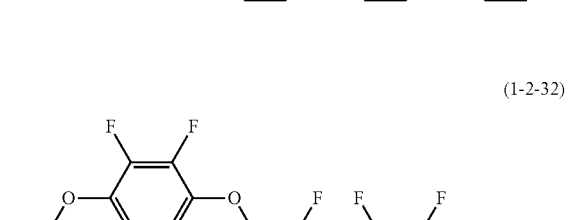
(1-2-33)
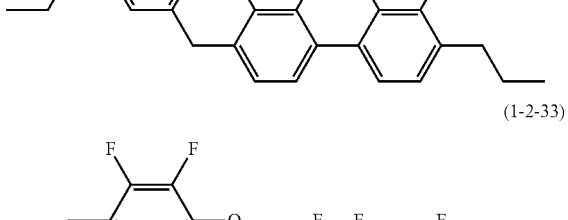
(1-2-34)
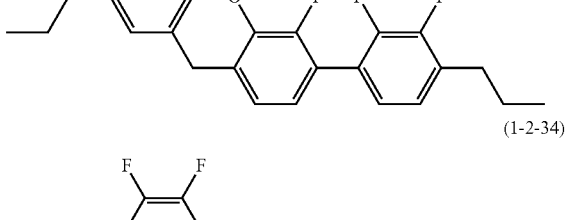
(1-2-35)
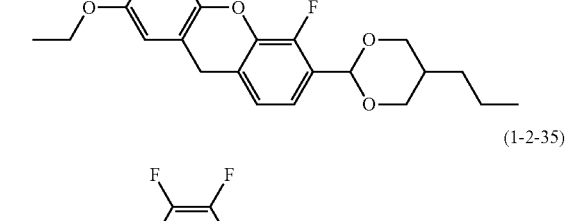
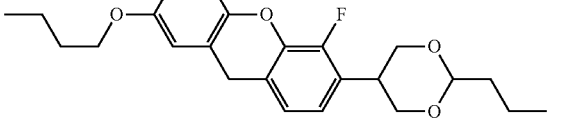

-continued
(1-2-36)
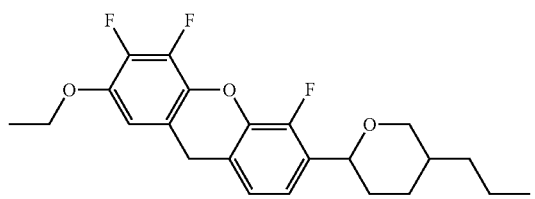
(1-2-46)
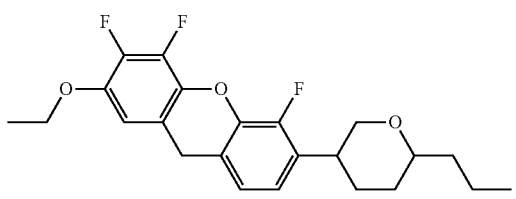
(1-2-37)
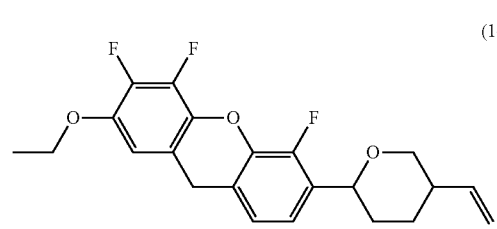
(1-2-47)
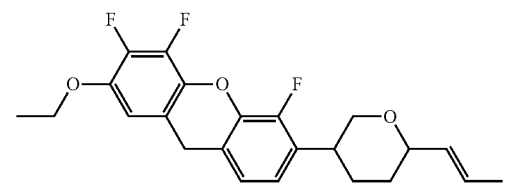
(1-2-38)
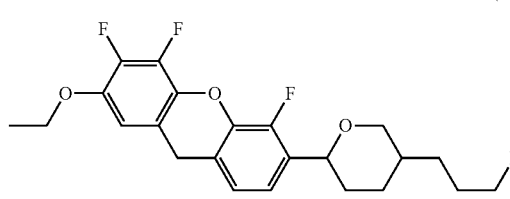
(1-2-48)
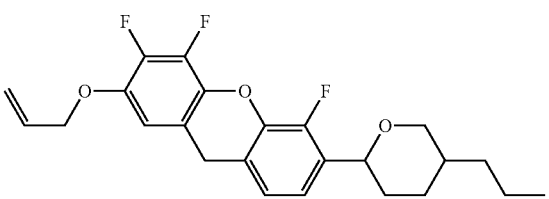
(1-2-39)
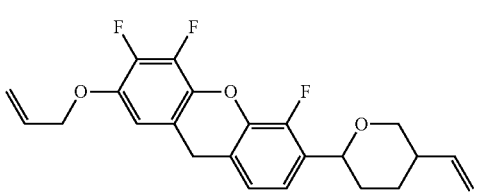
(1-2-49)
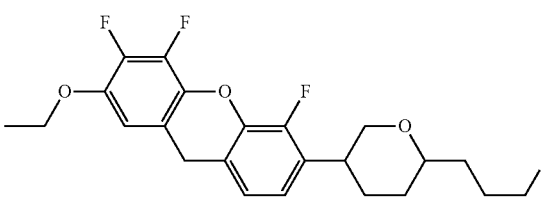
(1-2-40)
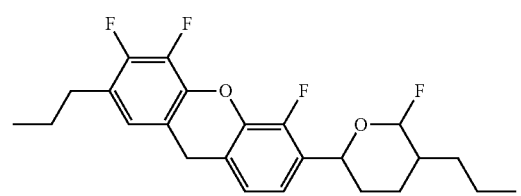
(1-2-50)

(1-2-41)
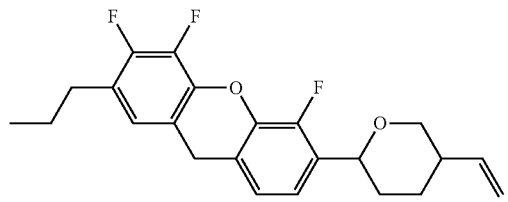
(1-2-42)
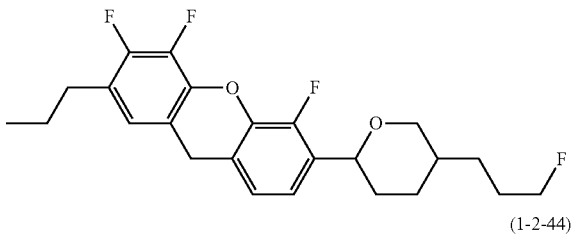
(1-2-43)
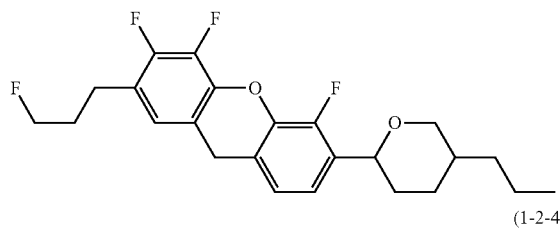
(1-2-44)
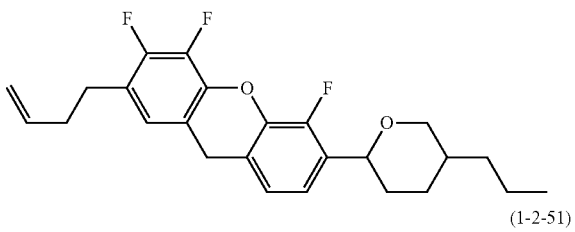
(1-2-45)
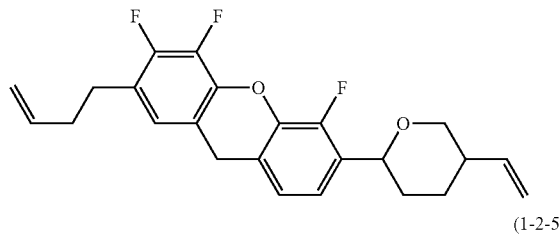
(1-2-51)
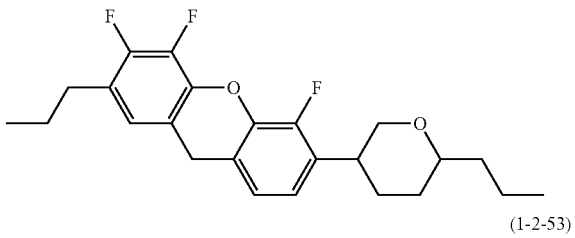
(1-2-52)
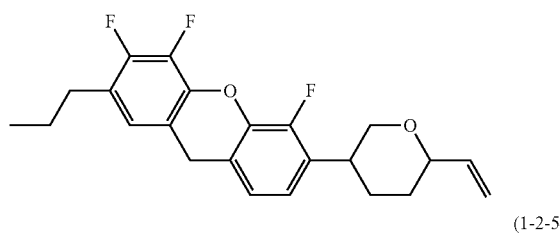
(1-2-53)
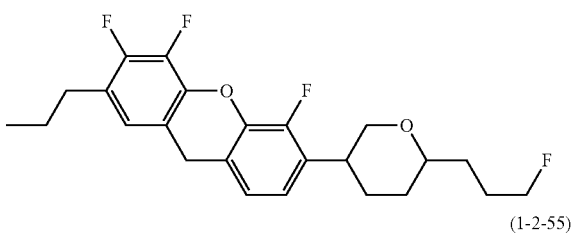
(1-2-54)
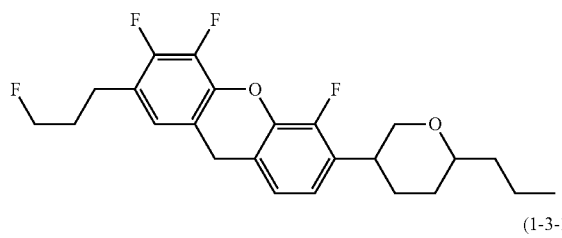
(1-2-55)
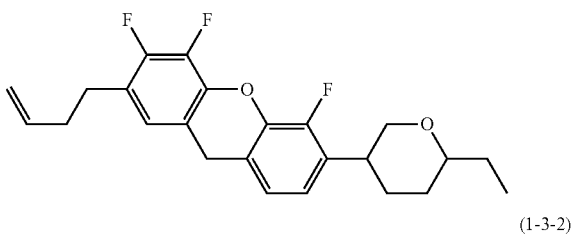
(1-3-1)
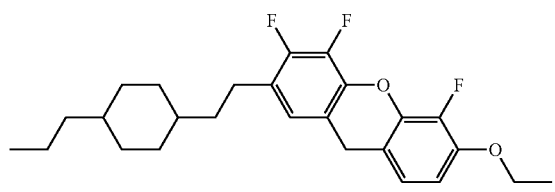
C 141 (N 98.4) I
$T_{NI}$ = 84.6° C., $\Delta\varepsilon$ = -12.4, $\Delta n$ = 0.147
(1-3-2)
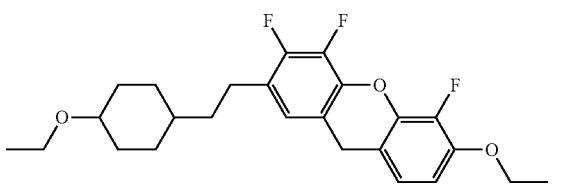
(1-3-3)
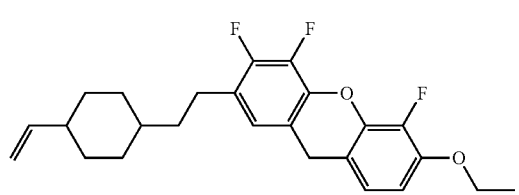
(1-3-5)
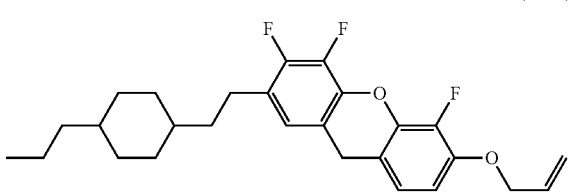

-continued
(1-3-6)
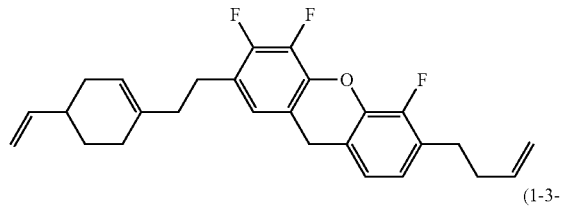
(1-3-7)
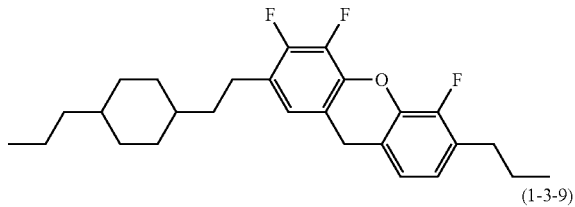
(1-3-8)
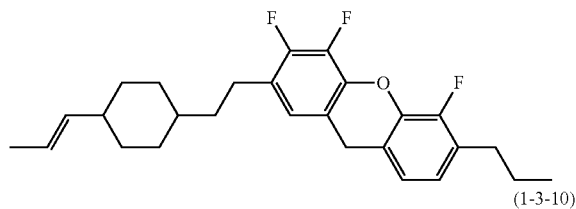
(1-3-9)
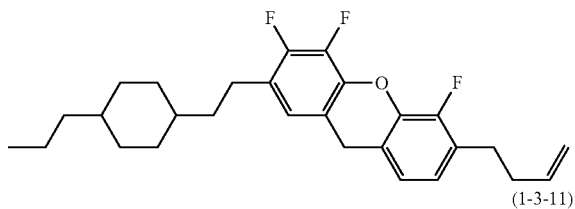
(1-3-10)
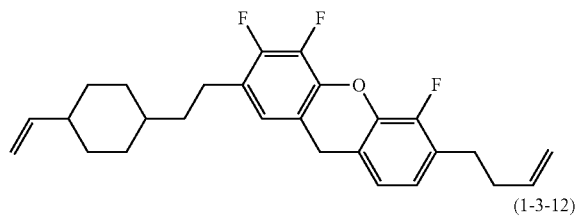
(1-3-11)
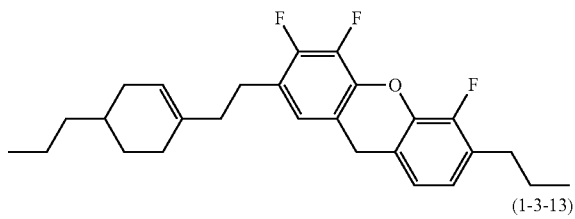
(1-3-12)
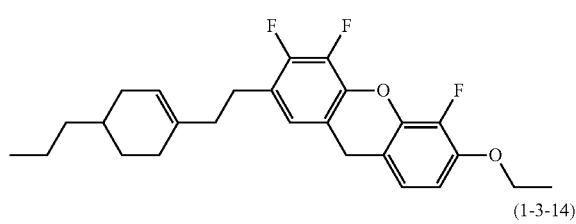
(1-3-13)
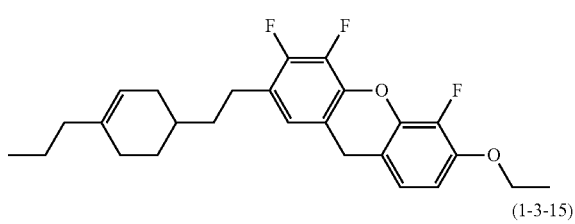
(1-3-14)
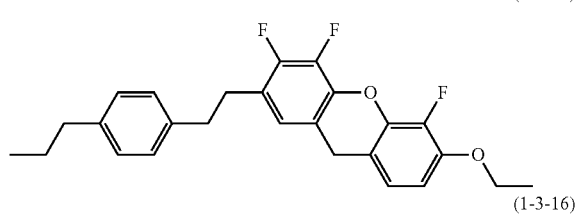
(1-3-15)
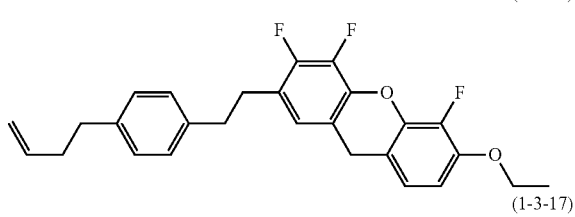
(1-3-16)
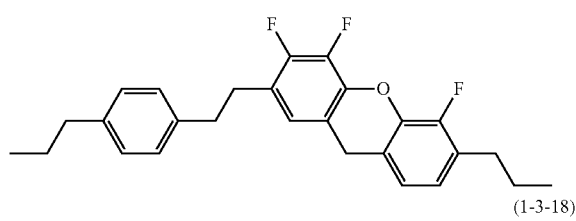
(1-3-17)
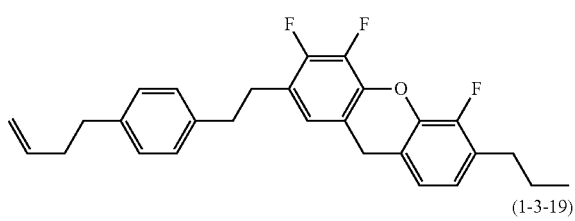
(1-3-18)
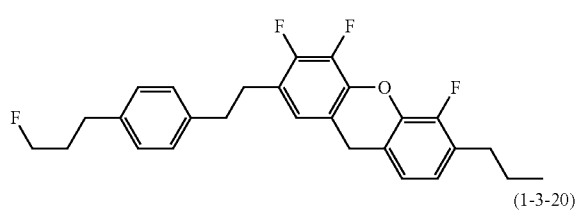
(1-3-19)
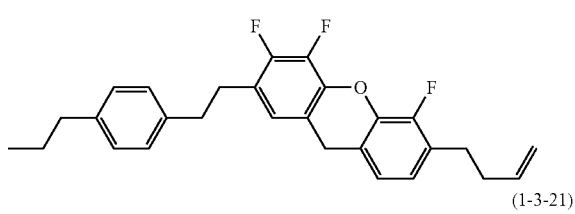
(1-3-20)
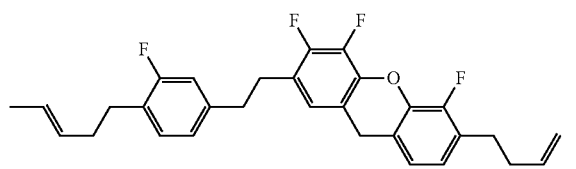
(1-3-21)
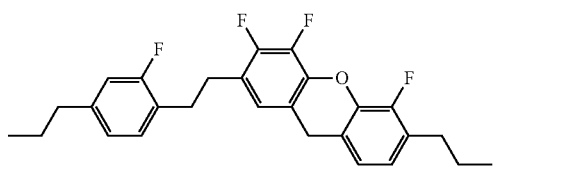

-continued
(1-3-22)
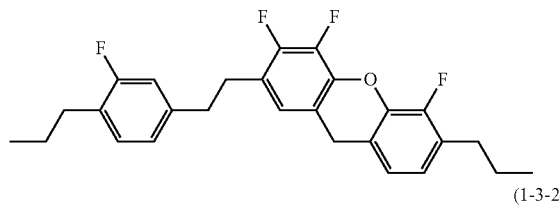
(1-3-23)
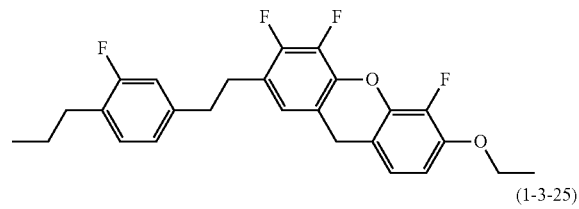
(1-3-24)
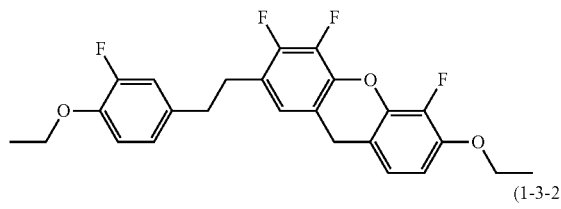
(1-3-25)
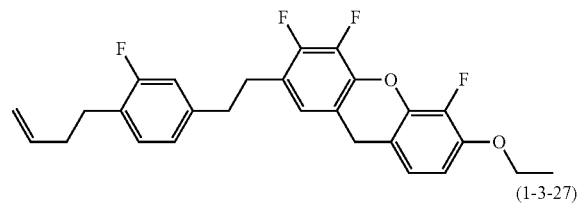
(1-3-26)
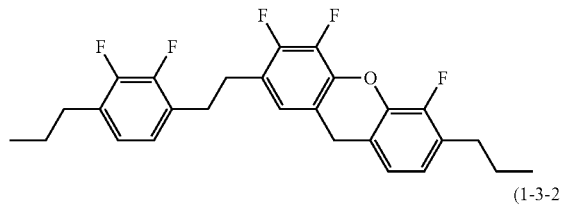
(1-3-27)
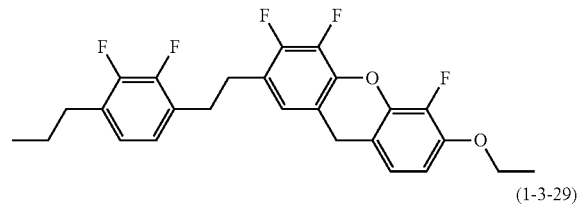
(1-3-28)
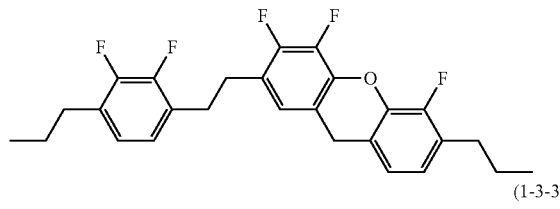
(1-3-29)
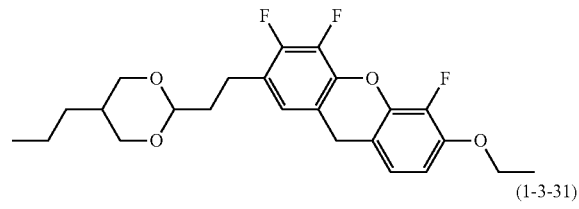
(1-3-30)
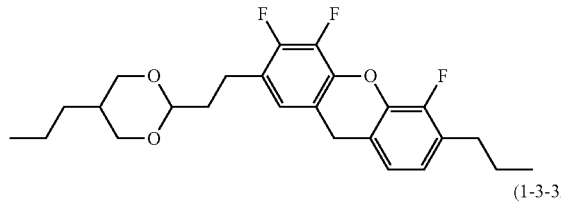
(1-3-31)
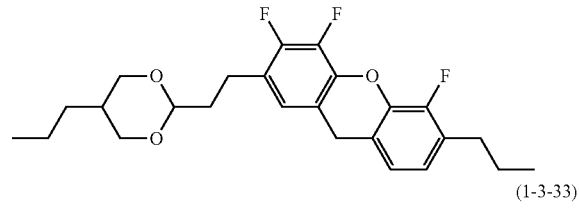
(1-3-32)
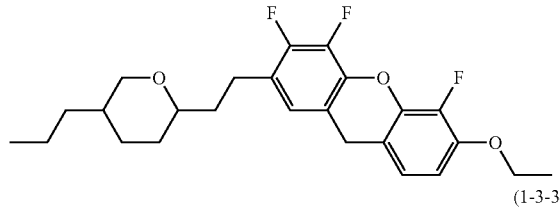
(1-3-33)
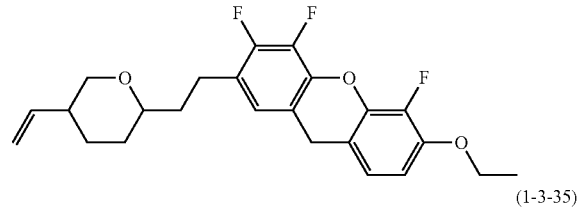
(1-3-34)
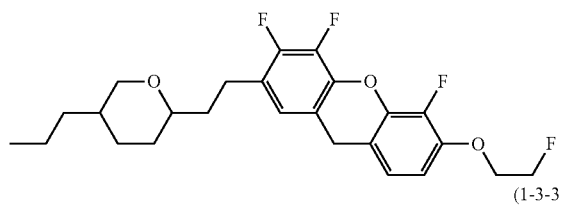
(1-3-35)
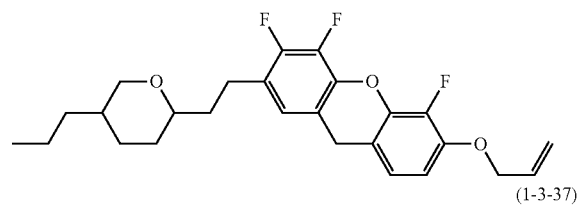
(1-3-36)
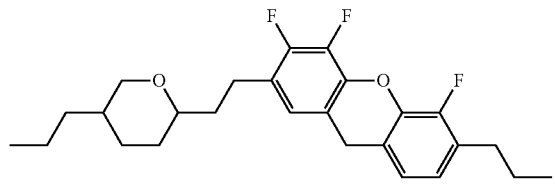
(1-3-37)
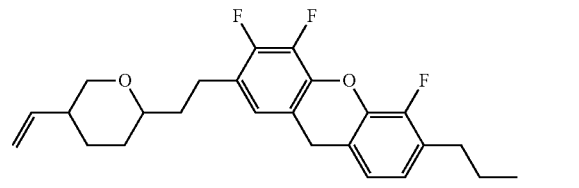

-continued
(1-3-38)
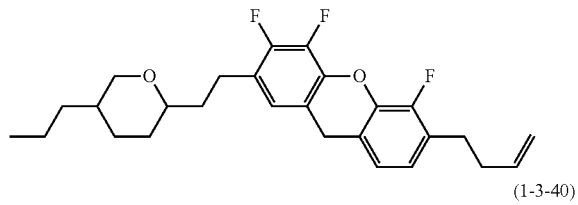
(1-3-39)
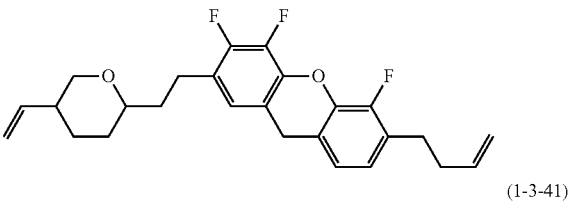
(1-3-40)
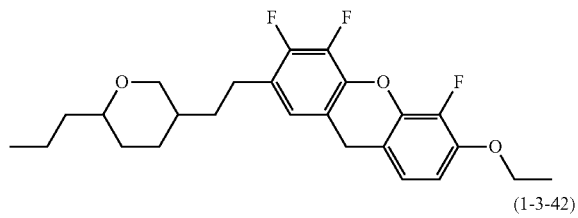
(1-3-41)
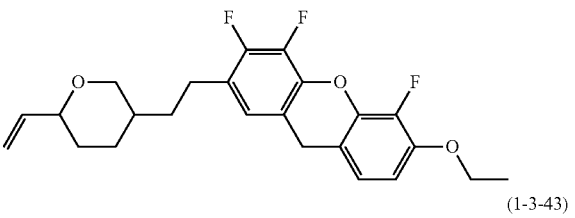
(1-3-42)
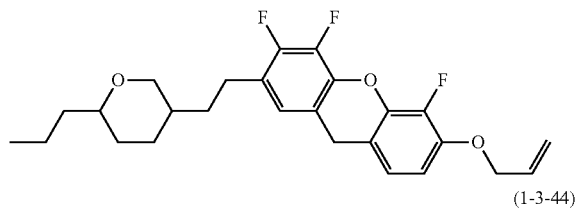
(1-3-43)
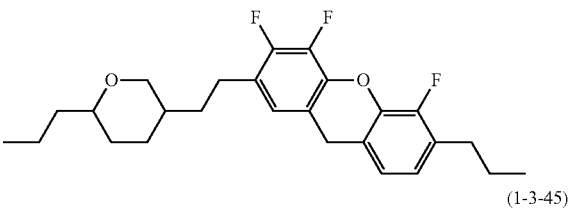
(1-3-44)
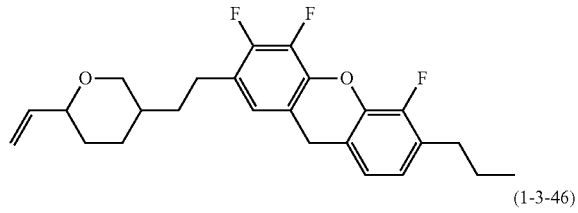
(1-3-45)
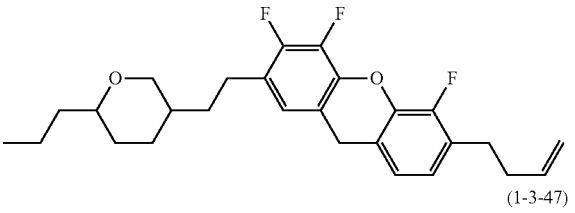
(1-3-46)
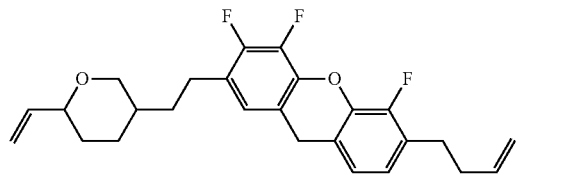
(1-3-47)
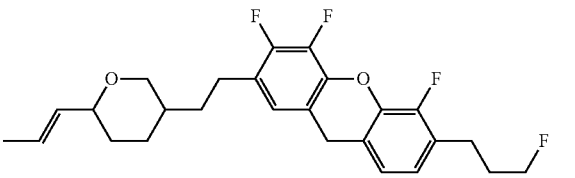
(1-4-1)
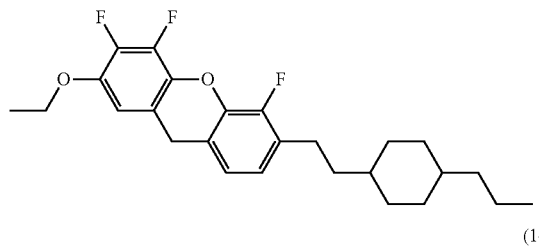
(1-4-2)
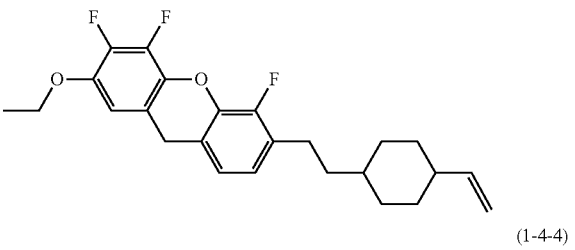
(1-4-3)
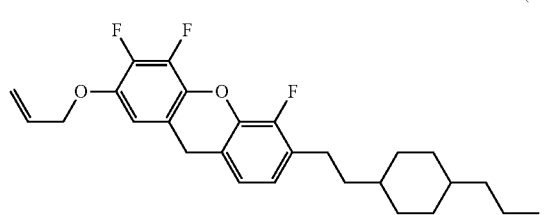
(1-4-4)
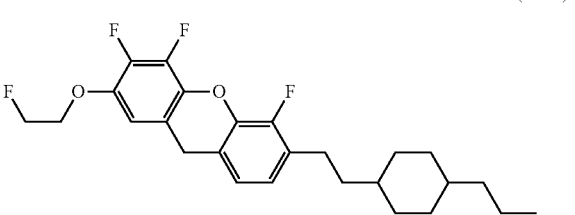

-continued
(1-4-5)
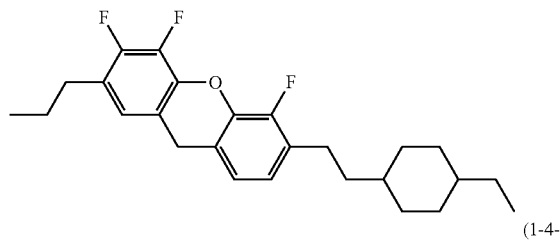
(1-4-6)
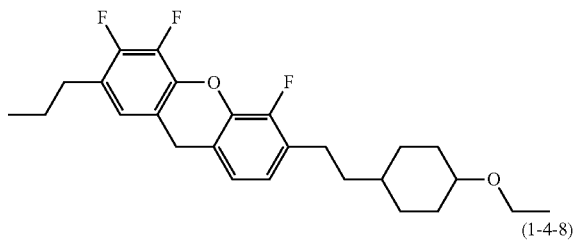
(1-4-7)
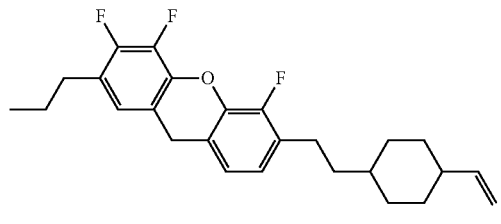
(1-4-8)
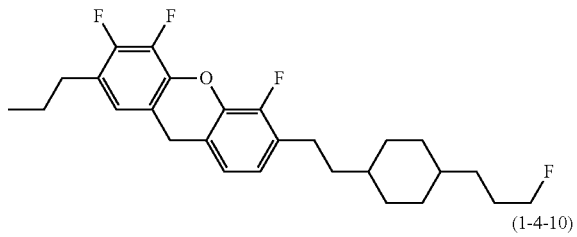
(1-4-9)
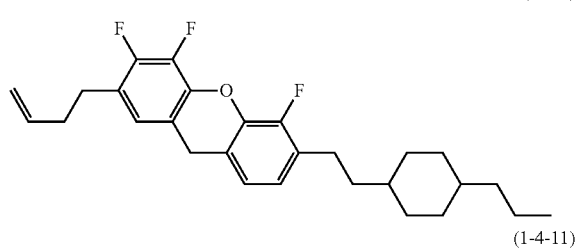
(1-4-10)
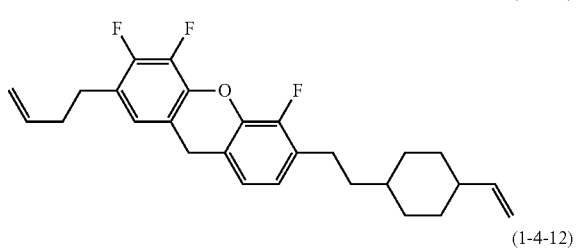
(1-4-11)
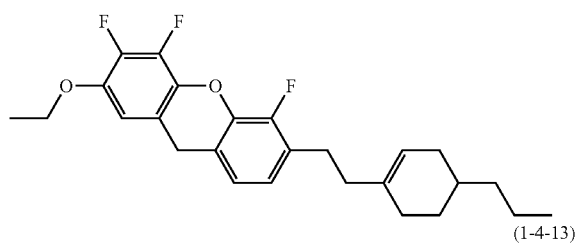
(1-4-12)
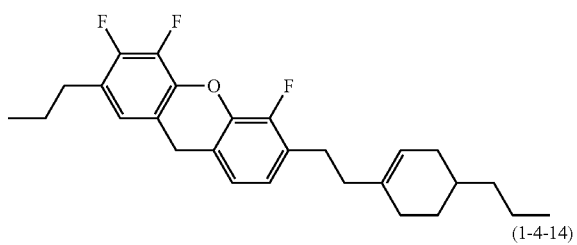
(1-4-13)
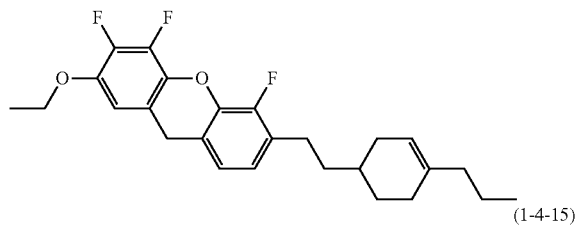
(1-4-14)
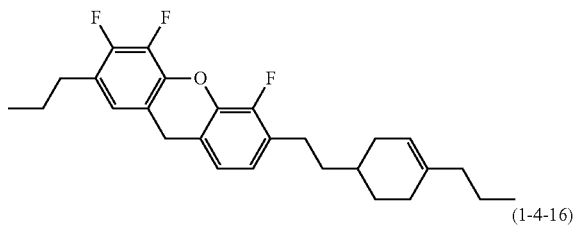
(1-4-15)
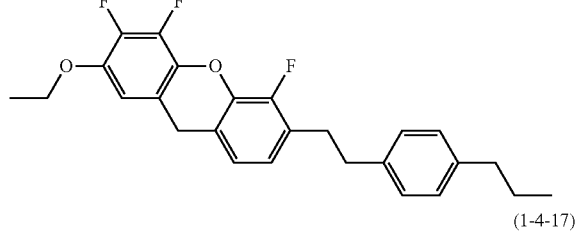
(1-4-16)
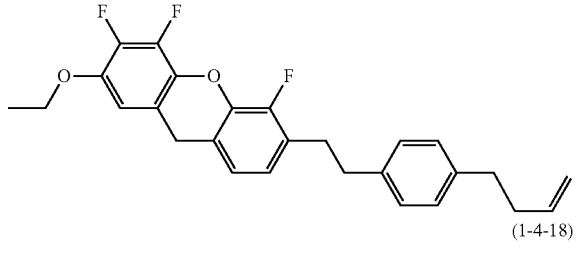
(1-4-17)
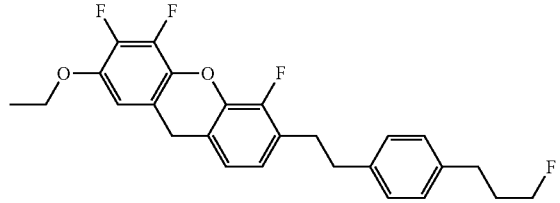
(1-4-18)
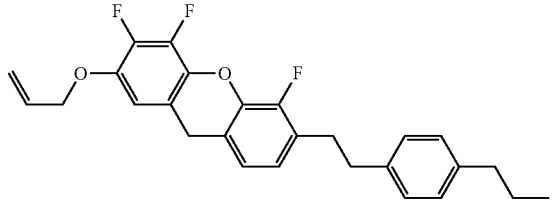

-continued
(1-4-19)
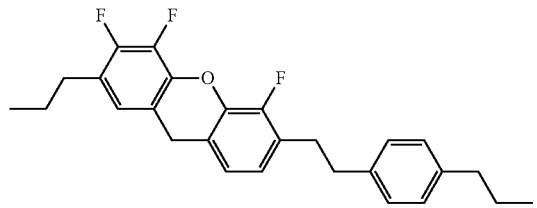
(1-4-20)
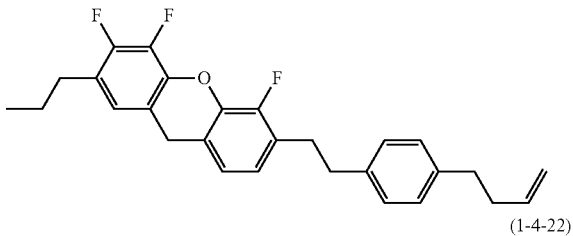
(1-4-21)
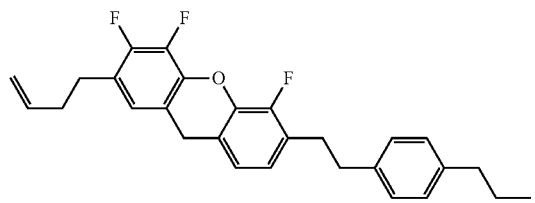
(1-4-22)
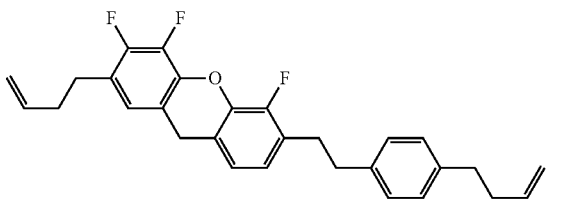
(1-4-23)
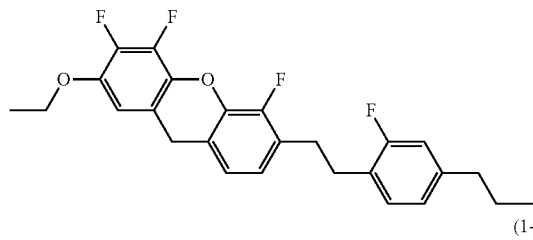
(1-4-24)
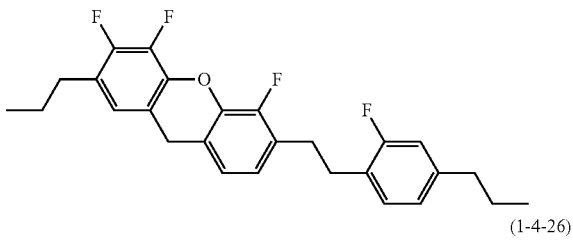
(1-4-25)
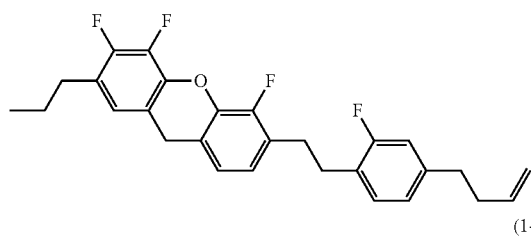
(1-4-26)
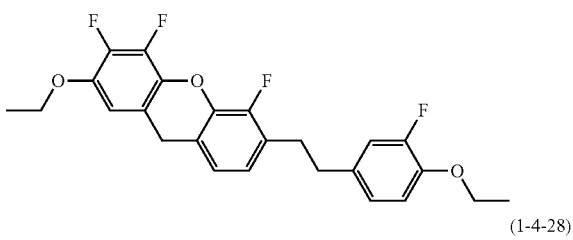
(1-4-27)
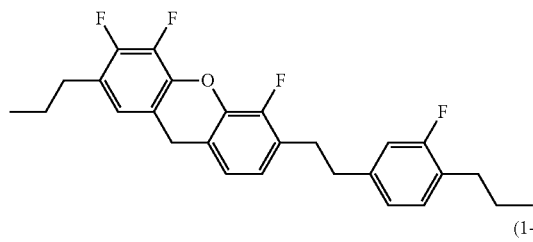
(1-4-28)
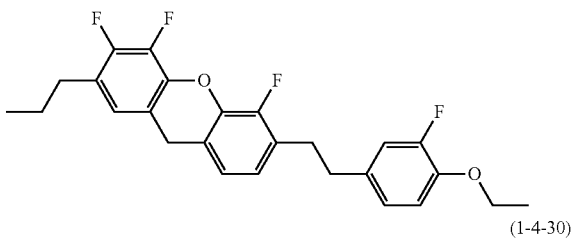
(1-4-29)
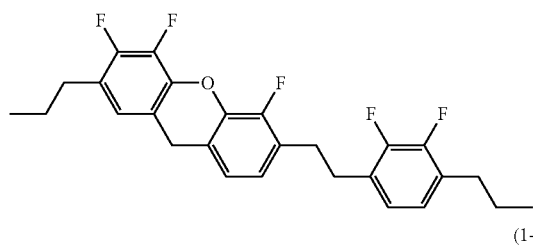
(1-4-30)
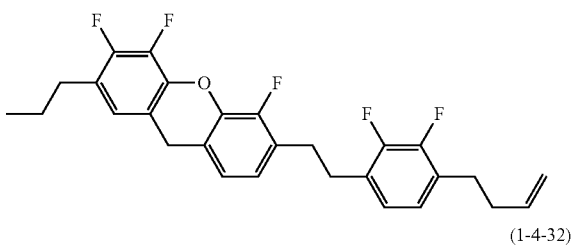
(1-4-31)
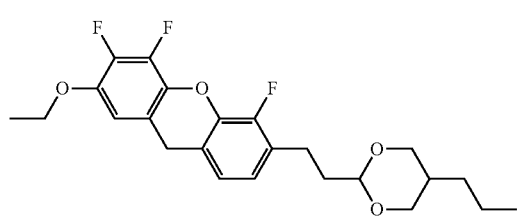
(1-4-32)
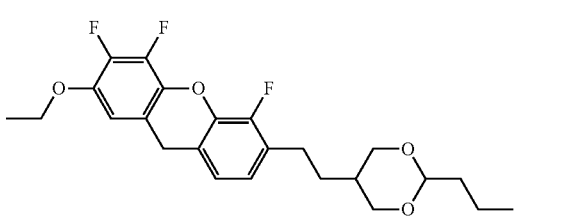

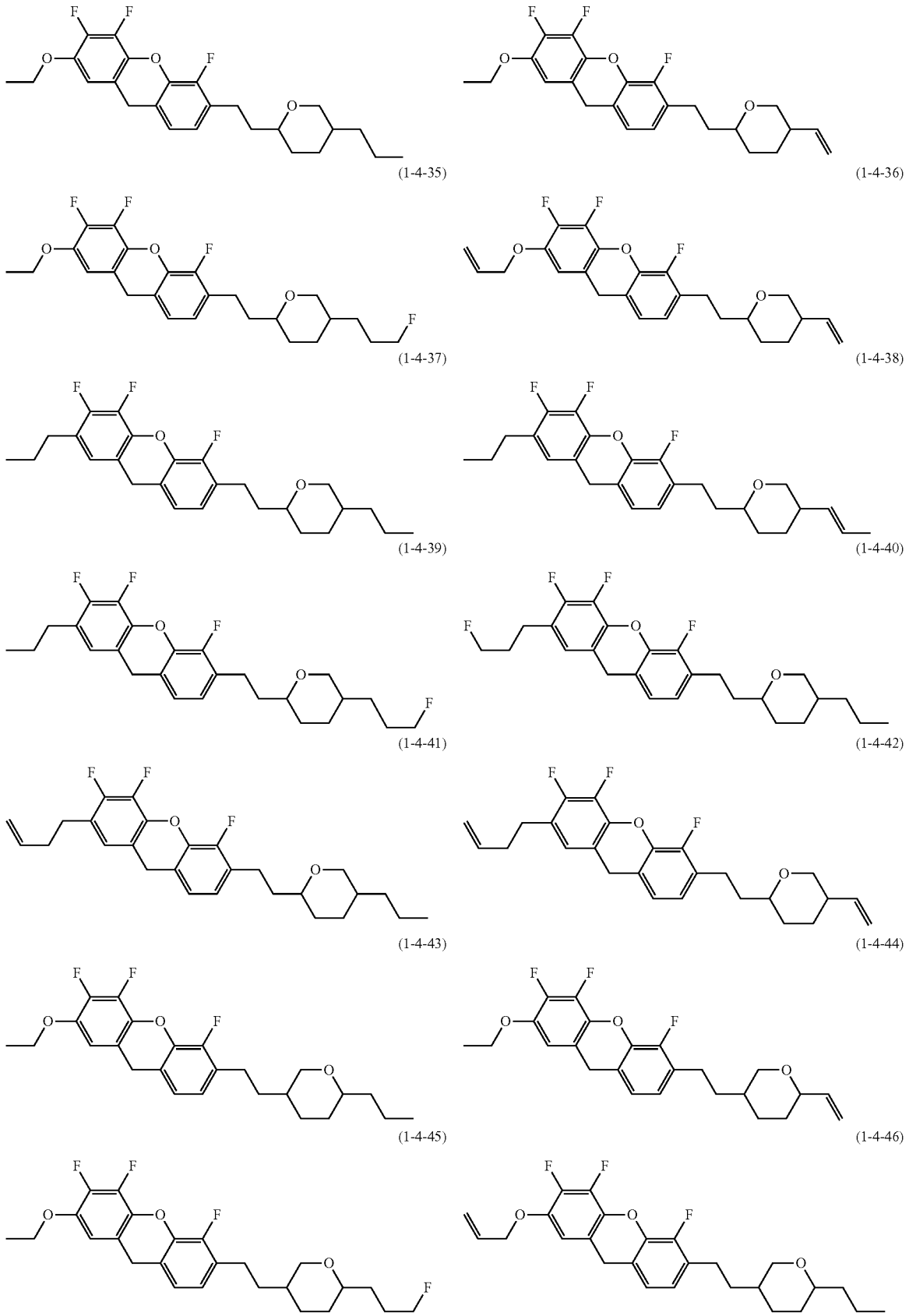

(1-4-47)
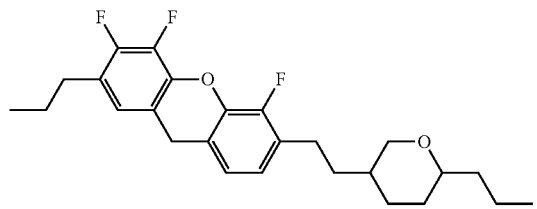
(1-4-48)
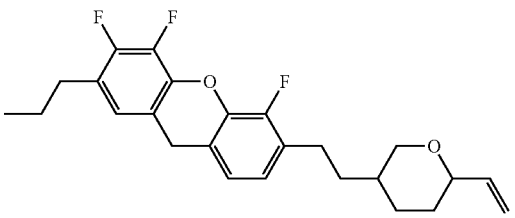
(1-4-49)
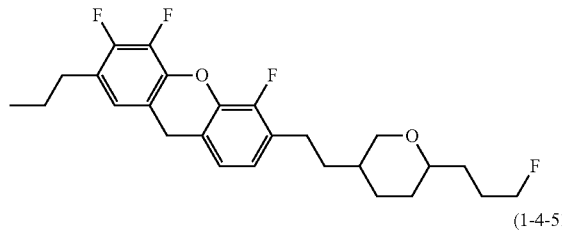
(1-4-50)
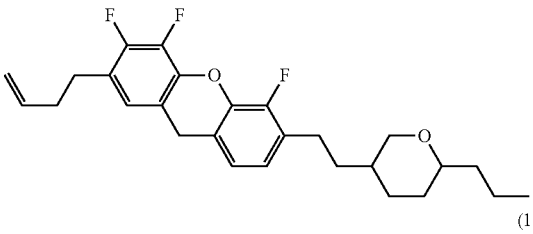
(1-4-51)
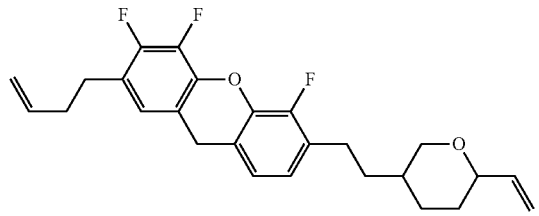
(1-5-1)
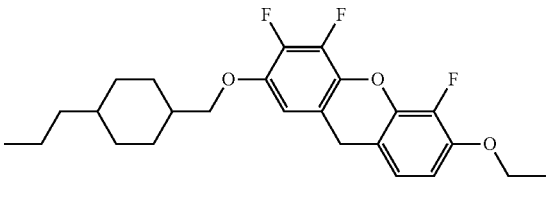 [SMILES: CCCC1CCC(COc2cc3c(c(F)c2F)Oc2c(ccc(OCC)c2F)C3)CC1]
C 101 (N 97.6) I
$T_{NI}$ = 94.6° C., $\Delta\varepsilon$ = −14.3, $\Delta n$ = 0.135
(1-5-2)
C 124 ($S_A$ 66.4 N 97.6) I
$T_{NI}$ = 94.6° C., $\Delta\varepsilon$ = −14.0, $\Delta n$ = 0.129
(1-5-3)
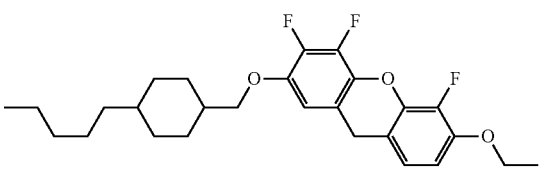
C 118 (N 104) I
$T_{NI}$ = 101° C., $\Delta\varepsilon$ = −13.2, $\Delta n$ = 0.135
(1-5-4)
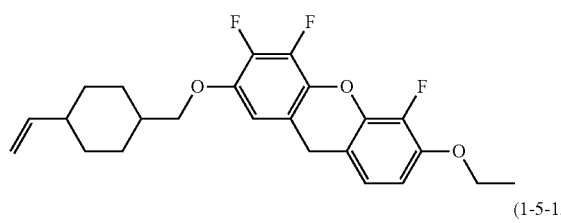
(1-5-5)
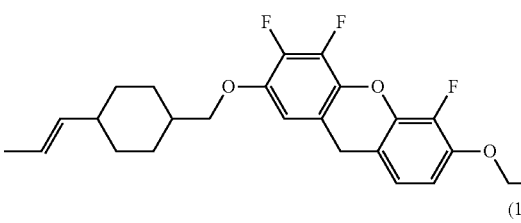
(1-5-13)
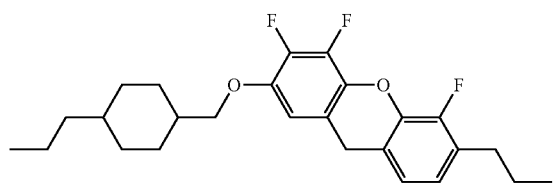
C 94.6 ($S_A$ 53.4 N 66.0) I
$T_{NI}$ = 63.3° C., $\Delta\varepsilon$ = −10.4, $\Delta n$ = 0.115
(1-5-14)
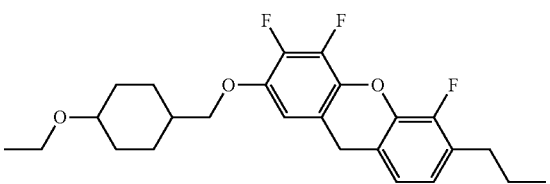

-continued
(1-5-15)
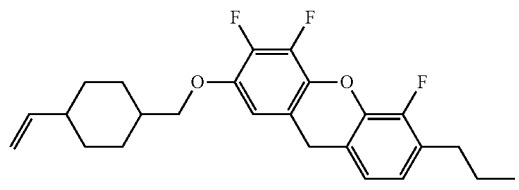
(1-5-16)
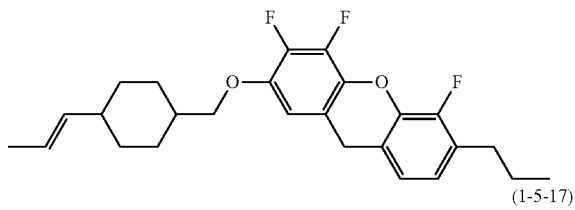
(1-5-17)
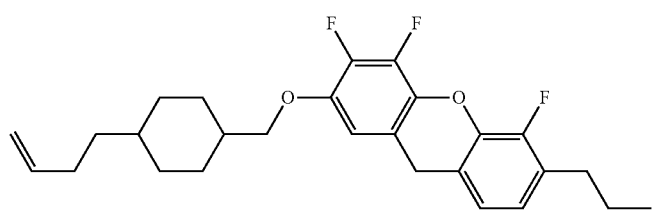
-continued
(1-5-1)
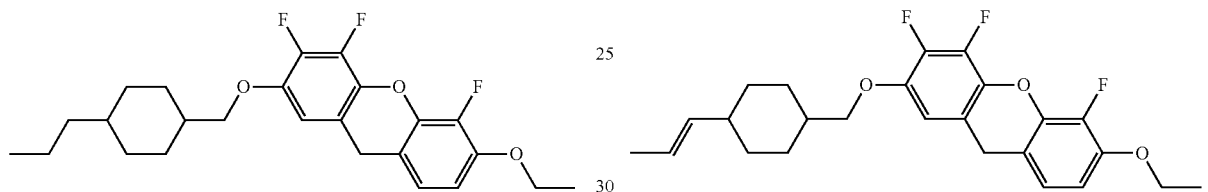
C 101 (N 97.6) I
$T_{NI}$ = 94.6° C., $\Delta\varepsilon$ = −14.3, $\Delta n$ = 0.135
(1-5-2)
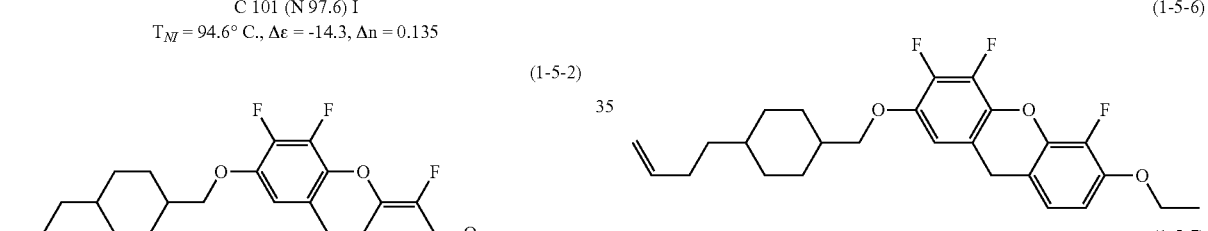
C 124 ($S_A$ 66.4 N 97.6) I
$T_{NI}$ = 94.6° C., $\Delta\varepsilon$ = −14.0, $\Delta n$ = 0.129
(1-5-3)
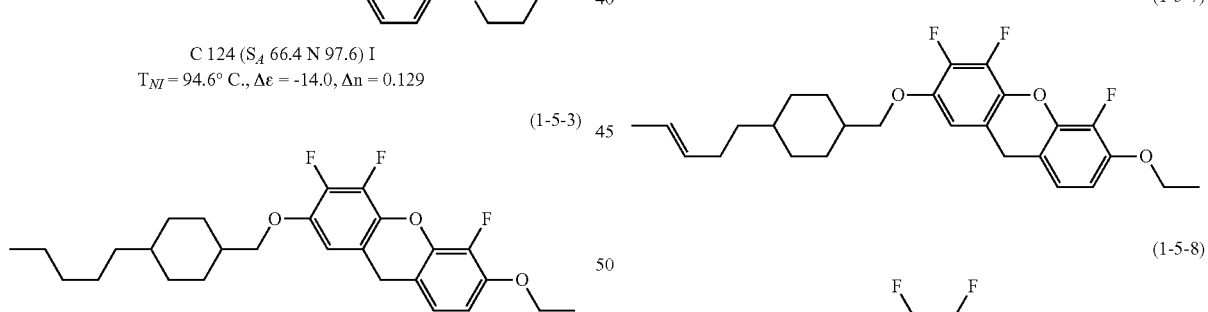
C 118 (N 104) I
$T_{NI}$ = 101° C., $\Delta\varepsilon$ = −13.2, $\Delta n$ = 0.135
(1-5-4)
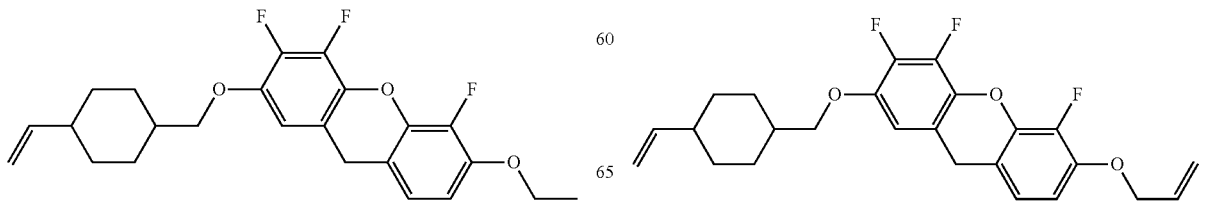
(1-5-5)
(1-5-6)
(1-5-7)
(1-5-8)
(1-5-9)

(1-5-10)
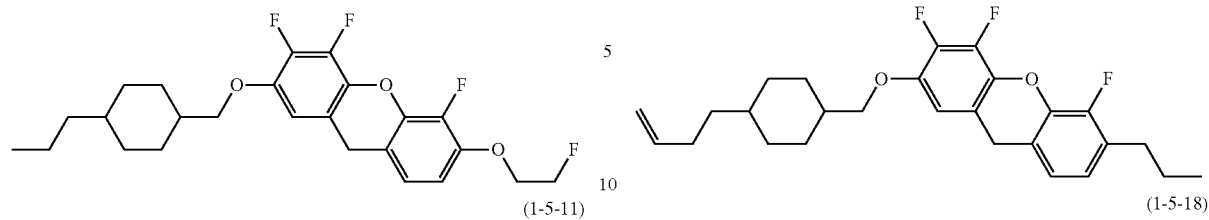
(1-5-11)
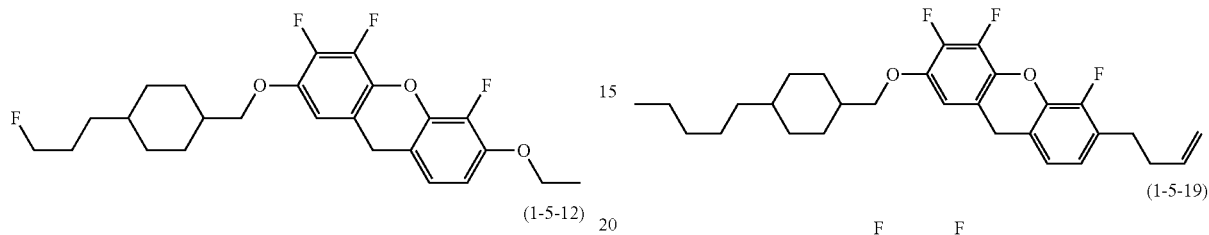
(1-5-12)
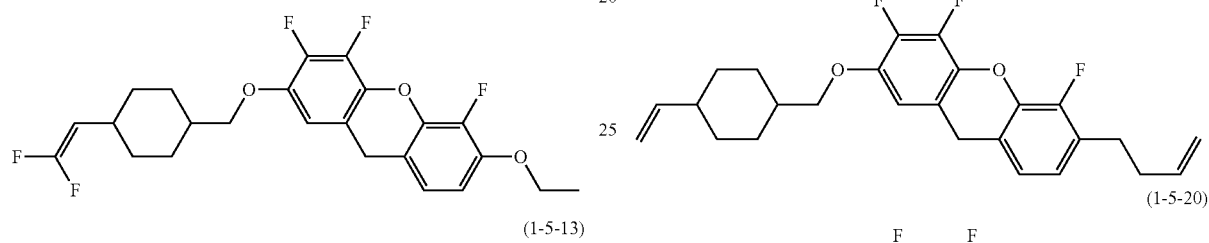
(1-5-13)
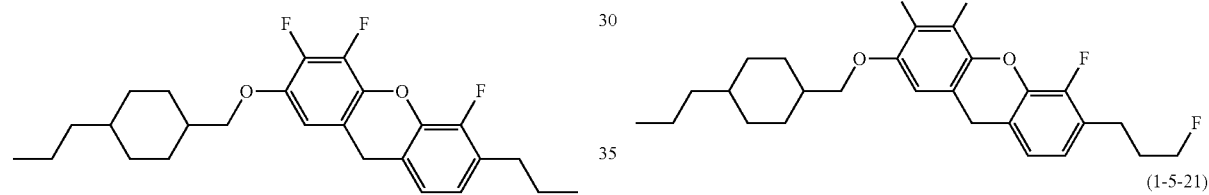
C 94.6 (S$_A$ 53.4 N 66.0) I
T$_{NI}$ = 63.3° C., Δε = −10.4, Δn = 0.115
(1-5-14)
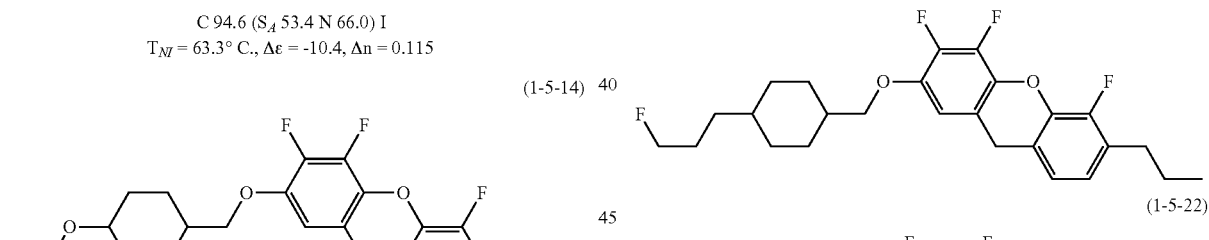
(1-5-15)
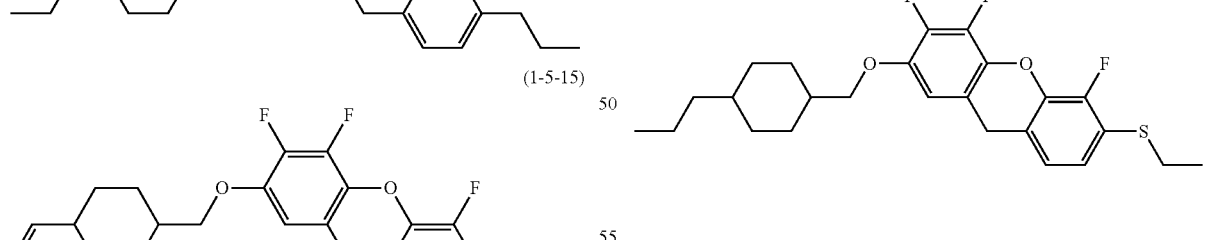
(1-5-16)
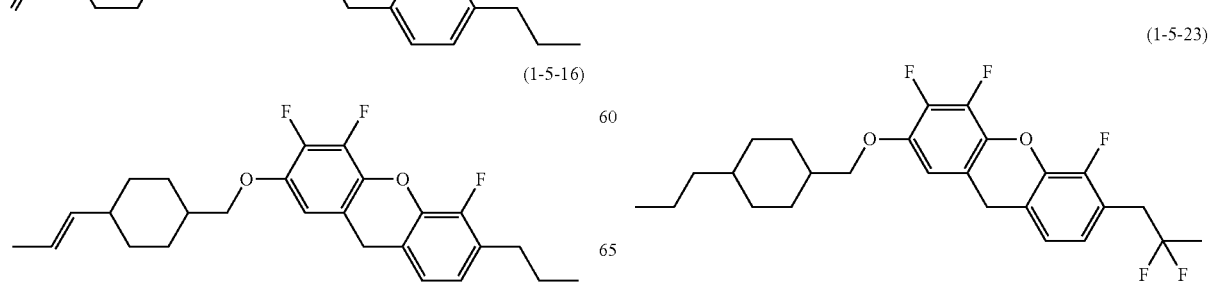
(1-5-17)
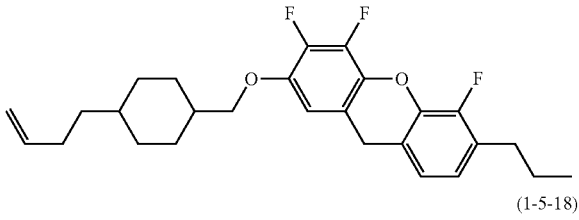
(1-5-18)
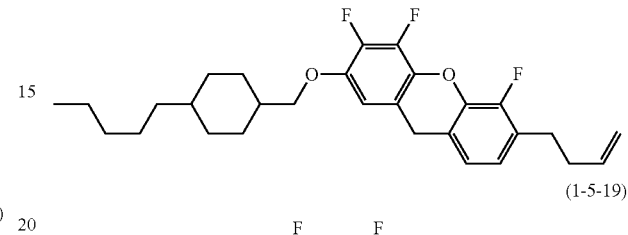
(1-5-19)
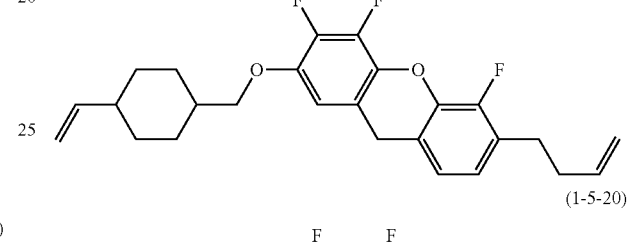
(1-5-20)
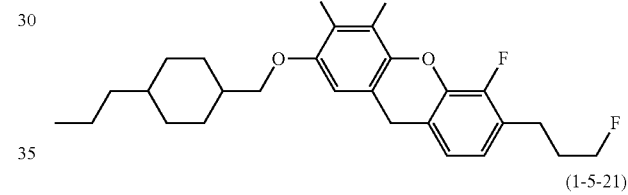
(1-5-21)
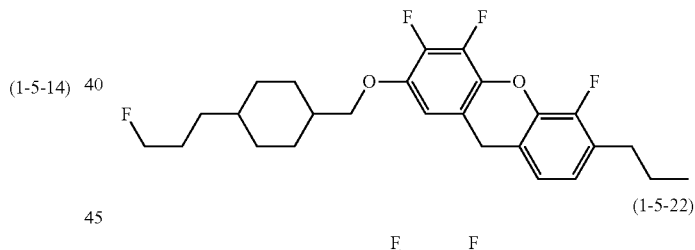
(1-5-22)
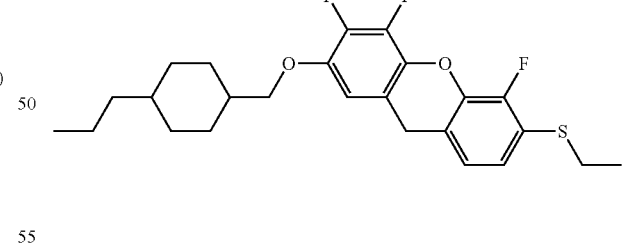
(1-5-23)
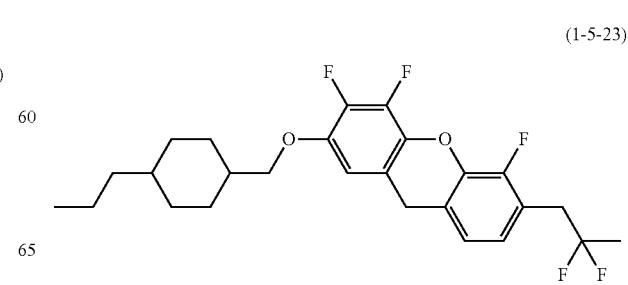

(1-5-24)
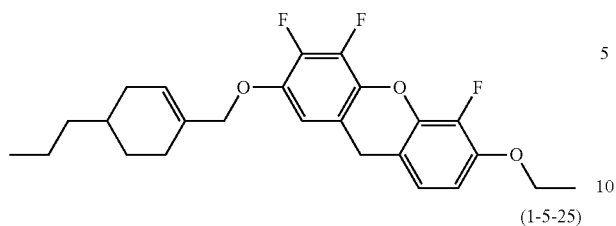
(1-5-25)
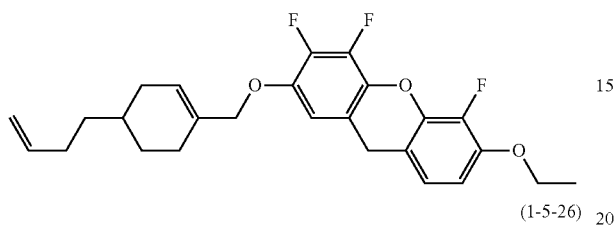
(1-5-26)
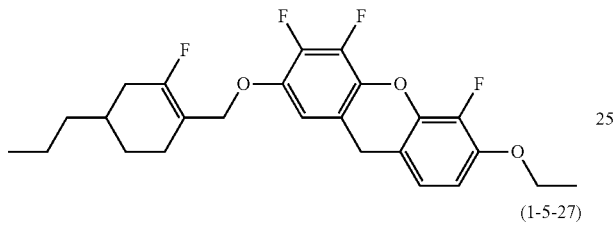
(1-5-27)
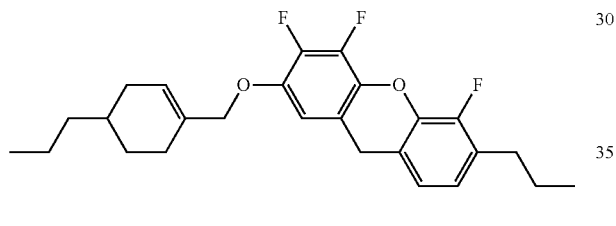
(1-5-28)
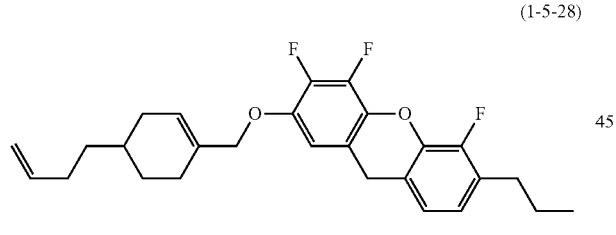
(1-5-29)
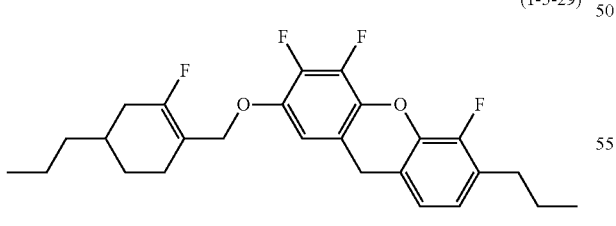
(1-5-30)
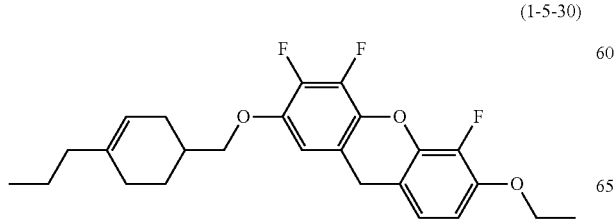
(1-5-31)
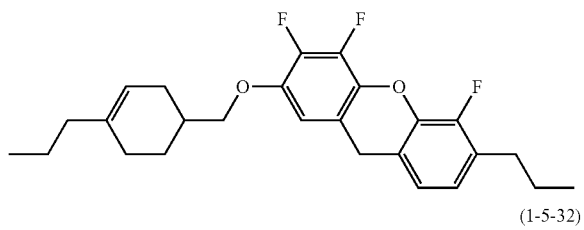
(1-5-32)
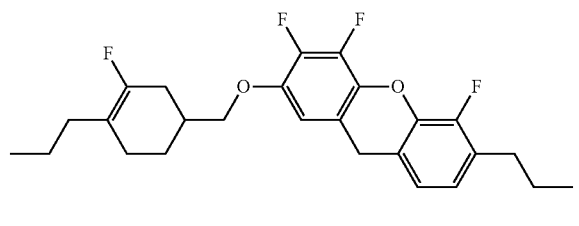
(1-5-33)
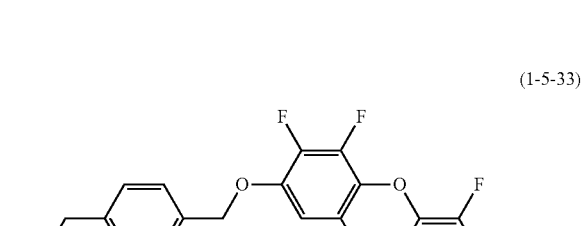
(1-5-34)
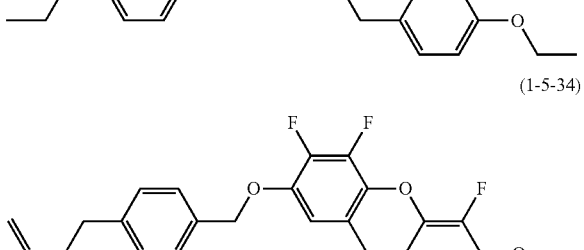
(1-5-35)
(1-5-36)
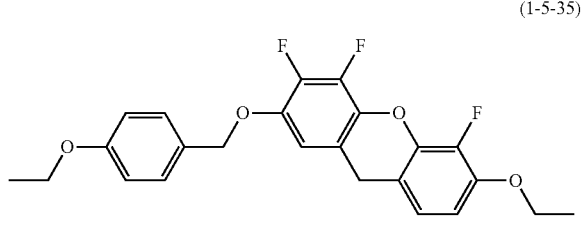
(1-5-37)

(1-5-38)
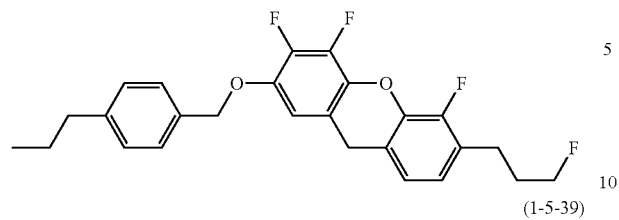
(1-5-39)
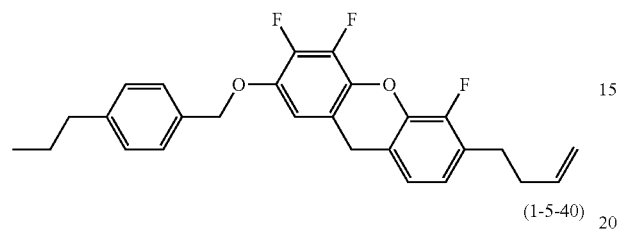
(1-5-40)
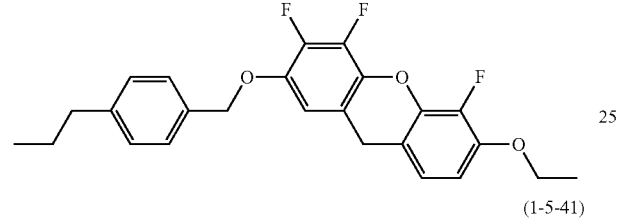
(1-5-41)
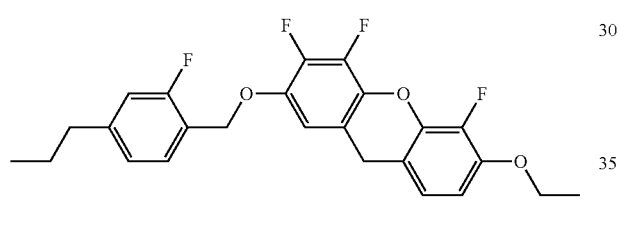
(1-5-42)
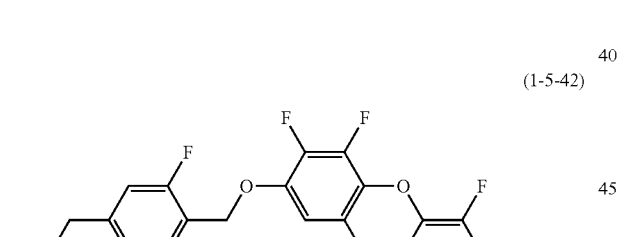
(1-5-43)
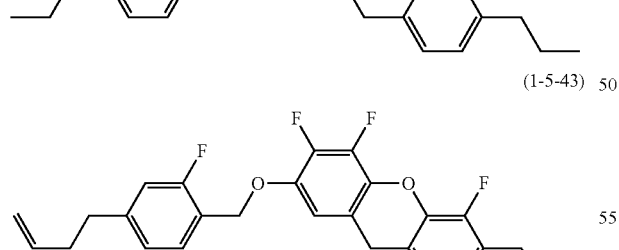
(1-5-44)
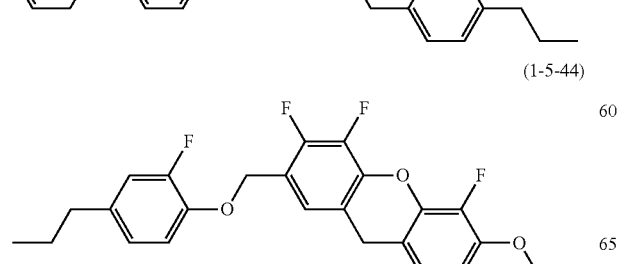
(1-5-45)
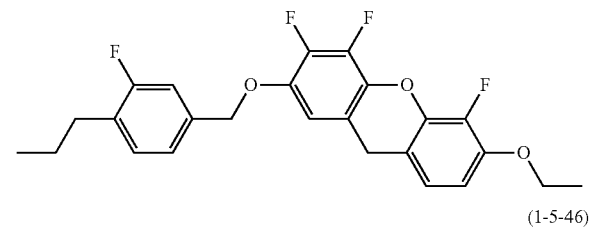
(1-5-46)
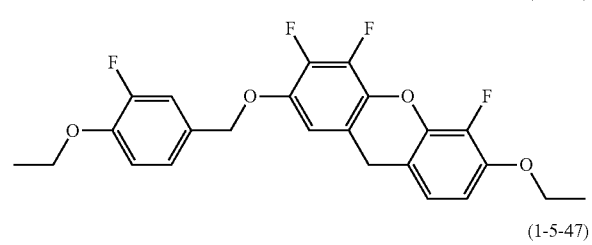
(1-5-47)
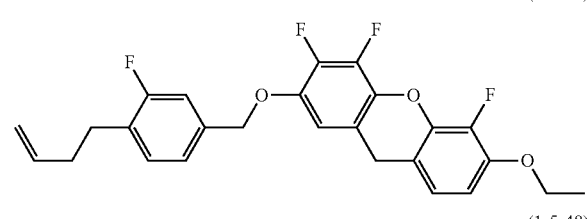
(1-5-48)
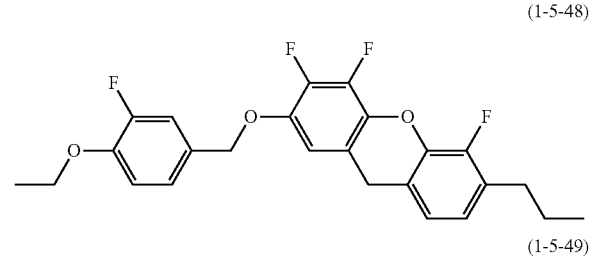
(1-5-49)
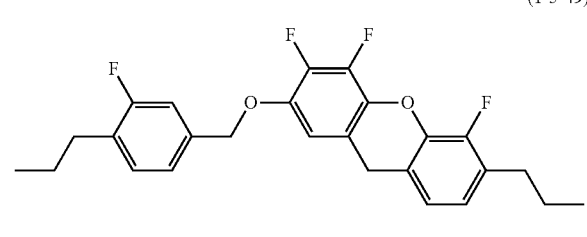
(1-5-50)
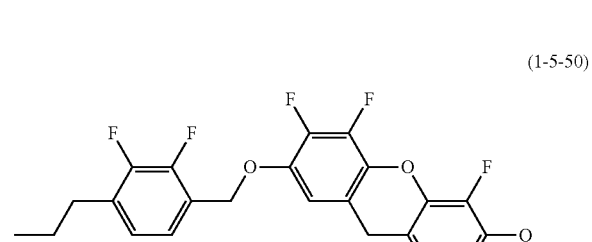
(1-5-51)
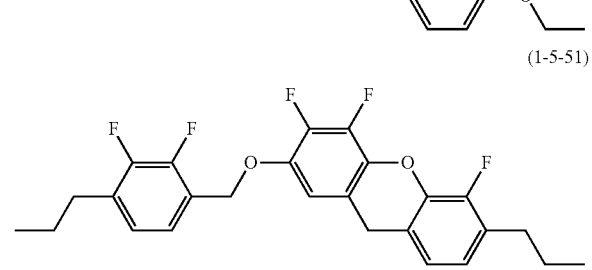

(1-5-52)
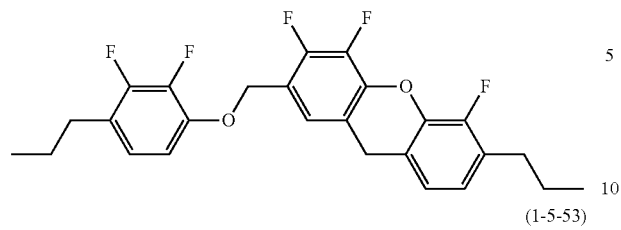
(1-5-53)
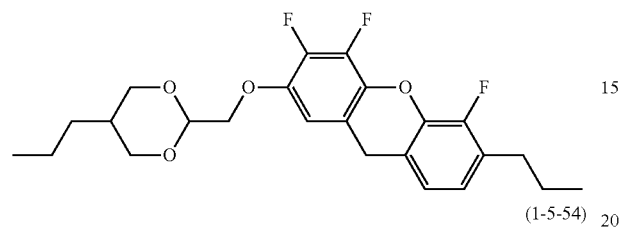
(1-5-54)
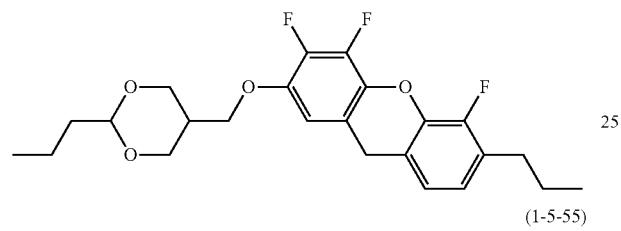
(1-5-55)
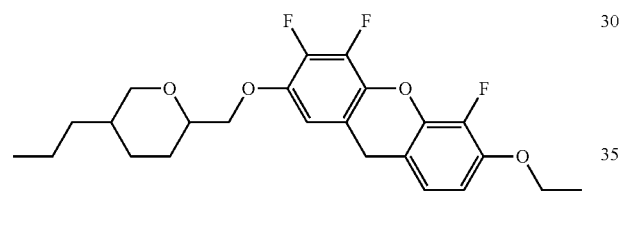
(1-5-56)
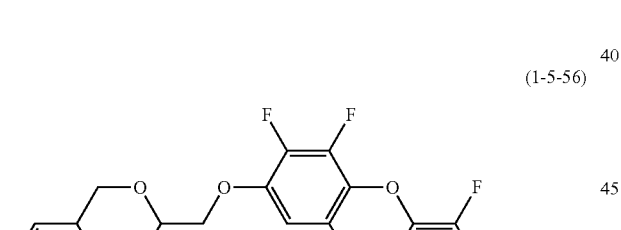
(1-5-57)
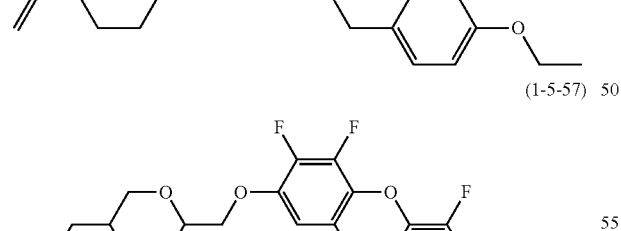
(1-5-58)
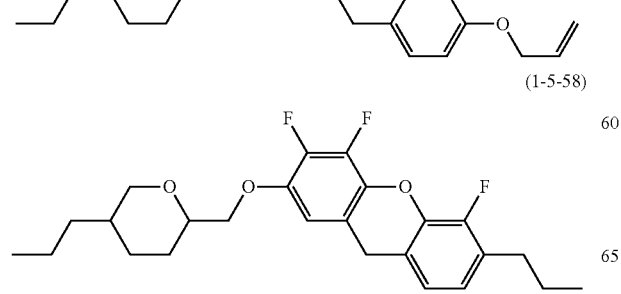
(1-5-59)
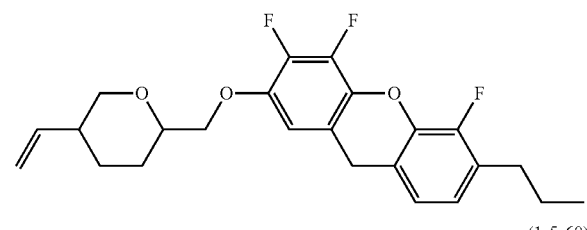
(1-5-60)
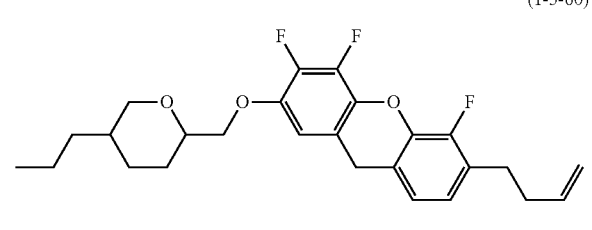
(1-5-61)
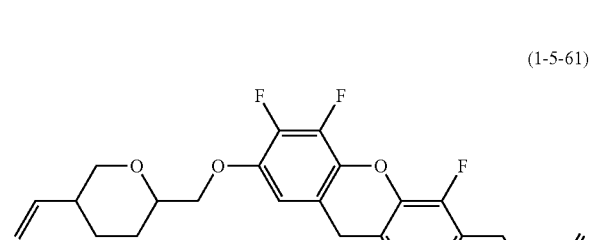
(1-5-62)
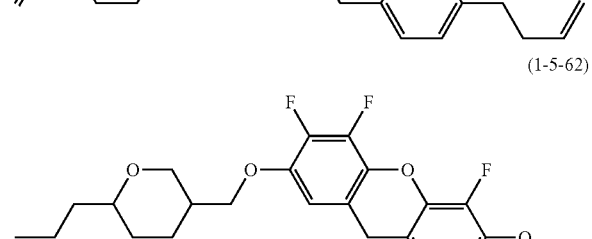
(1-5-63)
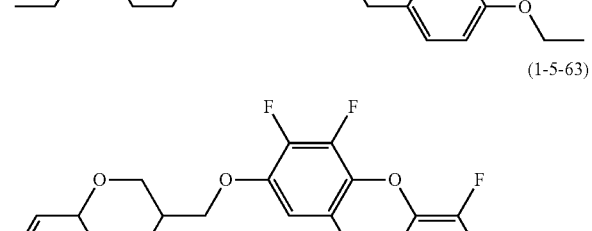
(1-5-64)
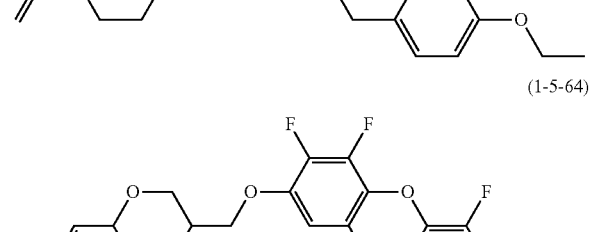
(1-5-65)
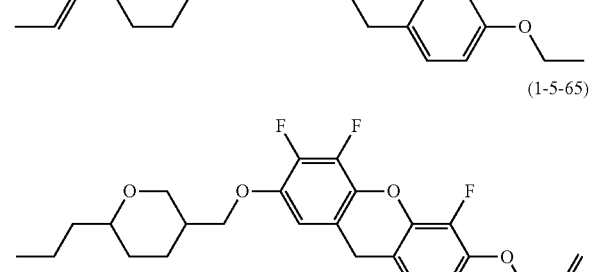

(1-5-66)
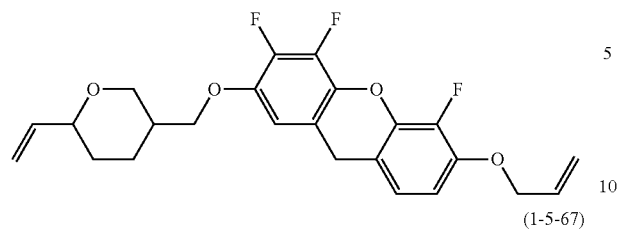
(1-5-67)
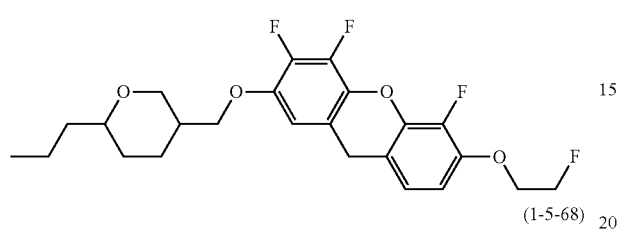
(1-5-68)
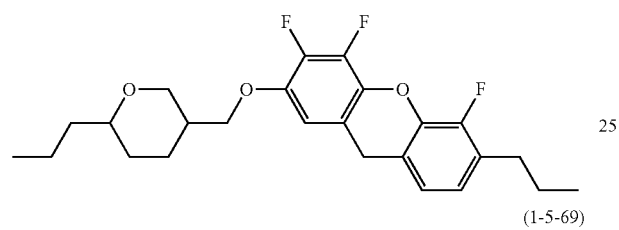
(1-5-69)
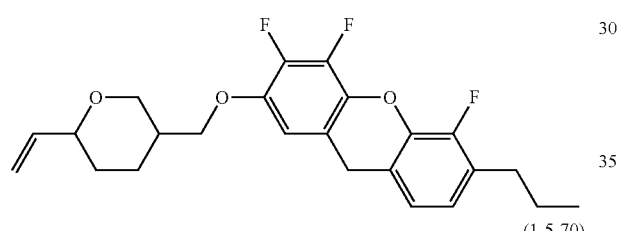
(1-5-70)
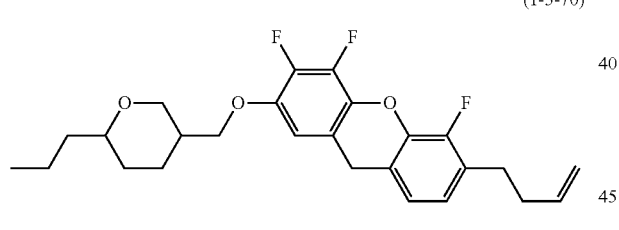
(1-5-71)
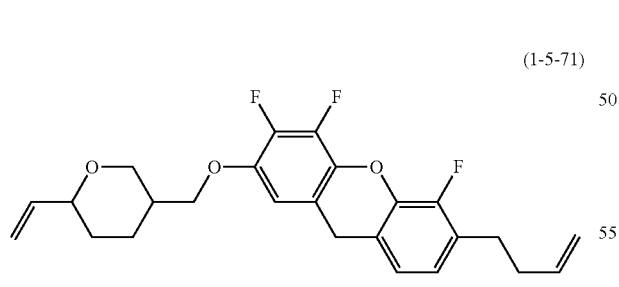
(1-5-72)
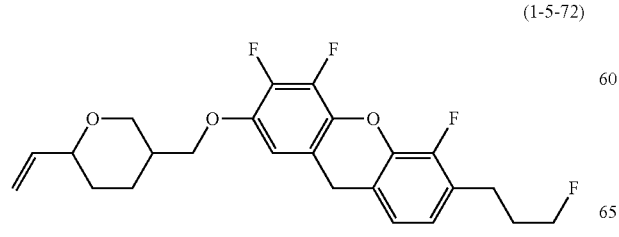
(1-6-1)
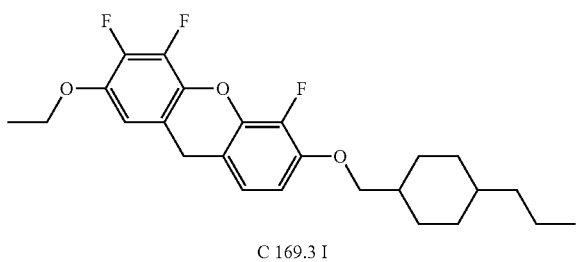
(1-6-2)
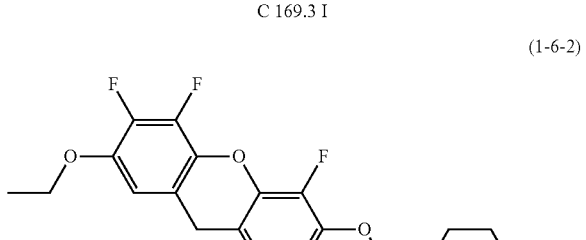
(1-6-3)
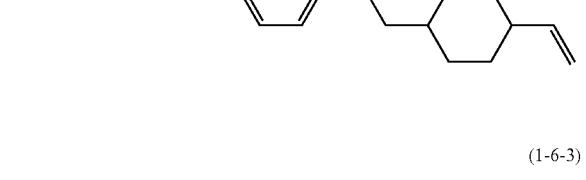
(1-6-4)
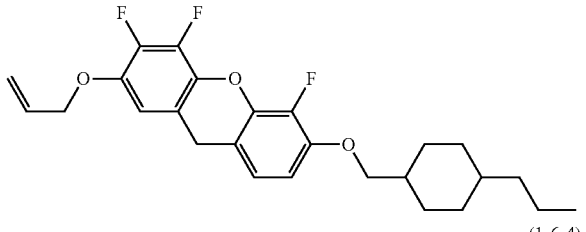
(1-6-5)
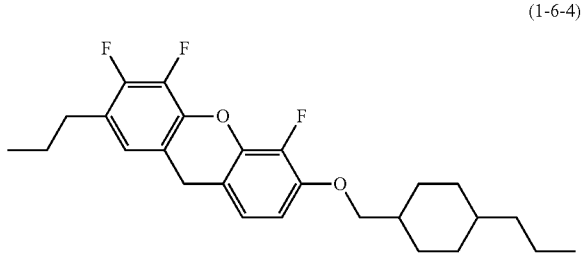
(1-6-6)
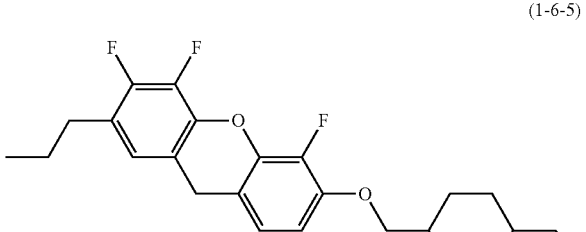
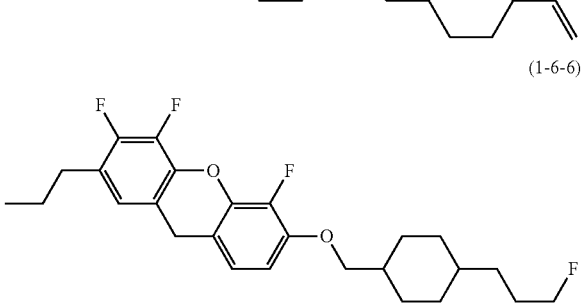

(1-6-7)
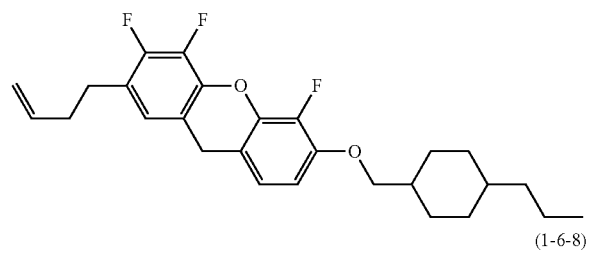
(1-6-8)
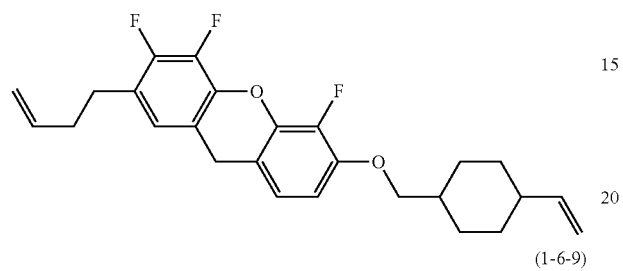
(1-6-9)
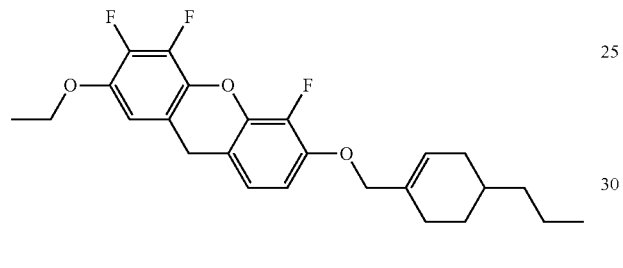
(1-6-10)
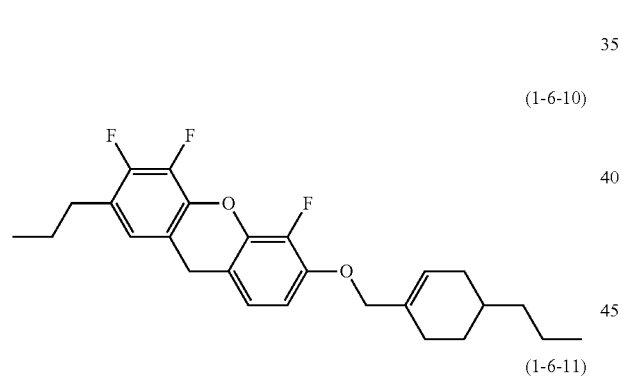
(1-6-11)
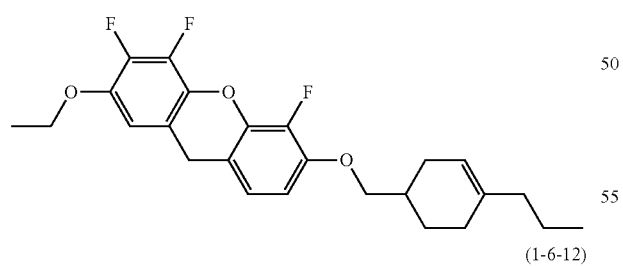
(1-6-12)
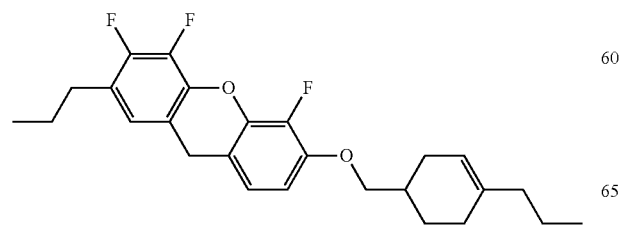
(1-6-13)
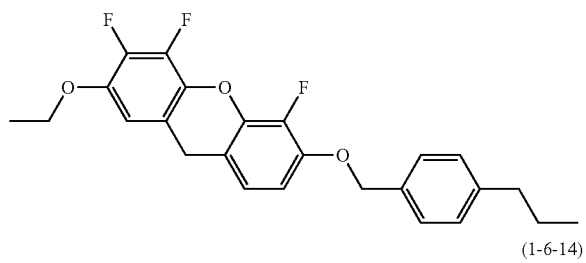
(1-6-14)
(1-6-15)
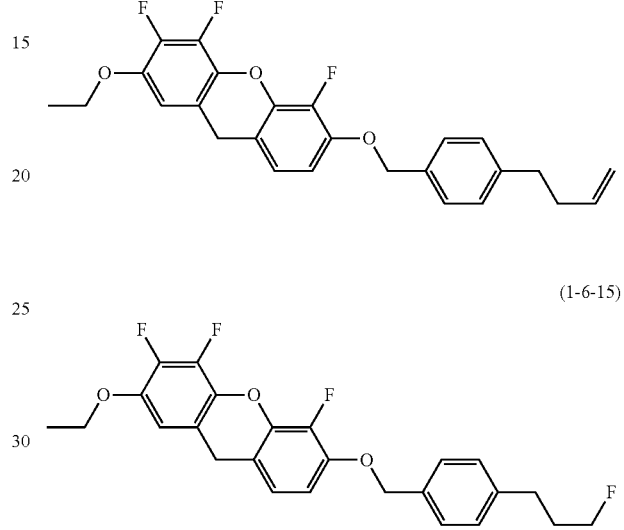
(1-6-16)
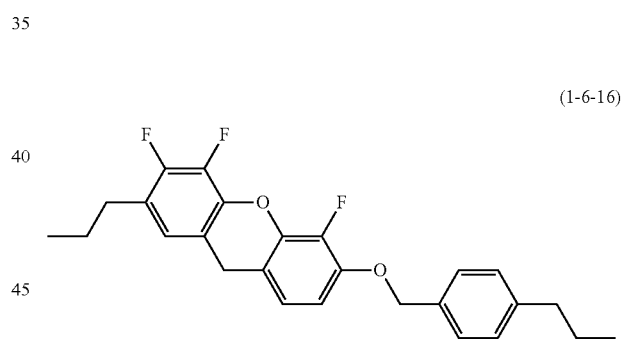
(1-6-17)
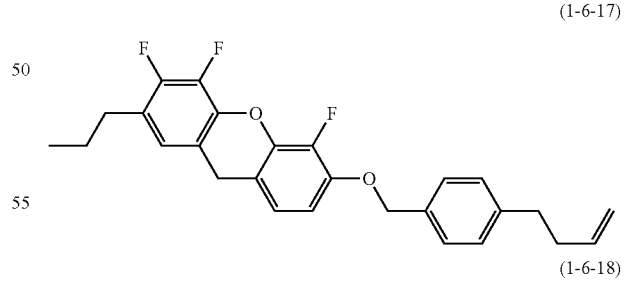
(1-6-18)
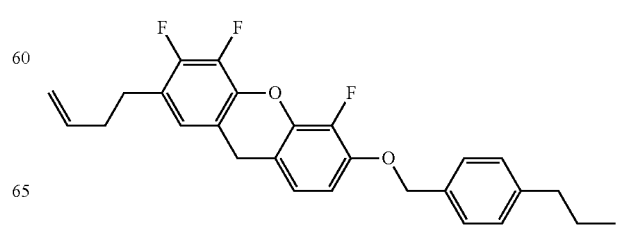

-continued
(1-6-19)
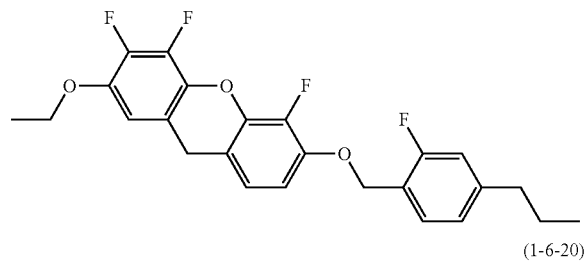
(1-6-20)
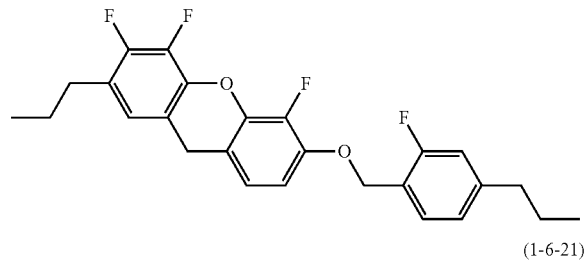
(1-6-21)
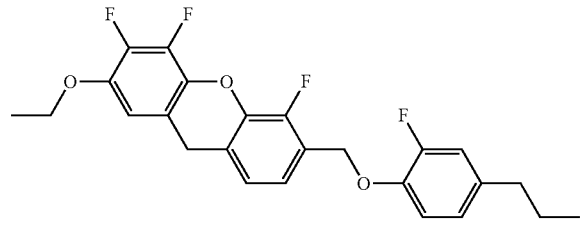
(1-6-22)
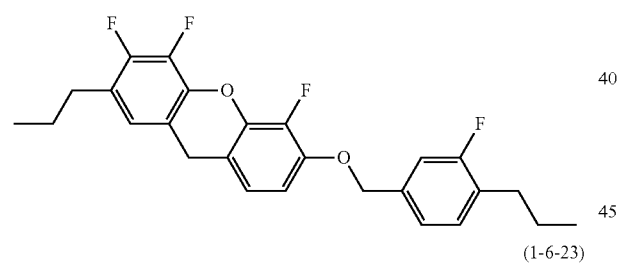
(1-6-23)
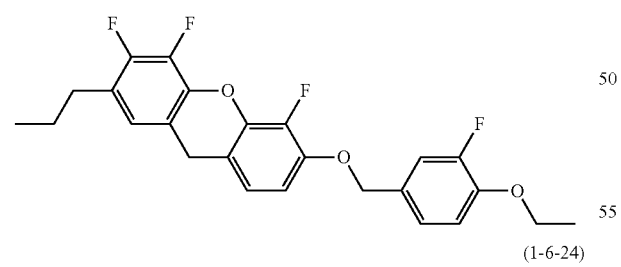
(1-6-24)
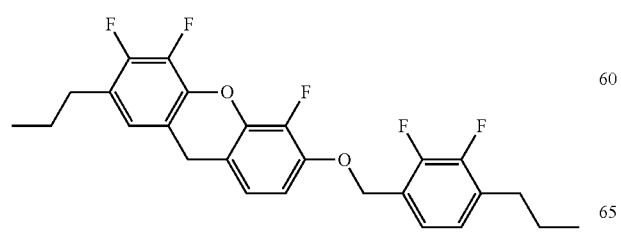
-continued
(1-6-25)
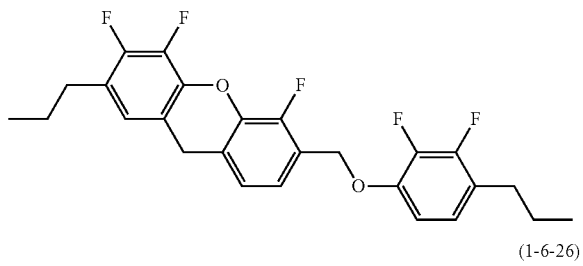
(1-6-26)
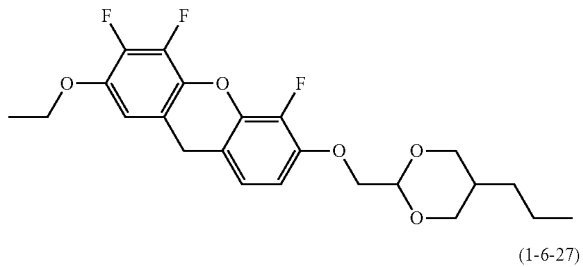
(1-6-27)
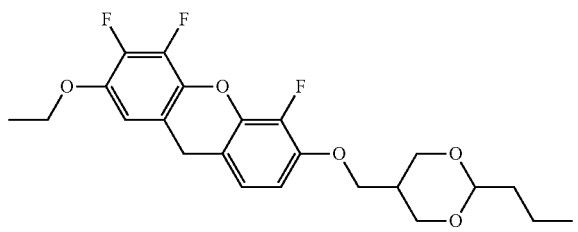
(1-6-28)
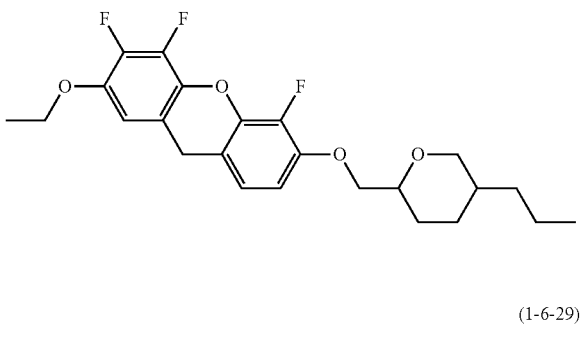
(1-6-29)
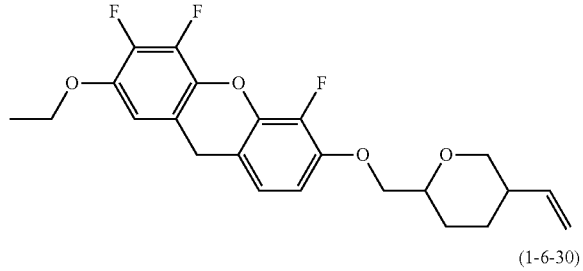
(1-6-30)
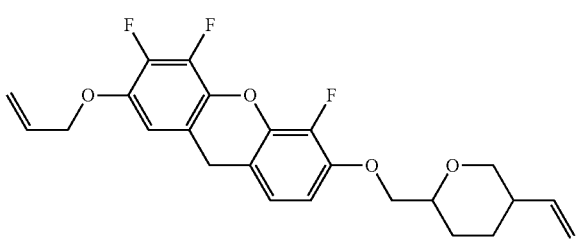

-continued
(1-6-31)
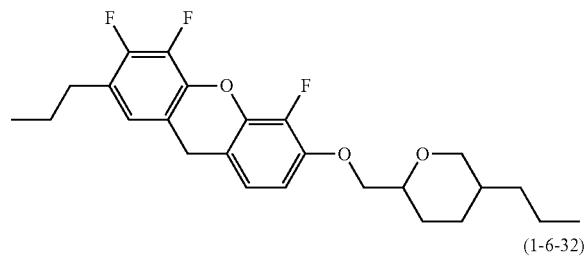
(1-6-32)
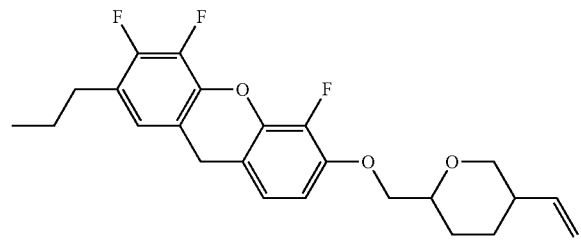
(1-6-33)
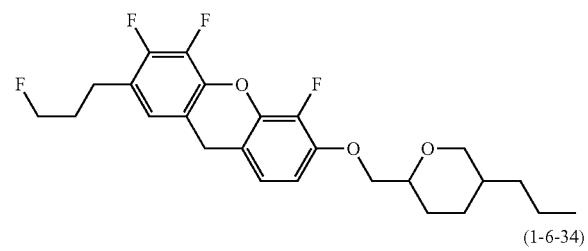
(1-6-34)
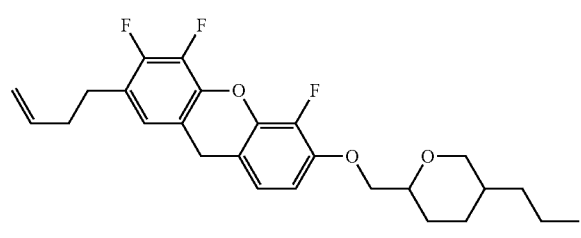
(1-6-35)
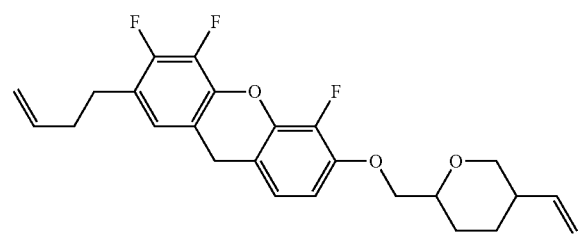
(1-6-36)
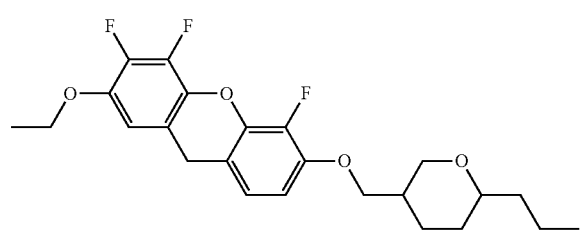
-continued
(1-6-37)
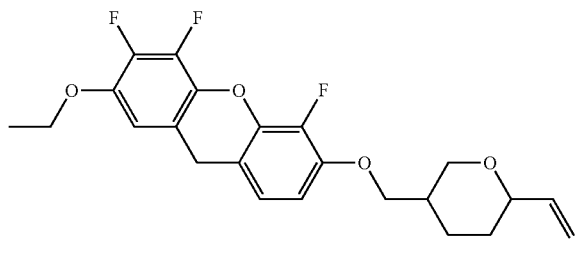
(1-6-38)
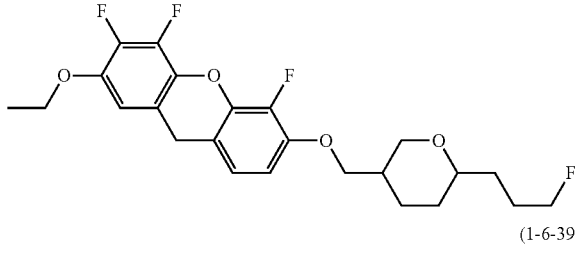
(1-6-39)
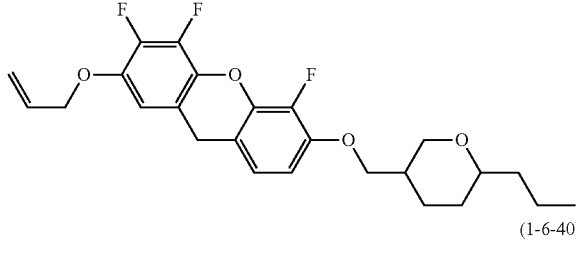
(1-6-40)
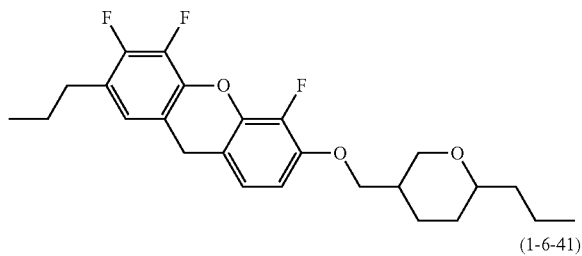
(1-6-41)
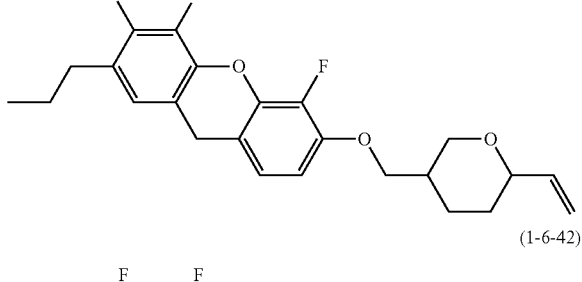
(1-6-42)

(1-6-43)
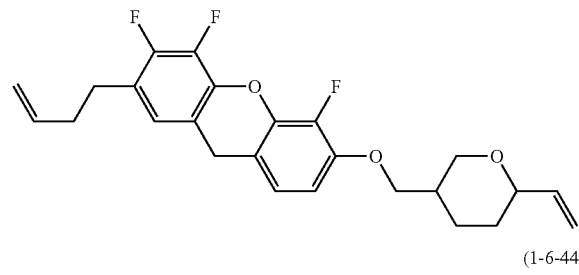
(1-6-44)
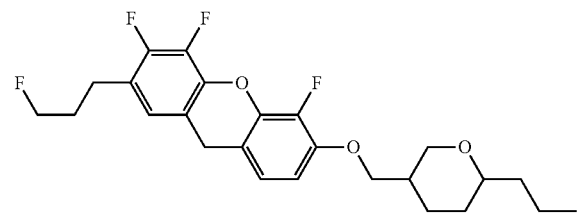
(1-7-1)
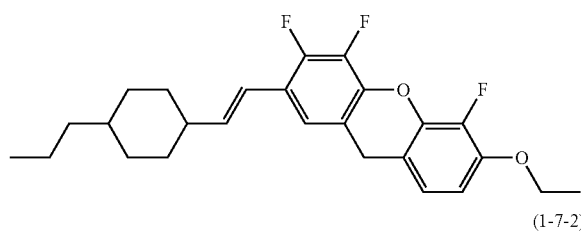
(1-7-2)
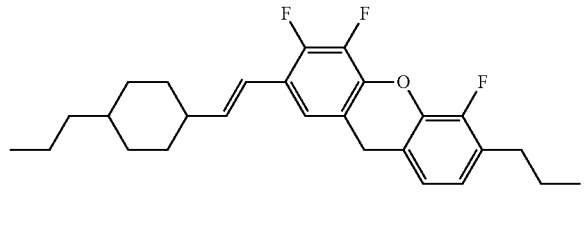
(1-7-3)
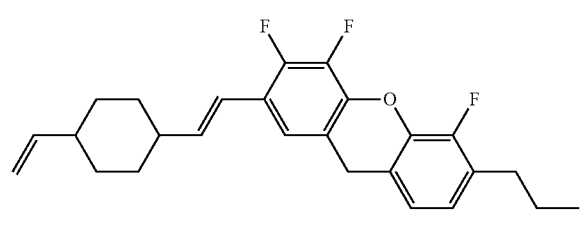
(1-7-4)
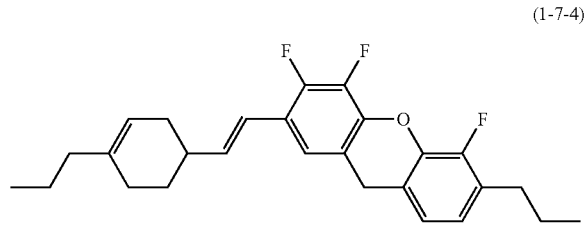
(1-7-5)
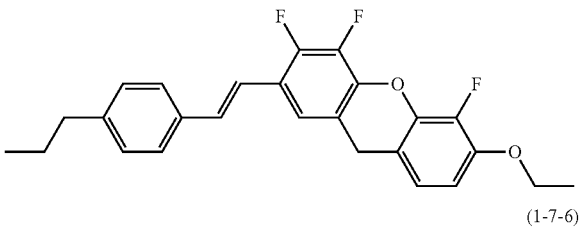
(1-7-6)
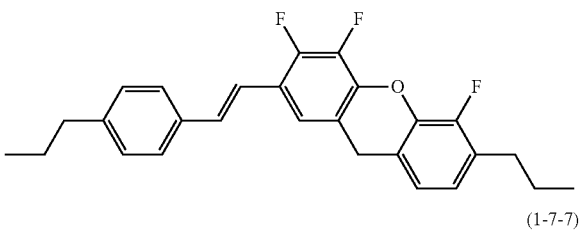
(1-7-7)
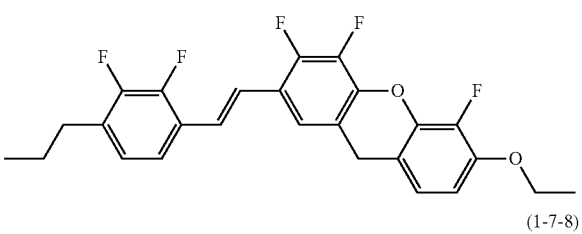
(1-7-8)
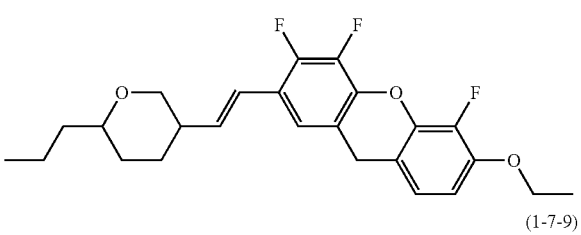
(1-7-9)
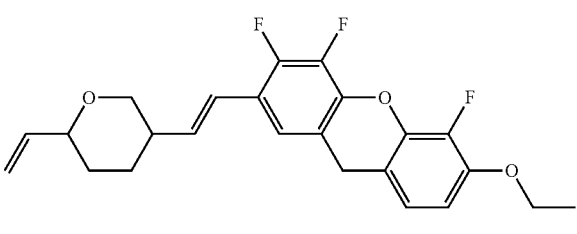
(1-7-10)
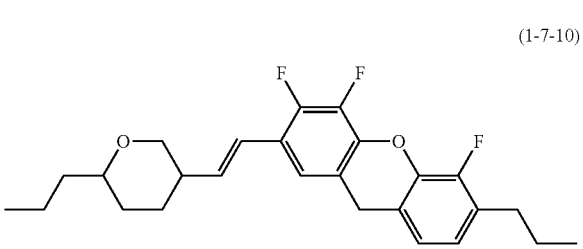
(1-7-11)
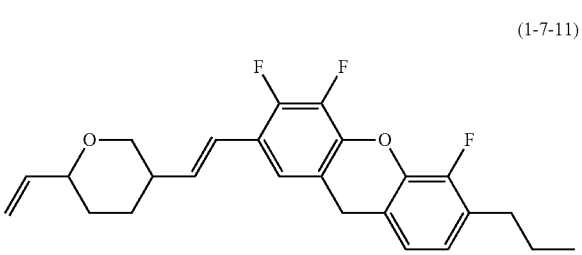

(1-7-12)
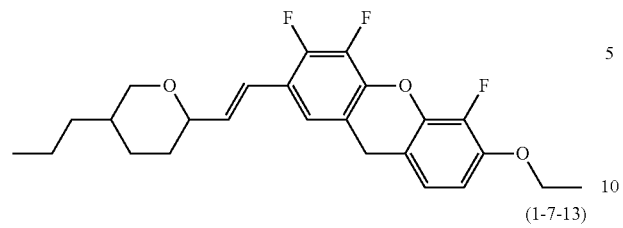
(1-7-13)
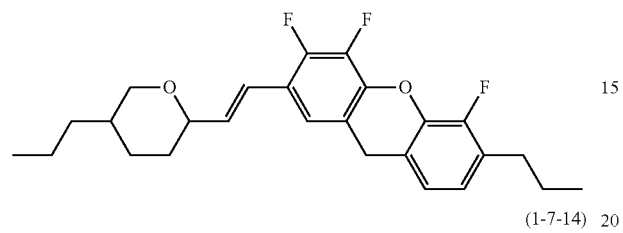
(1-7-14)
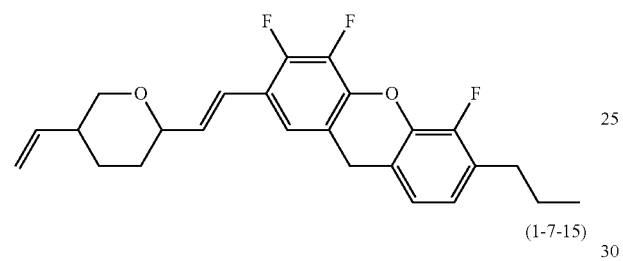
(1-7-15)
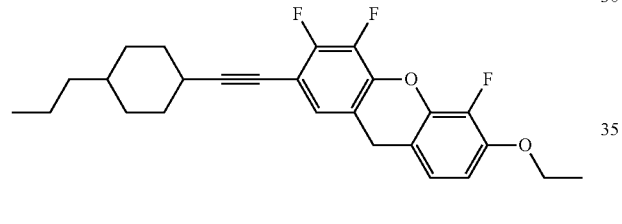
(1-7-16)
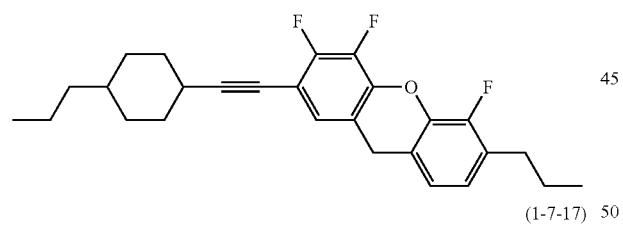
(1-7-17)
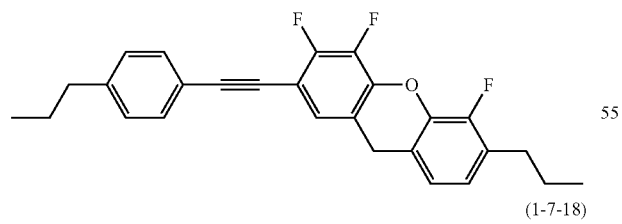
(1-7-18)
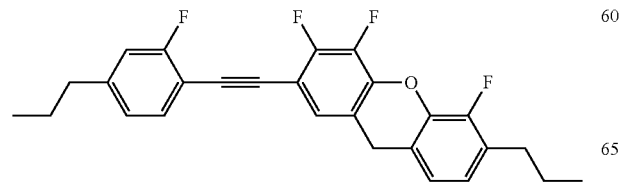
(1-7-19)
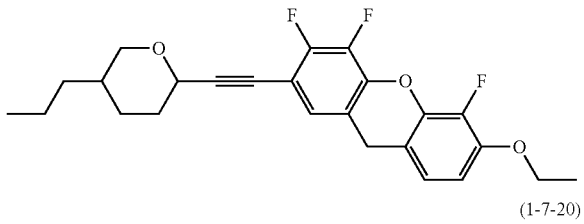
(1-7-20)
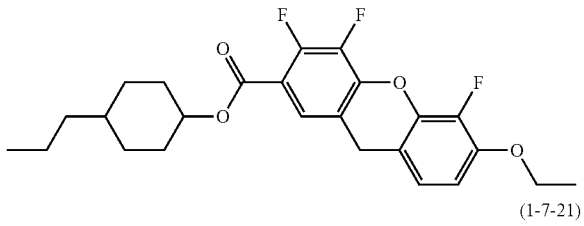
(1-7-21)
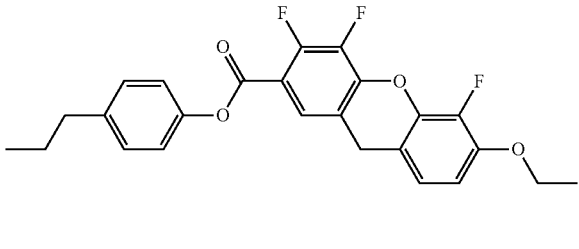
(1-7-22)
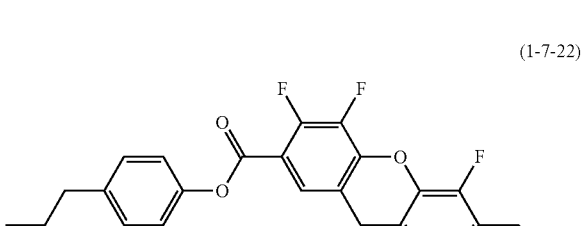
(1-7-23)
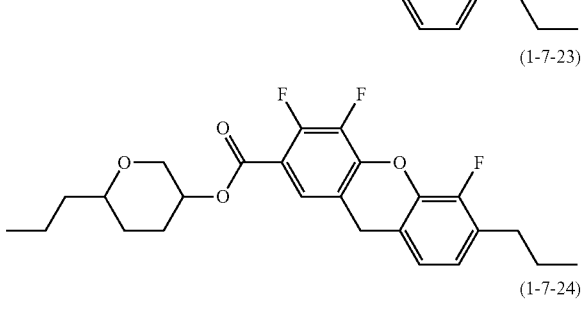
(1-7-24)
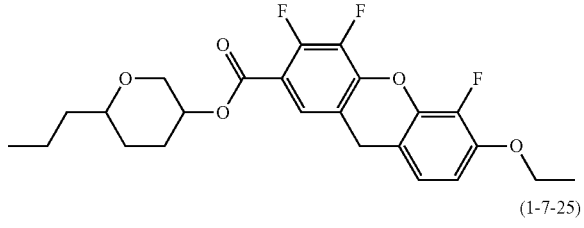
(1-7-25)
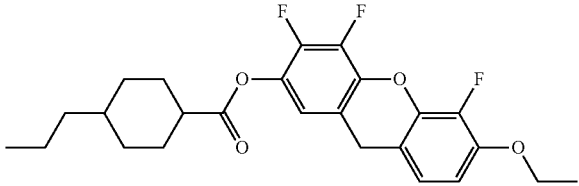

(1-7-26)
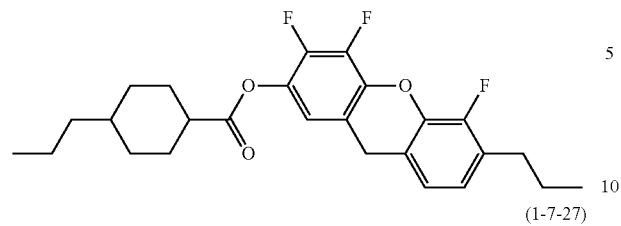
(1-7-27)
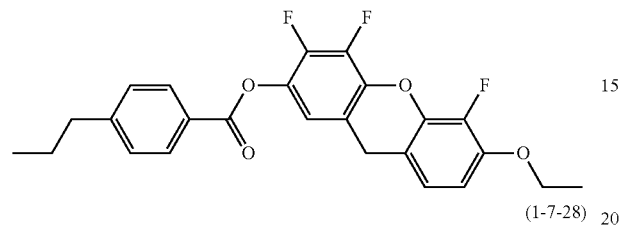
(1-7-28)
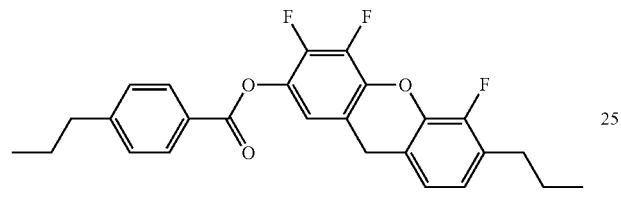
(1-7-29)
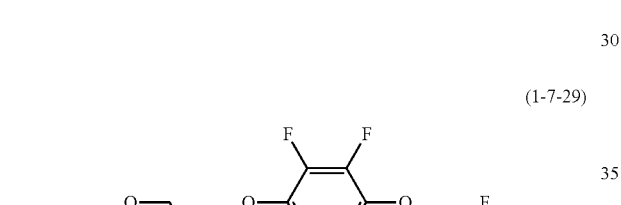
(1-7-30)
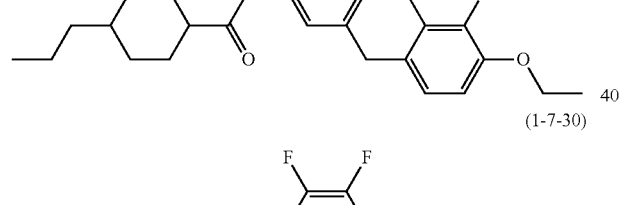
(1-7-31)
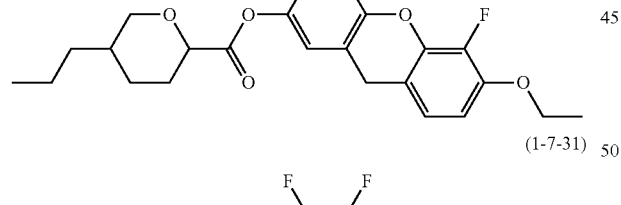
(1-7-32)
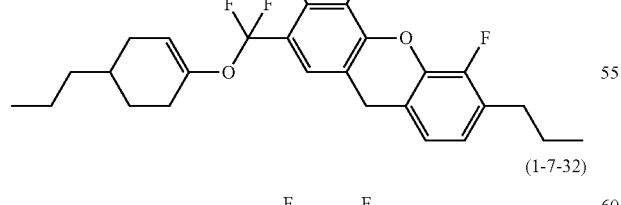
(1-7-33)
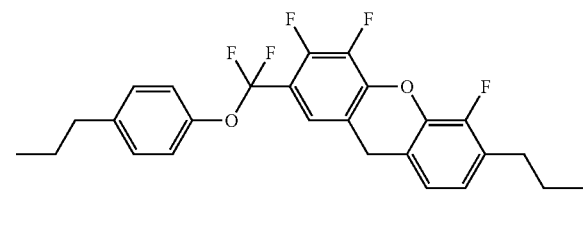
(1-7-34)
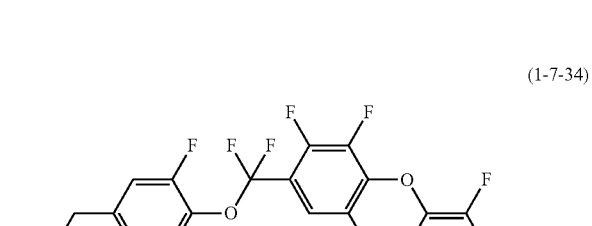
(1-7-35)
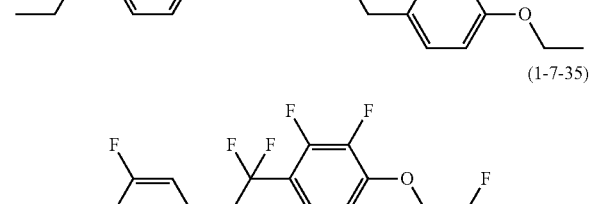
(1-7-36)
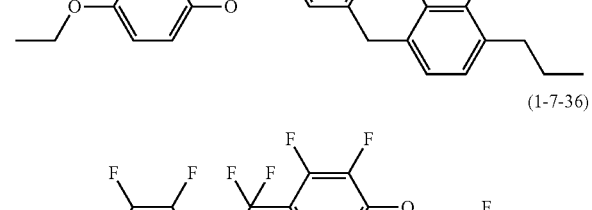
(1-7-37)
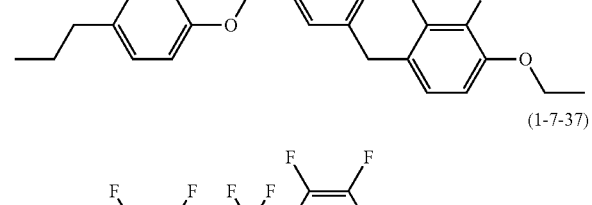
(1-7-38)
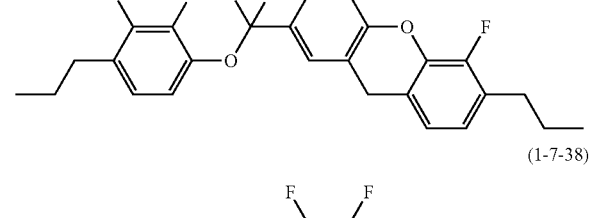
(1-7-39)
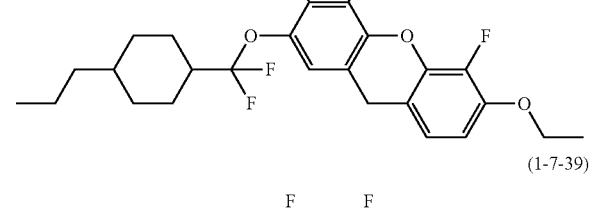

(1-7-40) 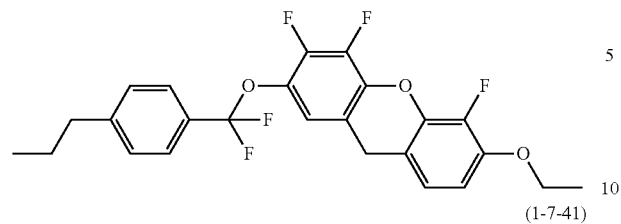
(1-7-41) 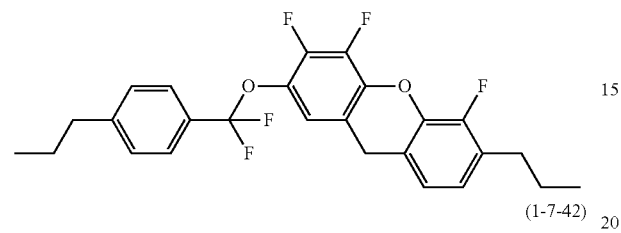
(1-7-42) 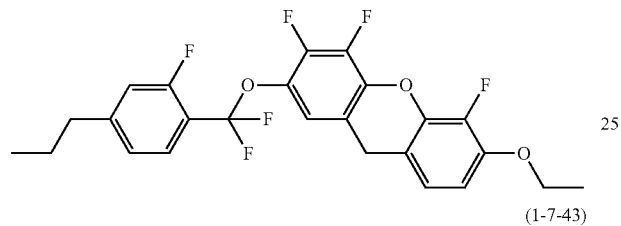
(1-7-43) 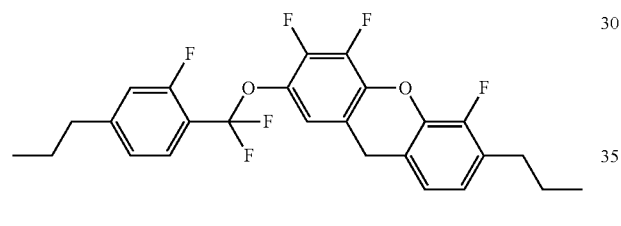
(1-7-44) 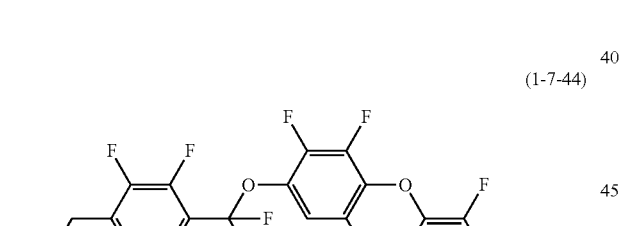
(1-7-45) 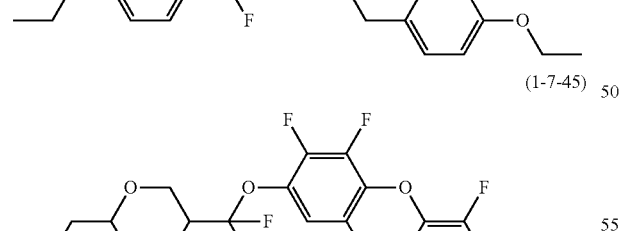
(1-7-46) 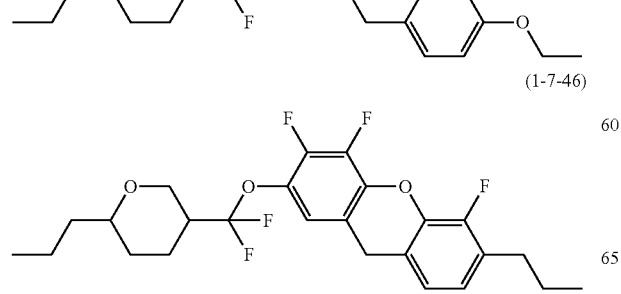
(1-7-47) 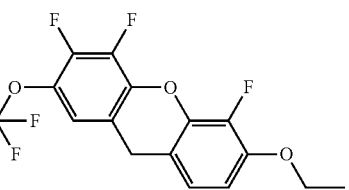
(1-7-48) 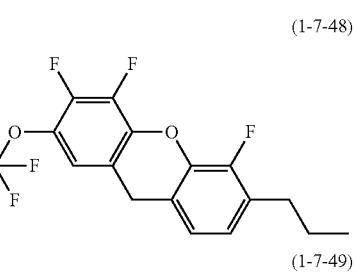
(1-7-49) 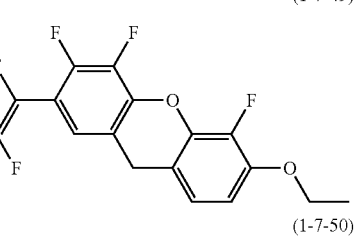
(1-7-50) 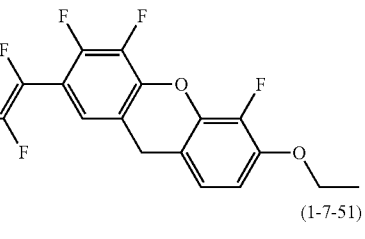
(1-7-51) 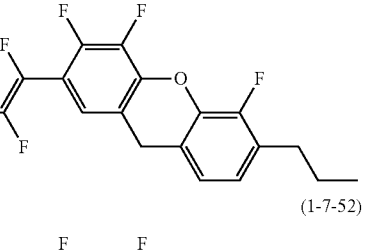
(1-7-52) 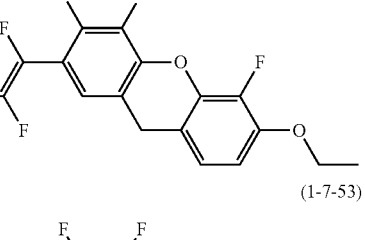
(1-7-53) 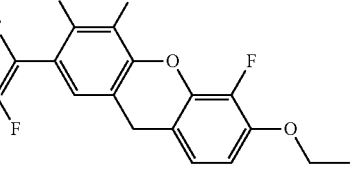

(1-7-54)
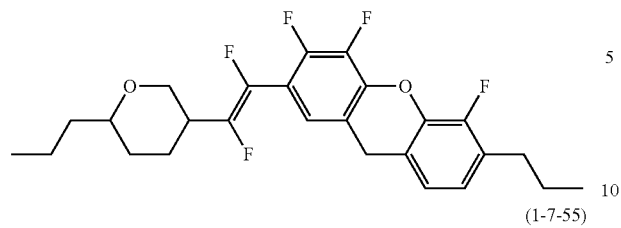
(1-7-55)
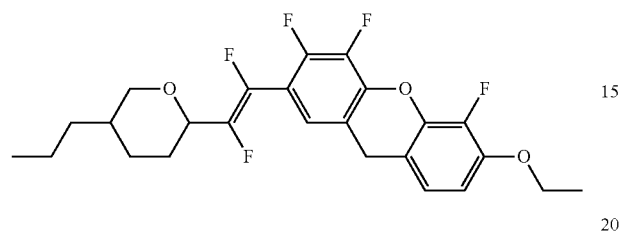
(1-7-56)
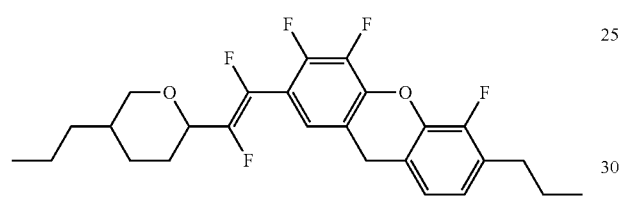
(1-8-1)
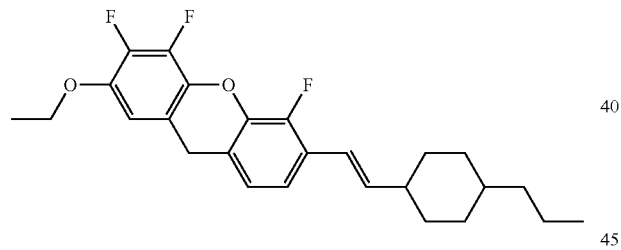
(1-8-2)
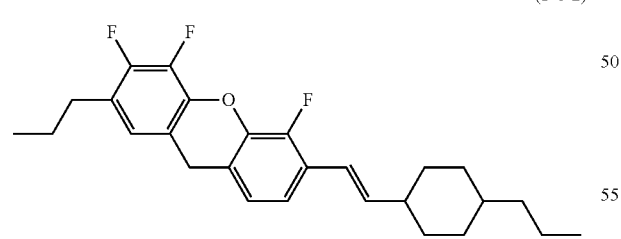
(1-8-3)
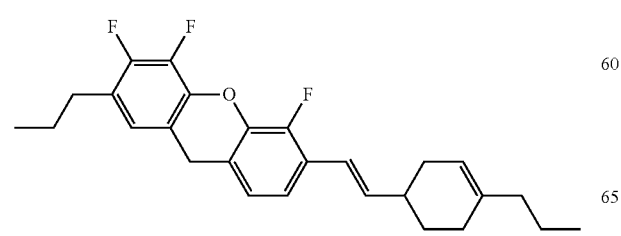
(1-8-4)
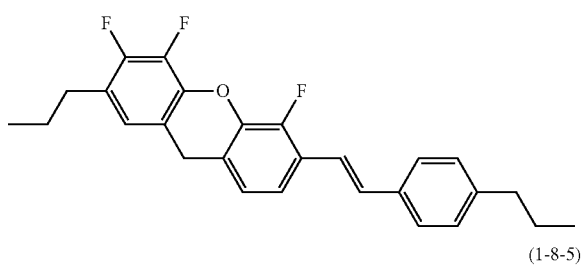
(1-8-5)
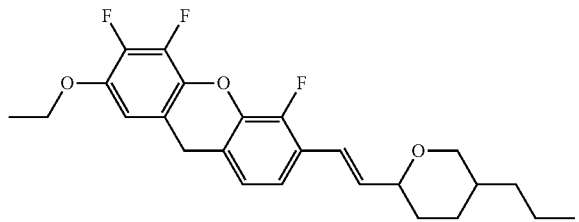
(1-8-6)
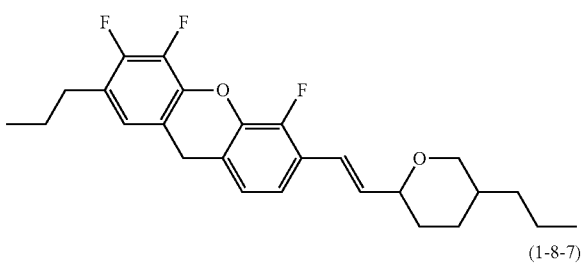
(1-8-7)
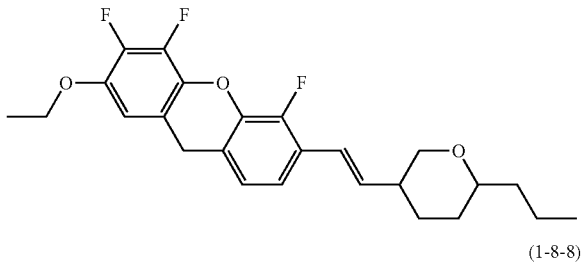
(1-8-8)
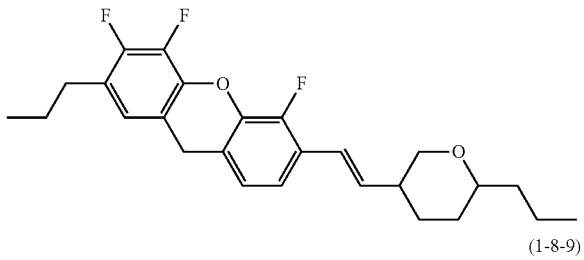
(1-8-9)
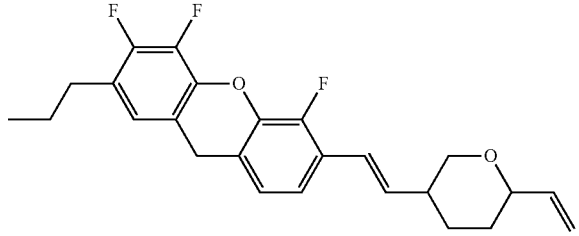

-continued (1-8-10)

(1-8-11)

(1-8-12)

(1-8-13)

(1-8-14)

(1-8-15)

(1-8-16)

-continued (1-8-17)

(1-8-18)

(1-8-19)

(1-8-20)

(1-8-21)

(1-8-22)

(1-8-23)
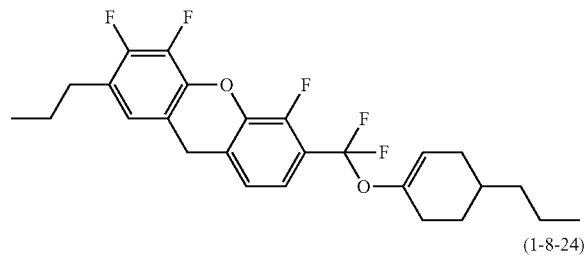
(1-8-24)
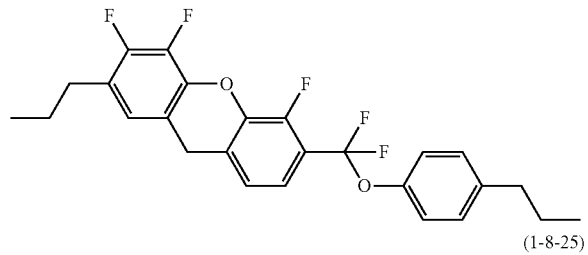
(1-8-25)
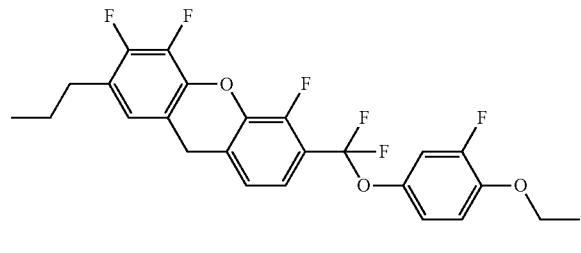
(1-8-26)
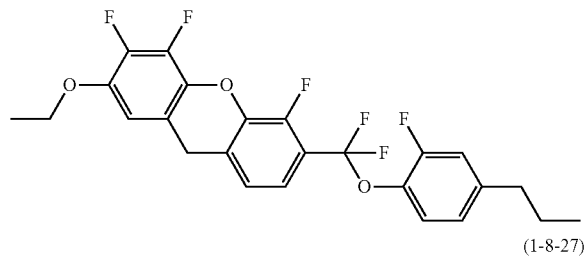
(1-8-27)
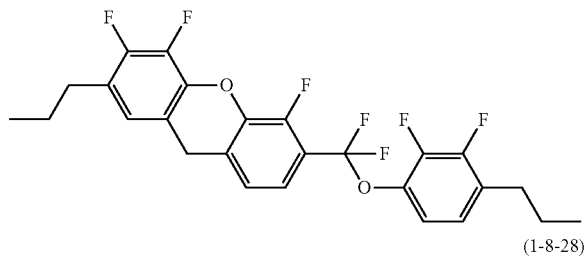
(1-8-28)
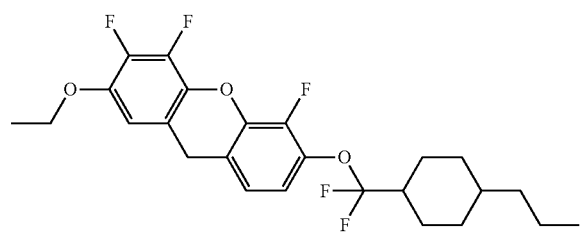
(1-8-29)
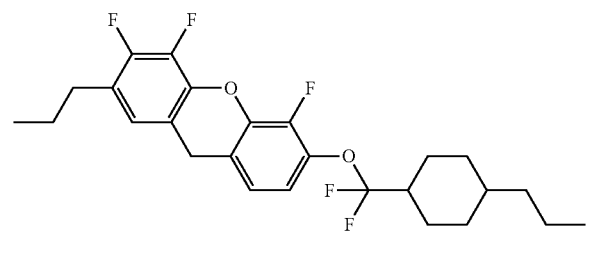
(1-8-30)
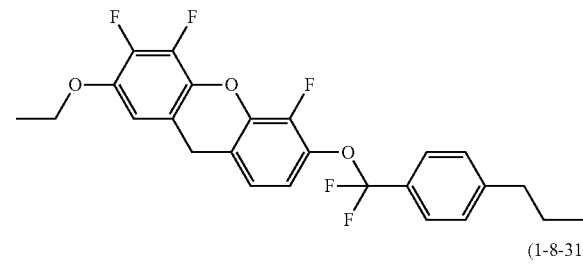
(1-8-31)
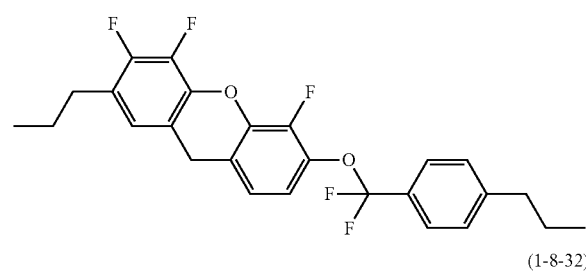
(1-8-32)
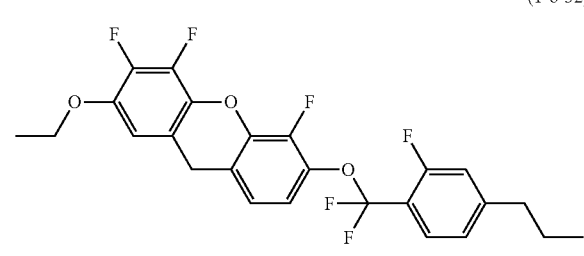
(1-8-33)
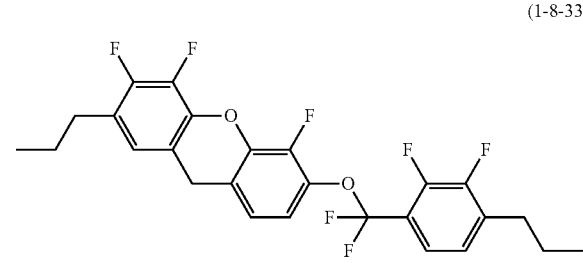
(1-8-34)
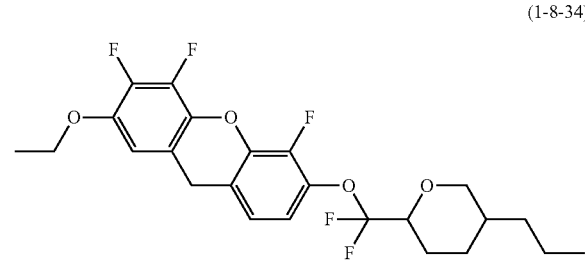

(1-8-35)
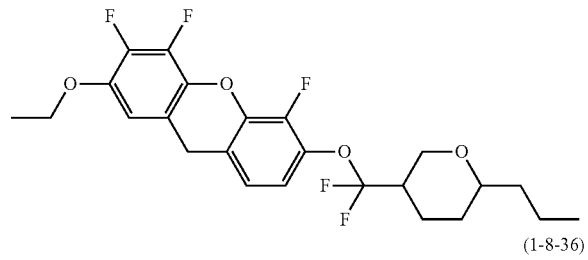
(1-8-36)
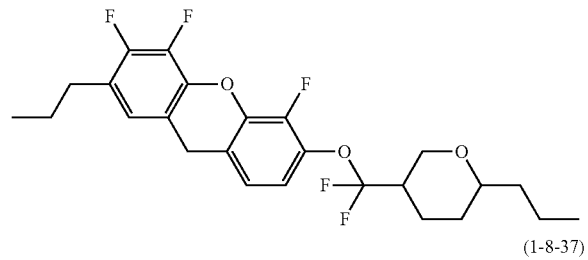
(1-8-37)
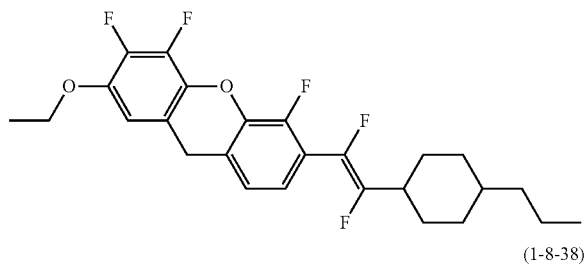
(1-8-38)
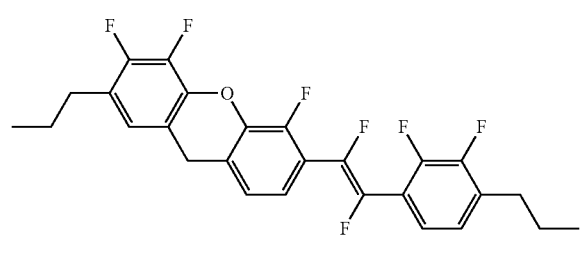
(1-8-39)
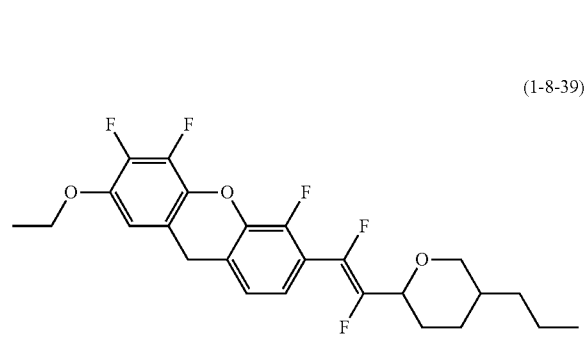
(1-8-40)
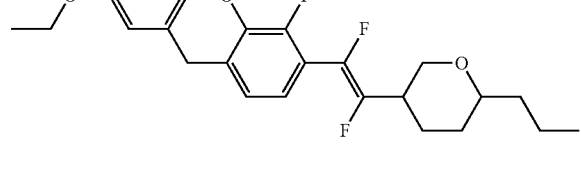
(1-9-1)
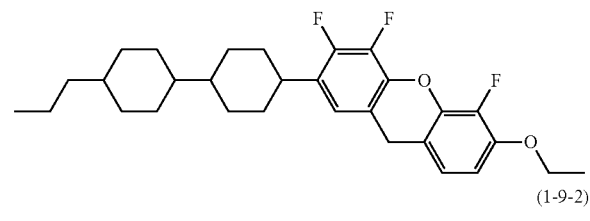
(1-9-2)
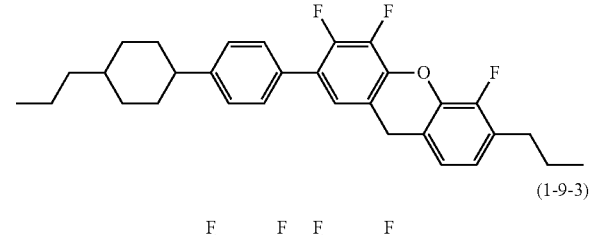
(1-9-3)
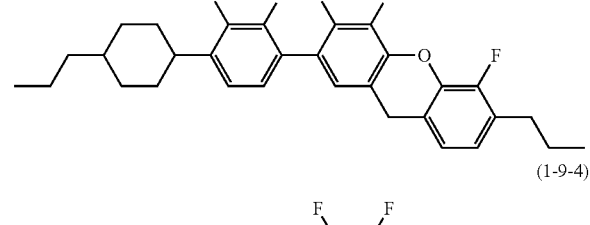
(1-9-4)
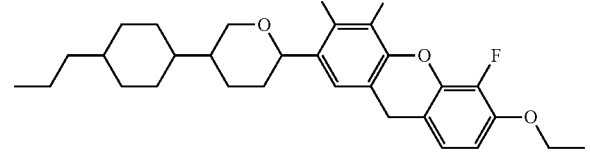
(1-9-5)
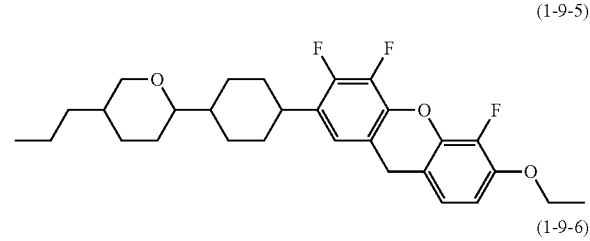
(1-9-6)
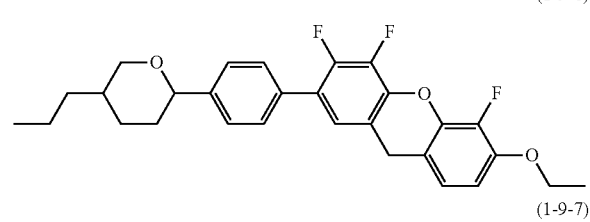
(1-9-7)
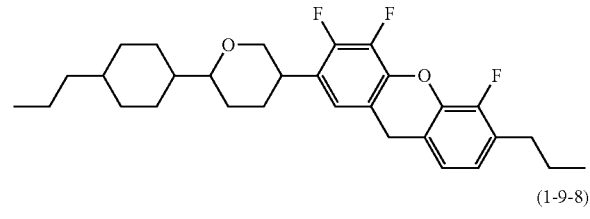
(1-9-8)
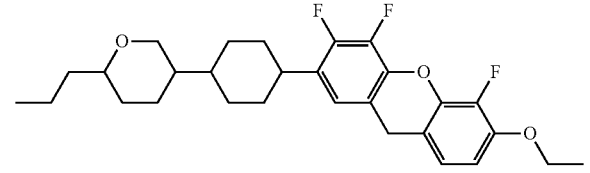

(1-9-9)
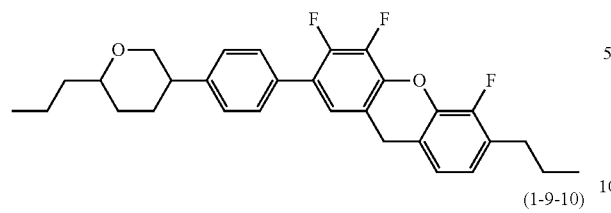
(1-9-10)
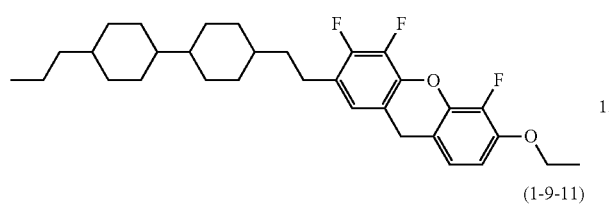
(1-9-11)
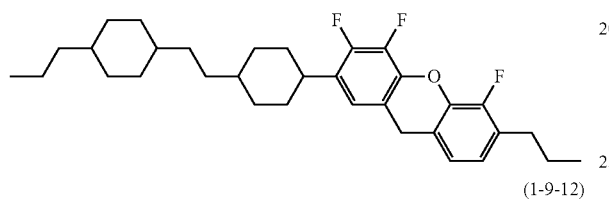
(1-9-12)
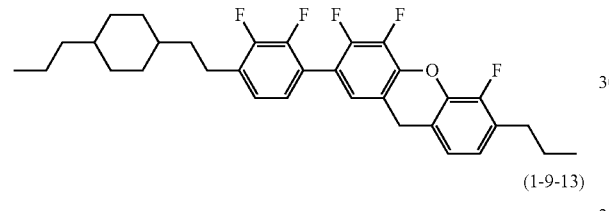
(1-9-13)
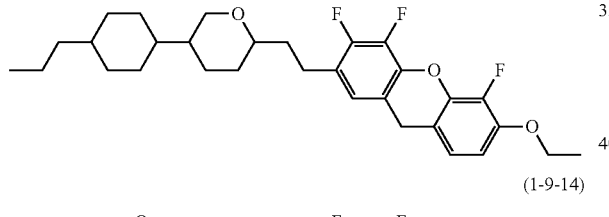
(1-9-14)
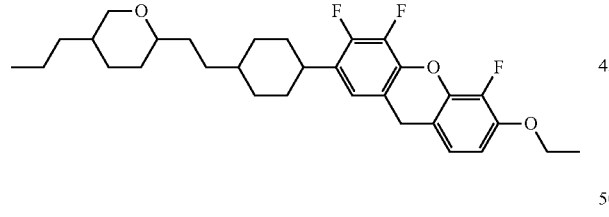
(1-9-15)
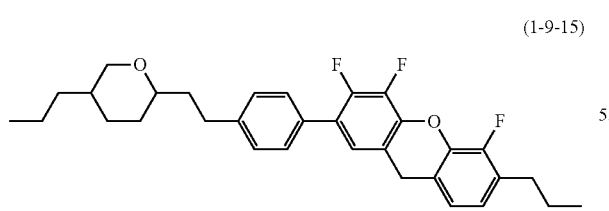
(1-9-16)
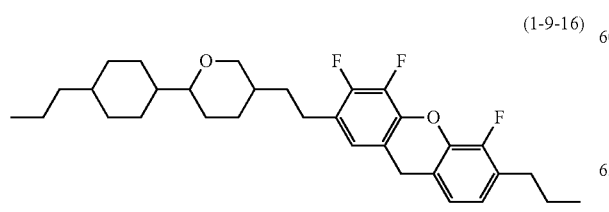
(1-9-17)
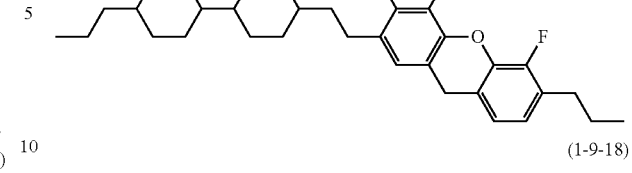
(1-9-18)
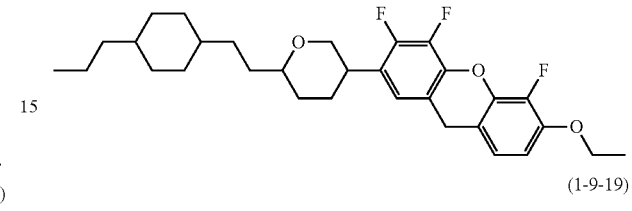
(1-9-19)
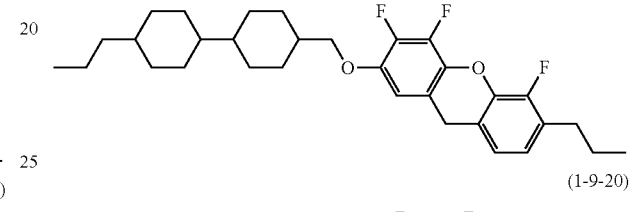
(1-9-20)
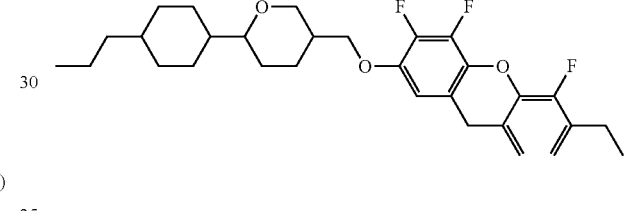
(1-9-21)
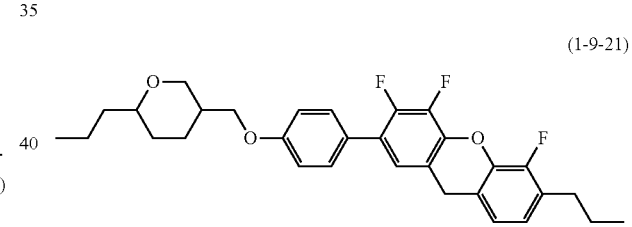
(1-9-22)
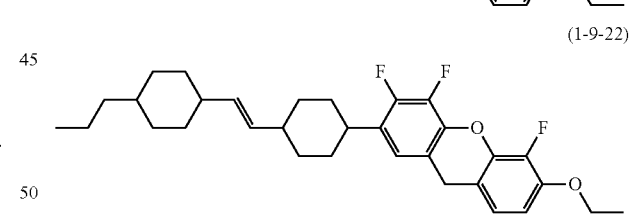
(1-9-23)
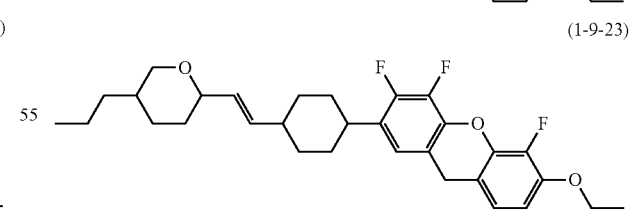
(1-9-24)
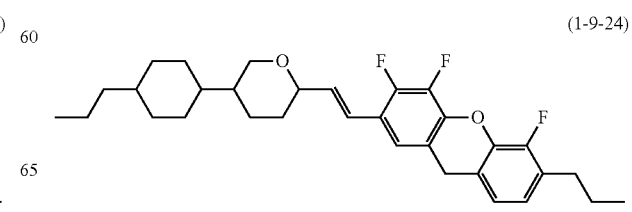

(1-9-25) 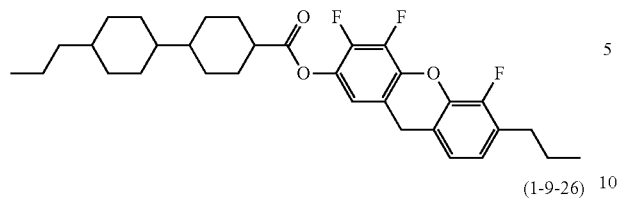
(1-9-26) 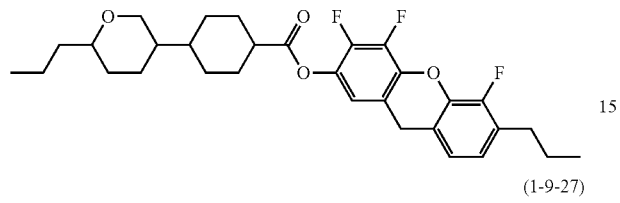
(1-9-27) 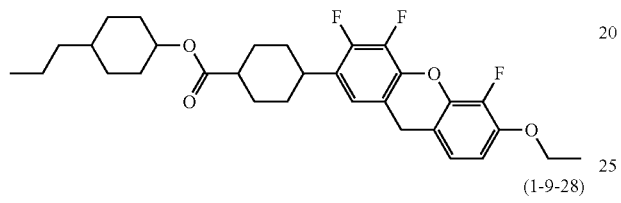
(1-9-28) 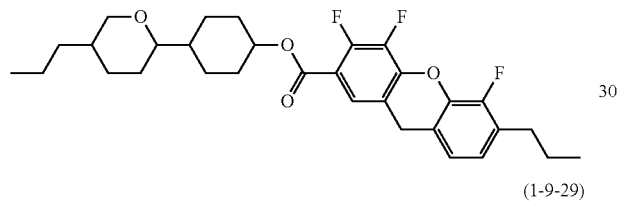
(1-9-29) 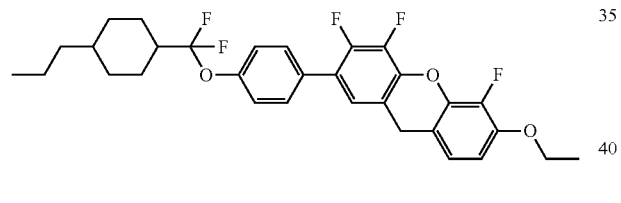
(1-9-30) 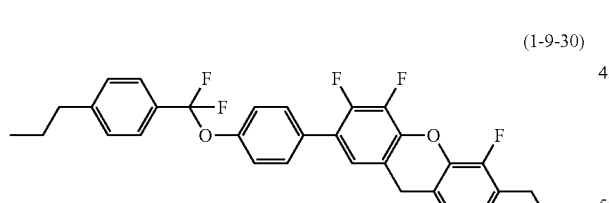
(1-9-31) 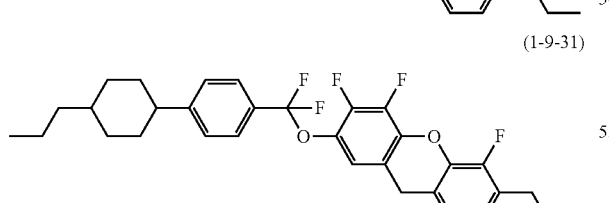
(1-9-32) 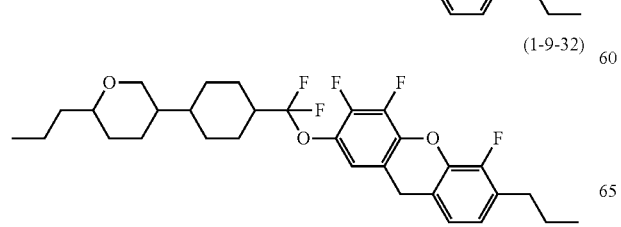
(1-9-33) 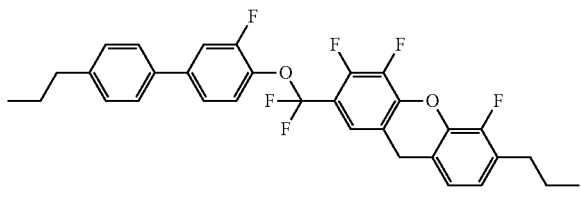
(1-9-34) 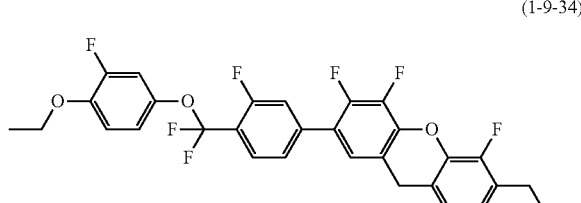
(1-9-35) 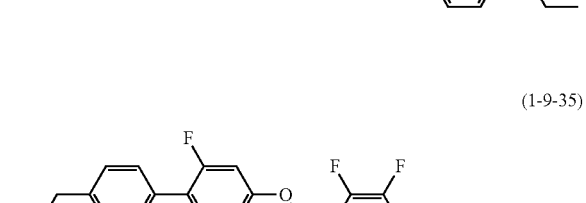
(1-9-36) 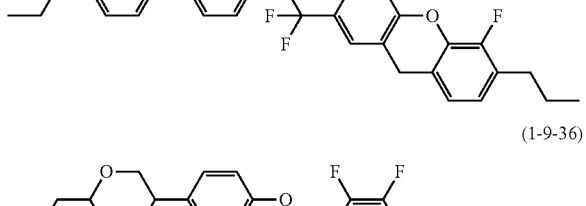
(1-9-37) 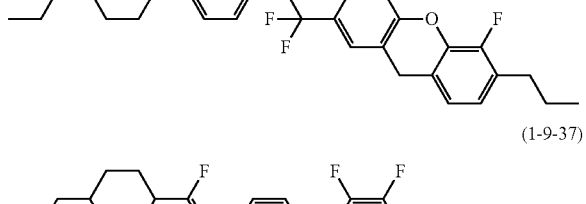
(1-10-1) 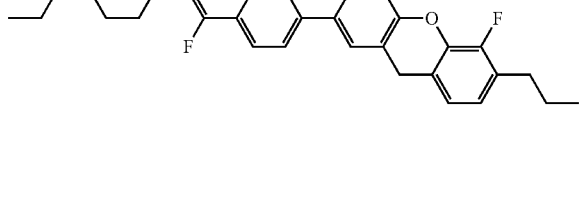
(1-10-2) 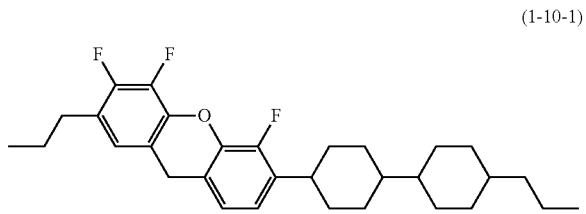
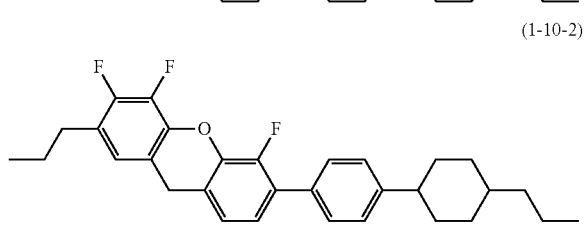

-continued
(1-10-3)
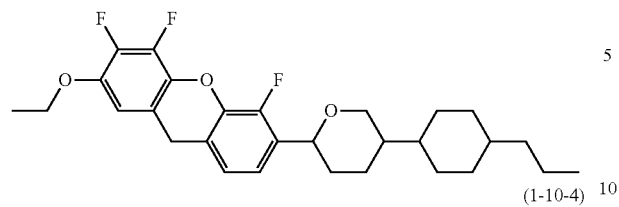
(1-10-4)
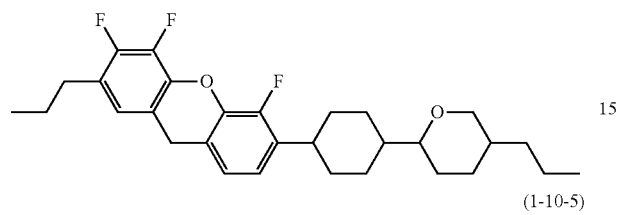
(1-10-5)
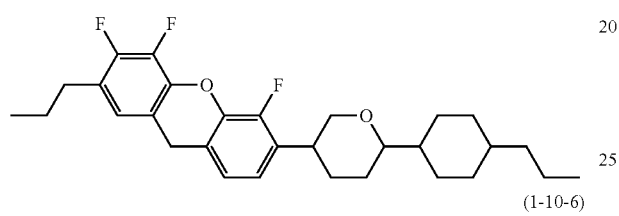
(1-10-6)
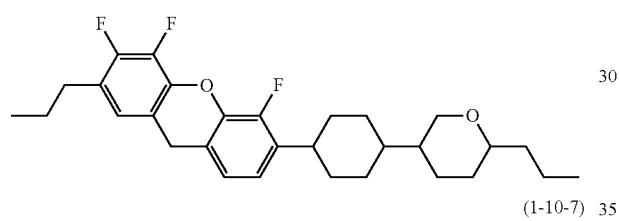
(1-10-7)
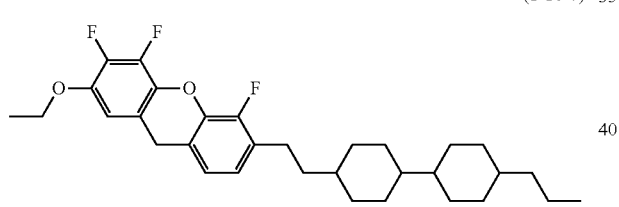
(1-10-8)
(1-10-9)
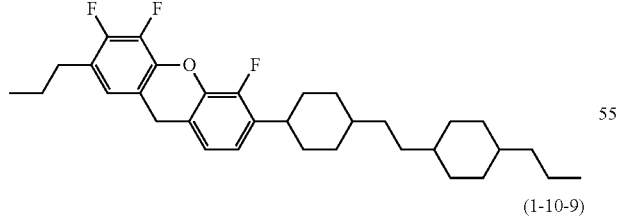
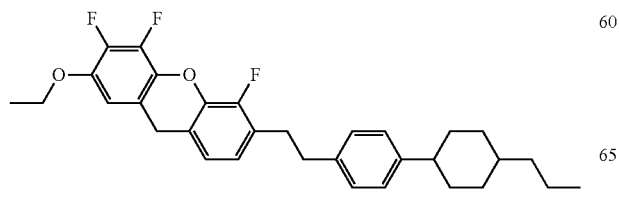
-continued
(1-10-10)
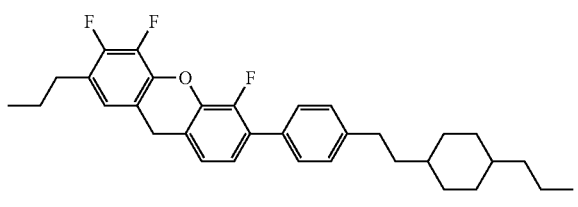
(1-10-11)
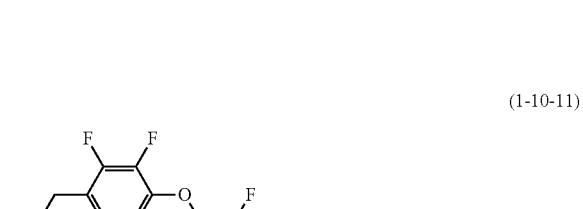
(1-10-12)
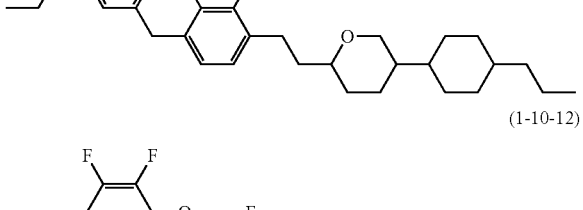
(1-10-13)
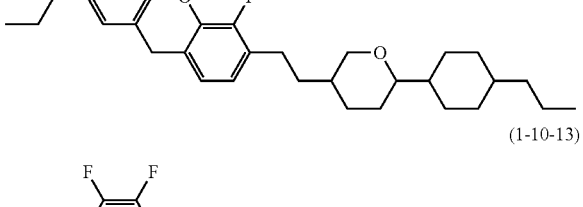
(1-10-14)
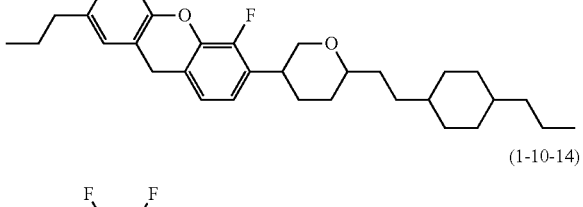
(1-10-15)
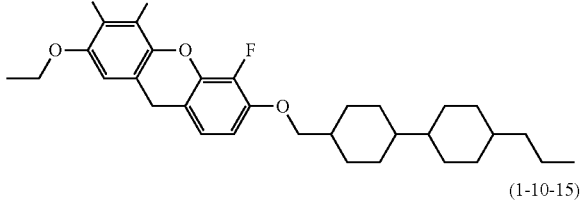
(1-10-16)
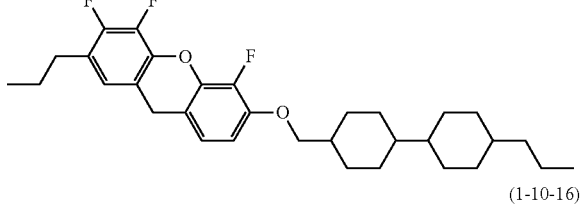
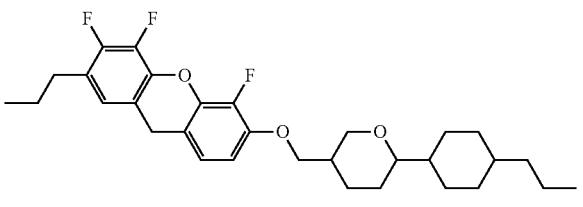

(1-10-16)
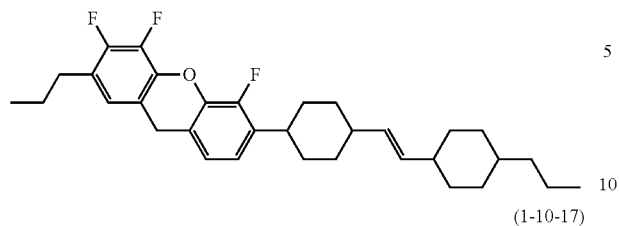
(1-10-17)
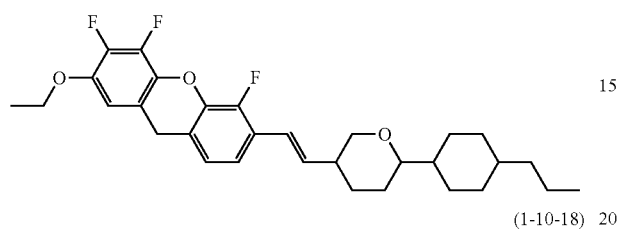
(1-10-18)
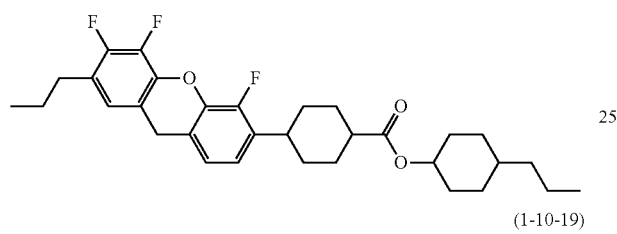
(1-10-19)
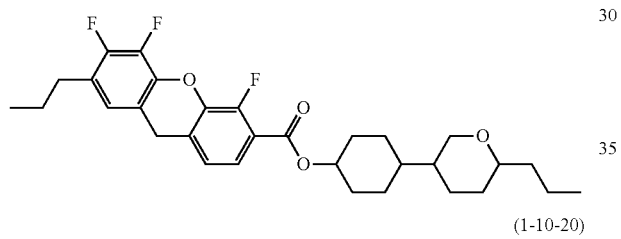
(1-10-20)
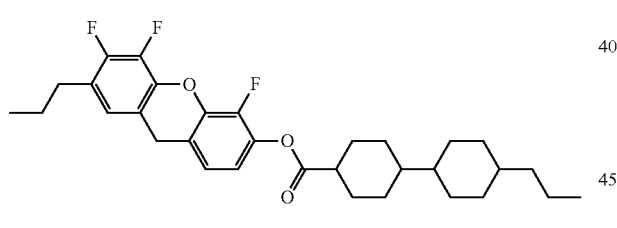
(1-10-21)
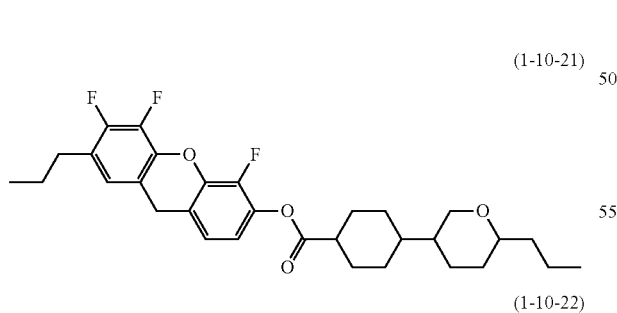
(1-10-22)
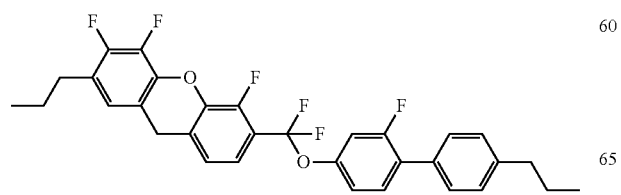
(1-10-23)
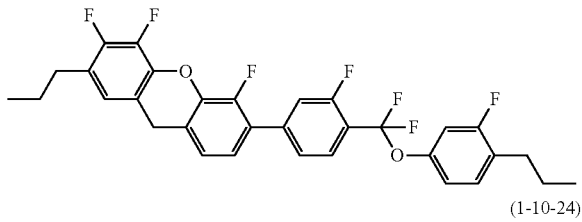
(1-10-24)
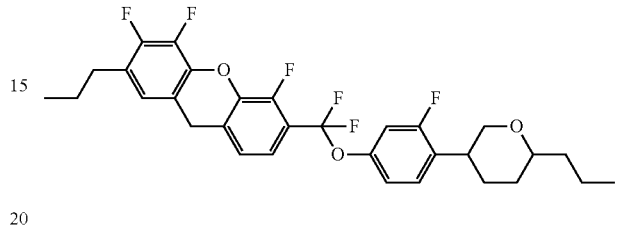
(1-10-25)
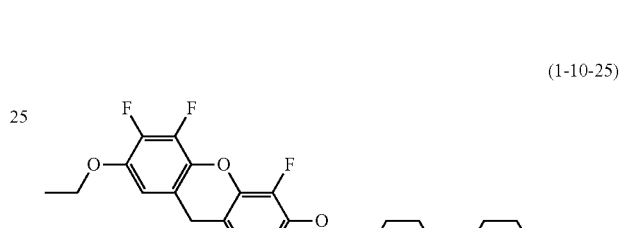
(1-10-26)
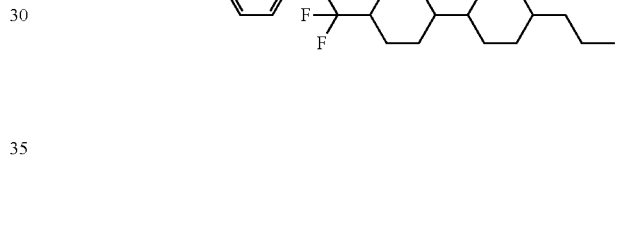
(1-10-27)
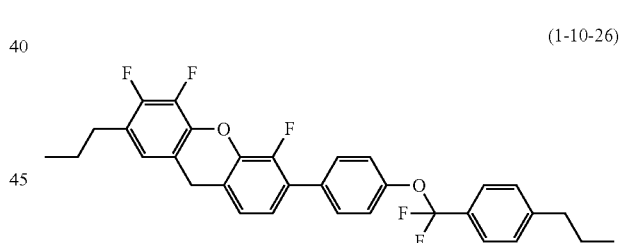
(1-10-28)
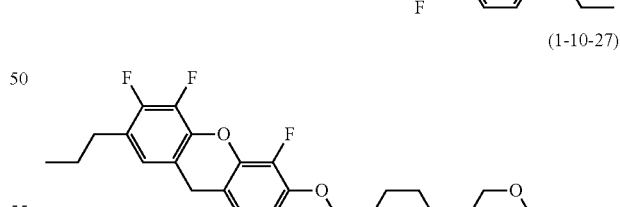
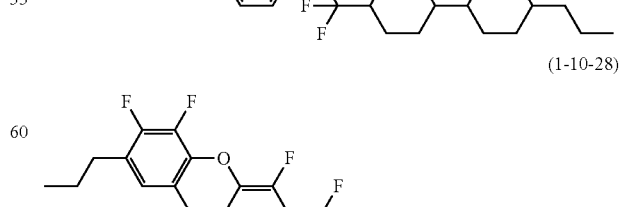

(1-11-1)
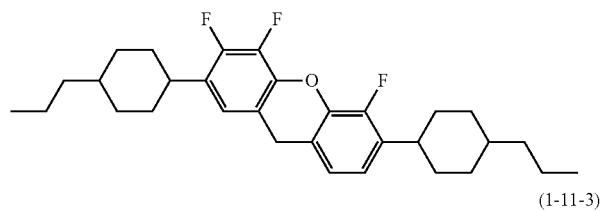
(1-11-2)
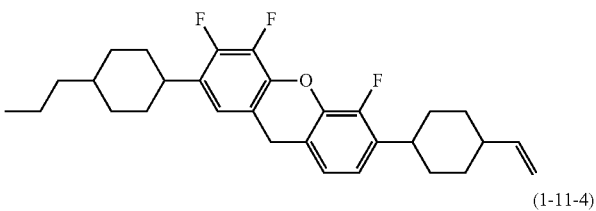
(1-11-3)
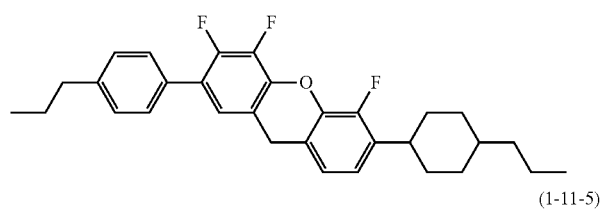
(1-11-4)
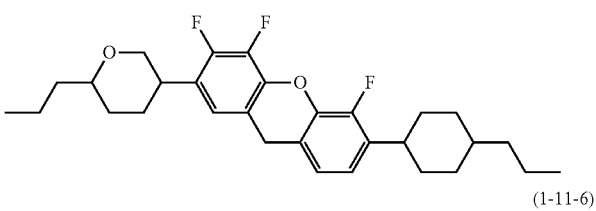
(1-11-5)
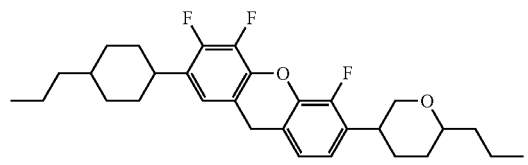
(1-11-6)
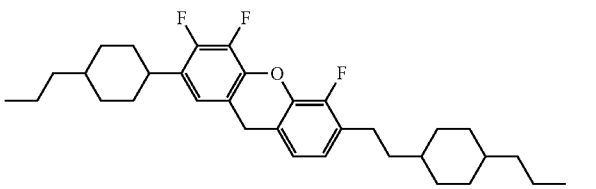
(1-11-7)
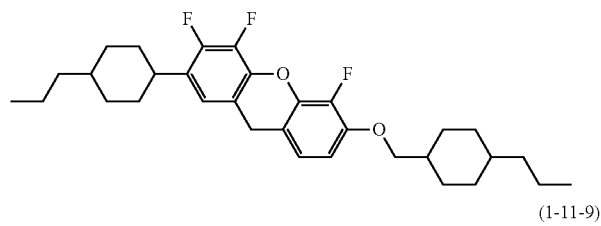
(1-11-8)
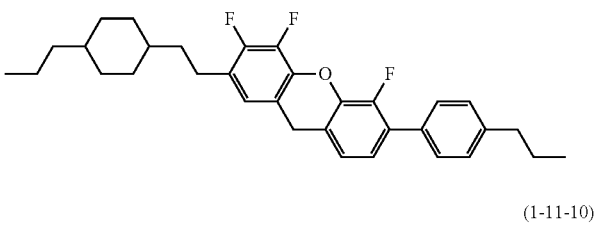
(1-11-9)
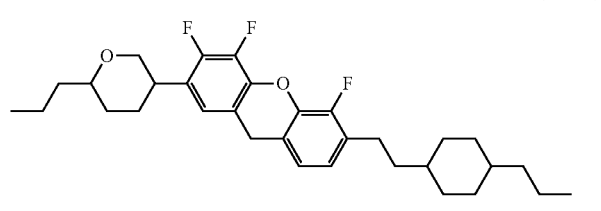
(1-11-10)
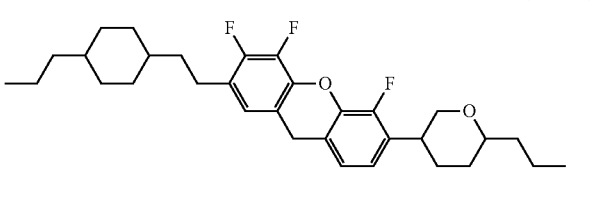
(1-11-11)
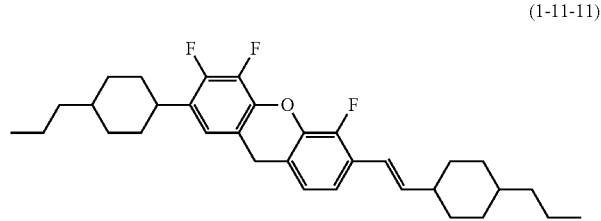
(1-11-12)
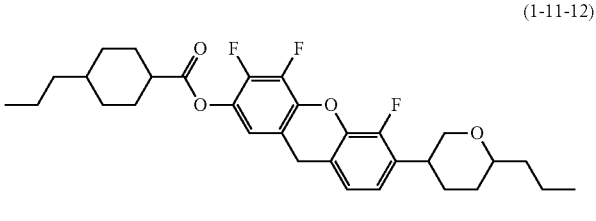
(1-11-13)
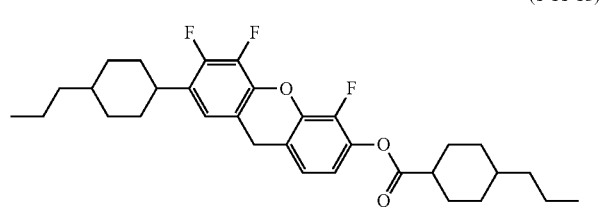
(1-11-14)

-continued
(1-11-15)
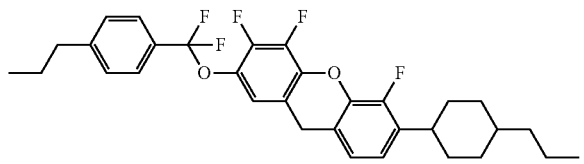
(1-11-16)
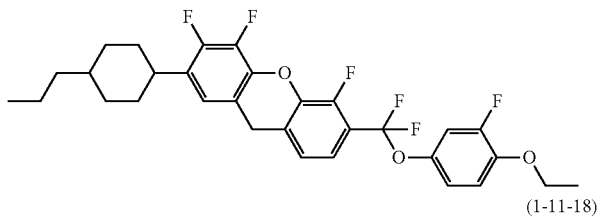
(1-11-17)
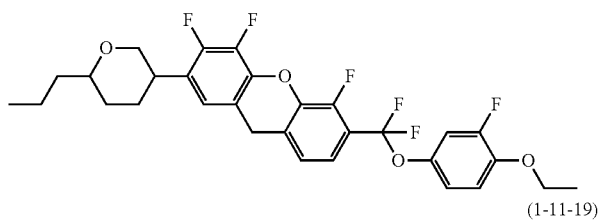
(1-11-18)
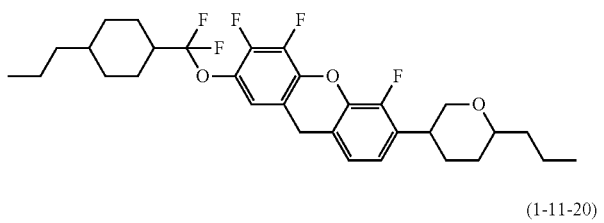
(1-11-19)
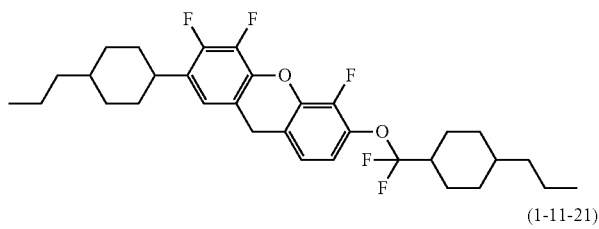
(1-11-20)
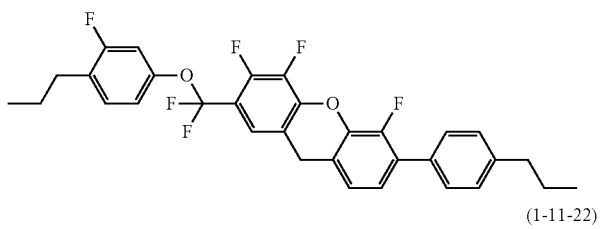
(1-11-21)
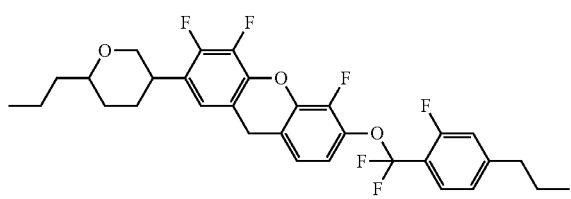
(1-11-22)
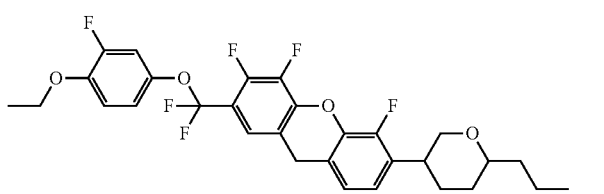
(1-11-23)
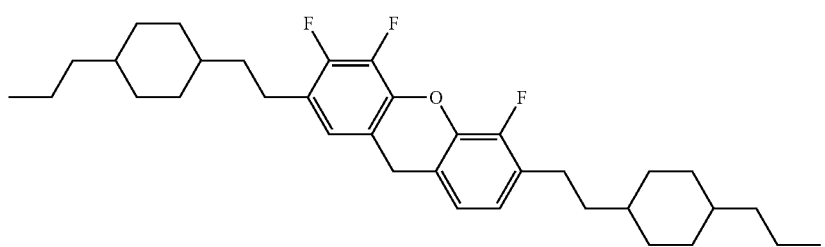
(1-11-24)
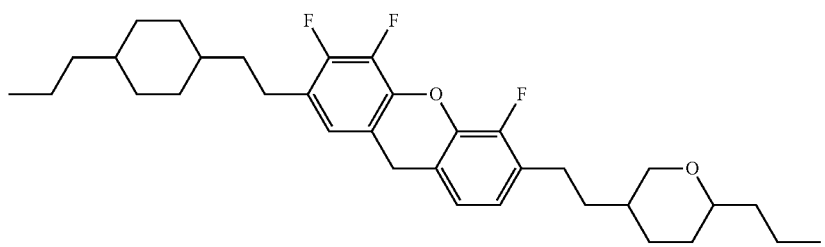
(1-11-25)

(1-11-26)

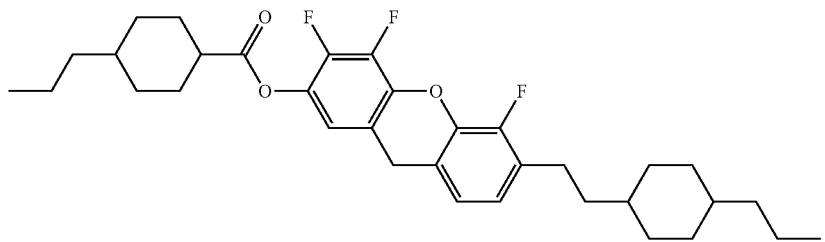

(1-11-27)

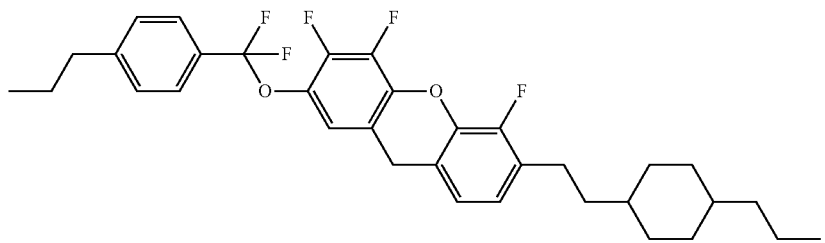

Comparative Example 1

As a comparative compound, compound (C-1) was prepared. The reason is that the compound is described in JP 2005-314417 A.

Synthesis of Comparative Compound (C-1)

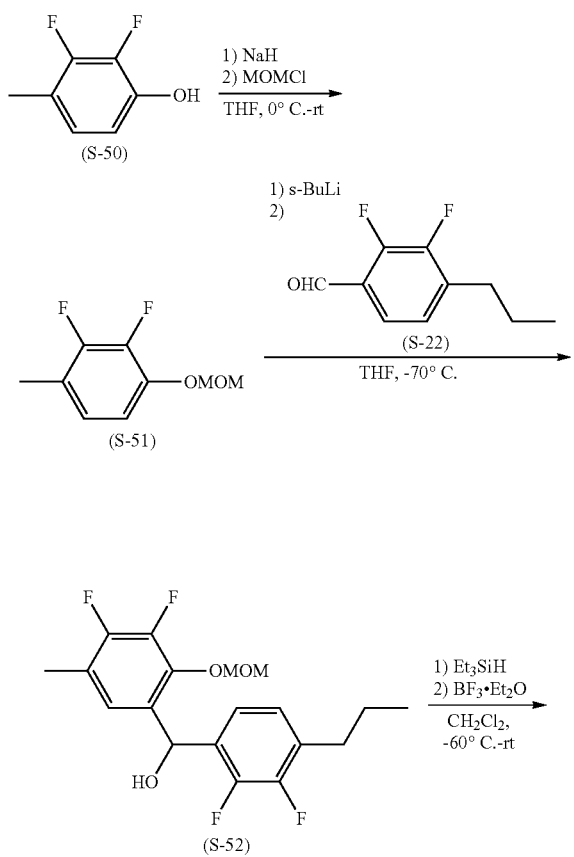

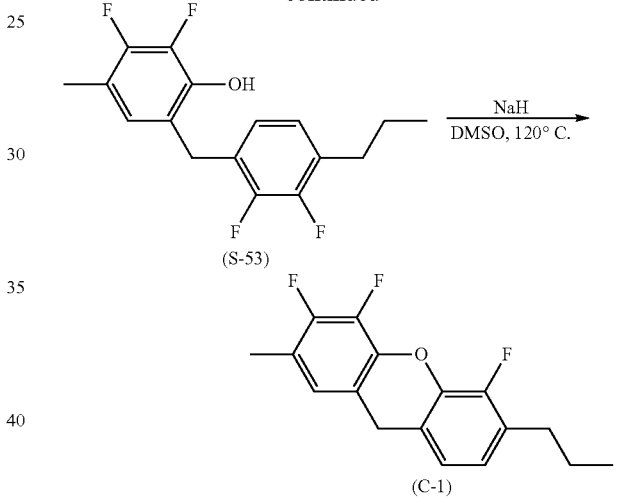

First Step

Under a nitrogen atmosphere, sodium hydride (2.13 g) and THF (35 mL) were put in a reaction vessel and the resulting mixture was cooled to 0° C. A THF solution (15 mL) of compound (S-50) (17.6 g) was slowly added thereto and the resulting mixture was stirred for 1 hour, and then chloromethyl methyl ether (3.71 mL) was slowly added thereto, and temperature was increased to room temperature. The reaction mixture was poured into water, and a water layer was subjected to extraction with diethyl ether. A combined organic layer was washed with water and saturated brine, and dried over anhydrous magnesium sulfate. The resulting solution was concentrated under reduced pressure, and the resulting residue was purified by silica gel chromatography (heptane:ethyl acetate=4:1 in a volume ratio) to obtain compound (S-51) (6.30 g; 82%).

Second Step

Under a nitrogen atmosphere, compound (S-51) (6.30 g) and THF (60 mL) were put in a reaction vessel and the resulting mixture was cooled to −70° C. Then, s-butyllithium (1.07 M cyclohexane solution, 37.6 mL) was slowly added thereto and the resulting mixture was stirred for 1 hour, and then a THF solution (35 mL) of compound (S-22) (5.25 g) was slowly added thereto, and the resulting mixture was heated to room temperature. The reaction mixture was poured into water, and a water layer was subjected to extraction with ethyl acetate. A combined organic layer was washed with water and saturated brine, and dried over anhydrous magnesium sulfate. The resulting solution was concentrated under reduced pressure, and the resulting residue was purified by silica gel chromatography (heptane: ethyl acetate=4:1 in a volume ratio) to obtain compound (S-52) (6.08 g; 57%).

Fifth Step

Under a nitrogen atmosphere, compound (S-52) (6.08 g) and dichloromethane (60 mL) were put in a reaction vessel, and the resulting mixture was cooled to −60° C. Triethylsilane (5.20 mL) was added thereto and the resulting mixture was stirred for 1 hour, and then a boron trifluoride-diethyl ether complex (12.4 mL) was slowly added thereto, and temperature was increased to room temperature. The reaction mixture was poured into ice water, and an organic layer was washed with water and saturated brine, and dried over anhydrous magnesium sulfate. The resulting solution was concentrated under reduced pressure, and the resulting residue was purified by silica gel chromatography (heptane: ethyl acetate=2:1 in a volume ratio) to obtain compound (S-53) (4.82 g; 95%).

Sixth Step

Under a nitrogen atmosphere, sodium hydride (0.74 g) and dimethylsulfoxide (60 mL) were put in a reaction vessel, a dimethyl sulfoxide solution (35 mL) of compound (S-53) (4.82 g) was slowly added thereto, and the resulting mixture was heated to 120° C. and stirred for 9 hours. The reaction mixture was poured into an ice-cooled 1 N hydrochloric acid solution, and a water layer was subjected to extraction with toluene. A combined organic layer was washed with water and saturated brine, and dried over anhydrous magnesium sulfate. The resulting solution was concentrated under reduced pressure, and the resulting residue was purified by silica gel chromatography (heptane:toluene=4:1 in a volume ratio). Further, the resulting material was purified by recrystallization from a mixed solvent of 2-propanol and ethyl acetate (volume ratio, 1:1) to obtain compound (C-1) (1.96 g; 43%).

Chemical shift δ (ppm; CDCl$_3$): 6.88-6.82 (m, 2H), 6.72 (d, J=6.8 Hz, 1H), 3.96 (s, 2H), 2.67-2.60 (m, 2H), 2.26 (d, J=2.0, 3H), 1.69-1.60 (m, 2H), 0.95 (t, J=7.4 Hz, 3H).

Physical properties of comparative compound (C-1) were as described below. For measurement of maximum temperature, optical anisotropy, dielectric anisotropy and viscosity, the sample in which the ratio of the compound to the base liquid crystal was 5% by weight: 95% by weight was used.

Transition temperature: C 112.5 I.

Maximum temperature ($T_{NI}$)=−53.4° C.; optical anisotropy (Δn)=0.097; dielectric anisotropy (Δ∈)=−7.2; viscosity (Δn)=67.0 mPa·s.

If physical properties of compounds (1-5-1) and (1-5-13) obtained in Examples 3 and 5 are compared with comparison compound (C-1), compounds (1-5-1) and (1-5-13) are found to be superb compounds having a larger negative dielectric anisotropy, a higher clearing point and a higher compatibility with other liquid crystal compounds and exhibiting a liquid crystal phase. The results are obtained due to an effect of having a ring structure bonded with a trifluoroxanthene skeleton.

1-2. Example of Composition (1)

Liquid crystal composition (1) of the invention will be described in detail by way of Examples. However, the invention is not limited by the Examples. The invention includes a mixture of the composition in Example 6 and the composition in Example 7. The invention also includes a mixture in which at least two compositions in Examples are mixed. Compounds described in Examples were expressed using symbols according to definitions in Table 1 below. In Table 1, a configuration of 1,4-cyclohexylene is trans. A parenthesized number next to a symbolized compound in Examples corresponds to the number of the compound. A symbol (-) means any other liquid crystal compound. A ratio (percentage) of a liquid crystal compound is expressed in terms of weight percentage (% by weight) based on the total weight of the liquid crystal composition. Values of physical properties of the composition were summarized in a last part. The physical properties were measured according to the methods described above, and were directly described without extrapolating the measured values.

TABLE 1

Method for Description of Compounds using Symbols
R—(A$_1$)—Z$_1$— . . . —Z$_n$—(A$_n$)—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |

| 2) Right-terminal Group - | Symbol |
|---|---|
| —$C_nH_{2n+1}$ | -n |
| —$OC_nH_{2n+1}$ | —On |
| —COOCH$_3$ | —EMe |
| —CH=CH$_2$ | —V |
| —CH=CH—$C_nH_{2n+1}$ | —Vn |
| —$C_nH_{2n}$—CH=CH$_2$ | —nV |
| —$C_mH_{2m}$—CH=CH—$C_nH_{2n+1}$ | —mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —CF=CH—CF$_3$ | —FVCF3 |
| —C≡N | —C |

| 3) Bonding Group —$Z_n$— | Symbol |
|---|---|
| —$C_nH_{2n}$— | n |
| —COO— | E |
| —CH=CH— | V |
| —CH$_2$O— | 1O |
| —OCH$_2$— | O1 |
| —CF$_2$O— | X |
| —C≡C— | T |

| 4) Ring Structure —$A_n$— | Symbol |
|---|---|
|  | H |
|  | B |

TABLE 1-continued

Method for Description of Compounds using Symbols
R—(A₁)—Z₁—...—Zₙ—(Aₙ)—R'

| Structure | Symbol |
|---|---|
| 1,4-phenylene with 3-F | B(F) |
| 1,4-phenylene with 2-F | B(2F) |
| 1,4-phenylene with 2,3-diF | B(F,F) |
| 1,4-phenylene with 2F,5F | B(2F,5F) |
| 1,4-phenylene with 2F,3F | B(2F,3F) |
| 1,4-phenylene with 2F,3Cl | B(2F,3CL) |
| 1,3-dioxane | G |
| tetrahydropyran (2,5) | dh |
| tetrahydropyran (2,6) | Dh |
| chromane with 7F,8F | Cro(7F,8F) |
| xanthene with 3F,4F,5F | Xt(3F,4F,5F) |
| cyclohexene | ch |

5) Examples of Description

Example 1  3-H1OXt(3F,4f,5F)—O2

Example 2  3-DhXt(3F,4F,5F)—O2

Example 6

| | | |
|---|---|---|
| 3-H1OXt(3F,4F,5F)-O2 | (1-5-1) | 3% |
| 2-HB-C | (5-1) | 5% |
| 3-HB-C | (5-1) | 12% |
| 3-HB-O2 | (13-5) | 12% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

NI = 102.7° C.; Δn = 0.102; Δε = 4.1; η = 21.3 mPa·s.

Example 7

| | | |
|---|---|---|
| 3-H1OXt(3F,4F,5F)-O4 | (1-5-2) | 3% |
| 5-HB-CL | (2-2) | 16% |
| 3-HH-4 | (13-1) | 12% |
| 3-HH-5 | (13-1) | 4% |
| 3-HHB-F | (3-1) | 4% |
| 3-HHB-CL | (3-1) | 3% |

-continued

| | | |
|---|---|---|
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 110.2° C.; Δn = 0.089; Δε = 3.3; η = 20.4 mPa · s.

Example 8

| | | |
|---|---|---|
| 3-H1OXt(3F,4F,5F)-3 | (1-5-13) | 3% |
| 5-HB-CL | (2-2) | 3% |
| 7-HB(F)-F | (2-3) | 7% |
| 3-HH-4 | (13-1) | 9% |
| 3-HH-EMe | (13-2) | 23% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 4% |

NI = 80.1° C.; Δn = 0.066; Δε = 4.7; η = 21.6 mPa · s.

Example 9

| | | |
|---|---|---|
| 3-HXt(3F,4F,5F)-O2 | (1-1-1) | 3% |
| 3-HB-O1 | (13-5) | 15% |
| 3-HH-4 | (13-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 10% |
| 3-HHB-1 | (14-1) | 6% |

NI = 84.6° C.; Δn = 0.091; Δε = −3.6; η = 36.7 mPa · s.

Example 10

| | | |
|---|---|---|
| 2O-Xt(3F,4F,5F)H-3 | (1-2-1) | 1% |
| 3-dhXt(3F,4F,5F)-3 | (1-1-61) | 3% |
| 3-HH-4 | (13-1) | 8% |
| 3-H2B(2F,3F)-O2 | (6-4) | 22% |
| 5-H2B(2F,3F)-O2 | (6-4) | 18% |
| 2-HHB(2F,3CL)-O2 | (7-12) | 2% |
| 3-HHB(2F,3CL)-O2 | (7-12) | 3% |
| 4-HHB(2F,3CL)-O2 | (7-12) | 2% |
| 5-HHB(2F,3CL)-O2 | (7-12) | 2% |
| 3-HBB(2F,3F)-O2 | (7-7) | 9% |
| 5-HBB(2F,3F)-O2 | (7-7) | 9% |
| V-HHB-1 | (14-1) | 6% |
| 3-HHB-3 | (14-1) | 6% |
| 3-HHEBH-3 | (15-6) | 3% |
| 3-HHEBH-4 | (15-6) | 3% |
| 3-HHEBH-5 | (15-6) | 3% |

NI = 92.8° C.; Δn = 0.101; Δε = −4.1; η = 32.2 mPa · s.

Example 11

| | | |
|---|---|---|
| 5-H1OXt(3F,4F,5F)-O2 | (1-5-3) | 3% |
| 2-HH-5 | (13-1) | 3% |
| 3-HH-4 | (13-1) | 15% |
| 3-HH-5 | (13-1) | 4% |
| 3-HB-O2 | (13-5) | 12% |
| 3-H2B(2F,3F)-O2 | (6-4) | 12% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 9% |
| 3-HHB-1 | (14-1) | 3% |
| 3-HHB-3 | (14-1) | 4% |
| 3-HHB-O1 | (14-1) | 3% |

NI = 78.5° C.; Δn = 0.095; Δε = −4.3; η = 22.1 mPa · s.

Example 12

| | | |
|---|---|---|
| 5-BXt(3F,4F,5F)-3 | (1-1-35) | 3% |
| 2-HH-3 | (13-1) | 21% |
| 3-HH-4 | (13-1) | 9% |
| 1-BB-3 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 10% |
| 3-HH1OB(2F,3F)-O2 | (7-5) | 21% |
| 3-HHB-1 | (14-1) | 5% |
| 3-HHB-O1 | (14-1) | 3% |
| 5-B(F)BB-2 | (14-8) | 2% |

Example 13

| | | |
|---|---|---|
| 3-DhXt(3F,4F,5F)-O2 | (1-1-66) | 3% |
| 2-HH-3 | (13-1) | 16% |
| 7-HB-1 | (13-5) | 10% |
| 5-HB-O2 | (13-5) | 8% |
| 3-HB(2F,3F)-O2 | (6-1) | 17% |
| 5-HB(2F,3F)-O2 | (6-1) | 16% |
| 3-HHB(2F,3CL)-O2 | (7-12) | 3% |
| 4-HHB(2F,3CL)-O2 | (7-12) | 3% |
| 5-HHB(2F,3CL)-O2 | (7-12) | 2% |
| 3-HH1OCro(7F,8F)-5 | (10-6) | 5% |
| 5-HBB(F)B-2 | (15-5) | 10% |
| 5-HBB(F)B-3 | (15-5) | 7% |

Example 14

| | | |
|---|---|---|
| 3-DhXt(3F,4F,5F)-3 | (1-1-71) | 3% |
| 1-BB-3 | (13-8) | 10% |
| 3-HH-V | (13-1) | 26% |
| 3-BB(2F,3F)-O2 | (6-3) | 13% |
| 3-HBB(2F,3F)-O2 | (7-7) | 10% |
| 2-HH1OB(2F,3F)-O2 | (7-5) | 10% |
| 3-HH1OB(2F,3F)-O2 | (7-5) | 14% |
| 3-HHB-1 | (14-1) | 8% |
| 5-B(F)BB-2 | (14-8) | 6% |

NI = 74.4° C.; Δn = 0.108; Δε = −3.3; η = 18.8 mPa · s.

Example 15

| | | |
|---|---|---|
| V-H1OXt(3F,4F,5F)-O2 | (1-5-4) | 3% |
| 3-GB(F)B(F,F)XB(F,F)-F | (4-57) | 5% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 41% |
| 3-HH-V1 | (13-1) | 7% |
| 3-HHEH-5 | (14-13) | 3% |
| 3-HHB-1 | (14-1) | 4% |
| V-HHB-1 | (14-1) | 2% |
| V2-BB(F)B-1 | (14-6) | 5% |
| 1V2-BB-F | (2-1) | 3% |
| 3-BB(F,F)XB(F,F)-F | (3-97) | 6% |
| 3-GB(F,F)XB(F,F)-F | (3-113) | 5% |
| 3-HHBB(F,F)-F | (4-6) | 3% |

Example 16

| | | |
|---|---|---|
| 3-dhXt(3F,4F,5F)-O2 | (1-1-57) | 3% |
| 2-HB-C | (5-1) | 5% |
| 3-HB-C | (5-1) | 12% |
| 3-HB-O2 | (13-5) | 12% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

Example 17

| | | |
|---|---|---|
| 5-HXt(3F,4F,5F)-3 | (1-1-11) | 3% |
| 2-HH-5 | (13-1) | 3% |
| 3-HH-4 | (13-1) | 15% |
| 3-HH-5 | (13-1) | 4% |
| 3-HB-O2 | (13-5) | 12% |
| 3-H2B(2F,3F)-O2 | (6-4) | 12% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 9% |
| 3-HHB-1 | (14-1) | 3% |
| 3-HHB-3 | (14-1) | 4% |
| 3-HHB-O1 | (14-1) | 3% |

NI = 77.5° C.; Δn = 0.094; Δε = −4.1; η = 21.4 mPa · s.

Example 18

| | | |
|---|---|---|
| 3-H2Xt(3F,4F,5F)-O2 | (1-3-1) | 3% |
| 2-HH-3 | (13-1) | 21% |
| 3-HH-4 | (13-1) | 9% |
| 1-BB-3 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 10% |
| 3-HH1OB(2F,3F)-O2 | (7-5) | 21% |
| 3-HHB-1 | (14-1) | 5% |
| 3-HHB-O1 | (14-1) | 3% |
| 5-B(F)BB-2 | (14-8) | 2% |

NI = 73.3° C.; Δn = 0.098; Δε = −3.3; η = 14.7 mPa · s.

Example 19

| | | |
|---|---|---|
| 5-H1OXt(3F,4F,5F)-2V | (1-5-18) | 3% |
| 2-HH-3 | (13-1) | 16% |
| 7-HB-1 | (13-5) | 10% |
| 5-HB-O2 | (13-5) | 8% |
| 3-HB(2F,3F)-O2 | (6-1) | 17% |
| 5-HB(2F,3F)-O2 | (6-1) | 16% |
| 3-HHB(2F,3CL)-O2 | (7-12) | 3% |
| 4-HHB(2F,3CL)-O2 | (7-12) | 3% |
| 5-HHB(2F,3CL)-O2 | (7-12) | 2% |
| 3-HH1OCro(7F,8F)-5 | (10-6) | 5% |
| 5-HBB(F)B-2 | (15-5) | 10% |
| 5-HBB(F)B-3 | (15-5) | 7% |

Example 20

| | | |
|---|---|---|
| 3-ch1OXt(3F,4F,5F)-O2 | (1-5-24) | 3% |
| 1-BB-3 | (13-8) | 10% |
| 3-HH-V | (13-1) | 26% |
| 3-BB(2F,3F)-O2 | (6-3) | 13% |
| 3-HBB(2F,3F)-O2 | (7-7) | 10% |
| 2-HH1OB(2F,3F)-O2 | (7-5) | 10% |
| 3-HH1OB(2F,3F)-O2 | (7-5) | 14% |
| 3-HHB-1 | (14-1) | 8% |
| 5-B(F)BB-2 | (14-8) | 6% |

INDUSTRIAL APPLICABILITY

A liquid crystal compound of the invention has a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. A liquid crystal composition of the invention contains the compound, and has a high maximum temperature of a nematic phase, a low minimum temperature of the nematic phase, a small viscosity, a suitable optical anisotropy, a large negative dielectric anisotropy, and a suitable elastic constant. The composition has a suitable balance regarding at least two of physical properties. A liquid crystal display device of the invention includes the composition, and has a wide temperature range in which the device can be used, a short response time, a large voltage holding ratio, a low threshold voltage, a large contrast ratio and a long service life. Therefore, the device can be widely applied to a display of a personal computer, a television and so forth.

What is claimed is:

1. A compound represented by formula (1-A) or (1-B):

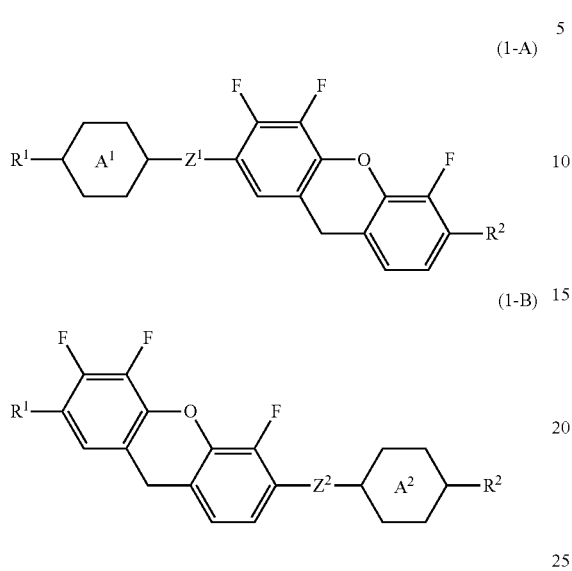

(1-A)

(1-B)

wherein, in formula (1-A) or (1-B),

R$^1$ and R$^2$ are independently alkyl having 1 to 15 carbons, and in the alkyl, at least one of —CH$_2$— may be replaced by —O—, at least one of —(CH$_2$)$_2$— may be replaced by —CH=CH—, and in the groups, at least one of hydrogen may be replaced by halogen;

ring A$^1$ and ring A$^2$ are independently 1,4-cyclohexylene, 1,4-cyclohexenylene, 1,4-phenylene, 1,4-phenylene in which at least one of hydrogen is replaced by fluorine, 1,3-dioxane-2,5-diyl or tetrahydropyran-2,5-diyl; and Z$^1$ and Z$^2$ are independently a single bond, —(CH$_2$)$_2$—, —CH=CH—, —COO—, —OCO—, —CH$_2$O—, —OCH$_2$—, —CF$_2$O—, or —OCF$_2$—.

2. The compound according to claim 1, wherein at least one of ring A$^1$ and ring A$^2$ is tetrahydropyran-2,5-diyl.

3. The compound according to claim 1, represented by any one of formulas (1-A-1) to (1-A-6) and formulas (1-B-1) to (1-B-6):

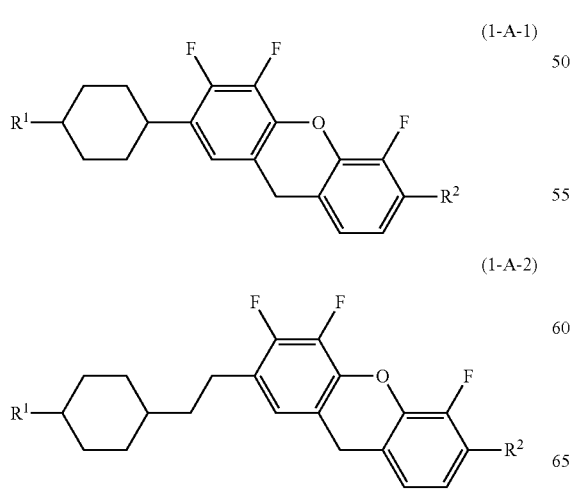

(1-A-1)

(1-A-2)

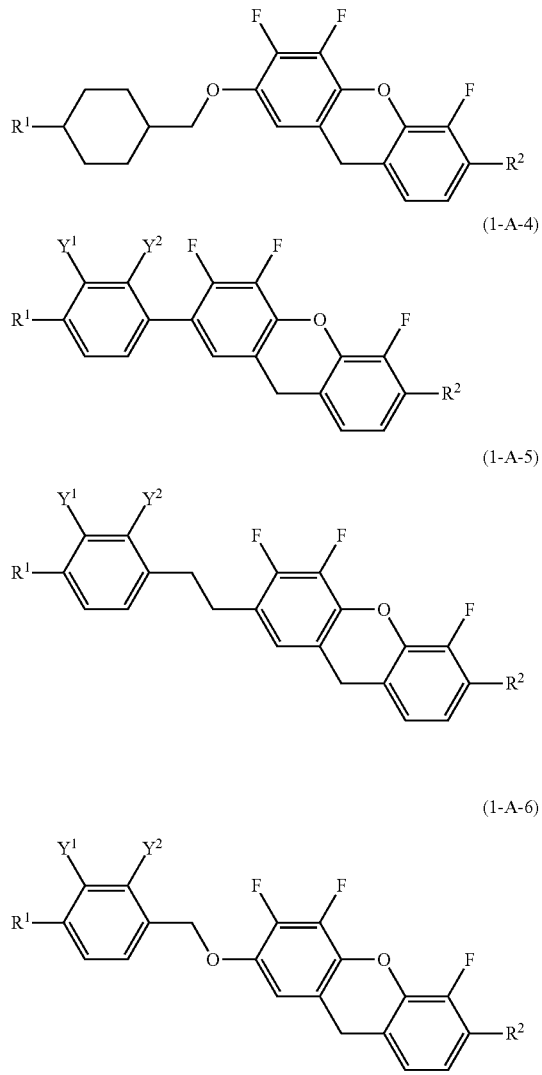

(1-A-3)

(1-A-4)

(1-A-5)

(1-A-6)

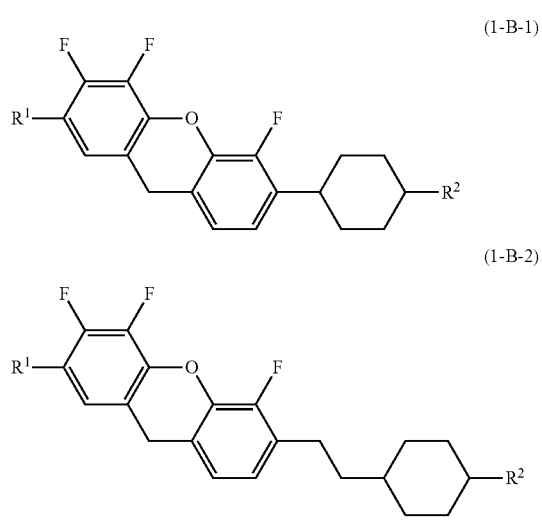

(1-B-1)

(1-B-2)

(1-B-3)
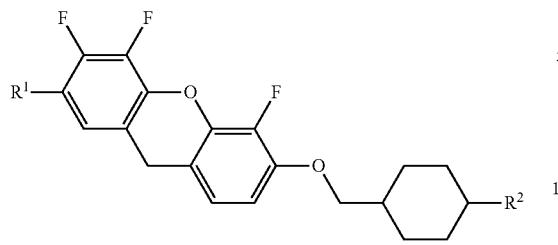
(1-B-4)
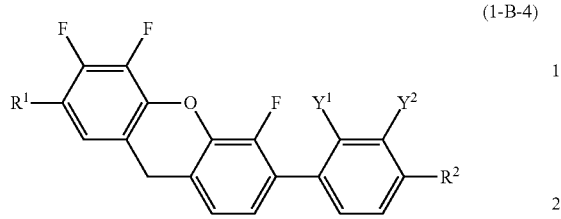
(1-B-5)
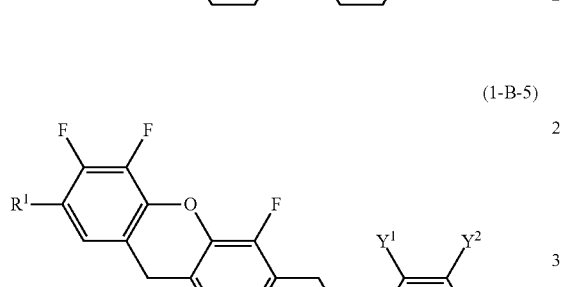
(1-B-6)
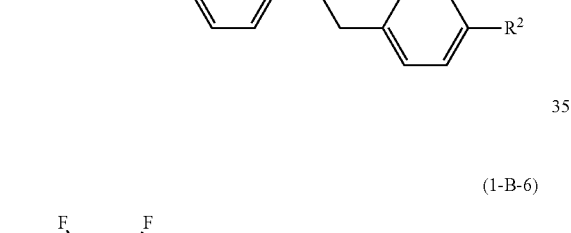
(1-C-1)
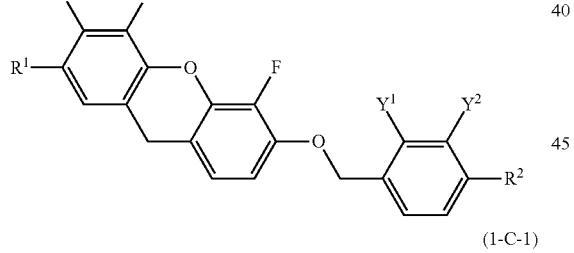
(1-C-2)
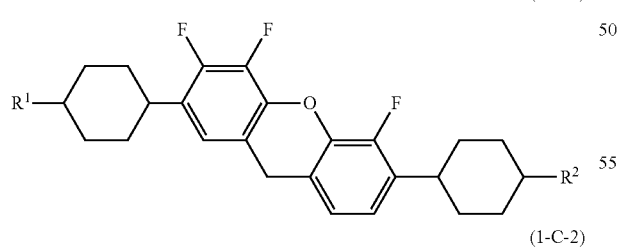
(1-C-3)
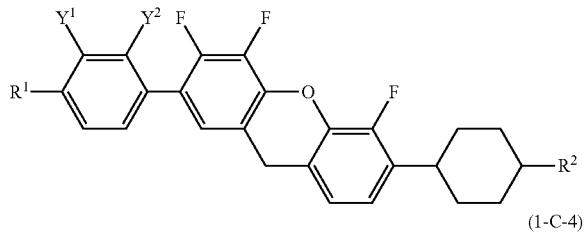
(1-C-4)
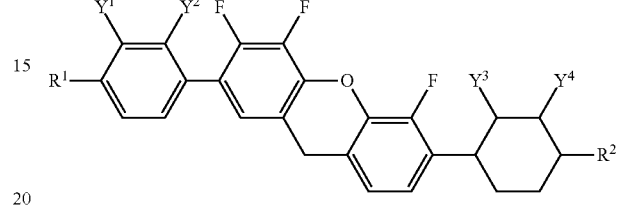
wherein, in formulas (1-A-1) to (1-A-6) and formulas (1-B-1) to (1-B-6), $R^1$ and $R^2$ are independently alkyl having 1 to 10 carbons, alkenyl having 2 to 10 carbons or alkoxy having 1 to 9 carbons, and $Y^1$, $Y^2$, $Y^3$ and $Y^4$ are independently hydrogen or fluorine.
4. The compound according to claim 1, represented by any one of formulas (1-A-7) to (1-A-12) and formulas (1-B-7) to (1-B-12):
(1-A-7)
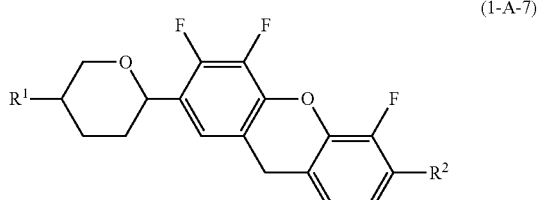
(1-A-8)
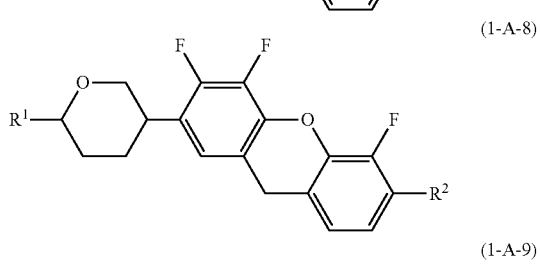
(1-A-9)
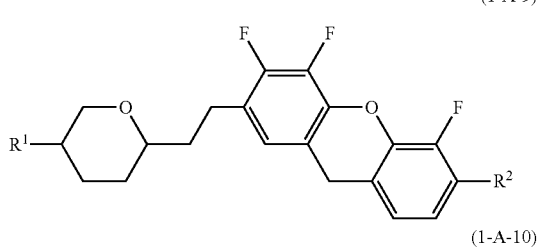
(1-A-10)
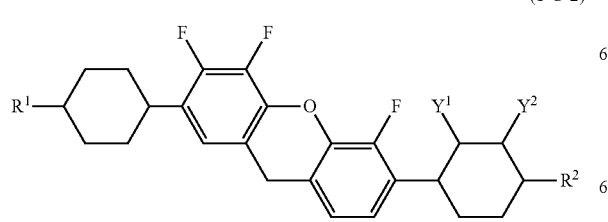
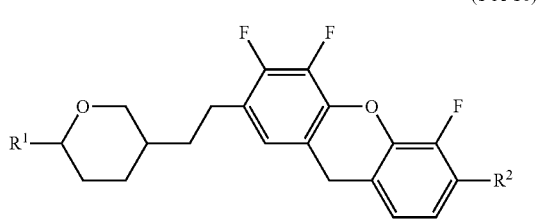

-continued (1-A-11)
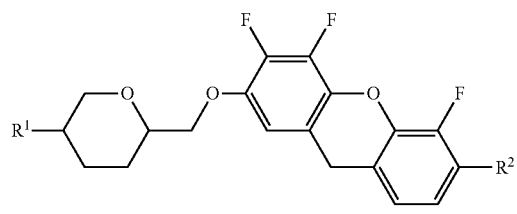

(1-A-12)
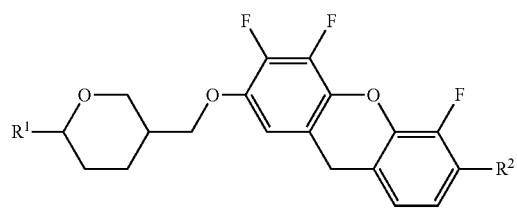

(1-B-7)
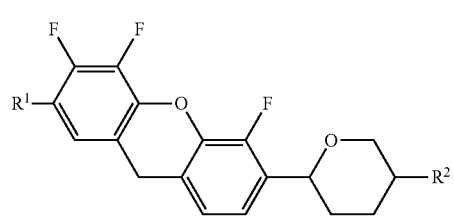

(1-B-8)
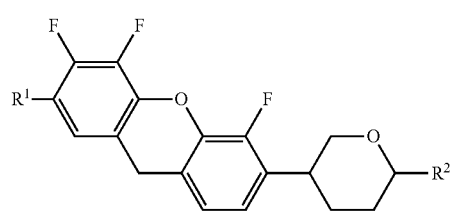

(1-B-9)
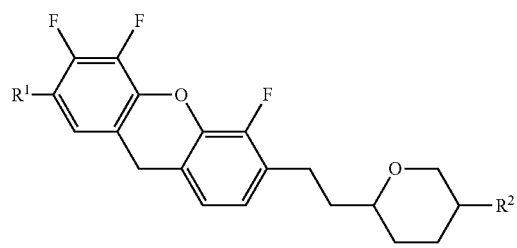

-continued (1-B-10)
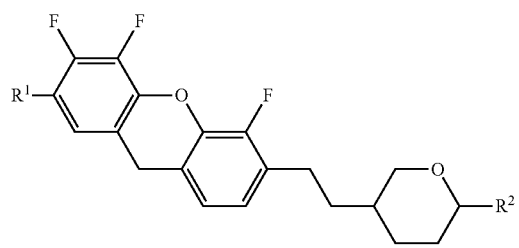

(1-B-11)
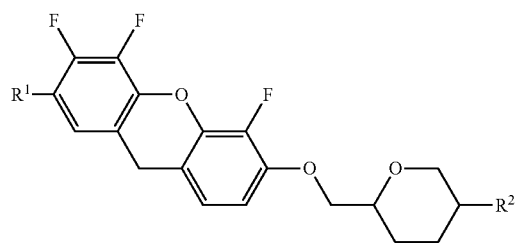

(1-B-12)
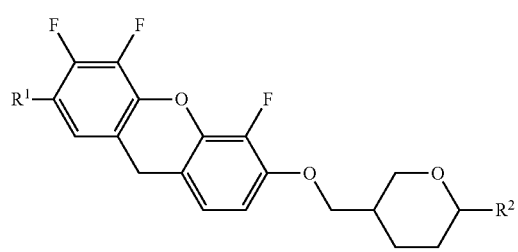

wherein, in formulas (1-A-7) to (1-A-12) and formulas (1-B-7) to (1-B-12), $R^1$ and $R^2$ are independently alkyl having 1 to 10 carbons, alkenyl having 2 to 10 carbons or alkoxy having 1 to 9 carbons.

5. A liquid crystal composition, containing at least one of the compounds according to claim 1.

6. The liquid crystal composition according to claim 5, further containing at least one compound selected from the group of compounds represented by formulas (6) to (12):

(6)
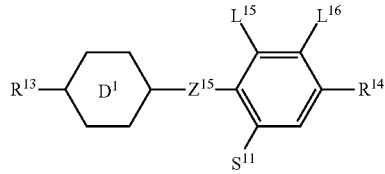

(7)
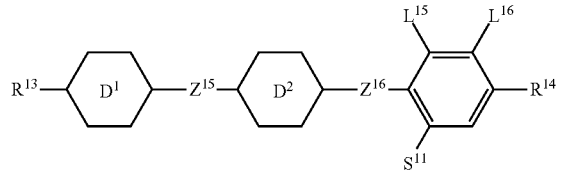

(8)
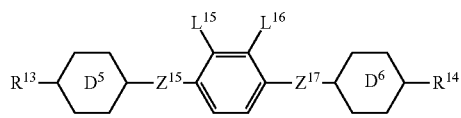

(9)
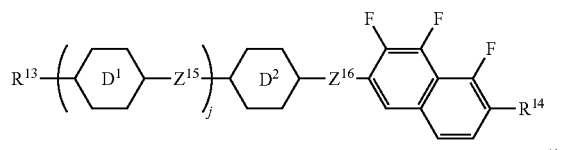

(10)
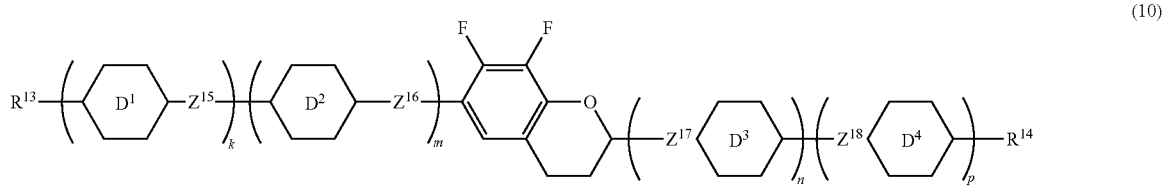

(11)
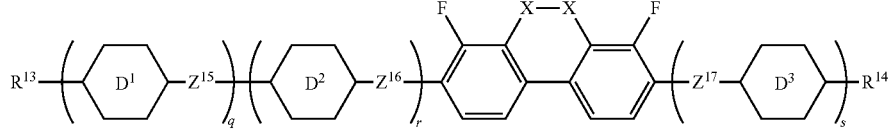

(12)
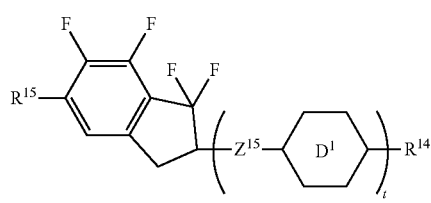

wherein, in formulas (6) to (12), $R^{13}$ is alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;

$R^{14}$ is alkyl having 1 to 10 carbons, and in the alkyl, at least one of —CH$_2$— may be replaced by —O— and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;

$S^{11}$ is hydrogen or methyl;

X is —CF$_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{17}$ and $Z^{18}$ are independently a single bond, —CH$_2$CH$_2$—, —COO—, —CH$_2$O—, —OCF$_2$— or —OCF$_2$CH$_2$CH$_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1,2 or 3, and t is 1,2 or 3.

7. The liquid crystal composition according to claim 5, further containing at least one compound selected from the group of compounds represented by formulas (13) to (15):

(13)
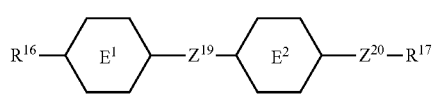

(14)
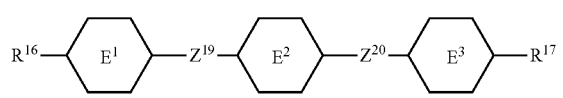

-continued

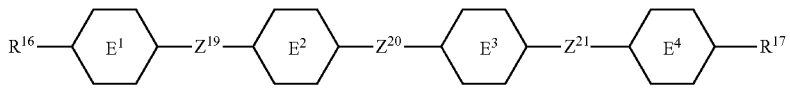
(15)

wherein, in formulas (13) to (15),
R$^{16}$ and R$^{17}$ are independently alkyl having 1 to 10 carbons or alkenyl having 2 to 10 carbons, and in the alkyl or the alkenyl, at least one of —CH$_2$— may be replaced by —O— and at least one of hydrogen may be replaced by fluorine;
ring E$^1$, ring E$^2$, ring E$^3$ and ring E$^4$ are independently 1,4-cyclohexylene, 1,4-phenylene, 2-fluoro-1,4-phenylene, 2,5-difluoro-1,4-phenylene or pyrimidine-2,5-diyl; and
Z$^{19}$, Z$^{20}$ and Z$^{21}$ are independently a single bond, —CH$_2$CH$_2$—, —CH═CH—, or —COO—.

8. The liquid crystal composition according to claim 5, further containing at least one compound selected from the group of compounds represented by formulas (2) to (4):

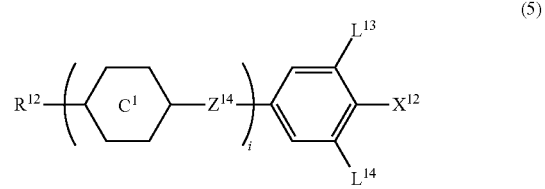
(5)

wherein, in formula (5),
R$^{12}$ is alkyl having 1 to 10 carbons or alkenyl having 2 to 10 carbons, and in the alkyl and alkenyl, at least one of hydrogen may be replaced by fluorine and at least one of —CH$_2$— may be replaced by —O—;

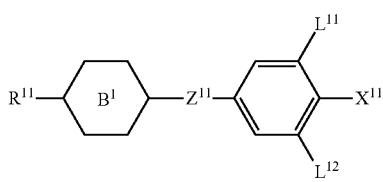
(2)

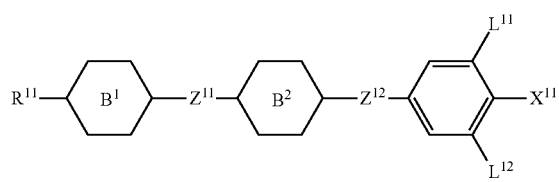
(3)

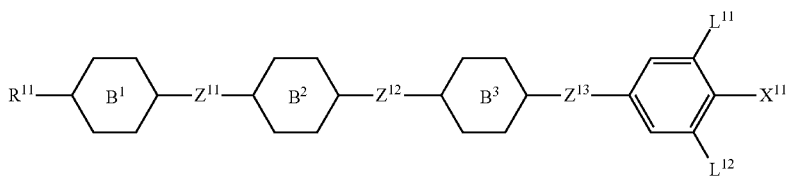
(4)

wherein, in formulas (2) to (4),
R$^{11}$ is alkyl having 1 to 10 carbons or alkenyl having 2 to 10 carbons, and in the alkyl and the alkenyl, at least one of hydrogen may be replaced by fluorine and at least one of —CH$_2$— may be replaced by —O—;
X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring B$^1$, ring B$^2$ and ring B$^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
Z$^{11}$, Z$^{12}$ and Z$^{13}$ are independently a single bond, —CH$_2$CH$_2$—, —CH═CH—, —C≡C—, —COO—, —CF$_2$O—, —OCF$_2$—, —CH$_2$O— or —(CH$_2$)$_4$—; and
L$^{11}$ and L$^{12}$ are independently hydrogen or fluorine.

9. The liquid crystal composition according to claim 5, further containing at least one compound selected from the group of compounds represented by formula (5):

X$^{12}$ is —C≡N or —C≡C—C≡N;
ring C$^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
Z$^{14}$ is a single bond, —CH$_2$CH$_2$—, —COO—, —CF$_2$O—, —OCF$_2$— or —CH$_2$O—;
L$^{13}$ and L$^{14}$ are independently hydrogen or fluorine; and
i is 1, 2, 3 or 4.

10. The liquid crystal composition according to claim 5, further containing at least one optically active compound and/or at least one polymerizable compound.

11. The liquid crystal composition according to claim 5, further containing at least one antioxidant and/or at least one ultraviolet light absorber.

12. A liquid crystal display device, including the liquid crystal composition according to claim 5.

* * * * *